(12) United States Patent
Blum et al.

(10) Patent No.: US 10,138,230 B2
(45) Date of Patent: Nov. 27, 2018

(54) AUTOTAXIN INHIBITORS

(71) Applicant: CANCER RESEARCH TECHNOLOGY LIMITED, London (GB)

(72) Inventors: Francesca Blum, Cambridge (GB); James Lindsay Carr, Cambridge (GB); Pritom Shah, Cambridge (GB); Maria Del Mar Jimenez Quesada, Cambridge (GB); Irene Farre Gutierrez, Cambridge (GB)

(73) Assignee: Cancer Research Technology Limited, London (GB)

( * ) Notice: Subject to any disclaimer, the term of this patent is extended or adjusted under 35 U.S.C. 154(b) by 0 days.

(21) Appl. No.: 15/547,776

(22) PCT Filed: Feb. 4, 2016

(86) PCT No.: PCT/GB2016/050267
§ 371 (c)(1),
(2) Date: Jul. 31, 2017

(87) PCT Pub. No.: WO2016/124938
PCT Pub. Date: Aug. 11, 2016

(65) Prior Publication Data
US 2018/0022742 A1   Jan. 25, 2018

(30) Foreign Application Priority Data

Feb. 4, 2015   (GB) .................................. 1501870.8
Feb. 18, 2015  (GB) .................................. 1502716.2

(51) Int. Cl.
| | | |
|---|---|---|
| C07D 417/14 | (2006.01) | |
| C07D 413/14 | (2006.01) | |
| C07D 401/14 | (2006.01) | |
| C07D 403/12 | (2006.01) | |
| C07D 417/12 | (2006.01) | |
| C07D 413/12 | (2006.01) | |
| C07D 405/14 | (2006.01) | |
| A61K 31/454 | (2006.01) | |
| A61K 31/5377 | (2006.01) | |
| A61K 31/433 | (2006.01) | |

(Continued)

(52) U.S. Cl.
CPC .......... *C07D 417/14* (2013.01); *A61K 31/433* (2013.01); *A61K 31/454* (2013.01); *A61K 31/496* (2013.01); *A61K 31/501* (2013.01); *A61K 31/5377* (2013.01); *A61K 31/55* (2013.01); *A61K 31/551* (2013.01); *A61K 31/553* (2013.01); *A61K 45/06* (2013.01); *C07D 401/14* (2013.01); *C07D 403/12* (2013.01); *C07D 405/14* (2013.01); *C07D 413/12* (2013.01); *C07D 413/14* (2013.01); *C07D 417/12* (2013.01)

(58) Field of Classification Search
CPC . C07D 403/12; C07D 403/14; A61K 31/4025
See application file for complete search history.

(56) References Cited

U.S. PATENT DOCUMENTS

| 6,184,225 B1 | 2/2001 | Thomas et al. |
| 6,291,455 B1 | 9/2001 | Thomas et al. |

(Continued)

FOREIGN PATENT DOCUMENTS

| WO | WO-0208213 A1 | 1/2002 |
| WO | WO 2008/109994 | 9/2008 |

(Continued)

OTHER PUBLICATIONS

West, Anthony R., Solid State Chemistry and Its Applications, Wiley, New York, 1988, 358.*
Barbayianni et al., "Autotaxin inhibitors; a patent review", Expert Opinion on Therapeutic Patents, Informa Healthcare, United Kingdom, (20130901), vol. 23, No. 9, pp. 1123-1132.
PCT International Search Report and Written Opinion for Application No. PCT/GB2016/050267 dated Mar. 30, 2016.
Aznavoorian, Sadie, et al. "Signal transduction for chemotaxis and haptotaxis by matrix molecules in tumor cells." *The Journal of cell biology* 110.4 (1990): 1427-1438.

(Continued)

*Primary Examiner* — Erich A Leeser
(74) *Attorney, Agent, or Firm* — Mintz Levin Cohn Ferris Glovsky and Popeo PC

(57) ABSTRACT

The present invention relates to compounds of formula (I): wherein $R_1$, $R_2$, $R_3$, $R_{4a}$, $R_{4b}$, $R_{4c}$, $R_{4d}$, L, A, Q, W and HET are each as defined herein. The compounds of the present invention are inhibitors of autotaxin (ATX) enzyme activity. The present invention also relates to processes for the preparation of these compounds, to pharmaceutical compositions comprising them, and to their use in the treatment of proliferative disorders, such as cancer, as well as other diseases or conditions (e.g. fibrosis) in which ATX activity is implicated.

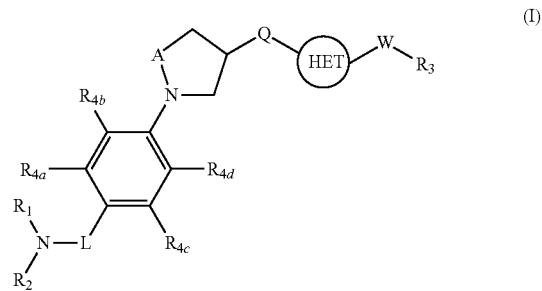

26 Claims, 3 Drawing Sheets

(51) Int. Cl.

| | |
|---|---|
| A61K 31/496 | (2006.01) |
| A61K 31/551 | (2006.01) |
| A61K 31/55 | (2006.01) |
| A61K 31/553 | (2006.01) |
| A61K 31/501 | (2006.01) |
| A61K 45/06 | (2006.01) |

(56) References Cited

U.S. PATENT DOCUMENTS

| | | | |
|---|---|---|---|
| 6,362,336 | B1 | 3/2002 | Lohmann et al. |
| 6,423,753 | B1 | 7/2002 | Dougherty |
| 6,897,210 | B2 | 5/2005 | Thomas et al. |
| 7,030,123 | B2 | 4/2006 | Arnould et al. |
| 7,135,502 | B1 | 11/2006 | Davis et al. |
| 7,696,214 | B2 | 4/2010 | Hennequin et al. |
| 7,875,727 | B2 | 1/2011 | Davis |
| 8,022,239 | B2 | 9/2011 | Parrill-Baker et al. |
| 8,268,891 | B1 | 9/2012 | Parrill-Baker et al. |
| 8,343,934 | B2 | 1/2013 | Parrill-Baker et al. |
| 8,492,560 | B2 | 7/2013 | Stokes et al. |
| 8,497,283 | B2 | 7/2013 | Schultz et al. |
| 8,530,650 | B2 | 9/2013 | Schiemann et al. |
| 8,552,001 | B2 | 10/2013 | Schiemann et al. |
| 8,557,824 | B2 | 10/2013 | Schiemann et al. |
| 8,673,882 | B2 | 3/2014 | Gupte et al. |
| 8,791,111 | B2 | 7/2014 | Schiemann et al. |
| 8,841,324 | B2 | 9/2014 | Staehle et al. |
| 8,969,555 | B2 | 3/2015 | Beauchamp et al. |
| 9,029,387 | B2 | 5/2015 | Staehle et al. |
| 9,260,416 | B2 | 2/2016 | Roppe et al. |
| 9,273,011 | B2 | 3/2016 | Gibson et al. |
| 9,394,317 | B2 | 7/2016 | Jones et al. |
| 9,452,997 | B2 | 9/2016 | Schiemann et al. |
| 9,499,485 | B2 | 11/2016 | Guckian et al. |
| 9,522,889 | B2 | 12/2016 | Guckian et al. |
| 9,549,911 | B2 | 1/2017 | Sang et al. |
| 9,550,774 | B2 | 1/2017 | Bleisch et al. |
| 9,550,798 | B2 | 1/2017 | Guckian et al. |
| 9,555,050 | B2 | 1/2017 | Guckian et al. |
| 9,630,945 | B2 | 4/2017 | Furminger et al. |
| 9,636,330 | B2 | 5/2017 | Ohata et al. |
| 9,670,204 | B2 | 6/2017 | Desroy et al. |
| 9,771,326 | B2 | 9/2017 | Peng et al. |
| 9,850,206 | B2 | 12/2017 | Peng et al. |
| 9,862,721 | B2 | 1/2018 | Ohata et al. |
| 2005/0277627 | A1 | 12/2005 | Arnould et al. |
| 2010/0016258 | A1 | 1/2010 | Lynch et al. |
| 2010/0249132 | A1 | 9/2010 | Schultz et al. |
| 2011/0230471 | A1 | 9/2011 | Staehle et al. |
| 2012/0115852 | A1 | 5/2012 | Schultz et al. |
| 2014/0171403 | A1* | 6/2014 | Legrand ............... A61K 31/337 514/210.18 |
| 2015/0203493 | A1 | 7/2015 | Guckian et al. |
| 2015/0376194 | A1 | 12/2015 | Hert et al. |
| 2016/0002247 | A1 | 1/2016 | Nagano et al. |
| 2017/0050960 | A1 | 2/2017 | Hert et al. |

FOREIGN PATENT DOCUMENTS

| | | |
|---|---|---|
| WO | WO-2011053597 A1 | 5/2011 |
| WO | WO-2013054185 A1 | 4/2013 |
| WO | WO-2015193669 A1 | 12/2015 |

OTHER PUBLICATIONS

Baumforth, Karl RN, et al. "Induction of autotaxin by the Epstein-Barr virus promotes the growth and survival of Hodgkin lymphoma cells." *Blood* 106.6 (2005): 2138-2146.

Boucharaba, Ahmed, et al. "Platelet-derived lysophosphatidic acid supports the progression of osteolytic bone metastases in breast cancer." *The Journal of clinical investigation* 114.12 (2004): 1714-1725.

Boucher, Jérémie, et al. "Potential involvement of adipocyte insulin resistance in obesity-associated up-regulation of adipocyte lysophospholipase D/autotaxin expression." *Diabetologia* 48.3 (2005): 569-577.

Choi, Ji Woong, et al. "LPA receptors: subtypes and biological actions." *Annual review of pharmacology and toxicology* 50 (2010): 157-186.

Cui, Peng, et al. "α-and β-substituted phosphonate analogs of LPA as autotaxin inhibitors." *Bioorganic & medicinal chemistry* 16.5 (2008): 2212-2225.

Cui, Peng, et al. "Synthesis and biological evaluation of phosphonate derivatives as autotaxin (ATX) inhibitors." *Bioorganic & medicinal chemistry letters* 17.6 (2007): 1634-1640.

Ferry, Gilles, et al. "S32826, a nanomolar inhibitor of autotaxin: discovery, synthesis and applications as a pharmacological tool." *Journal of Pharmacology and Experimental Therapeutics* 327.3 (2008): 809-819.

Gajewiak, Joanna, et al. "Synthesis, pharmacology, and cell biology of sn-2-aminooxy analogues of lysophosphatidic acid." *Organic letters* 10.6 (2008): 1111-1114.

Hausman, D. B., et al. "The biology of white adipocyte proliferation." *Obesity reviews* 2.4 (2001): 239-254.

Houben, Anna JS, et al. "Autotaxin and LPA receptor signaling in cancer." *Cancer and Metastasis Reviews* 30.3-4 (2011): 557-565.

Inoue, Makoto, et al. "Autotaxin, a synthetic enzyme of lysophosphatidic acid (LPA), mediates the induction of nerve-injured neuropathic pain." *Molecular pain* 4.1 (2008): 6.

Inoue, Makoto, et al. "Initiation of neuropathic pain requires lysophosphatidic acid receptor signaling." *Nature medicine* 10.7 (2004): 712.

Jiang, Guowei, et al. "α-Substituted Phosphonate Analogues of Lysophosphatidic Acid (LPA) Selectively Inhibit Production and Action of LPA." *ChemMedChem* 2.5 (2007): 679-690.

Kanda, Hidenobu, et al. "Autotaxin, an ectoenzyme that produces lysophosphatidic acid, promotes the entry of lymphocytes into secondary lymphoid organs." *Nature immunology* 9.4 (2008): 415.

Knowlden, Sara, et al. "The autotaxin-LPA axis emerges as a novel regulator of lymphocyte homing and inflammation." *The Journal of Immunology* 192.3 (2014): 851-857.

Kremer, Andreas E., et al. "Serum autotaxin is increased in pruritus of cholestasis, but not of other origin, and responds to therapeutic interventions." *Hepatology* 56.4 (2012): 1391-1400.

Leblanc, Raphael, et al. "New insights into the autotaxin/LPA axis in cancer development and metastasis." *Experimental cell research* 333.2 (2015): 183-189.

Lin, Songbai, et al. "The absence of LPA2 attenuates tumor formation in an experimental model of colitis-associated cancer." *Gastroenterology* 136.5 (2009): 1711-1720.

Liu, Shuying, et al. "Expression of autotaxin and lysophosphatidic acid receptors increases mammary tumorigenesis, invasion, and metastases." *Cancer cell* 15.6 (2009): 539-550.

Marshall, Jean-Claude A., et al. "Effect of inhibition of the lysophosphatidic acid receptor 1 on metastasis and metastatic dormancy in breast cancer." *Journal of the National Cancer Institute* 104.17 (2012): 1306-1319.

Masuda, Akiko, et al. "Serum autotaxin measurement in haematological malignancies: a promising marker for follicular lymphoma." *British journal of haematology* 143.1 (2008): 60-70.

Moolenaar, Wouter H., et al. "Autotaxin in embryonic development." *Biochimica et Biophysica Acta (BBA)—Molecular and Cell Biology of Lipids* 1831.1 (2013): 13-19.

Murakami, Masanori, et al. "Identification of the orphan GPCR, P2Y 10 receptor as the sphingosine-1-phosphate and lysophosphatidic acid receptor." *Biochemical and biophysical research communications* 371.4 (2008): 707-712.

Nakamura, Kazuhiro, et al. "Serum lysophospholipase D/autotaxin may be a new nutritional assessment marker: study on prostate cancer patients." *Annals of clinical biochemistry* 44.6 (2007): 549-556.

Nakao, Momoko, et al. "Serum autotaxin levels correlate with pruritus in patients with atopic dermatitis." *The Journal of investigative dermatology* 134.6 (2014): 1745.

(56) References Cited

OTHER PUBLICATIONS

Nakasaki, Tae, et al. "Involvement of the lysophosphatidic acid-generating enzyme autotaxin in lymphocyte-endothelial cell interactions." *The American journal of pathology* 173.5 (2008): 1566-1576.

Nishimura, Satoshi, et al. "ENPP2 contributes to adipose tissue expansion and insulin resistance in diet-induced obesity." *Diabetes* 63.12 (2014): 4154-4164.

Pamuklar, Zehra, et al. "Autotaxin/lysopholipase D and lysophosphatidic acid regulate murine hemostasis and thrombosis." *Journal of Biological Chemistry* 284.11 (2009): 7385-7394.

Pradere, Jean-Philippe, et al. "LPA1 receptor activation promotes renal interstitial fibrosis." *Journal of the American Society of Nephrology* 18.12 (2007): 3110-3118.

Reynolds, G., et al. "The autotaxin-lysophosphatidate axis plays a key role in the pathogenesis of Hepatitis C virus-associated Hepatocellular carcinoma." *Virchows Archiv.* vol. 465. 233 Spring St, New York, NY 10013 USA: Springer, 2014.

Saga, Hiroshi, et al. "A novel highly potent autotaxin/ENPP2 inhibitor produces prolonged decreases in plasma lysophosphatidic acid formation in vivo and regulates urethral tension." *PLoS One* 9.4 (2014): e93230.

Siess, Wolfgang, et al. "Lysophosphatidic acid mediates the rapid activation of platelets and endothelial cells by mildly oxidized low density lipoprotein and accumulates in human atherosclerotic lesions." *Proceedings of the National Academy of Sciences* 96.12 (1999): 6931-6936.

Siess, Wolfgang, et al. "Thrombogenic and atherogenic activities of lysophosphatidic acid." *Journal of cellular biochemistry* 92.6 (2004): 1086-1094.

Tabata, Ken-ichi, et al. "The orphan GPCR GPR87 was deorphanized and shown to be a lysophosphatidic acid receptor." *Biochemical and biophysical research communications* 363.3 (2007): 861-866.

Tager, Andrew M., et al. "The lysophosphatidic acid receptor LPA 1 links pulmonary fibrosis to lung injury by mediating fibroblast recruitment and vascular leak." *Nature medicine* 14.1.

Taghavi, P., et al. "In vitro genetic screen identifies a cooperative role for LPA signaling and c-Myc in cell transformation." *Oncogene* 27.54 (2008): 6806.

Tigyi, Gabor. "Physiological responses to lysophosphatidic acid and related glycero-phospholipids." *Prostaglandins & other lipid mediators* 64.1-4 (2001): 47-62.

Van Meeteren, Laurens A., et al. "Inhibition of autotaxin by lysophosphatidic acid and sphingosine 1-phosphate." *Journal of Biological Chemistry* 280.22 (2005): 21155-21161.

Van Meeteren, Laurens A., et al. "Regulation and biological activities of the autotaxin-LPA axis." *Progress in lipid research* 46.2 (2007): 145-160.

Watanabe, Naoko, et al. "Both plasma lysophosphatidic acid and serum autotaxin levels are increased in chronic hepatitis C." *Journal of clinical gastroenterology* 41.6 (2007): 616-623.

Wu, Jian-Min, et al. "Autotaxin expression and its connection with the TNF-alpha-NF-κB axis in human hepatocellular carcinoma." *Molecular cancer* 9.1 (2010): 71.

Zhang, Honglu, et al. "Dual activity lysophosphatidic acid receptor pan-antagonist/autotaxin inhibitor reduces breast cancer cell migration in vitro and causes tumor regression in vivo." *Cancer research* 69.13 (2009): 5441-5449.

Zhang, Yafeng, et al. "Autotaxin through lysophosphatidic acid stimulates polarization, motility, and transendothelial migration of naive T cells." *The Journal of Immunology* 189.8 (2012): 3914-3924.

Zhao, Hongjuan, et al. "Distinctive gene expression of prostatic stromal cells cultured from diseased versus normal tissues." *Journal of cellular physiology* 210.1 (2007): 111-121.

Zu Heringdorf, Dagmar Meyer, et al. "Lysophospholipid receptors: signalling, pharmacology and regulation by lysophospholipid metabolism." *Biochimica et Biophysica Acta (BBA)-Biomembranes* 1768.4 (2007): 923-940 (2008): 45.

\* cited by examiner

AUTOTAXIN INHIBITORS

CROSS-REFERENCE TO RELATED APPLICATIONS

This application is a U.S. national stage application of International Patent Application No. PCT/GB2016/050267, filed on Feb. 4, 2016, which claims priority to GB Application No. 1501870.8, filed on Feb. 4, 2015, and GB Application No. 1502716.2, filed on Feb. 18, 2015, the content of each of these applications is incorporated herein in its entirety by reference.

FIELD OF THE INVENTION

The present invention relates to certain compounds that function as inhibitors of autotaxin (ATX) enzyme activity. The present invention also relates to processes for the preparation of these compounds, to pharmaceutical compositions comprising them, and to their use in the treatment of proliferative disorders, such as cancer, as well as other diseases or conditions (e.g. fibrosis) in which ATX activity is implicated.

BACKGROUND OF THE INVENTION

Autotaxin (ATX), also known as ectonucleotide pyrophosphatase/phosphodiesterase family member 2 (ENPP2), is a secreted lysophospholipase D (lysoPLD) that cleaves choline from lysophosphatidylcholine (LPC) forming lysophosphatidic acid (LPA), a potent mitogen and motily factor that has been implicated in the pathophysiology of cancer (Liu et al., 2009) (Houben and Moolenaar, 2011) (Leblanc and Peyruchaud, 2014) and many other biological processes such as vascular development lymphocyte homing and inflammation (see, e.g., Van Meeteren et al., 2007) (Moolenaar et al., 2013) (Knowlden and Georas, 2014). LPA consists of a single fatty acyl chain, a glycerol backbone and a free phosphate group. The great variety of cellular and biological actions of LPA is explained by the fact that the six known LPA receptors show broad tissue expression and can couple to at least six distinct G proteins, which, in turn, feed into multiple effector systems (Choi et al., 2010).

ATX is processed along the classical export pathway and secreted as a catalytically active glycoprotein. ATX's major lipid substrate, LPC, is secreted by the liver and is abundantly present in plasma and interstitial fluids.

As previously indicated, ATX is implicated in cancer and numerous other disease states. The role of ATX in cancer and various other disease states is summarised below.

ATX and Cancer

ATX is widely expressed, with highest mRNA levels detected in lymph nodes, brain, kidney, testis, pancreas, lung and liver. ATX is found overexpressed in several common human cancers, while many established tumour cell lines express ATX to varying levels (see references above). Expression is also detected in stromal cells, including macrophages, fibroblasts and endothelial cells.

ATX is an attractive target for the treatment of cancer because it acts extracellularly and stimulates the metastatic cascade at multiple levels. In addition, ATX has been implicated in inflammatory processes by regulating lymphocyte homing (Kanda et al, 2008; Zhang et al, 2012; Knowlden and Georas, 2014).

ATX is thought to act in an autocrine/paracrine manner to promote tumour progression, i.e., by providing an invasive and angiogenic microenvironment for malignant cells. A causal link between the ATX-LPA axis and cancer is supported by a growing number of studies (for a review, see Van Meeteren et al., 2007; Houben A J, Moolenaar W H (2011). Cancer Metastasis Rev. 30:557-65.) (Leblanc and Peyruchaud, 2015).

Overexpressed ATX promotes tumour aggressiveness, metastasis and angiogenesis in mice (Liu et al., 2009).

ATX is overexpressed in various human cancers, including glioblastoma, lung and breast cancer, renal cell carcinoma and Hodgkin lymphoma. Furthermore, ATX is upregulated in stromal cells from cancer patients. (See, e.g., Zhao et al., 2007).

ATX mediates the EBV-induced growth and survival of Hodgkin lymphoma cells, while ATX knockdown reduces lymphoma cell growth and viability. (See, e.g., Baumforth et al., 2005).

Inducible overexpression of LPA1 receptors in breast carcinoma cells promotes tumour growth and bone metastasis, while LPA1 knockdown reduces tumour progression (Bouchabara et al., 2006).

ATX and LPA receptors have transforming potential both in vitro and in mice. (See, e.g., Taghavi et al., 2008. Liu et al. (2009) Cancer Cell. 15:539-50).

Inhibition of the LPA1 receptor reduces metastasis and metastatic dormancy in breast cancer. (Marshall et al., 2012).

Serum ATX levels in patients with B-cell neoplasms, especially follicular lymphoma (FL), are higher than those in healthy subjects (see, e.g., Masuda et al., 2008). Serum ATX in FL patients was associated with tumour burden and changed in parallel with the patients' clinical courses. Plasma LPA levels in FL patients correlated well with ATX levels. Since tumour cells from FL patients expressed ATX, secreted ATX from lymphoma cells probably underlies the increase in serum ATX. Thus, serum ATX is a promising marker for FL.

ATX/lysoPLD activity is also significantly elevated in malignant effusions from ovarian cancer patients. Furthermore, serum ATX activity decreases after prostate cancer surgery and may reflect postoperative damage or nutritional status. See, e.g., Nakamura et al., 2007.

Dual ATX and pan-LPA receptor inhibitors inhibit breast cancer cell migration and invasion and cause tumour regression in breast cancer xenograft model. (See, e.g., Zhang et al., 2009).

Overexpression of ATX or LPA receptors in breast cancer epithelium causes high frequency of late-onset mammary carcinomas. (See, e.g., Liu et al., 2009).

LPA2 knockout mice have reduced incidence of chemically induced colon carcinoma. (See, e.g., Lin et al., 2009).

ATX and Inflammation

High ATX expression is found in the high endothelial venules (HEVs) of lymphoid organs and in venules at sites of chronic inflammation, where it may play a role in T cell trafficking across the endothelial walls during inflammation. (See, e.g., Kanda et al., 2008). Intravenous injection of enzymatically inactive ATX attenuated the homing of T cells to lymphoid tissues, probably through competition with endogenous ATX. These results suggest that ATX is a potential target for anti-inflammatory therapy.

Along similar lines, Japanese investigators recently showed that injection of neutralizing monoclonal antibodies against ATX into mice reduced plasma LPA levels to zero. (See, e.g., Nakasaki et al., 2008). It thus appears that plasma LPA can be depleted by targeting ATX. These results suggest that ATX is a potential target for anti-inflammatory therapy.

ATX and Diabetes Melitus

ATX expression is significantly up-regulated in adipose tissue from patients exhibiting both insulin resistance and impaired glucose tolerance (see, for example, Boucher et al., 2005). This suggests that ATX may serve as a therapeutic target in obesity-associated type 2 diabetes (Nishimura S, et al. (2014). ENPP2 Contributes to Adipose Tissue Expansion and Insulin Resistance in Diet-Induced Obesity. Diabetes 63:4154-64).

ATX and Hypertension, Atherosclerosis and Thrombosis

LPA accumulates in the lipid core of human atherosclerotic plaques and is the primary platelet-activating lipid constituent of the plaques (see, for example, Siess et al., 1999). Furthermore, due to its ability to stimulate the proliferation of vascular smooth muscle cells, LPA may play an important role in the development of both hypertension and atherosclerosis (see, for example, Siess et al., 2004). Recent evidence shows that plasma ATX associates with platelets during aggregation and concentrates in arterial thrombus (see, for example, Pamuklar et al., 2009). Thus, unbalanced LPA homeostasis is a potential risk factor for thrombosis. Therefore, LPA-lowering ATX inhibitors may prove useful in the treatment of both hypertension and atherosclerosis.

ATX and Fibrosis

Mice lacking the LPA1 receptor are markedly protected from pulmonary fibrosis and mortality (see, e.g., Tager et al., 2008). The absence of LPA1 leads to reduced fibroblast recruitment and vascular leak, two responses that are excessive when injury leads to fibrosis rather than to repair. Thus, the ATX-LPA axis represents a therapeutic target for diseases in which aberrant responses to injury contribute to fibrosis, such as idiopathic pulmonary fibrosis, as well as renal interstitial fibrosis (see, e.g., Pradere et al., 2007), hepatic fibrosis and skin fibrosis.

ATX and Pain

Mice lacking the LPA1 receptor are also protected against injury-induced neuropathic pain and related behaviour (see, e.g., Inoue et al., 2004). Heterozygous Enpp2(+/−) mice, which have 50% ATX protein compared to wild-type mice, show approx. 50% recovery of nerve injury-induced neuropathic pain (see, e.g., Inoue et al., 2008). Therefore, targeting ATX (and its downstream LPA signaling pathways) represents a novel way to prevent nerve injury-induced neuropathic pain.

ATX and Urethral Obstructive Disease

Smooth muscle contraction is known to be promoted by lysophosphatidic acid and inhibition of ATX has been shown to decrease intraurethral pressure accompanied by urethral relaxation (see e.g. Saga et al., 2014). Therefore, targeting ATX (and its downstream LPA signaling pathways) represents a useful method for the treatment of urethral obstructive disease such as benign prostatic hyperplasia.

ATX and Pruritus

Serum ATX levels have been reported to correlate with pruritus of cholestasis (Kremer et al., 2012). Serum ATX levels have also been shown to correlate with pruritus in patients with atopic dermatitis (Nakao et al., 2014). This suggests that targeting ATX (and its downstream LPA signaling pathways) represents a useful method for the treatment of pruritus.

ATX and Hepatitis C and B/Human Hepatocellular Carcinoma

Serum ATX activity and plasma LPA levels are increased in chronic hepatitis C (HCV) in association with liver fibrosis (Watanabe et al, 2007). ATX and genes related to ATX signalling pathway were up regulated in human hepatocellular carcinoma (HCC) patients co-infected with HCV (Wu et al, 2010). It has recently been reported that ATX expression in tumour cells is specifically associated with HCV and that ATX plays a key role in HCV replication. (Reynolds et al, 2014). Recent studies have also reported the ATX-LPA signalling axis to play an essential role in the lifecycle of both chronic hepatitis B (HBV) and chronic hepatitis C (HCV) (WO2015193669). Thus, ATX-LPA is also a potential therapeutic target for the treatment of hepatitis B and hepatitis C.

ATX Inhibitors

Potent and selective ATX inhibitors are now needed as a starting point for the development of targeted anti-ATX therapy. Direct targeting of LPA receptors seems to be a less attractive strategy, since there are at least six distinct LPA receptors that show overlapping activities (see Choi et al. (2010). Since it was reported that ATX is subject to product inhibition by LPA and sphingosine-1-phosphate (S1P) (see, e.g., van Meeteren et al., 2005), various synthetic phospho- and phosphonate lipids have been explored as ATX inhibitors (see, e.g., Gajewiak et al., 2008; Cui et al, 2007; Jiang et al., 2007; Ferry et al., 2008; Zhang et al., 2009; Cui et al., 2008). However, these inhibitors have the inherent danger of inadvertently activating downstream LPA/S1P receptors, thereby inducing the opposite of the intended effect. Furthermore, lipids offer relatively few avenues for chemical diversification and usually have poor pharmacokinetic properties.

Non-lipid inhibitors of ATX have recently been identified and some of which are described in the following patents: WO2009046841; WO2009046804; WO2009046842; WO 2010115491; WO2010060532; WO2010063352; WO2010112116; WO2010112124; US2010/0016258; WO201040080; WO2011006569; WO2011044978; WO2011116867; WO2011053597; WO2011002918; WO2012166415; WO2012005227; WO2012127885; U.S. Pat. No. 8,268,891; WO2012100018; WO2013061297; WO2013054185; WO2014018881; WO2014018887; WO2014081756; WO2014152725; WO2014110000; WO2014168824; WO2014018891; WO2014025708; WO2014025709; WO2014081752; WO2014139882; WO2014143583; WO2014097151; WO 2014048865; WO2014139978; WO 2014133112.

SUMMARY OF THE INVENTION

In one aspect, the present invention provides a compound as defined herein, or a pharmaceutically acceptable salt or solvate thereof.

In another aspect, the present invention provides a pharmaceutical composition as defined herein which comprises a compound as defined herein, or a pharmaceutically acceptable salt or solvate thereof, and one or more pharmaceutically acceptable excipients.

In another aspect, the present invention provides a compound as defined herein, or a pharmaceutically acceptable salt or solvate thereof, or a pharmaceutical composition as defined herein, for use in therapy.

In another aspect, the present invention provides a compound as defined herein, or a pharmaceutically acceptable salt or solvate thereof, or a pharmaceutical composition as defined herein, for use in the treatment of a proliferative condition.

In another aspect, the present invention provides a compound as defined herein, or a pharmaceutically acceptable salt or solvate thereof, or a pharmaceutical composition as defined herein, for use in the treatment of cancer. In a particular embodiment, the cancer is a human cancer.

In another aspect, the present invention provides a compound as defined herein, or a pharmaceutically acceptable salt or solvate thereof, or a pharmaceutical composition as defined herein, for use in the treatment of inflammation.

In another aspect, the present invention provides a compound as defined herein, or a pharmaceutically acceptable salt or solvate thereof, or a pharmaceutical composition as defined herein, for use in the treatment of diabetes mellitus.

In another aspect, the present invention provides a compound as defined herein, or a pharmaceutically acceptable salt or solvate thereof, or a pharmaceutical composition as defined herein, for use in the treatment of hypertension, Atherosclerosis or Thrombosis.

In another aspect, the present invention provides a compound as defined herein, or a pharmaceutically acceptable salt or solvate thereof, or a pharmaceutical composition as defined herein, for use in the treatment of pain. In a particular embodiment, the pain is neuropathic pain.

In another aspect, the present invention provides a compound as defined herein, or a pharmaceutically acceptable salt or solvate thereof, or a pharmaceutical composition as defined herein, for use in the treatment of urethral obstructive disease. In a particular embodiment, the urethral obstructive disease is benign prostatic hyperplasia.

In another aspect, the present invention provides a compound as defined herein, or a pharmaceutically acceptable salt or solvate thereof, or a pharmaceutical composition as defined herein, for use in the treatment of pruritus.

In another aspect, the present invention provides a compound as defined herein, or a pharmaceutically acceptable salt or solvate thereof, or a pharmaceutical composition as defined herein, for use in the treatment of hepatitis B and/or C.

In another aspect, the present invention provides a compound as defined herein, or a pharmaceutically acceptable salt or solvate thereof, or a pharmaceutical composition as defined herein, for use in the treatment of fibrosis, including lung, renal, hepatic and skin fibrosis.

In another aspect, the present invention provides a compound as defined herein, or a pharmaceutically acceptable salt or solvate thereof, or a pharmaceutical composition as defined herein, for use in the production of an ATX inhibitory effect.

In another aspect, the present invention provides the use of a compound as defined herein, or a pharmaceutically acceptable salt or solvate thereof, in the manufacture of a medicament for use in the treatment of a proliferative condition.

In another aspect, the present invention provides the use of a compound as defined herein, or a pharmaceutically acceptable salt or solvate thereof, in the manufacture of a medicament for use in the treatment of cancer. Suitably, the medicament is for use in the treatment of human cancers.

In another aspect, the present invention provides the use of a compound as defined herein, or a pharmaceutically acceptable salt or solvate thereof, in the manufacture of a medicament for use in the production of an ATX inhibitory effect.

In another aspect, the present invention provides a method of inhibiting ATX in vitro or in vivo, said method comprising contacting a cell with an effective amount of a compound as defined herein, or a pharmaceutically acceptable salt or solvate thereof.

In another aspect, the present invention provides a method of inhibiting cell proliferation in vitro or in vivo, said method comprising contacting a cell with an effective amount of a compound as defined herein, or a pharmaceutically acceptable salt or solvate thereof.

In another aspect, the present invention provides a method of treating a proliferative disorder in a patient in need of such treatment, said method comprising administering to said patient a therapeutically effective amount of a compound as defined herein, or a pharmaceutically acceptable salt or solvate thereof, or a pharmaceutical composition as defined herein.

In another aspect, the present invention provides a method of treating cancer in a patient in need of such treatment, said method comprising administering to said patient a therapeutically effective amount of a compound as defined herein, or a pharmaceutically acceptable salt or solvate thereof, or a pharmaceutical composition as defined herein.

In another aspect, the present invention provides a method of treating fibrosis in a patient in need of such treatment, said method comprising administering to said patient a therapeutically effective amount of a compound as defined herein, or a pharmaceutically acceptable salt or solvate thereof, or a pharmaceutical composition as defined herein. Suitably, the method is for the treatment of lung, renal, hepatic or skin fibrosis.

The present invention further provides a method of synthesising a compound, or a pharmaceutically acceptable salt or solvate thereof, as defined herein.

In another aspect, the present invention provides a compound as defined herein, or a pharmaceutically acceptable salt or solvate thereof, obtainable by, or obtained by, or directly obtained by a method of synthesis as defined herein.

In another aspect, the present invention provides novel intermediates as defined herein which are suitable for use in any one of the synthetic methods as set out herein.

Preferred, suitable, and optional features of any one particular aspect of the present invention are also preferred, suitable, and optional features of any other aspect.

DETAILED DESCRIPTION OF THE INVENTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t-butyl. A similar convention applies to other radicals, for example "phenyl(1-6C)alkyl" includes phenyl(1-4C)alkyl, benzyl, 1-phenylethyl and 2-phenylethyl.

The term "(m-nC)" or "(m-nC) group" used alone or as a prefix, refers to any group having m to n carbon atoms.

An "alkylene," "alkenylene," or "alkynylene" group is an alkyl, alkenyl, or alkynyl group that is positioned between and serves to connect two other chemical groups. Thus, "(1-6C)alkylene" means a linear saturated divalent hydrocarbon radical of one to six carbon atoms or a branched saturated divalent hydrocarbon radical of three to six carbon atoms, for example, methylene, ethylene, propylene, 2-methylpropylene, pentylene, and the like.

"(2-6C)alkenylene" means a linear divalent hydrocarbon radical of two to six carbon atoms or a branched divalent hydrocarbon radical of three to six carbon atoms, containing at least one double bond, for example, as in ethenylene, 2,4-pentadienylene, and the like.

"(2-6C)alkynylene" means a linear divalent hydrocarbon radical of two to six carbon atoms or a branched divalent hydrocarbon radical of three to six carbon atoms, containing at least one triple bond, for example, as in ethynylene, propynylene, and butynylene and the like.

"(3-8C)cycloalkyl" means a hydrocarbon ring containing from 3 to 8 carbon atoms, for example, cyclopropyl, cyclobutyl, cyclopentyl, cyclohexyl, cycloheptyl or bicyclo [2.2.1]heptyl.

"(3-8C)cycloalkenyl" means a hydrocarbon ring containing at least one double bond, for example, cyclobutenyl, cyclopentenyl, cyclohexenyl or cycloheptenyl, such as 3-cyclohexen-1-yl, or cyclooctenyl.

"(3-8C)cycloalkyl-(1-6C)alkylene" means a (3-8C)cycloalkyl group covalently attached to a (1-6C)alkylene group, both of which are defined herein.

The term "halo" or "halogeno" refers to fluoro, chloro, bromo and iodo.

The term "heterocyclyl", "heterocyclic" or "heterocycle" means a non-aromatic saturated or partially saturated monocyclic, fused, bridged, or spiro bicyclic heterocyclic ring system(s). Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

By "bridged ring systems" is meant ring systems in which two rings share more than two atoms, see for example *Advanced Organic Chemistry*, by Jerry March, 4$^{th}$ Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane and quinuclidine.

By "spiro bi-cyclic ring systems" we mean that the two ring systems share one common spiro carbon atom, i.e. the heterocyclic ring is linked to a further carbocyclic or heterocyclic ring through a single common spiro carbon atom. Examples of spiro ring systems include 6-azaspiro[3.4] octane, 2-oxa-6-azaspiro[3.4]octane, 2-azaspiro[3.3]heptanes, 2-oxa-6-azaspiro[3.3]heptanes, 7-oxa-2-azaspiro[3.5] nonane, 6-oxa-2-azaspiro[3.4]octane, 2-oxa-7-azaspiro[3.5] nonane and 2-oxa-6-azaspiro[3.5]nonane.

"Heterocyclyl(1-6C)alkyl" means a heterocyclyl group covalently attached to a (1-6C)alkylene group, both of which are defined herein.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. The term heteroaryl includes both monovalent species and divalent species. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from:
a benzene ring fused to a 5- or 6-membered ring containing 1, 2 or 3 ring heteroatoms;
a pyridine ring fused to a 5- or 6-membered ring containing 1, 2 or 3 ring heteroatoms;
a pyrimidine ring fused to a 5- or 6-membered ring containing 1 or 2 ring heteroatoms;
a pyrrole ring fused to a 5- or 6-membered ring containing 1, 2 or 3 ring heteroatoms;
a pyrazole ring fused to a 5- or 6-membered ring containing 1 or 2 ring heteroatoms;
a pyrazine ring fused to a 5- or 6-membered ring containing 1 or 2 ring heteroatoms;
an imidazole ring fused to a 5- or 6-membered ring containing 1 or 2 ring heteroatoms;
an oxazole ring fused to a 5- or 6-membered ring containing 1 or 2 ring heteroatoms;
an isoxazole ring fused to a 5- or 6-membered ring containing 1 or 2 ring heteroatoms;
a thiazole ring fused to a 5- or 6-membered ring containing 1 or 2 ring heteroatoms;
an isothiazole ring fused to a 5- or 6-membered ring containing 1 or 2 ring heteroatoms;
a thiophene ring fused to a 5- or 6-membered ring containing 1, 2 or 3 ring heteroatoms;
a furan ring fused to a 5- or 6-membered ring containing 1, 2 or 3 ring heteroatoms;
a cyclohexyl ring fused to a 5- or 6-membered heteroaromatic ring containing 1, 2 or 3 ring heteroatoms; and
a cyclopentyl ring fused to a 5- or 6-membered heteroaromatic ring containing 1, 2 or 3 ring heteroatoms.

Particular examples of bicyclic heteroaryl groups containing a six membered ring fused to a five membered ring include but are not limited to benzfuranyl, benzthiophenyl, benzimidazolyl, benzoxazolyl, benzisoxazolyl, benzthiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

"Heteroaryl(1-6C)alkyl" means a heteroaryl group covalently attached to a (1-6C)alkylene group, both of which are defined herein. Examples of heteroaralkyl groups include pyridin-3-ylmethyl, 3-(benzofuran-2-yl)propyl, and the like.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In particular embodiment, an aryl is phenyl.

The term "aryl(1-6C)alkyl" means an aryl group covalently attached to a (1-6C)alkylene group, both of which are defined herein. Examples of aryl-(1-6C)alkyl groups include benzyl, phenylethyl, and the like.

This specification also makes use of several composite terms to describe groups comprising more than one functionality. Such terms will be understood by a person skilled in the art. For example heterocyclyl(m-nC)alkyl comprises (m-nC)alkyl substituted by heterocyclyl.

The term "optionally substituted" refers to either groups, structures, or molecules that are substituted and those that are not substituted. The term "wherein a/any CH, CH$_2$, CH$_3$ group or heteroatom (i.e. NH) within a R$^1$ group is optionally substituted" suitably means that (any) one of the hydrogen radicals of the R$^1$ group is substituted by a relevant stipulated group.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

Compounds of the Invention

In one aspect, the present invention relates compounds, or a pharmaceutically acceptable salts or solvates thereof, having the structural formula (I) shown below:

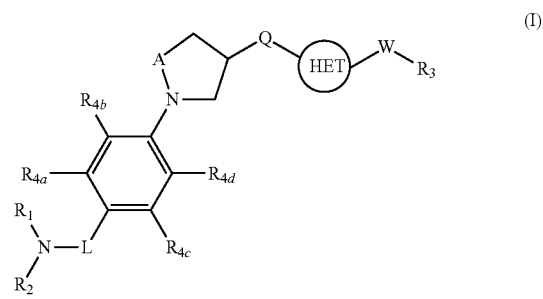

wherein:
R$_1$ and R$_2$ are independently selected from H, (1-8C)alkyl, (4-7C)cycloalkyl, 4-7 membered heterocyclyl, 5-6 membered heteroaryl, —S(O)$_y$R$_a$ or C(O)R$_a$, wherein R$_a$ is selected from H, (1-4C)alkyl or (1-4C)alkoxy, y is 0, 1 or 2, and wherein any (1-8C)alkyl, (4-7C)cycloalkyl, 4-7 membered heterocyclyl or 5-6 membered heteroaryl is optionally substituted by one or more substituents selected from oxo, (1-4C)alkyl, halo, cyano, nitro, hydroxyl, amino, (1-4C)haloalkyl, (1-4C)alkoxy, (1-4C)haloalkoxy, carboxyl, carbamoyl, sulphamoyl, NR$_b$R$_c$, OR$_b$, C(O)R$_b$, C(O)OR$_b$, OC(O)R$_b$, C(O)N(R$_b$)R$_c$, N(R$_b$)C(O)R$_c$, S(O)$_y$R$_b$ (where y is 0, 1 or 2), SO$_2$N(R$_b$)R$_c$, N(R$_b$)SO$_2$R$_c$ or (CH$_2$)$_z$NR$_b$R$_c$ (where z is 1, 2 or 3), (4-6C)heterocycyl, 6 membered aryl or 5 or 6 membered heteroaryl, wherein R$_b$ and R$_c$ are each independently selected from H or (1-4C)alkyl; or R$_1$ and R$_2$ are linked such that, together with the nitrogen atom to which they are attached, they form a 4 to 10 membered mono or bicyclic heterocyclic ring which is optionally substituted by one or more substituents selected from oxo, (1-4C)alkyl, halo, cyano, nitro, hydroxyl, amino, (1-4C)haloalkyl, (1-4C)alkoxy, (1-4C)haloalkoxy, carboxyl, carbamoyl, sulphamoyl, NR$_d$R$_e$, OR$_d$, C(O)R$_d$, C(O)OR$_d$, OC(O)R$_d$, C(O)N(R$_e$)R$_d$, N(R$_e$)C(O)R$_d$, S(O)$_y$R$_d$ (where y is 0, 1 or 2), SO$_2$N(R$_e$)R$_d$, N(R$_e$)SO$_2$R$_d$ or (CH$_2$)$_z$NR$_d$R$_e$ (where z is 1, 2 or 3), (4-6C)heterocycyl, 6 membered aryl or 5 or 6 membered heteroaryl, wherein R$_d$ and R$_e$ are each independently selected from H or (1-4C)alkyl;

L is a (1-3C)alkylene optionally substituted by fluoro, (1-2C)alkyl or oxo;

R$_{4a}$, R$_{4b}$, R$_{4c}$ and R$_{4d}$ are each independently selected from H, halo, (1-2C)alkyl, cyano, nitro, hydroxyl, amino, (1-2C)haloalkyl, (1-2C)alkoxy, or (1-2C)haloalkoxy;

A is C(=X) or CR$_f$R$_g$;
wherein X is O, NH or S; and
R$_f$ and R$_g$ are independently selected from H or (1-2C)alkyl;

Q is selected from —NH—S(O)$_y$—, —S(O)$_y$—NH—, —C(O)NR$_h$—, —NR$_h$C(O)—, —NR$_h$—S(O)(NH)—, —S(O)(NH)—NR$_h$—, —C(O)O—, —OC(O)—, —CH$_2$CH$_2$—, —CH$_2$NR$_h$— or —NR$_h$CH$_2$—, wherein y is 0, 1 or 2 and R$_h$ is selected from H or (1-2C)alkyl; HET is a 5 or 6 membered nitrogen containing heteroaryl optionally substituted with one or more substituents selected from H, (1-4C)alkyl, halo, cyano, nitro, hydroxyl, amino, (1-4C)haloalkyl, (1-4C)alkoxy, (1-4C)haloalkoxy, carboxyl, carbamoyl, amido or sulphamoyl;

W is either a group of the formula:

-Q$_1$-R$_i$— wherein:
Q$_1$ is attached to HET and is —C(O)— or —CH$_2$—; and
R$_i$ is attached to R$_3$ and is selected from —CHR$_j$—, —NR$_j$—, or —O—, wherein R$_j$ is selected from H or (1-2C)alkyl;
or W is a group of the formula:

—R$_k$-Q$_2$- wherein:
Q$_2$ is attached to R$_3$ and is selected from —C(O)— or —CH$_2$—; and
R$_k$ is attached to HET and is selected from CHR$_l$, NR$_l$, O or S(O)$_y$, wherein y is 0, 1 or 2 and R$_l$ is H or (1-4C)alkyl;

R$_3$ is selected from (1-6C)alkyl, phenyl, (4-8C)carbocyclyl, heteroaryl or heterocyclyl, each of which is optionally substituted with one or more substituents selected from (1-4C)alkyl, halo, (1-4C)haloalkyl, (1-4C)alkoxy, (1-4C)haloalkoxy, (3-6C)cycloalkyl, (3-6C)cycloalkyl(1-2C)alkyl, (2-4C)alkenyl or (2-4C)alkynyl.

Particular compounds of the invention include, for example, compounds of the formula (I), or pharmaceutically acceptable salts and/or solvates thereof, wherein, unless otherwise stated, each of R$_1$, R$_2$, R$_3$, R$_{4a}$, R$_{4b}$, R$_{4c}$, R$_{4d}$, L, A, Q, HET, W and any associated substituent group has any of the meanings defined hereinbefore or in any of paragraphs (1) to (49) hereinafter:—

(1) R$_1$ and R$_2$ are independently selected from H, (1-8C)alkyl, (4-7C)cycloalkyl, 4-7 membered heterocyclyl, 5-6 membered heteroaryl, —S(O)$_y$R$_a$ or C(O)R$_a$, wherein R$_a$ is selected from H, (1-4C)alkyl or (1-4C)alkoxy, y is 0, 1 or 2, and wherein any (1-8C)alkyl, (4-7C)cycloalkyl, 4-7 membered heterocyclyl or 5-6 membered heteroaryl is optionally substituted by one or more substituents selected from oxo, (1-4C)alkyl, halo, cyano, nitro, hydroxyl, amino, (1-4C)fluoroalkyl, (1-4C)alkoxy, (1-4C)fluoroalkoxy, carboxyl, carbamoyl, sulphamoyl, NR$_b$R$_c$, OR$_b$, C(O)R$_b$, C(O)OR$_b$, OC(O)R$_b$, C(O)N(R$_b$)R$_c$, N(R$_b$)C(O)R$_c$, S(O)$_y$R$_b$ (where y is 0, 1 or 2), (4-6C)heterocycyl, 6 membered aryl or 5 or 6 membered heteroaryl, wherein R$_b$ and R$_c$ are each independently selected from H or (1-4C)alkyl; or R$_1$ and R$_2$ are linked such that, together with the nitrogen atom to which they are attached, they form a 4 to 10 membered mono or bicyclic heterocyclic ring which is optionally substituted by one or more substituents selected from oxo, (1-4C)alkyl, halo, cyano, nitro, hydroxyl, amino, (1-4C)haloalkyl, (1-4C)alkoxy, (1-4C)haloalkoxy, carboxyl, carbamoyl, sulphamoyl, NR$_d$R$_e$, OR$_d$, C(O)R$_d$, C(O)OR$_d$, OC(O)R$_d$, C(O)N(R$_e$)R$_d$, N(R$_e$)C(O)R$_d$, S(O)$_y$R$_d$ (where y is 0, 1 or 2), (4-6C)heterocycyl, 6 membered aryl or 5 or 6 membered heteroaryl, wherein R$_d$ and R$_e$ are each independently selected from H or (1-4C)alkyl;

(2) R$_1$ and R$_2$ are independently selected from H, (1-8C)alkyl, (4-7C)cycloalkyl, 4-7 membered heterocyclyl, 5-6 membered heteroaryl, —S(O)$_y$R$_a$ or C(O)R$_a$, wherein R$_a$ is selected from H, (1-4C)alkyl or (1-4C)alkoxy, y is 0, 1 or 2, and wherein any (1-8C)alkyl, (4-7C)cycloalkyl, 4-7 membered heterocyclyl or 5-6 membered heteroaryl is optionally substituted by one or more substituents selected from oxo, (1-4C)alkyl, halo, cyano, nitro, hydroxyl, amino, (1-4C)fluoroalkyl, (1-4C)alkoxy, (1-4C)fluoroalkoxy, carboxyl, carbamoyl, sulphamoyl or NR$_b$R$_c$, wherein R$_b$ and R$_c$ are each independently selected from H or (1-4C)alkyl; or R$_1$ and R$_2$ are linked such that, together with the nitrogen atom to which they are attached, they form a 4 to 10 membered mono or bicyclic heterocyclic ring which is optionally substituted by one or more substituents selected from oxo, (1-4C)alkyl, halo, cyano, nitro, hydroxyl, amino, (1-4C)fluoroalkyl, (1-4C)alkoxy, (1-4C)fluoroalkoxy, carboxyl, carbamoyl, sulphamoyl, NR$_d$R$_e$, OR$_d$, C(O)R$_d$, C(O)OR$_d$, OC(O)R$_d$, C(O)N(R$_e$)R$_d$, N(R$_e$)C(O)R$_d$, S(O)$_y$R$_d$ (where y is 0, 1 or 2), (4-6C)heterocycyl, 6 membered aryl or 5 or 6 membered heteroaryl, wherein R$_d$ and R$_e$ are each independently selected from H or (1-4C)alkyl;

(3) R$_1$ and R$_2$ are independently selected from H, (1-6C)alkyl, (4-7C)cycloalkyl, 4-7 membered heterocyclyl, 5-6 membered heteroaryl, —S(O)$_y$R$_a$ or C(O)R$_a$, wherein R$_e$ is selected from H, (1-4C)alkyl or (1-4C)alkoxy, y is 0, 1 or 2, and wherein any (1-6C)alkyl, (4-7C)cycloalkyl, 4-7 membered heterocyclyl or 5-6 membered heteroaryl is optionally substituted by one or more substituents selected from oxo, (1-4C)alkyl, halo, cyano, nitro, hydroxyl, amino, (1-4C)fluoroalkyl, (1-4C)alkoxy, (1-4C) fluoroalkoxy, carboxyl, carbamoyl, sulphamoyl or NR$_b$R$_c$, wherein R$_b$ and R$_c$ are each independently selected from H or (1-4C)alkyl; or R$_1$ and R$_2$ are linked such that, together with the nitrogen atom to which they are attached, they form a 4 to 10 membered mono or bicyclic heterocyclic ring which is optionally substituted by one or more substituents selected from oxo, (1-4C)alkyl, halo, cyano, nitro, hydroxyl, amino, (1-4C)fluoroalkyl, (1-4C)alkoxy, (1-4C)fluoroalkoxy, carboxyl, carbamoyl, sulphamoyl, NR$_d$R$_e$, C(O)OR$_d$, OC(O)R$_d$, C(O)N(R$_e$)R$_d$, N(R$_e$)C(O)R$_d$, S(O)$_y$R$_d$ (where y is 0, 1 or 2), 6 membered aryl or 5 or 6 membered heteroaryl, wherein R$_d$ and R$_e$ are each independently selected from H or (1-4C)alkyl;

(4) R$_1$ and R$_2$ are independently selected from H, (1-6C)alkyl, 4-7 membered heterocyclyl, 5-6 membered heteroaryl, —S(O)$_y$R$_a$ or C(O)R$_a$, wherein R$_a$ is selected from H, (1-2C)alkyl or (1-2C)alkoxy, y is 0, 1 or 2, and wherein any (1-6C)alkyl, (4-7C)cycloalkyl, 4-7 membered heterocyclyl or 5-6 membered heteroaryl is optionally substituted by one or more substituents selected from oxo, (1-4C)alkyl, halo, cyano, nitro, hydroxyl, amino, (1-4C)fluoroalkyl, (1-4C)alkoxy, (1-4C)fluoroalkoxy, carboxyl, carbamoyl, sulphamoyl, or NR$_b$R$_c$, wherein R$_b$ and R$_c$ are each independently selected from H or (1-4C)alkyl; or R$_1$ and R$_2$ are linked such that, together with the nitrogen atom to which they are attached, they form a 4 to 10 membered mono or bicyclic heterocyclic ring which is optionally substituted by one or more substituents selected from oxo, (1-4C)alkyl, halo, cyano, nitro, hydroxyl, amino, (1-2C)fluoroalkyl, (1-2C)alkoxy, (1-2C)fluoroalkoxy, carboxyl, carbamoyl, sulphamoyl, NR$_d$R$_e$, C(O)OR$_d$, OC(O)R$_d$, C(O)N(R$_e$)R$_d$, N(R$_e$)C(O)R$_d$ or S(O)$_y$R$_d$ (where y is 0, 1 or 2), wherein R$_d$ and R$_e$ are each independently selected from H or (1-4C)alkyl;

(5) R$_1$ and R$_2$ are independently selected from H, (1-6C)alkyl, 4-7 membered heterocyclyl, —S(O)$_y$R$_a$ or C(O)R$_a$, wherein R$_a$ is selected from H or (1-2C)alkyl, y is 0, 1 or 2, and wherein any (1-6C)alkyl, or 4-7 membered heterocyclyl is optionally substituted by one or more substituents selected from oxo, (1-2C)alkyl, halo, cyano, nitro, hydroxyl, amino, CF$_3$, (1-2C)alkoxy, OCF$_3$, carboxyl, carbamoyl, sulphamoyl, or NR$_b$R$_c$, wherein R$_b$ and R$_c$ are each independently selected from H or (1-4C)alkyl; or R$_1$ and R$_2$ are linked such that, together with the nitrogen atom to which they are attached, they form a 4 to 10 membered mono or bicyclic heterocyclic ring which is optionally substituted by one or more substituents selected from oxo, (1-2C)alkyl, halo, cyano, nitro, hydroxyl, amino, CF$_3$, OMe, OCF$_3$, carboxyl, carbamoyl, sulphamoyl, NR$_d$R$_e$, C(O)OR$_d$, wherein R$_d$ and R$_e$ are each independently selected from H or (1-4C)alkyl;

(6) R$_1$ and R$_2$ are independently selected from H, (1-6C)alkyl, 4-6 membered heterocyclyl, —S(O)$_2$R$_a$ or C(O)R$_a$, wherein R$_a$ is selected from H or (1-2C)alkyl, and wherein any (1-6C)alkyl, or 4-6 membered heterocyclyl is optionally substituted by one or more substituents selected from oxo, (1-2C)alkyl, halo, cyano, nitro, hydroxyl, amino, CF$_3$, (1-2C)alkoxy or OCF$_3$; or R$_1$ and R$_2$ are linked such that, together with the nitrogen atom to which they are attached, they form a 4 to 10 membered mono or bicyclic heterocyclic ring which is optionally substituted by one or more substituents selected from oxo, (1-2C)alkyl, halo, cyano, nitro, hydroxyl, amino, CF$_3$, OMe, OCF$_3$, C(O)OR$_d$, wherein R$_d$ is selected from H or (1-4C)alkyl;

(7) R$_1$ and R$_2$ are independently selected from H, (1-6C)alkyl, 4-6 membered heterocyclyl, —S(O)$_2$R$_a$ or C(O)R$_a$, wherein R$_a$ is selected from H or (1-2C)alkyl, and wherein any (1-6C)alkyl, or 4-6 membered heterocyclyl is optionally substituted by one or more substituents selected from methyl, fluoro, hydroxyl, CF$_3$, OMe or OCF$_3$; or R$_1$ and R$_2$ are linked such that, together with the nitrogen atom to which they are attached, they form a 4 to 10 membered mono or bicyclic heterocyclic ring which is optionally substituted by one or more substituents selected from oxo, methyl, fluoro, hydroxyl, CF$_3$, OMe, OCF$_3$, C(O)OR$_d$, wherein R$_d$ is selected from H or (1-4C)alkyl;

(8) R$_1$ and R$_2$ are independently selected from H, (1-6C)alkyl, 4-6 membered heterocyclyl, —S(O)$_2$R$_a$ or C(O)R$_a$, wherein R$_a$ is selected from H or methyl, and wherein any (1-6C)alkyl, or 4-6 membered heterocyclyl is optionally substituted by one or more substituents selected from methyl, fluoro or hydroxyl; or R$_1$ and R$_2$ are linked such that, together with the nitrogen atom to which they are attached, they form a 4 to 10 membered mono or bicyclic heterocyclic ring which is optionally substituted by one or more substituents selected from oxo, methyl, fluoro, hydroxyl or C(O)OR$_d$, wherein R$_d$ is selected from H or (1-4C)alkyl;

(9) R$_1$ and R$_2$ are linked such that, together with the nitrogen atom to which they are attached, they form a 4 to 6 membered mono heterocyclic ring which is optionally substituted by one or more substituents selected from oxo, methyl, fluoro, hydroxyl or C(O)OR$_d$, wherein R$_d$ is selected from H or (1-4C)alkyl;

(10) L is a methylene optionally substituted by fluoro, (1-2C)alkyl or oxo;

(11) L is a methylene optionally substituted by fluoro, methyl or oxo;

(12) L is a methylene optionally substituted by methyl;

(13) L is a methylene;

(14) R$_{4a}$, R$_{4b}$, R$_{4c}$ and R$_{4d}$ are each independently selected from H, halo, (1-2C)alkyl, cyano, nitro, hydroxyl, amino, (1-2C)fluoroalkyl, (1-2C)alkoxy, or (1-2C)fluoroalkoxy;

(15) R$_{4a}$, R$_{4b}$, R$_{4c}$ and R$_{4d}$ are each independently selected from H, halo, (1-2C)alkyl, (1-2C)fluoroalkyl, (1-2C)alkoxy, or (1-2C)fluoroalkoxy;

(16) R$_{4a}$, R$_{4b}$, R$_{4c}$ and R$_{4d}$ are each independently selected from H, fluoro, methyl, CF$_3$, OMe, or OCF$_3$;

(17) R$_{4a}$, R$_{4b}$, R$_{4c}$ and R$_{4d}$ are each independently selected from H, fluoro, methyl or CF$_3$;

(18) R$_{4a}$, R$_{4b}$, R$_{4c}$ and R$_{4d}$ are each independently selected from H or fluoro;

(19) R$_{4a}$, R$_{4b}$ and R$_{4c}$ are H, and R$_{4d}$ is selected from H or fluoro;

(20) A is C(=X) or CR$_f$R$_g$;

wherein X is O, or S; and

R$_f$ and R$_g$ are independently selected from H or methyl;

(21) A is C(=X) or $CR_fR_g$;
  wherein X is O, or NH; and
  $R_f$ and $R_g$ are independently selected from H or methyl;
(22) A is C(=O) or $CR_fR_g$;
  wherein $R_f$ and $R_g$ are independently selected from H or methyl;
(23) A is C(=O) or $CH_2$;
(24) A is C(=O);
(25) Q is selected from —NH—S(O)$_y$—, —S(O)$_y$—NH—, —C(O)NR$_h$—, —NR$_h$C(O)—, —C(O)O—, —OC(O), —CH$_2$CH$_2$—, —CH$_2$NR$_h$— or —NR$_h$CH$_2$—, wherein y is 0, 1 or 2 and R$_h$ is selected from H or (1-2C)alkyl;
(26) Q is selected from —NH—S(O)$_y$—, —S(O)$_y$—NH—, —C(O)NR$_h$—, —NR$_h$C(O)—, —C(O)O—, —OC(O), —CH$_2$NR$_h$— or —NR$_h$CH$_2$—, wherein y is 0, 1 or 2 and R$_h$ is selected from H or methyl;
(27) Q is selected from —C(O)NR$_h$—, —NR$_h$C(O)—, —CH$_2$NR$_h$— or —NR$_h$CH$_2$—, wherein R$_h$ is selected from H or methyl;
(28) Q is selected from —C(O)NH—, —NHC(O)—, —CH$_2$NH— or —NHCH$_2$;
(29) HET is a 5 or 6 membered nitrogen-containing heteroaryl optionally substituted with one or more substituents selected from H, (1-4C)alkyl, halo, cyano, nitro, hydroxyl, amino, (1-4C)fluoroalkyl, (1-4C)alkoxy, (1-4C)fluoroalkoxy, carboxyl, carbamoyl, amido or sulphamoyl;
(30) HET is a 5 or 6 membered nitrogen-containing heteroaryl optionally substituted with one or more substituents selected from H, (1-4C)alkyl, halo, cyano, nitro, hydroxyl, amino, (1-2C)fluoroalkyl, (1-2C)alkoxy or (1-2C)fluoroalkoxy;
(31) HET is a 5 or 6 membered nitrogen-containing heteroaryl optionally substituted with one or more substituents selected from H, (1-4C)alkyl, halo, hydroxyl, amino, $CF_3$, OMe or $OCF_3$;
(32) HET is a 5 or 6 membered nitrogen-containing heteroaryl optionally substituted with one or more substituents selected from H, methyl, fluoro hydroxyl, amino, $CF_3$, OMe or $OCF_3$;
(33) HET is a 5 or 6 membered nitrogen-containing heteroaryl optionally substituted with one or more substituents selected from H, methyl, fluoro or $CF_3$;
(34) HET is a 5 or 6 membered nitrogen-containing heteroaryl;
(35) HET is a 5 membered nitrogen-containing heteroaryl;
(36) HET is selected from 1,3,4-thiadiazole, pyrazole, pyridizine, isoxazole, thiazole, 1-methyl-pyrazole or oxadiazole;
(37) HET is 1,3,4-thiadiazole;
(38) W is either a group of the formula:

-$Q_1$-$R_i$— wherein:
  $Q_1$ is attached to HET and is —C(O)— or —CH$_2$—; and
  $R_i$ is attached to $R_3$ and is selected from —CHR$_j$—, —NR$_j$—, or —O—, wherein R$_j$ is selected from H or methyl;
  or W is a group of the formula:

—$R_k$-$Q_2$- wherein:
  $Q_2$ is attached to $R_3$ and is selected from —C(O)— or —CH$_2$—; and
  $R_k$ is attached to HET and is selected from CHR$_l$, NR$_l$, O or S(O)$_y$, wherein y is 0, 1 or 2 and R$_l$ is H or methyl;
(39) W is either a group of the formula:

-$Q_1$-$R_i$— wherein:
  $Q_1$ is attached to HET and is —C(O)— or —CH$_2$—; and
  $R_i$ is attached to $R_3$ and is selected from —CHR$_j$— or —O—, wherein R$_j$ is selected from H or methyl;
  or W is a group of the formula:

—$R_k$-$Q_2$- wherein:
  $Q_2$ is attached to $R_3$ and is selected from —C(O)— or —CH$_2$—; and
  $R_k$ is attached to HET and is selected from NR$_l$, O or S(O)$_y$, wherein y is 0, 1 or 2 and R$_l$ is H or methyl;
(40) W is either a group of the formula:

-$Q_1$-$R_i$— wherein:
  $Q_1$ is attached to HET and is —C(O)— or —CH$_2$—; and
  $R_i$ is attached to $R_3$ and is selected from —CH$_2$— or —O;
  or W is a group of the formula:

—$R_k$-$Q_2$- wherein:
  $Q_2$ is attached to $R_3$ and is selected from —C(O)— or —CH$_2$—; and
  $R_k$ is attached to HET and is selected from NH, or S(O)$_y$, wherein y is 0, 1 or 2;
(41) W is either a group of the formula:

-$Q_1$-$R_i$— wherein:
  $Q_1$ is attached to HET and is —CH$_2$—; and
  $R_i$ is attached to $R_3$ and is selected from —CH$_2$— or —O;
  or W is a group of the formula:

—$R_k$-$Q_2$- wherein:
  $Q_2$ is attached to $R_3$ and is selected from —CH$_2$—; and
  $R_k$ is attached to HET and is NH or S;
(42) W is —CH$_2$CH$_2$—;
(43) $R_3$ is selected from (1-6C)alkyl, phenyl, (4-8C)carbocyclyl, heteroaryl or heterocyclyl, each of which is optionally substituted with one or more substituents selected from (1-4C)alkyl, halo, (1-4C)fluoroalkyl, (1-4C)alkoxy, (1-4C)fluoroalkoxy, (3-6C)cycloalkyl, (3-6C)cycloalkyl(1-2C)alkyl, (2-4C)alkenyl or (2-4C)alkynyl;
(44) $R_3$ is selected from (1-6C)alkyl, phenyl, (4-8C)carbocyclyl, 5- or 6-membered heteroaryl or 4- to 6-membered heterocyclyl, each of which is optionally substituted with one or more substituents selected from (1-4C)alkyl, halo, (1-4C)fluoroalkyl, (1-4C)alkoxy, (1-4C)fluoroalkoxy, cyclopropyl, cyclobutyl, (2-4C)alkenyl or (2-4C)alkynyl;
(45) $R_3$ is selected from (1-6C)alkyl, phenyl, (4-8C)carbocyclyl, 5- or 6-membered heteroaryl or 4- to 6-membered heterocyclyl, each of which is optionally substituted with one or more substituents selected from (1-4C)alkyl, halo, (1-2C)fluoroalkyl, (1-2C)alkoxy or (1-2C)fluoroalkoxy;
(46) $R_3$ is selected from (1-6C)alkyl, phenyl, (4-8C)carbocyclyl, or 4- to 6-membered heterocyclyl, each of which is optionally substituted with one or more substituents selected from (1-2C)alkyl, halo, $CF_3$ OMe or $OCF_3$;
(47) $R_3$ is selected from (1-4C)alkyl, phenyl, (5-6C)carbocyclyl, or 5- to 6-membered heterocyclyl, each of which is optionally substituted with one or more substituents selected from methyl, halo, $CF_3$ or OMe;

(48) $R_3$ is selected from a phenyl, or 5- to 6-membered heterocyclyl, each of which is optionally substituted with one or more substituents selected from methyl, halo, $CF_3$ or OMe;

(49) $R_3$ is selected a phenyl, optionally substituted with one or more substituents selected from methyl, halo, $CF_3$ or OMe.

Suitably, a heteroaryl or heterocyclyl group as defined herein is a monocyclic heteroaryl or heterocyclyl group comprising one, two or three heteroatoms selected from N, O or S.

Suitably, a heteroaryl is a 5- or 6-membered heteroaryl ring comprising one, two or three heteroatoms selected from N, O or S.

Suitably, a heterocyclyl group is a 4-, 5- or 6-membered heterocyclyl ring comprising one, two or three heteroatoms selected from N, O or S. Most suitably, a heterocyclyl group is a 5- or 6-membered ring comprising one, two or three heteroatoms selected from N, O or S [e.g. morpholinyl (e.g. 4-morpholinyl), oxetane, methyloxetane (e.g. 3-methyloxetane), pyrrolidinone (e.g. pyrrolidin-2-one)].

Suitably an aryl group is phenyl.

Suitably, $R_1$ and $R_2$ are as defined in any one of paragraphs (1) to (9) above. Most preferably, $R_1$ and $R_2$ are as defined in paragraph (9).

Suitably, L is as defined in any one of paragraphs (10) to (13) above. Most suitably, L is methylene.

Suitably, $R_{4a}$, $R_{4b}$, $R_{4c}$ and $R_{4d}$ are as defined in any one of paragraphs (14) to (19) above. Most preferably, $R_{4a}$, $R_{4b}$, $R_{4c}$ and $R_{4d}$ are as defined in paragraph (19).

Suitably, A is as defined in any one of paragraphs (20) to (24) above. Most suitably, A is as defined in paragraph (24).

Suitably, Q is as defined in any one of paragraphs (25) to (28) above. Most suitably, Q is as defined in paragraph (28).

Suitably, HET is as defined in any one of paragraphs (29) to (37) above. Most suitably, HET is as defined in paragraph (37).

Suitably, W is as defined in any one of paragraphs (38) to (42) above. Most suitably, W is as defined in paragraph (42).

Suitably, $R_3$ is as defined in any one of paragraphs (43) to (49) above. Most suitably, W is as defined in paragraph (49).

In a particular group of compounds of the invention, L is methylene and $R_{4a}$, $R_{4b}$ and $R_{4c}$ are H, i.e. the compounds have the structural formula Ia (a sub-definition of formula (I)) shown below:

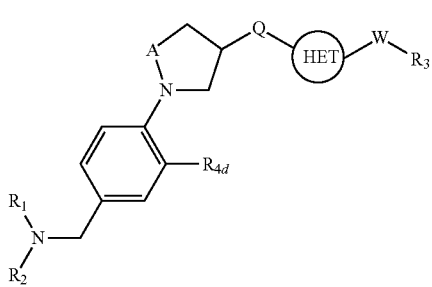

Ia wherein $R_1$, $R_2$, $R_3$, $R_{4d}$, A, Q, HET and W each have any one of the meanings defined herein; or a pharmaceutically acceptable salt, hydrate and/or solvate thereof.

In an embodiment of the compounds of formula Ia:
$R_1$ and $R_2$ are as defined in any one of paragraphs (1) to (9) above;
$R_{4d}$ is as defined in any one of paragraphs (14) to (19);
A is as defined in any one of paragraphs (20) to (24) above;
Q is as defined in any one of paragraphs (25) to (28) above;
HET is as defined in any one of paragraphs (29) to (37) above;
W is as defined in any one of paragraphs (38) to (42) above; and
$R_3$ is as defined in any one of paragraphs (43) to (49) above.

In an embodiment of the compounds of formula Ia:
$R_1$ and $R_2$ are as defined in paragraph (9) above;
$R_{4d}$ is as defined in paragraph (19);
A is as defined in paragraph (24) above;
Q is as defined in paragraph (28) above;
HET is as defined in paragraph (37) above;
W is as defined in paragraph (42) above; and
$R_3$ is as defined in paragraphs (49) above.

In a particular group of compounds of the invention, L is methylene, $R_{4a}$, $R_{4b}$ and $R_{4c}$ are H and A is C(=O), i.e. the compounds have the structural formula Ib (a sub-definition of formula (I)) shown below:

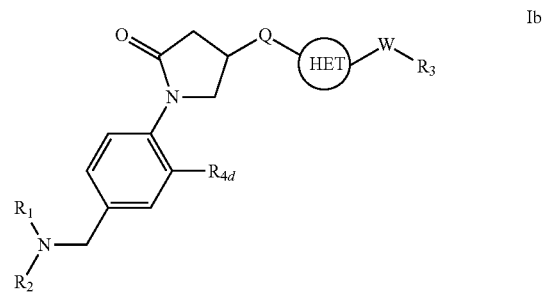

Ib wherein $R_1$, $R_2$, $R_3$, $R_{4d}$, Q, HET and W each have any one of the meanings defined herein; or a pharmaceutically acceptable salt, hydrate and/or solvate thereof.

In an embodiment of the compounds of formula Ib:
$R_1$ and $R_2$ are as defined in any one of paragraphs (1) to (9) above;
$R_{4d}$ is as defined in any one of paragraphs (14) to (19);
Q is as defined in any one of paragraphs (25) to (28) above;
HET is as defined in any one of paragraphs (29) to (37) above;
W is as defined in any one of paragraphs (38) to (42) above; and
$R_3$ is as defined in any one of paragraphs (43) to (49) above.

In an embodiment of the compounds of formula Ib:
$R_1$ and $R_2$ are as defined in paragraph (9) above;
$R_{4d}$ is as defined in paragraph (19);
Q is as defined in paragraph (28) above;
HET is as defined in paragraph (37) above;
W is as defined in paragraph (42) above; and
$R_3$ is as defined in paragraphs (49) above.

In a particular group of compounds of the invention, L is methylene, $R_{4a}$, $R_{4b}$ and $R_{4c}$ are H, W is $CH_2CH_2$ and A is C(=O), i.e. the compounds have the structural formula Ic (a sub-definition of formula (I)) shown below:

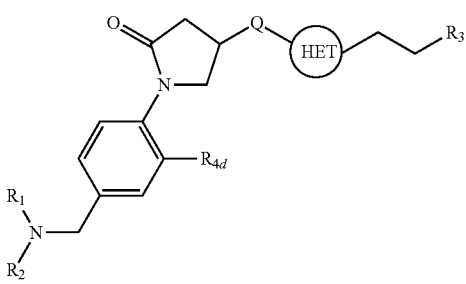

Ic wherein $R_1$, $R_2$, $R_3$, $R_{4d}$, Q and HET each have any one of the meanings defined herein; or a pharmaceutically acceptable salt, hydrate and/or solvate thereof.

In an embodiment of the compounds of formula Ic:
$R_1$ and $R_2$ are as defined in any one of paragraphs (1) to (9) above;
$R_{4d}$ is as defined in any one of paragraphs (14) to (19);
Q is as defined in any one of paragraphs (25) to (28) above;
HET is as defined in any one of paragraphs (29) to (37) above; and
$R_3$ is as defined in any one of paragraphs (43) to (49) above.

In an embodiment of the compounds of formula Ic:
$R_1$ and $R_2$ are as defined in paragraph (9) above;
$R_{4d}$ is as defined in paragraph (19);
Q is as defined in paragraph (28) above;
HET is as defined in paragraph (37) above; and
$R_3$ is as defined in paragraphs (49) above.

In a particular group of compounds of the invention, L is methylene, $R_{4a}$, $R_{4b}$ and $R_{4c}$ are H, W is $CH_2CH_2$, Q is —NHCO—, HET is as shown below and A is C(=O), i.e. the compounds have the structural formula Id (a sub-definition of formula (I)) shown below:

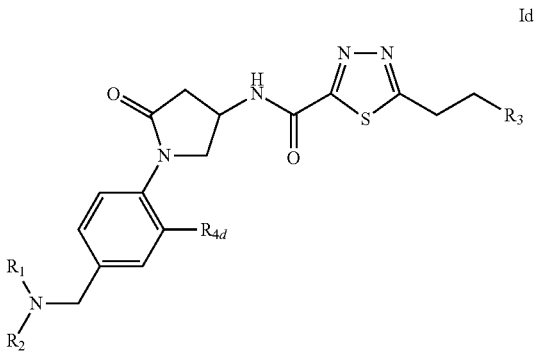

Id wherein $R_1$, $R_2$, $R_3$ and $R_{4d}$, each have any one of the meanings defined herein; or a pharmaceutically acceptable salt, hydrate and/or solvate thereof.

In an embodiment of the compounds of Id:
$R_1$ and $R_2$ are as defined in any one of paragraphs (1) to (9) above;
$R_{4d}$ is as defined in any one of paragraphs (14) to (19); and
$R_3$ is as defined in any one of paragraphs (43) to (49) above.

In an embodiment of the compounds of formula Id:
$R_1$ and $R_2$ are as defined in paragraph (9) above;
$R_{4d}$ is as defined in paragraph (19); and
$R_3$ is as defined in paragraphs (49) above.

In a particular group of compounds of the invention, the compound of formula I has the following stereochemistry shown in formula Ie below:

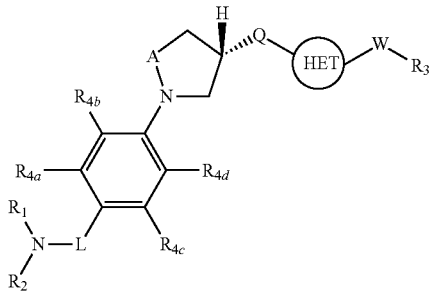

Ie wherein $R_1$, $R_2$, $R_3$, $R_{4a}$, $R_{4b}$, $R_{4c}$, $R_{4d}$, L, A, Q, HET and W each have any one of the meanings defined herein; or a pharmaceutically acceptable salt, hydrate and/or solvate thereof.

In an embodiment of the compounds of formula Ie:
$R_1$ and $R_2$ are as defined in any one of paragraphs (1) to (9) above;
L is as defined in any one of paragraphs (10) to (13) above;
$R_{4a}$, $R_{4b}$, $R_{4c}$ and $R_{4d}$ are as defined in any one of paragraphs (14) to (19);
A is as defined in any one of paragraphs (20) to (24) above;
Q is as defined in any one of paragraphs (25) to (28) above;
HET is as defined in any one of paragraphs (29) to (37) above;
W is as defined in any one of paragraphs (38) to (42) above; and
$R_3$ is as defined in any one of paragraphs (43) to (49) above.

In an embodiment of the compounds of formula Ie:
$R_1$ and $R_2$ are as defined in paragraph (9) above;
L is as defined in paragraph (13) above;
$R_{4a}$, $R_{4b}$, $R_{4c}$ and $R_{4d}$ are as defined in paragraph (19);
A is as defined in paragraph (24) above;
Q is as defined in paragraph (28) above;
HET is as defined in paragraph (37) above;
W is as defined in paragraph (42) above; and
$R_3$ is as defined in paragraphs (49) above.

In a particular group of compounds of the invention, the compound of formula I has the following stereochemistry shown in formula If below:

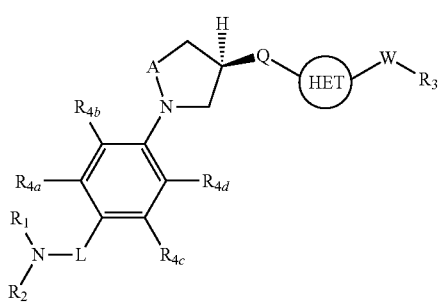

If wherein $R_1$, $R_2$, $R_3$, $R_{4a}$, $R_{4b}$, $R_{4c}$, $R_{4d}$, L, A, Q, HET and W each have any one of the meanings defined herein; or a pharmaceutically acceptable salt, hydrate and/or solvate thereof.

In an embodiment of the compounds of formula If:
$R_1$ and $R_2$ are as defined in any one of paragraphs (1) to (9) above;
L is as defined in any one of paragraphs (10) to (13) above;
$R_{4a}$, $R_{4b}$, $R_{4c}$ and $R_{4d}$ are as defined in any one of paragraphs (14) to (19);
A is as defined in any one of paragraphs (20) to (24) above;
Q is as defined in any one of paragraphs (25) to (28) above;
HET is as defined in any one of paragraphs (29) to (37) above;
W is as defined in any one of paragraphs (38) to (42) above; and
$R_3$ is as defined in any one of paragraphs (43) to (49) above.

In an embodiment of the compounds of formula If:
$R_1$ and $R_2$ are as defined in paragraph (9) above;
L is as defined in paragraph (13) above;
$R_{4a}$, $R_{4b}$, $R_{4c}$ and $R_{4d}$ are as defined in paragraph (19);
A is as defined in paragraph (24) above;
Q is as defined in paragraph (28) above;
HET is as defined in paragraph (37) above;
W is as defined in paragraph (42) above; and
$R_3$ is as defined in paragraphs (49) above.

Particular compounds of the present invention include any of the compounds exemplified in the present application, or a pharmaceutically acceptable salt or solvate thereof, and, in particular, any of the following:

(3S)—N-[5-[2-(4-chlorophenyl)ethyl]-1,3,4-thiadiazol-2-yl]-1-[4-[[methyl(tetrahydrofuran-3-yl)amino]methyl]phenyl]-5-oxo-pyrrolidine-3-carboxamide;

(3S)—N-[5-[2-(4-chlorophenyl)ethyl]-1,3,4-thiadiazol-2-yl]-1-[4-[[methyl(oxetan-3-yl)amino]methyl]phenyl]-5-oxo-pyrrolidine-3-carboxamide;

(3S)—N-[5-[2-(4-chlorophenyl)ethyl]-1,3,4-thiadiazol-2-yl]-1-[4-(morpholinomethyl)phenyl]-5-oxo-pyrrolidine-3-carboxamide;

(3S)—N-[5-[2-(4-chlorophenyl)ethyl]-1,3,4-thiadiazol-2-yl]-1-[4-[[methyl(tetrahydropyran-4-yl)amino]methyl]phenyl]-5-oxo-pyrrolidine-3-carboxamide;

(3S)-1-[4-(azepan-1-ylmethyl)phenyl]-N-[5-[2-(4-chlorophenyl)ethyl]-1,3,4-thiadiazol-2-yl]-5-oxo-pyrrolidine-3-carboxamide;

(3S)—N-[5-[2-(4-chlorophenyl)ethyl]-1,3,4-thiadiazol-2-yl]-1-[4-[(4-methyl-1-piperidyl)methyl]phenyl]-5-oxo-pyrrolidine-3-carboxamide;

(3S)—N-[5-[2-(4-chlorophenyl)ethyl]-1,3,4-thiadiazol-2-yl]-5-oxo-1-[4-(1-piperidylmethyl)phenyl]pyrrolidine-3-carboxamide;

(3S)—N-[5-[2-(4-chlorophenyl)ethyl]-1,3,4-thiadiazol-2-yl]-1-[4-[[2-methoxyethyl(methyl)amino]methyl]phenyl]-5-oxo-pyrrolidine-3-carboxamide;

N-[5-[2-(4-chlorophenyl)ethyl]-1,3,4-thiadiazol-2-yl]-1-[4-[(4-methyl-1-piperidyl)methyl]phenyl]-5-oxo-pyrrolidine-3-carboxamide;

N-[5-(2-cyclohexylethyl)-1,3,4-thiadiazol-2-yl]-1-[4-(1,4-oxazepan-4-ylmethyl)phenyl]-5-oxo-pyrrolidine-3-carboxamide;

(3S)-1-[4-(morpholinomethyl)phenyl]-5-oxo-N-[5-[2-[4-(trifluoromethyl)phenyl]ethyl]-1,3,4-thiadiazol-2-yl]pyrrolidine-3-carboxamide;

N-[5-[2-(4-chlorophenyl)ethyl]-1,3,4-thiadiazol-2-yl]-1-[4-(diethylaminomethyl)phenyl]-5-oxo-pyrrolidine-3-carboxamide;

N-[5-[2-(4-chlorophenyl)ethyl]-1,3,4-thiadiazol-2-yl]-5-oxo-1-[4-(1-piperidylmethyl)phenyl]pyrrolidine-3-carboxamide;

N-[5-[2-(4-chlorophenyl)ethyl]-1,3,4-thiadiazol-2-yl]-1-[4-[[2-methoxyethyl(methyl)amino]methyl]phenyl]-5-oxo-pyrrolidine-3-carboxamide;

N-[5-[2-(4-chlorophenyl)ethyl]-1,3,4-thiadiazol-2-yl]-1-[4-(1,4-oxazepan-4-ylmethyl)phenyl]-5-oxo-pyrrolidine-3-carboxamide;

N-[5-[2-(4-chlorophenyl)ethyl]-1,3,4-thiadiazol-2-yl]-1-[4-[(4-hydroxy-1-piperidyl)methyl]phenyl]-5-oxo-pyrrolidine-3-carboxamide;

(3S)-1-[4-(3-azabicyclo[3.1.0]hexan-3-ylmethyl)phenyl]-N-[5-[2-(4-chlorophenyl)ethyl]-1,3,4-thiadiazol-2-yl]-5-oxo-pyrrolidine-3-carboxamide;

(3S)—N-[5-[2-(4-chlorophenyl)ethyl]-1,3,4-thiadiazol-2-yl]-1-[4-(1,4-oxazepan-4-ylmethyl)phenyl]-5-oxo-pyrrolidine-3-carboxamide;

N-[5-[2-(4-chlorophenyl)ethyl]-1,3,4-thiadiazol-2-yl]-5-oxo-1-[4-[(tetrahydropyran-4-ylamino)methyl]phenyl]pyrrolidine-3-carboxamide;

N-[5-(2-cyclohexylethyl)-1,3,4-thiadiazol-2-yl]-5-oxo-1-[4-(1-piperidylmethyl)phenyl]pyrrolidine-3-carboxamide;

N-[5-(2-cyclopentylethyl)-1,3,4-thiadiazol-2-yl]-1-[4-(morpholinomethyl)phenyl]-5-oxo-pyrrolidine-3-carboxamide;

(3S)—N-[5-[2-(4-fluorophenyl)ethyl]-1,3,4-thiadiazol-2-yl]-1-[4-(morpholinomethyl)phenyl]-5-oxo-pyrrolidine-3-carboxamide;

N-[5-[2-(4-chlorophenyl)ethyl]-1,3,4-thiadiazol-2-yl]-1-[4-[[methyl(propyl)amino]methyl]phenyl]-5-oxo-pyrrolidine-3-carboxamide;

1-[4-(3-azabicyclo[3.1.0]hexan-3-ylmethyl)phenyl]-N-[5-[2-(4-chlorophenyl)ethyl]-1,3,4-thiadiazol-2-yl]-5-oxo-pyrrolidine-3-carboxamide;

N-[5-[2-(4-chlorophenyl)ethyl]-1,3,4-thiadiazol-2-yl]-1-[4-[[methyl(tetrahydropyran-4-yl)amino]methyl]phenyl]-5-oxo-pyrrolidine-3-carboxamide;

N-[5-[2-(4-chlorophenyl)ethyl]-1,3,4-thiadiazol-2-yl]-1-[4-[[ethyl(isobutyl)amino]methyl]phenyl]-5-oxo-pyrrolidine-3-carboxamide;

N-[5-(2-cyclopentylethyl)-1,3,4-thiadiazol-2-yl]-1-[4-[(4-fluoro-1-piperidyl)methyl]phenyl]-5-oxo-pyrrolidine-3-carboxamide;

1-[4-(azepan-1-ylmethyl)phenyl]-N-[5-[2-(4-chlorophenyl)ethyl]-1,3,4-thiadiazol-2-yl]-5-oxo-pyrrolidine-3-carboxamide;

N-[5-(2-cyclopentylethyl)-1,3,4-thiadiazol-2-yl]-1-[4-[(3,3-difluoro-1-piperidyl)methyl]phenyl]-5-oxo-pyrrolidine-3-carboxamide;

N-[5-[2-(4-chlorophenyl)ethyl]-1,3,4-thiadiazol-2-yl]-1-[4-[(dipropylamino)methyl]phenyl]-5-oxo-pyrrolidine-3-carboxamide;

N-[5-[2-(4-chlorophenyl)ethyl]-1,3,4-thiadiazol-2-yl]-1-[4-[(4-methylpiperazin-1-yl)methyl]phenyl]-5-oxo-pyrrolidine-3-carboxamide;

1-[4-(morpholinomethyl)phenyl]-5-oxo-N-[5-(2-phenylethyl)thiazol-2-yl]pyrrolidine-3-carboxamide;

N-[5-[2-(4-chlorophenyl)ethyl]-1,3,4-thiadiazol-2-yl]-1-[4-[[(2S,6R)-2,6-dimethylmorpholin-4-yl]methyl]phenyl]-5-oxo-pyrrolidine-3-carboxamide;

N-[5-[2-(4-chlorophenyl)ethyl]-1,3,4-thiadiazol-2-yl]-1-[4-[[ethyl(propyl)amino]methyl]phenyl]-5-oxo-pyrrolidine-3-carboxamide;

N-[5-[2-(4-chlorophenyl)ethyl]-1,3,4-thiadiazol-2-yl]-1-[4-(morpholinomethyl)phenyl]-5-oxo-pyrrolidine-3-carboxamide;

N-[5-(2-cyclopentylethyl)-1,3,4-thiadiazol-2-yl]-1-[4-(1,4-oxazepan-4-ylmethyl)phenyl]-5-oxo-pyrrolidine-3-carboxamide;

N-[5-(2-cyclopentylethyl)-1,3,4-thiadiazol-2-yl]-1-[4-[(4,4-difluoro-1-piperidyl)methyl]phenyl]-5-oxo-pyrrolidine-3-carboxamide;

N-[3-[2-(4-chlorophenyl)ethyl]-1H-pyrazol-5-yl]-1-[4-(morpholinomethyl)phenyl]-5-oxo-pyrrolidine-3-carboxamide;

N-[5-[2-(4-chlorophenyl)ethyl]-1,3,4-thiadiazol-2-yl]-1-[4-[[(2S,6S)-2,6-dimethylmorpholin-4-yl]methyl]phenyl]-5-oxo-pyrrolidine-3-carboxamide;

(3S)—N-[6-[2-(4-fluorophenyl)ethyl]pyridazin-3-yl]-1-[4-[[methyl(tetrahydropyran-4-yl)amino]methyl]phenyl]-5-oxo-pyrrolidine-3-carboxamide;

N-[5-[2-(4-chlorophenyl)ethyl]-1,3,4-thiadiazol-2-yl]-1-[4-[[ethyl(isopropyl)amino]methyl]phenyl]-5-oxo-pyrrolidine-3-carboxamide;

5-[2-(4-chlorophenyl)ethyl]-N-[1-[4-(morpholinomethyl)phenyl]-5-oxo-pyrrolidin-3-yl]-1,3,4-thiadiazole-2-carboxamide;

5-[2-(4-chlorophenyl)ethyl]-N-[1-[4-(1,4-oxazepan-4-ylmethyl)phenyl]-5-oxo-pyrrolidin-3-yl]-1,3,4-thiadiazole-2-carboxamide;

5-[2-(4-chlorophenyl)ethyl]-N-[(3R)-1-[4-(morpholinomethyl)phenyl]-5-oxo-pyrrolidin-3-yl]-1,3,4-thiadiazole-2-carboxamide;

5-[2-(4-chlorophenyl)ethyl]-N-[(3R)-1-[4-(morpholinomethyl)phenyl]pyrrolidin-3-yl]-1,3,4-thiadiazole-2-carboxamide;

5-[2-(4-chlorophenyl)ethyl]-N-[(3R)-5-oxo-1-[4-(1-piperidylmethyl)phenyl]pyrrolidin-3-yl]-1,3,4-thiadiazole-2-carboxamide;

5-[2-(4-chlorophenyl)ethyl]-N-[(3S)-5-oxo-1-[4-(1-piperidylmethyl)phenyl]pyrrolidin-3-yl]-1,3,4-thiadiazole-2-carboxamide;

N-[1-[4-(azepan-1-ylmethyl)phenyl]-5-oxo-pyrrolidin-3-yl]-5-[2-(4-chlorophenyl)ethyl]-1,3,4-thiadiazole-2-carboxamide;

5-[2-(4-chlorophenyl)ethyl]-N-[(3S)-1-[4-(morpholinomethyl)phenyl]-5-oxo-pyrrolidin-3-yl]-1,3,4-thiadiazole-2-carboxamide;

5-[2-(4-chlorophenyl)ethyl]-N-[1-[4-[(4-methyl-1-piperidyl)methyl]phenyl]-5-oxo-pyrrolidin-3-yl]-1,3,4-thiadiazole-2-carboxamide;

5-[2-(4-chlorophenyl)ethyl]-N-[(3S)-1-[4-[(4-methyl-1-piperidyl)methyl]phenyl]-5-oxo-pyrrolidin-3-yl]-1,3,4-thiadiazole-2-carboxamide;

5-[2-(4-chlorophenyl)ethyl]-N-[(3R)-1-[4-[(4-methyl-1-piperidyl)methyl]phenyl]-5-oxo-pyrrolidin-3-yl]-1,3,4-thiadiazole-2-carboxamide 5-[2-(4-chlorophenyl)ethyl]-N-[5-oxo-1-[4-(1-piperidylmethyl)phenyl]pyrrolidin-3-yl]-1,3,4-thiadiazole-2-carboxamide;

N-[1-[4-(3-azabicyclo[3.1.0]hexan-3-yl methyl)phenyl]-5-oxo-pyrrolidin-3-yl]-5-[2-(4-chlorophenyl)ethyl]-1,3,4-thiadiazole-2-carboxamide;

5-[2-(4-chlorophenyl)ethyl]-N-[(3R)-5-oxo-1-[4-[(3-oxopiperazin-1-yl)methyl]phenyl]pyrrolidin-3-yl]-1,3,4-thiadiazole-2-carboxamide;

5-[2-(4-chlorophenyl)ethyl]-N-[1-[4-[[2-methoxyethyl(methyl)amino]methyl]phenyl]-5-oxo-pyrrolidin-3-yl]-1,3,4-thiadiazole-2-carboxamide;

5-[2-(4-chlorophenyl)ethyl]-N-[(3R)-5-oxo-1-[4-(1-piperidylmethyl)phenyl]pyrrolidin-3-yl]isoxazole-3-carboxamide;

5-[2-(4-chlorophenyl)ethyl]-N-[5-oxo-1-[4-(1-piperidylmethyl)phenyl]pyrrolidin-3-yl]isoxazole-3-carboxamide;

5-[2-(4-chlorophenyl)ethyl]-N-[(3S)-5-oxo-1-[4-(1-piperidylmethyl)phenyl]pyrrolidin-3-yl]isoxazole-3-carboxamide;

(3S)—N-[5-[2-(4-chlorophenyl)ethyl]isoxazol-3-yl]-5-oxo-1-[4-(1-piperidylmethyl)phenyl]pyrrolidine-3-carboxamide;

N-[5-(2-cyclohexylethyl)-1,3,4-thiadiazol-2-yl]-1-[4-(morpholinomethyl)phenyl]-5-oxo-pyrrolidine-3-carboxamide;

(3S)—N-[6-[2-(4-fluorophenyl)ethyl]pyridazin-3-yl]-1-[4-[[methyl(tetrahydrofuran-3-yl)amino]methyl]phenyl]-5-oxo-pyrrolidine-3-carboxamide;

N-[6-[2-(4-fluorophenyl)ethyl]pyridazin-3-yl]-1-[4-(morpholinomethyl)phenyl]-5-oxo-pyrrolidine-3-carboxamide;

N-[5-[2-(4-methoxyphenyl)ethyl]-1,3,4-thiadiazol-2-yl]-1-[4-(morpholinomethyl)phenyl]-5-oxo-pyrrolidine-3-carboxamide;

N-[5-[2-(4-chlorophenyl)ethyl]-1,3,4-thiadiazol-2-yl]-5-oxo-1-[4-(pyrrolidin-1-ylmethyl)phenyl]pyrrolidine-3-carboxamide;

(3S)—N-[5-[2-(4-chlorophenyl)ethyl]isoxazol-3-yl]-1-[4-[[methyl(tetrahydrofuran-3-yl)amino]methyl]phenyl]-5-oxo-pyrrolidine-3-carboxamide;

4-[[[5-[2-(4-chlorophenyl)ethyl]-1,3,4-thiadiazol-2-yl]amino]methyl]-1-[4-(morpholinomethyl)phenyl]pyrrolidin-2-one;

N-[5-[(4-fluorophenyl)methylsulfanyl]-1,3,4-thiadiazol-2-yl]-1-[4-(morpholinomethyl)phenyl]-5-oxo-pyrrolidine-3-carboxamide;

(3S)—N-[6-[2-(4-fluorophenyl)ethyl]pyridazin-3-yl]-1-[4-[[methyl(oxetan-3-yl)amino]methyl]phenyl]-5-oxo-pyrrolidine-3-carboxamide;

N-[5-[2-(4-chlorophenyl)ethyl]-1,3,4-thiadiazol-2-yl]-1-[4-(1,4-diazepan-1-ylmethyl)phenyl]-5-oxo-pyrrolidine-3-carboxamide;

tert-butyl 4-[[4-[4-[[5-[2-(4-chlorophenyl)ethyl]-1,3,4-thiadiazol-2-yl]carbamoyl]-2-oxo-pyrrolidin-1-yl]phenyl]methyl]piperazine-1-carboxylate;

1-[4-(morpholinomethyl)phenyl]-5-oxo-N-[5-(2-phenylethyl)isoxazol-3-yl]pyrrolidine-3-carboxamide;

N-[5-[2-(4-chlorophenyl)ethyl]-1,3,4-thiadiazol-2-yl]-1-[4-[[isopropyl(methyl)amino]methyl]phenyl]-5-oxo-pyrrolidine-3-carboxamide;

N-[5-[2-(4-chlorophenyl)ethyl]-1,3,4-thiadiazol-2-yl]-5-oxo-1-[4-(piperazin-1-ylmethyl)phenyl]pyrrolidine-3-carboxamide;

(3R)—N-[5-[2-(4-chlorophenyl)ethyl]-1,3,4-thiadiazol-2-yl]-1-[4-(morpholinomethyl)phenyl]-5-oxo-pyrrolidine-3-carboxamide;

1-[4-(morpholinomethyl)phenyl]-5-oxo-N-[6-(2-phenylethyl)pyridazin-3-yl]pyrrolidine-3-carboxamide;

(3R)—N-[5-[2-(4-chlorophenyl)ethyl]-1,3,4-thiadiazol-2-yl]-5-oxo-1-[4-(1-piperidylmethyl)phenyl]pyrrolidine-3-carboxamide;

(3S)-5-oxo-1-[4-(I-piperidylmethyl)phenyl]-N-[5-(2-tetrahydropyran-2-ylethyl)-1,3,4-thiadiazol-2-yl]pyrrolidine-3-carboxamide;

(3S)-1-[4-(morpholinomethyl)phenyl]-5-oxo-N-[5-(2-tetrahydropyran-2-ylethyl)-1,3,4-thiadiazol-2-yl]pyrrolidine-3-carboxamide;

N-[5-(2-cyclopentylethyl)-1,3,4-thiadiazol-2-yl]-5-oxo-1-[4-(1-piperidylmethyl)phenyl]pyrrolidine-3-carboxamide;

5-[2-(4-chlorophenyl)ethyl]-N-[(3S)-1-[4-(morpholinomethyl)phenyl]pyrrolidin-3-yl]-1,3,4-thiadiazole-2-carboxamide;

5-[2-(4-fluorophenyl)ethyl]-N-[5-oxo-1-[4-(1-piperidylmethyl)phenyl]pyrrolidin-3-yl]-1,3,4-thiadiazole-2-carboxamide;

5-[2-(4-chlorophenyl)ethyl]-N-[(3R)-1-[4-[(4-hydroxy-4-methyl-1-piperidyl)methyl]phenyl]-5-oxo-pyrrolidin-3-yl]-1,3,4-thiadiazole-2-carboxamide;

5-[2-(4-chlorophenyl)ethyl]-N-[(3R)-1-[4-[[(3-hydroxy-3-methyl-butyl)amino]methyl]phenyl]-5- oxo-pyrrolidin-3-yl]-1,3,4-thiadiazole-2-carboxamide hydrochloride;

5-[2-(4-chlorophenyl)ethyl]-N-[(3R)-1-[4-[[(3-hydroxy-3-methyl-butyl)-methyl-amino]methyl]phenyl]-5-oxo-pyrrolidin-3-yl]-1,3,4-thiadiazole-2-carboxamide;

N-[5-oxo-1-[4-(1-piperidylmethyl)phenyl]pyrrolidin-3-yl]-5-(2-phenylethyl)-1,3,4-thiadiazole-2-carboxamide;

5-[2-(4-fluorophenyl)ethyl]-N-[(3R)-5-oxo-1-[4-(1-piperidylmethyl)phenyl]pyrrolidin-3-yl]isoxazole-3-carboxamide;

5-[2-(4-fluorophenyl)ethyl]-N-[(3S)-5-oxo-1-[4-(1-piperidylmethyl)phenyl]pyrrolidin-3-yl]isoxazole-3-carboxamide;

N-[5-oxo-1-[4-(1-piperidylmethyl)phenyl]pyrrolidin-3-yl]-5-(2-phenylethyl)isoxazole-3-carboxamide;

1-[4-(morpholinomethyl)phenyl]-5-oxo-N-[5-(2-phenylethyl)-1,3,4-thiadiazol-2-yl]pyrrolidine-3-carboxamide;

N-[5-[2-(4-chlorophenyl)ethyl]-1,3,4-thiadiazol-2-yl]-1-[4-[(dimethylamino)methyl]phenyl]-5-oxo-pyrrolidine-3-carboxamide;

(3S)—N-[6-[2-(4-fluorophenyl)ethyl]pyridazin-3-yl]-5-oxo-1-[4-(1-piperidylmethyl)phenyl]pyrrolidine-3-carboxamide;

1-[4-(morpholinomethyl)phenyl]-5-oxo-N-[5-(2-phenylethyl)-1H-pyrazol-3-yl]pyrrolidine-3-carboxamide;

(3S)—N-[6-[2-(4-fluorophenyl)ethyl]pyridazin-3-yl]-1-[4-(morpholinomethyl)phenyl]-5-oxo-pyrrolidine-3-carboxamide;

N-[5-(3-methylpentyl)-1,3,4-thiadiazol-2-yl]-1-[4-(morpholinomethyl)phenyl]-5-oxo-pyrrolidine-3-carboxamide;

N-[5-(3-methylpentyl)-1,3,4-thiadiazol-2-yl]-5-oxo-1-[4-(1-piperidylmethyl)phenyl]pyrrolidine-3-carboxamide;

4-[[5-[2-(4-chlorophenyl)ethyl]-1,3,4-thiadiazol-2-yl]methylamino]-1-[4-(morpholinomethyl)phenyl]pyrrolidin-2-one;

N-[[4-[4-[[5-[2-(4-chlorophenyl)ethyl]-1,3,4-thiadiazol-2-yl]carbamoyl]-2-oxo-pyrrolidin-1-yl]phenyl]methyl]-1-methyl-piperidine-4-carboxamide;

(3S)-1-[4-(morpholinomethyl)phenyl]-5-oxo-N-[5-(2-tetrahydrofuran-2-ylethyl)-1,3,4-thiadiazol-2-yl]pyrrolidine-3-carboxamide;

N-[5-(cyclohexoxymethyl)thiazol-2-yl]-1-[4-(morpholinomethyl)phenyl]-5-oxo-pyrrolidine-3-carboxamide;

1-[4-(morpholinomethyl)phenyl]-5-oxo-N-[5-(2-tetrahydropyran-4-ylethyl)-1,3,4-thiadiazol-2-yl]pyrrolidine-3-carboxamide;

5-oxo-1-[4-(1-piperidylmethyl)phenyl]-N-[5-(2-tetrahydropyran-4-ylethyl)-1,3,4-thiadiazol-2-yl]pyrrolidine-3-carboxamide;

(3S)-5-oxo-1-[4-(1-piperidylmethyl)phenyl]-N-[5-(2-tetrahydropyran-4-ylethyl)-1,3,4-thiadiazol-2-yl]pyrrolidine-3-carboxamide;

(3S)-5-oxo-1-[4-(1-piperidylmethyl)phenyl]-N-[5-(2-tetrahydrofuran-2-ylethyl)-1,3,4-thiadiazol-2-yl]pyrrolidine-3-carboxamide;

N-[5-[2-(4-chlorophenyl)ethyl]-1-methyl-pyrazol-3-yl]-1-[4-(morpholinomethyl)phenyl]-5-oxo-pyrrolidine-3-carboxamide;

5-[2-(4-chlorophenyl)ethyl]-N-[(3R)-1-[4-[(4-methylpiperazin-1-yl)methyl]phenyl]-5-oxo-pyrrolidin-3-yl]-1,3,4-thiadiazole-2-carboxamide;

N-[5-oxo-1-[4-(1-piperidylmethyl)phenyl]pyrrolidin-3-yl]-5-(2-phenylethyl)-1,3,4-oxadiazole-2-carboxamide;

5-[2-(2-furyl)ethyl]-N-[5-oxo-1-[4-(1-piperidylmethyl)phenyl]pyrrolidin-3-yl]-1,3,4-thiadiazole-2-carboxamide;

5-[(4-chlorophenyl)methylamino]-N-[5-oxo-1-[4-(1-piperidylmethyl)phenyl]pyrrolidin-3-yl]-1,3,4-thiadiazole-2-carboxamide;

N-[5-oxo-1-[4-(1-piperidylmethyl)phenyl]pyrrolidin-3-yl]-5-(2-phenylethyl)thiazole-2-carboxamide;

N-[5-oxo-1-[4-(1-piperidylmethyl)phenyl]pyrrolidin-3-yl]-3-(2-phenylethyl)isoxazole-5-carboxamide;

N-[3-[2-(4-methoxyphenyl)ethyl]isoxazol-5-yl]-1-[4-(morpholinomethyl)phenyl]-5-oxo-pyrrolidine-3-carboxamide;

1-[4-(morpholinomethyl)phenyl]-5-oxo-N-[3-(2-phenylethyl)isoxazol-5-yl]pyrrolidine-3-carboxamide;

1-[4-(morpholinomethyl)phenyl]-5-oxo-N-[2-(2-phenylethyl)thiazol-5-yl]pyrrolidine-3-carboxamide;

N-[5-[2-(4-chlorophenyl)ethyl]-2-methyl-pyrazol-3-yl]-1-[4-(morpholinomethyl)phenyl]-5-oxo-pyrrolidine-3-carboxamide;

1-[4-(aminomethyl)phenyl]-N-[5-[2-(4-chlorophenyl)ethyl]-1,3,4-thiadiazol-2-yl]-5-oxo-pyrrolidine-3-carboxamide;

N-[5-oxo-1-[4-(1-piperidylmethyl)phenyl]pyrrolidin-3-yl]-3-(2-phenylethyl)-1H-pyrazole-5-carboxamide;

N-[5-oxo-1-[4-(1-piperidylmethyl)phenyl]pyrrolidin-3-yl]-6-(2-phenylethyl)pyridazine-3-carboxamide;

N-[5-oxo-1-[4-(1-piperidylmethyl)phenyl]pyrrolidin-3-yl]-2-(2-phenylethyl)thiazole-5-carboxamide;

N-[5-[2-(4-methoxyphenyl)ethyl]-1,3,4-oxadiazol-2-yl]-1-[4-(morpholinomethyl)phenyl]-5-oxo-pyrrolidine-3-carboxamide;

1-[4-(4-{5-[2-(4-Chloro-phenyl)-ethyl]-[1,3,4]thiadiazol-2-ylcarbamoyl}-2-oxo-pyrrolidin-1-yl)-3-fluoro-benzyl]-piperidinium; chloride;

4-[4-(4-{5-[2-(4-Chloro-phenyl)-ethyl]-[1,3,4]thiadiazol-2-ylcarbamoyl}-2-oxo-pyrrolidin-1-yl)-3-fluoro-benzyl]-morpholin-4-ium; chloride;

1-[4-(4-{5-[2-(4-Chloro-phenyl)-ethyl]-[1,3,4]thiadiazol-2-ylcarbamoyl}-2-oxo-pyrrolidin-1-yl)-3-fluoro-benzyl]-4-methyl-piperidinium; chloride;

1-{4-[(Ethyl-methyl-amino)-methyl]-phenyl}-5-oxo-pyrrolidine-3-carboxylic acid {5-[2-(4-chloro-phenyl)-ethyl]-[1,3,4]thiadiazol-2-yl}-amide;

(3S)—N-[5-[2-(4-chlorophenyl)ethyl]-1,3,4-thiadiazol-2-yl]-1-[4-(2-oxa-7-azaspiro[3.4]octan-7-ylmethyl)phenyl]-5-oxo-pyrrolidine-3-carboxamide;

(3S)—N-[5-[2-(4-chlorophenyl)ethyl]-1,3,4-thiadiazol-2-yl]-1-[4-(2-oxa-6-azaspiro[3.3]heptan-6-ylmethyl)phenyl]-5-oxo-pyrrolidine-3-carboxamide;

5-[2-(4-chlorophenyl)ethyl]-N-[(3R)-1-[4-(methanesulfonamidomethyl)phenyl]-5-oxo-pyrrolidin-3-yl]-1,3,4-thiadiazole-2-carboxamide; or 1-(4-Morpholin-4-ylmethyl-phenyl)-5-oxo-pyrrolidine-3-carboxylic acid {5-[2-(4-fluoro-phenyl)-ethyl]-[1,3,4]thiadiazol-2-yl}-amide; hydrochloride.

The various functional groups and substituents making up the compounds of the formula (I) are typically chosen such that the molecular weight of the compound of the formula (I) does not exceed 1000. More usually, the molecular weight of the compound will be less than 900, for example less than 800, or less than 750, or less than 700, or less than 650. More preferably, the molecular weight is less than 600 and, for example, is 550 or less.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric methane sulfonate or maleic acid. In addition, a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, trimethylamine, piperidine, morpholine or tris-(2-hydroxyethyl)amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess antiproliferative activity.

The present invention also encompasses compounds of the invention as defined herein which comprise one or more isotopic substitutions. For example, H may be in any isotopic form, including 1H, 2H(D), and 3H (T); C may be in any isotopic form, including 12C, 13C, and 14C; and O may be in any isotopic form, including 16O and 18O; and the like.

It is also to be understood that certain compounds of the formula (I) may exist in solvated as well as unsolvated forms such as, for example, hydrated forms. It is to be understood that the invention encompasses all such solvated forms that possess antiproliferative activity.

It is also to be understood that certain compounds of the formula I may exhibit polymorphism, and that the invention encompasses all such forms that possess antiproliferative activity.

Compounds of the formula I may exist in a number of different tautomeric forms and references to compounds of the formula I include all such forms. For the avoidance of doubt, where a compound can exist in one of several tautomeric forms, and only one is specifically described or shown, all others are nevertheless embraced by formula I. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

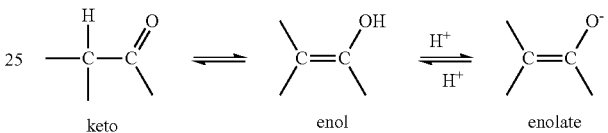

keto  enol  enolate

Compounds of the formula I containing an amine function may also form N-oxides. A reference herein to a compound of the formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example Advanced Organic Chemistry, by Jerry March, 4th Edition, Wiley Interscience, pages. More particularly, N-oxides can be made by the procedure of L. W. Deady (Syn. Comm. 1977, 7, 509-514) in which the amine compound is reacted with m-chloroperoxybenzoic acid (mCPBA), for example, in an inert solvent such as dichloromethane.

The compounds of formula (I) may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the formula (I) and in-vivo cleavable amide derivatives that may be formed at a carboxy group or an amino group in a compound of the formula (I).

Accordingly, the present invention includes those compounds of the formula (I) as defined hereinbefore when made available by organic synthesis and when made available within the human or animal body by way of cleavage of a pro-drug thereof. Accordingly, the present invention includes those compounds of the formula I that are produced by organic synthetic means and also such compounds that are produced in the human or animal body by way of metabolism of a precursor compound, that is a compound of the formula (I) may be a synthetically-produced compound or a metabolically-produced compound.

A suitable pharmaceutically acceptable pro-drug of a compound of the formula (I) is one that is based on reasonable medical judgement as being suitable for administration to the human or animal body without undesirable pharmacological activities and without undue toxicity.

Various forms of pro-drug have been described, for example in the following documents:—
a) Methods in Enzymology, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, Advanced Drug Delivery Reviews, 8, 1-38 (1992);
e) H. Bundgaard, et al., Journal of Pharmaceutical Sciences, 77, 285 (1988);
f) N. Kakeya, et al., Chem. Pharm. Bull., 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the formula I that possesses a carboxy group is, for example, an in vivo cleavable ester thereof. An in vivo cleavable ester of a compound of the formula I containing a carboxy group is, for example, a pharmaceutically acceptable ester which is cleaved in the human or animal body to produce the parent acid. Suitable pharmaceutically acceptable esters for carboxy include C1-6alkyl esters such as methyl, ethyl and tert-butyl, C1-6alkoxymethyl esters such as methoxymethyl esters, C1-6alkanoyloxymethyl esters such as pivaloyloxymethyl esters, 3-phthalidyl esters, C3-8cycloalkylcarbonyloxy-C1-6alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and C1-6alkoxycarbonyloxy-C1-6alkyl esters such as methoxycarbonyloxymethyl and 1-methoxycarbonyloxyethyl esters.

A suitable pharmaceutically acceptable pro-drug of a compound of the Formula (I) that possesses a hydroxy group is, for example, an in vivo cleavable ester or ether thereof. An in vivo cleavable ester or ether of a compound of the formula I containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include C1-10alkanoyl groups such as acetyl, benzoyl, phenylacetyl and substituted benzoyl and phenylacetyl groups, C1-10alkoxycarbonyl groups such as ethoxycarbonyl, N,N—(C1-6)2carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(C1-4alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the formula (I) that possesses a carboxy group is, for example, an in vivo cleavable amide thereof, for example an amide formed with an amine such as ammonia, a C1-4alkylamine such as methylamine, a (C1-4alkyl) 2amine such as dimethylamine, N-ethyl-N-methylamine or diethylamine, a C1-4alkoxy-C2-4alkylamine such as 2-methoxyethylamine, a phenyl-C1-4alkylamine such as benzylamine and amino acids such as glycine or an ester thereof.

A suitable pharmaceutically acceptable pro-drug of a compound of the formula I that possesses an amino group is, for example, an in vivo cleavable amide derivative thereof. Suitable pharmaceutically acceptable amides from an amino group include, for example an amide formed with C1-10alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(C1-4alkyl)piperazin-1-ylmethyl.

The in vivo effects of a compound of the formula (I) may be exerted in part by one or more metabolites that are formed within the human or animal body after administration of a compound of the formula (I). As stated hereinbefore, the in vivo effects of a compound of the formula (I) may also be exerted by way of metabolism of a precursor compound (a pro-drug).

Though the present invention may relate to any compound or particular group of compounds defined herein by way of optional, preferred or suitable features or otherwise in terms of particular embodiments, the present invention may also relate to any compound or particular group of compounds that specifically excludes said optional, preferred or suitable features or particular embodiments.

Suitably, the present invention excludes any individual compounds not possessing the biological activity defined herein.

Synthesis

The compounds of the present invention can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

It will be appreciated that during the synthesis of the compounds of the invention in the processes defined herein, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The methodology employed to synthesise a compound of formula (I) will vary depending on the nature of $R_1$, $R_2$, $R_3$, $R_{4a}$, $R_{4b}$, $R_{4c}$, $R_{4d}$, L, A, Q, HET, W and any substituent groups associated therewith. Suitable processes for their preparation are described further in the accompanying Examples.

Once a compound of formula (I) has been synthesised by any one of the processes defined herein, the processes may then further comprise the additional steps of:

(i) removing any protecting groups present;
(ii) converting the compound formula (I) into another compound of formula (I);
(iii) forming a pharmaceutically acceptable salt, hydrate or solvate thereof; and/or
(iv) forming a prodrug thereof.

An example of (ii) above is when a compound of formula (I) is synthesised and then one or more of the groups $R_1$, $R_2$, $R_3$, $R_{4a}$, $R_{4b}$, $R_{4c}$, $R_{4d}$, L, A, Q, HET and W, may be further reacted to change the nature of the group and provide an alternative compound of formula (I).

For example, the compound can be reacted to convert any R group into a substituent group other than hydrogen.

The resultant compounds of formula (I) can be isolated and purified using techniques well known in the art.

In one aspect of the present invention, the compounds of formula (I), or a pharmaceutically acceptable salt or solvate thereof, may be synthesised by a method comprising either:

a) reacting a compound of formula A:

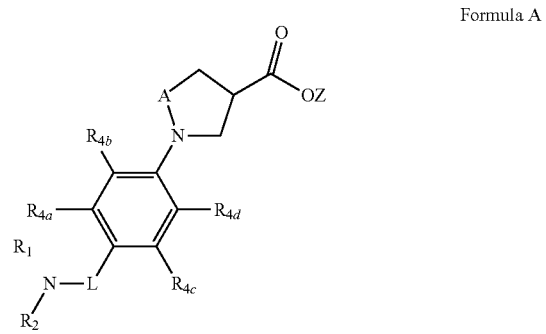

Formula A wherein $R_1$, $R_2$, $R_{4a}$, $R_{4b}$, $R_{4c}$, $R_{4d}$, L and A are as defined hereinabove, and Z is either H or $[M]^+$, where M is selected from Li or Na;

with any suitable amide coupling agent, and a compound of formula B;

Formula B wherein HET, W and $R_3$ are as defined hereinabove;

b) reacting a compound of formula C:

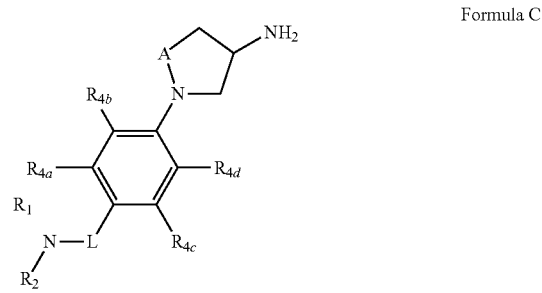

Formula C wherein $R_1$, $R_2$, $R_{4a}$, $R_{4b}$, $R_{4c}$, $R_{4d}$, L and A are as defined hereinabove; with any suitable amide coupling agent, and a compound of formula D;

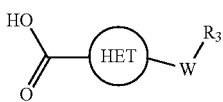

Formula D wherein HET, W and R$_3$ are as defined hereinabove;
c) reacting a compound of formula E:

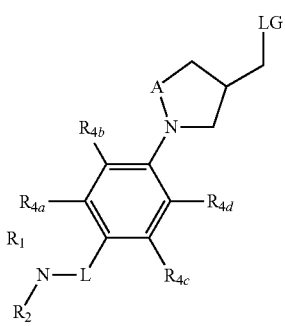

Formula E wherein R$_1$, R$_2$, R$_{4a}$, R$_{4b}$, R$_{4c}$, R$_{4d}$, L and A are as defined hereinabove, and LG is a suitable leaving group (e.g. halo or SO$_3$Me);
with a compound of Formula B:

wherein HET, W and R$_3$ are as defined hereinabove;
optionally thereafter, and if necessary:
  i) removing any protecting groups present;
  ii) converting the compound formula I into another compound of formula I; and/or
  iii) forming a pharmaceutically acceptable salt or solvate thereof.

Biological Activity

The ATX enzyme assay (Quanta Red assay) described in accompanying Example section may be used to measure the pharmacological effects of the compounds of the present invention.

Although the pharmacological properties of the compounds of formula I vary with structural change, as expected, the compounds of the invention were found to be active in this ATX assay.

In general, the compounds of the invention demonstrate an IC50 of 10 µM or less in the ATX enzyme assay described herein, with preferred compounds of the invention demonstrating an IC50 of 1 µM or less, more preferred compounds demonstrating an IC50 of 500 nM or less, and the most preferred compounds of the invention demonstrating an IC50 of 100 nM or less.

Pharmaceutical Compositions

According to a further aspect of the invention there is provided a pharmaceutical composition which comprises a compound of the invention as defined hereinbefore, or a pharmaceutically acceptable salt, hydrate or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy is an amount sufficient to treat or prevent a proliferative condition referred to herein, slow its progression and/or reduce the symptoms associated with the condition.

The amount of active ingredient that is combined with one or more excipients to produce a single dosage form will necessarily vary depending upon the individual treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula I will naturally vary according to the nature and severity of the conditions, the age and sex of the animal or patient and the route of administration, according to well known principles of medicine.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

The present invention provides compounds that function as inhibitors of ATX.

The present invention therefore provides a method of inhibiting ATX enzyme activity in vitro or in vivo, said method comprising contacting a cell and/or circulating ATX with an effective amount of a compound, or a pharmaceutically acceptable salt, hydrate or solvate thereof, as defined herein.

The present invention also provides a method of treating a disease or disorder in which ATX activity is implicated in a patient in need of such treatment, said method comprising administering to said patient a therapeutically effective amount of a compound, or a pharmaceutically acceptable salt, hydrate or solvate thereof, or a pharmaceutical composition as defined herein.

The present invention further provides a method of inhibiting cell proliferation, in vitro or in vivo, said method comprising contacting a cell and/or circulating ATX with an effective amount of a compound, or a pharmaceutically acceptable salt, hydrate or solvate thereof, as defined herein.

The present invention further provides a method of treating a proliferative disorder in a patient in need of such treatment, said method comprising administering to said patient a therapeutically effective amount of a compound as defined herein, or a pharmaceutically acceptable salt, hydrate or solvate thereof, or a pharmaceutical composition as defined herein.

The present invention further provides a method of treating or preventing cancer in a patient in need of such treatment, said method comprising administering to said patient a therapeutically effective amount of a compound as defined herein, or a pharmaceutically acceptable salt, hydrate or solvate thereof, or a pharmaceutical composition as defined herein.

The present invention further provides a method of treating or preventing invasive and/or metastatic cancer disease in a patient in need of such treatment, said method comprising administering to said patient a therapeutically effective amount of a compound as defined herein, or a pharmaceutically acceptable salt, hydrate or solvate thereof, or a pharmaceutical composition as defined herein.

The present invention further provides a method of treating or preventing fibrosis in a patient in need of such treatment, said method comprising administering to said patient a therapeutically effective amount of a compound as defined herein, or a pharmaceutically acceptable salt, hydrate or solvate thereof, or a pharmaceutical composition as defined herein. Suitably, the present invention provides a method of treating or preventing lung, renal, hepatic or skin fibrosis, most suitably, lung and hepatic fibrosis.

The present invention further provides a compound as defined herein, or a pharmaceutically acceptable salt, hydrate or solvate thereof, or a pharmaceutical composition as defined herein, for use in therapy.

The present invention further provides a compound as defined herein, or a pharmaceutically acceptable salt, hydrate or solvate thereof, or a pharmaceutical composition as defined herein, for use in the treatment of a proliferative condition.

The present invention provides a compound as defined herein, or a pharmaceutically acceptable salt, hydrate or solvate thereof, or a pharmaceutical composition as defined herein, for use in the treatment of cancer. In a particular embodiment, the cancer is human cancer.

The present invention further provides a compound as defined herein, or a pharmaceutically acceptable salt, hydrate or solvate thereof, or a pharmaceutical composition as defined herein, for use in the treatment of invasive and/or metastatic cancer disease. In a particular embodiment, the invasive and/or metastatic cancer is a human invasive and/or metastatic cancer.

The present invention provides a compound, or a pharmaceutically acceptable salt, hydrate or solvate thereof as defined herein, or a pharmaceutical composition as defined herein, for use in the inhibition of ATX enzyme activity.

The present invention provides a compound or a pharmaceutically acceptable salt, hydrate or solvate thereof as defined herein, or a pharmaceutical composition as defined herein, for use in the treatment of a disease or disorder in which ATX activity is implicated.

The present invention provides a use of a compound or a pharmaceutically acceptable salt, hydrate or solvate thereof as defined herein, or a pharmaceutical composition as defined herein, in the manufacture of a medicament for the treatment of a proliferative condition.

The present invention provides a use of a compound, or a pharmaceutically acceptable salt, hydrate or solvate thereof, as defined herein in the manufacture of a medicament for the treatment of cancer. Suitably, the medicament is for use in the treatment of human cancers.

The present invention further provides a use of a compound, or a pharmaceutically acceptable salt, hydrate or solvate thereof, as defined herein in the manufacture of a medicament for the treatment of invasive and/or metastatic cancer. Suitably, the medicament is for use in the treatment of human invasive and/or metastatic cancer disease.

The present invention provides a use of a compound, or a pharmaceutically acceptable salt, hydrate or solvate thereof, as defined herein in the manufacture of a medicament for the inhibition of ATX enzyme activity.

The present invention provides a use of a compound, or a pharmaceutically acceptable salt, hydrate or solvate thereof, as defined herein in the manufacture of a medicament for the treatment of a disease or disorder in which ATX activity is implicated.

The term "proliferative disorder" are used interchangeably herein and pertain to an unwanted or uncontrolled cellular proliferation of excessive or abnormal cells which is undesired, such as, neoplastic or hyperplastic growth, whether in vitro or in vivo. Examples of proliferative conditions include, but are not limited to, benign, pre-malignant and malignant cellular proliferation, including but not limited to, malignant neoplasms and tumours, cancers, leukemias, psoriasis, bone diseases, fibroproliferative disorders (e.g., of connective tissues), and atherosclerosis. Any type of cell may be treated, including but not limited to, lung, colon, breast, ovarian, prostate, liver, pancreas, brain, bladder, kidney, bone, nerves and skin.

In an embodiment of the invention, the proliferative disorder is a benign disorder, such as, for example, neuroblastoma or fibrosis.

The anti-proliferative, anti-metastatic and anti-invasive effects of the compounds of the present invention have particular application in the treatment of human cancers (by virtue of their inhibition of ATX enzyme activity).

In an embodiment of the invention, the anti-proliferative, anti-metastatic and anti-invasive effects of the compounds of the present invention have particular application in the treatment and/or prevention of invasive and/or metastatic cancers, such as, for example bladder cancer, invasive breast cancer, kidney cancer, ovarian cancer and glioma (e.g. glioblastoma). Suitably, the anti-proliferative, anti-metastatic and anti-invasive effects of the compounds of the present invention have particular application in the treatment and/or prevention of bladder cancer, invasive breast cancer and/or glioma (e.g. glioblastoma).

The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures or within an organ), or the promotion of apoptosis (programmed cell death).

In a particular embodiment of the invention, the proliferative, metastatic and/or invasive condition to be treated is cancer. Suitably, the condition to be treated is highly invasive or metastatic cancer.

In another aspect, the present invention provides a compound as defined herein, or a pharmaceutically acceptable salt or solvate thereof, or a pharmaceutical composition as defined herein, for use in the treatment of inflammation.

In another aspect, the present invention provides a compound as defined herein, or a pharmaceutically acceptable salt or solvate thereof, or a pharmaceutical composition as defined herein, for use in the treatment of diabetes mellitus.

In another aspect, the present invention provides a compound as defined herein, or a pharmaceutically acceptable salt or solvate thereof, or a pharmaceutical composition as defined herein, for use in the treatment of hypertension, Atherosclerosis or Thrombosis.

In another aspect, the present invention provides a compound as defined herein, or a pharmaceutically acceptable salt or solvate thereof, or a pharmaceutical composition as defined herein, for use in the treatment of pain. In a particular embodiment, the pain is neuropathic pain.

In another aspect, the present invention provides a compound as defined herein, or a pharmaceutically acceptable salt or solvate thereof, or a pharmaceutical composition as defined herein, for use in the treatment of urethral obstructive disease. In a particular embodiment, the urethral obstructive disease is benign prostatic hyperplasia.

In another aspect, the present invention provides a compound as defined herein, or a pharmaceutically acceptable salt or solvate thereof, or a pharmaceutical composition as defined herein, for use in the treatment of pruritus.

In another aspect, the present invention provides a compound as defined herein, or a pharmaceutically acceptable salt or solvate thereof, or a pharmaceutical composition as defined herein, for use in the treatment of hepatitis C and/or B.

In another aspect, the present invention provides a compound as defined herein, or a pharmaceutically acceptable salt or solvate thereof, or a pharmaceutical composition as defined herein, for use in the treatment of fibrosis including lung, renal, hepatic and skin fibrosis.

Routes of Administration

The compounds of the invention or pharmaceutical compositions comprising these compounds may be administered to a subject by any convenient route of administration, whether systemically/peripherally or topically (i.e., at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The treatment defined herein may be applied as a sole therapy for the treatment of the specified condition or may involve, in addition to the compound of the invention, one or more additional therapies (including treatment with another therapeutic agent, surgery or other therapeutic interventions such as radiotherapy in the oncology setting).

Typically, the other therapeutic agent used in combination with a compound of the present invention will be one or more therapeutic agents used as the standard of care for the treatment of the disease or condition concerned. The other therapeutic agent may include, for example, another drug used for the treatment of the condition concerned, or an agent that modulates the biological response to the compound of the invention, such as, for example, an immunomodulatory agent.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

Cancer Therapy

The antiproliferative treatment defined hereinbefore may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. (Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy) quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In a particular embodiment, the antiproliferative treatment defined hereinbefore may involve, in addition to the compound of the invention, conventional surgery or radiotherapy or chemotherapy.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination for use in the treatment of a cancer (for example a cancer involving a solid tumour) comprising a compound of the invention as defined hereinbefore, or a pharmaceutically acceptable salt, hydrate or solvate thereof, and another anti-tumour agent.

According to this aspect of the invention there is provided a combination for use in the treatment of a proliferative condition, such as cancer (for example a cancer involving a solid tumour), comprising a compound of the invention as defined hereinbefore, or a pharmaceutically acceptable salt, hydrate or solvate thereof, and any one of the anti-tumour agents listed herein above.

In a further aspect of the invention there is provided a compound of the invention or a pharmaceutically acceptable salt, hydrate or solvate thereof, for use in the treatment of cancer in combination with another anti-tumour agent, optionally selected from one listed herein above.

According to a further aspect of the invention there is provided a pharmaceutical composition which comprises a compound of the invention, or a pharmaceutically acceptable salt, hydrate or solvate thereof, in combination with an anti-tumour agent (optionally selected from one listed herein above), in association with a pharmaceutically acceptable diluent or carrier.

Inflammation Therapy

In another aspect of the invention, there is provided a combination for use in the treatment of inflammation, comprising a compound of the invention as defined hereinbefore, or a pharmaceutically acceptable salt, hydrate or solvate thereof, and another anti-inflammatory agent and/or analgesic agent.

In a further aspect of the invention there is provided a compound of the invention or a pharmaceutically acceptable salt, hydrate or solvate thereof, for use in the treatment of inflammation in combination with another anti-inflammatory and/or analgesic agent.

According to a further aspect of the invention there is provided a pharmaceutical composition which comprises a compound of the invention, or a pharmaceutically acceptable salt, hydrate or solvate thereof, and another anti-inflammatory and/or analgesic agent, in association with a pharmaceutically acceptable diluent or carrier.

Diabetes Mellitus Therapy

In another embodiment of the invention, there is provided a combination for use in the treatment of diabetes mellitus (for example type II diabetes), comprising a compound of the invention as defined hereinbefore, or a pharmaceutically acceptable salt, hydrate or solvate thereof, and another anti-diabetic agent.

In a further aspect of the invention there is provided a compound of the invention or a pharmaceutically acceptable salt, hydrate or solvate thereof, for use in the treatment of diabetes mellitus in combination with another anti-diabetic agent.

According to a further aspect of the invention there is provided a pharmaceutical composition which comprises a compound of the invention, or a pharmaceutically acceptable salt, hydrate or solvate thereof, and another antidiabetic agent, in association with a pharmaceutically acceptable diluent or carrier.

Hypertension, Atherosclerosis and/or Thrombosis Therapy

In another embodiment of the invention, there is provided a combination for use in the treatment of hypertension, atherosclerosis and/or thrombosis, comprising a compound of the invention as defined hereinbefore, or a pharmaceutically acceptable salt, hydrate or solvate thereof, and one or more additional medicaments for the treatment of said conditions.

In a further aspect of the invention there is provided a compound of the invention or a pharmaceutically acceptable salt, hydrate or solvate thereof, for use in the treatment of hypertension, atherosclerosis and/or thrombosis in combination with another agent for the treatment of said conditions.

According to a further aspect of the invention there is provided a pharmaceutical composition which comprises a compound of the invention, or a pharmaceutically acceptable salt, hydrate or solvate thereof, and another agent for the treatment of hypertension, atherosclerosis and/or thrombosis, in association with a pharmaceutically acceptable diluent or carrier.

Urethral Obstructive Disease

In another embodiment of the invention, there is provided a combination for use in the treatment of urethral obstructive disease (for example benign prostatic hyperplasia), comprising a compound of the invention as defined hereinbefore, or a pharmaceutically acceptable salt, hydrate or solvate thereof, and another medicament for the treatment of urethral obstructive disease.

In a further aspect of the invention there is provided a compound of the invention or a pharmaceutically acceptable salt, hydrate or solvate thereof, for use in the treatment of urethral obstructive disease (for example benign prostatic hyperplasia), in combination with another agent for the treatment of said condition.

According to a further aspect of the invention there is provided a pharmaceutical composition which comprises a compound of the invention, or a pharmaceutically acceptable salt, hydrate or solvate thereof, and another agent for the treatment of urethral obstructive disease (for example benign prostatic hyperplasia), in association with a pharmaceutically acceptable diluent or carrier.

Pruritis Therapy

In another embodiment of the invention, there is provided a combination for use in the treatment of pruritus, comprising a compound of the invention as defined hereinbefore, or a pharmaceutically acceptable salt, hydrate or solvate thereof, and another antipruritic agent.

In a further aspect of the invention there is provided a compound of the invention or a pharmaceutically acceptable salt, hydrate or solvate thereof, for use in the treatment of pruritus, in combination with another anti-pruritic agent.

According to a further aspect of the invention there is provided a pharmaceutical composition which comprises a compound of the invention, or a pharmaceutically acceptable salt, hydrate or solvate thereof, and another antipruritic agent, in association with a pharmaceutically acceptable diluent or carrier.

Pain Therapy

In another embodiment of the invention, there is provided a combination for use in the treatment of pain (for example neuropathic pain) comprising a compound of the invention as defined hereinbefore, or a pharmaceutically acceptable salt, hydrate or solvate thereof, and another analgesic and/or anti-inflammatory agent.

In a further aspect of the invention there is provided a compound of the invention or a pharmaceutically acceptable salt, hydrate or solvate thereof, for use in the treatment of pain (for example neuropathic pain) in combination with another analgesic and/or anti-inflammatory agent.

According to a further aspect of the invention there is provided a pharmaceutical composition which comprises a compound of the invention, or a pharmaceutically acceptable salt, hydrate or solvate thereof, and another analgesic agent and/or anti-inflammatory, in association with a pharmaceutically acceptable diluent or carrier.

Hepatitis B and/or C

In another embodiment of the invention, there is provided a combination for use in the treatment of hepatitis B and/or C comprising a compound of the invention as defined hereinbefore, or a pharmaceutically acceptable salt, hydrate or solvate thereof, and another anti-hepatitis B and/or C agent.

In a further aspect of the invention there is provided a compound of the invention or a pharmaceutically acceptable salt, hydrate or solvate thereof, for use in the treatment of hepatitis B and/or C in combination with another anti-hepatitis B and/or C agent.

According to a further aspect of the invention there is provided a pharmaceutical composition which comprises a compound of the invention, or a pharmaceutically acceptable salt, hydrate or solvate thereof, and another anti-hepatitis B and/or C agent, in association with a pharmaceutically acceptable diluent or carrier.

Fibrosis

In another embodiment of the invention, there is provided a combination for use in the treatment of fibrosis (for example lung, renal, hepatic and skin fibrosis) comprising a compound of the invention as defined hereinbefore, or a pharmaceutically acceptable salt, hydrate or solvate thereof, and another anti-fibrotic agent.

In a further aspect of the invention there is provided a compound of the invention or a pharmaceutically acceptable salt, hydrate or solvate thereof, for use in the treatment of fibrosis (for example lung, renal, hepatic and skin fibrosis) in combination with another anti-fibrotic agent.

According to a further aspect of the invention there is provided a pharmaceutical composition which comprises a compound of the invention, or a pharmaceutically acceptable salt, hydrate or solvate thereof, and another anti-fibrotic agent, in association with a pharmaceutically acceptable diluent or carrier.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

EXAMPLES

Description of Drawings

Embodiments of the invention will be described, by way of example only, with reference to the accompanying drawings, in which.

GENERAL EXPERIMENTAL

Figure 1:
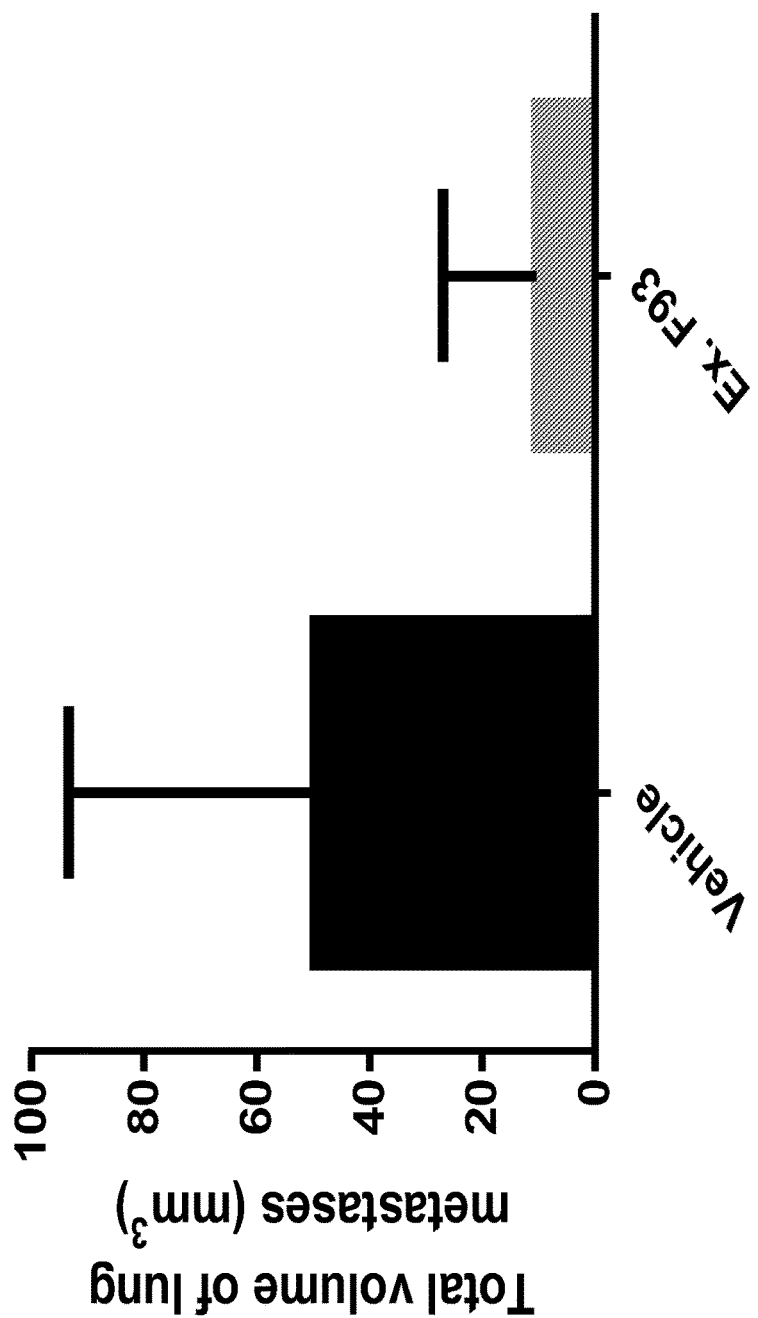
FIG. 1 shows the total volume of lung metastases for Example F93 compared to the vehicle, in the 4T1 orthotopic metastatic breast cancer model, described hereinbelow.

Analytical Methods
NMR
Proton NMR spectra were recorded using either:
an Oxford Instruments AS400 9.4 Tesla 400 MHz magnet with either a 5 mm BBO or PH SEF 400SB F-H-D-05 probe and an AVANCE/DPX400 console machine at 400 MHz;
a 300 MHz Bruker spectrometer; or
a 500 MHz Bruker spectrometer.

For all methods, NMR solutions were typically prepared in either $CDCl_3$, $CD_3OD$ or $DMSO-d_6$. Shifts are reported in ppm values relative to an internal standard of tetramethylsilane (TMS) or residual protic solvent. The following abbreviations are used to describe the splitting patterns: s (singlet), d (doublet), t (triplet), q (quartet), qn (quintet), m (multiplet), dd (doublet-doublet), ddd (doublet-doublet-doublet), dt (doublet-triplet), dq (doublet-quartet), sx (sextet), br (broad signal). Deuterated solvents were obtained from the Sigma-Aldrich Chemical Company, Goss or Fluorochem.
LCMS Method 1 employed Waters 515 pumps, a Waters 2525 mixer and a Waters 2998 UV detector. The detection was done between 210 nm and 400 nm. The mass spectrometer was a Waters micromass ZQ which detected masses between 100 and 700 g/mol. A Waters SunFire, 5 micron pore size, C18 column of dimensions 50×4.60 mm was used. The injection volume was 10 µL. The flow rate was 1.5 mL/min. The mobile phases of water and MeOH contained 0.1% formic acid. The elution was started at 85% water: 15% MeOH, changed linearly to 15% water: 85% MeOH over 4.5 minutes. These conditions were held for 1 minute before the eluent level was returned to the starting conditions of 85% water: 15% MeOH over 6 seconds. These conditions were held for 1.4 minutes to allow equilibration of the column before the next sample was injected. The run lasted 7 minutes in total.

Method 2 employed Waters 515 pumps, a Waters 2525 mixer and a Waters 2487 UV detector. The detection was done at 254 nm. The mass spectrometer was a Waters micromass ZQ which detected masses between 100 and 700 g/mol. A Waters SunFire, 5 micron pore size, C18 column of dimensions 50×4.60 mm was used. The injection volume was 10 µL. The flow rate was 1.5 mL/min. The mobile phases of water and MeOH contained 0.1% formic acid. The elution was started at 85% water: 15% MeOH, changing linearly to 15% water: 85% MeOH over 3 minutes. These conditions were held for 2.5 minutes before the eluent level was returned to the starting conditions of 85% water: 15% MeOH over 6 seconds. These conditions were held for 1.4 minutes to allow equilibration of the column before the next sample was injected. The run lasted 7 minutes in total.

Method 3 employed Waters 515 pumps, a Waters 2545 mixer and a Waters 2996 UV detector. The detection was done between 210 nm and 650 nm. The mass spectrometer used was a Waters 3100 which detected masses between 100 and 700 g/mol. A Waters XBridge, 5 micron pore size, C18 column of dimensions 50×4.60 mm was used. The injection volume was 10 µL. The flow rate was 1.5 mL/min. The mobile phases were water (pH 10, 0.03% ammonium hydroxide) and MeOH (0.03% ammonium hydroxide). The elution was started at 85% water: 15% MeOH, changing linearly to 15% water: 85% MeOH over 4.5 minutes. These conditions were held for 1 minute before the eluent level was returned to the starting conditions of 85% water: 15% MeOH over 6 seconds. These conditions were held for 1.4 minutes to allow equilibration of the column before the next sample was injected. The run lasted 7 minutes in total.

Method 4 employed Waters 515 pumps, a Waters 2545 mixer and a Waters 2996 UV detector. The detection was done between 210 nm and 650 nm. The mass spectrometer used was a Waters 3100 which detected masses between 100 and 700 g/mol. A Waters XBridge, 5 micron pore size, C18 column of dimensions 50×4.60 mm was used. The injection volume was 10 µL. The flow rate was 1.5 mL/min. The mobile phases were water (pH 10, 0.03% ammonium hydroxide) and MeOH (0.03% ammonium hydroxide). The elution was started at 85% water: 15% MeOH, changing linearly to 2% water: 98% MeOH over 3 minutes. These conditions were held for 2.5 minutes before the eluent level was returned to the starting conditions of 85% water: 15% ACN over 6 seconds. These conditions were held for 1.4 minutes to allow equilibration of the column before the next sample was injected. The run lasted 7 minutes in total.

Method 5 employed a Waters 515 pumps, a Waters 2545 mixer, an Alliance e2695 liquid handler and SFO mixer and a Waters 2998 UV detector. The detection was done between 210 nm and 600 nm. The mass spectrometer was an Acquity SQ which detected masses between 100 and 700 g/mol. A Waters SunFire, 5 micron pore size, C18 of dimensions 50×4.60 mm was used. The injection volume was 10 µl. The mobile phase consisted of a mixture of water and ACN containing 0.1% formic acid. The eluent flow rate was 1.5 ml/min, using 95% water: 5% ACN, changing linearly to 5% water:95% ACN over 5.0 minutes and then maintained at this mixture for 0.50 minutes before the eluent level was returned to the starting conditions of 95% water: 5% ACN over 6 seconds. These conditions were held for 1.4 minutes to allow equilibration of the column before the next sample was injected. The run lasted 7 minutes in total.

Method 6 employed a Waters 515 pumps, a Waters 2545 mixer, an Alliance e2695 liquid handler and SFO mixer and a Waters 2998 UV detector. The detection was done between 210 nm and 600 nm. The mass spectrometer was an Acquity SQ which detected masses between 100 and 700 g/mol. A Waters SunFire, 5 micron pore size, C18 of dimensions 50×4.60 mm was used. The injection volume was 10 µl. The mobile phase consisted of a mixture of water and ACN containing 0.1% formic acid. The eluent flow rate was 1.5 ml/min, using 95% water: 5% ACN, changing linearly to 5% water: 95% ACN over 10 min and then maintained at this mixture for 0.50 min before the eluent level was returned to the starting conditions of 95% water: 5% ACN over 6 seconds. These conditions were held for 1.4 minutes to allow equilibration of the column before the next sample was injected. The run lasted 12 minutes in total.

Method 7 employed Waters 515 pumps, a Waters 2525 mixer and a Waters 2998 detector. The detection was done between 210 nm and 400 nm. The mass spectrometer was a Waters micromass ZQ which detected masses between 100 and 700 g/mol. A Waters SunFire, 5 micron pore size, C18 column of dimensions 50×4.60 mm was used. The injection volume was 10 μL. The flow rate was 1.5 mL/min and the mobile phases of water and MeOH contained 0.1% formic acid. The elution was started at 85% water: 15% MeOH, changing linearly to 15% water: 85% MeOH over 3 minutes. These conditions were held for 2.5 minutes before the eluent level was returned to the starting conditions of 85% water: 15% MeOH over 6 seconds. These conditions were held for 1.4 minutes to allow equilibration of the column before the next sample was injected. The run lasted 7 minutes in total.

List of Abbreviations

° C. degrees Celsius
shift in parts per million
μL microliters
μm micrometers
$^1$H NMR proton nuclear magnetic resonance
2-MeTHF 2-methyl tetrahydrofuran
ACN acetonitrile
AcOH acetic acid
Boc tert-butyloxycarbonyl
$CCl_4$ carbon tetrachloride
$CDCl_3$ deuterated chloroform
$CD_3OD$ deuterated methanol
CDI 1,1'-carbonyldiimidazole
conc. concentrated
$Cs_2CO_3$ caesium carbonate
DCM dichloromethane
d.e. diastereomeric excess
DIPEA N,N-diisopropylethylamine
DMA dimethyl acetamide
DMF dimethyl formamide
DMSO dimethyl sulfoxide
DMSO-d6 deuterated dimethyl sulfoxide
EDC 1-ethyl-3-(3-dimethylaminopropyl)carbodiimide
e.e. enantiomeric excess
$Et_2O$ diethyl ether
EtOAc ethyl acetate
EtOH ethanol
FBS foetal bovine serum
g gram
$H_2O$ water
$H_2SO_4$ sulfuric acid
HATU 1-[bis(dimethylamino)methylene]-1H-1,2,3-triazolo[4,5-b]pyridinium 3-oxid hexafluorophosphate
HBTU O-(benzotriazol-1-yl)-N,N,N,N-tetramethyluronium hexafluorophosphate
HCl hydrochloric acid
HET heterocycle
HOBt hydroxybenzotriazole
$K_2CO_3$ potassium carbonate
KCN potassium cyanide
LCMS liquid chromatography mass spectrometry
Li lithium
$LiAlH_4$ lithium aluminium hydride
LiOH lithium hydroxide
M molar
MeOH methanol
mg milligram
$MgSO_4$ magnesium sulfate
MHz megahertz
MI molecular ion
$M^{+1}$ molecular ion plus one mass unit
$M^{-1}$ molecular ion minus one mass unit
min minutes
mL milliliters
mm millimeters
mmol millimoles
mol moles
MP-$CNBH_3$ polymer supported cyanoborohydride
MTBE methyl tert-butyl ether
MW microwave
$Na_2CO_3$ sodium carbonate
NaCl sodium chloride
NaH sodium hydride
$NaHCO_3$ sodium hydrogen carbonate
NaOH sodium hydroxide
NatOBu sodium tert-butoxide
NBS N-bromo succinimide
NCS N-chloro succinimide
$NEt_3$ triethylamine
$NH_2OH.HCl$ hydroxylamine hydrochloride
$NH_3$ ammonia
$NH_4Cl$ ammonium chloride
$NH_4HCO_3$ ammonium hydrogen carbonate
nm nanometers
NMM N-methyl morpholine
NMR nuclear magnetic resonance
PBS phosphate buffered saline
ppm parts per million
RPMI Roswell Park Memorial Institute
RT retention time
SCX Strong Cation Exchange (propylsulfonic acid bonded sorbent)
TBTU O-(benzotriazol-1-yl)-N,N,N',N'-tetramethyluronium tetrafluoroborate
$^t$BuOH tert-butanol
TFA trifluoroacetic acid
THF tetrahydrofuran
TMS trimethyl silane
TMS-Cl chlorotrimethylsilane
TsCl tosyl chloride
UV ultraviolet
General Methods

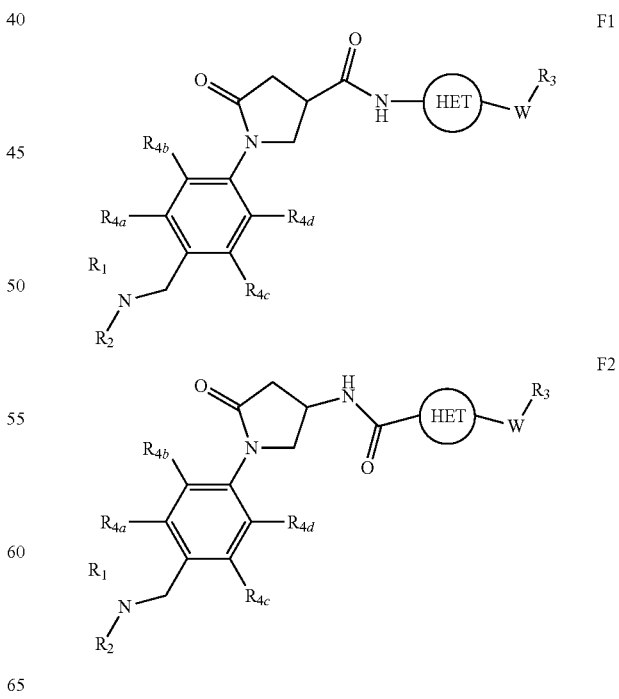

Compounds of general formula F1 (to include racemate and homochiral enantiomers) can be prepared by reacting a compound of general formula F3, which can be optionally the lithium salt or the hydrochloride salt (to include racemate and homochiral enantiomers) with a heterocyclic amine of general formula F4 in the presence of a suitable coupling agent such as HBTU, HATU, TBTU or EDC. The reaction may be conducted in a suitable solvent such as DMF in the presence of a tertiary amine base such as NEt$_3$ or NMM, optionally in the presence of HOBt. Alternatively compounds of general formula F1 may be prepared by reacting compounds of formula F3 with oxalyl chloride to give the corresponding acid chloride and then reacting with compounds of formula F4 in the presence of a suitable base such as NEt$_3$ in a suitable solvent such as DCM.

DMF in the presence of a tertiary amine base such as NEt$_3$ or NMM, optionally in the presence of HOBt.

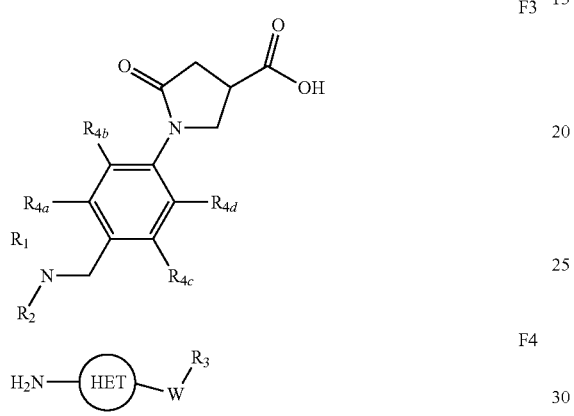

F3

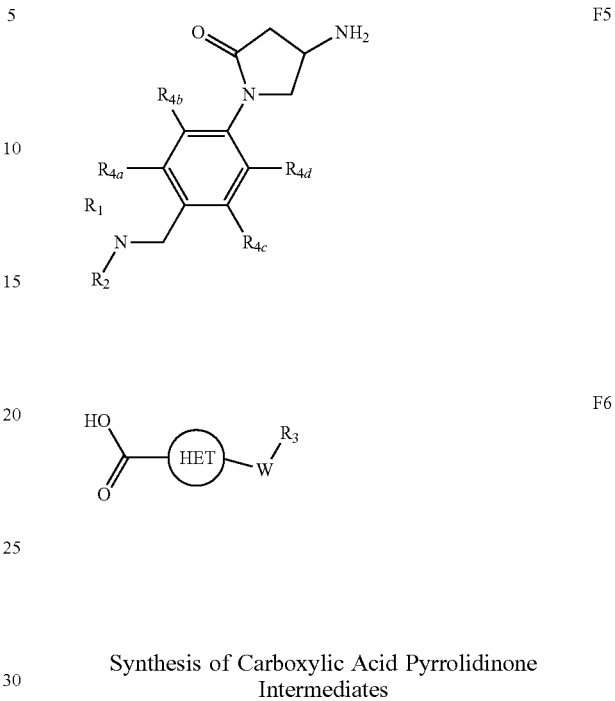

F5

F6

F4

Compounds of general formula F2 (to include racemate and homochiral enantiomers) can be prepared by reacting a compound of general formula F6 (or the corresponding lithium salt) with an amine of general formula F5 (to include racemate and homochiral enantiomers) in the presence of a suitable coupling agent such as HBTU, TBTU or EDC. The reaction may be conducted in a suitable solvent such as

Synthesis of Carboxylic Acid Pyrrolidinone Intermediates

Compounds of general formula F3 can be prepared as described in Scheme 1:

Scheme 1

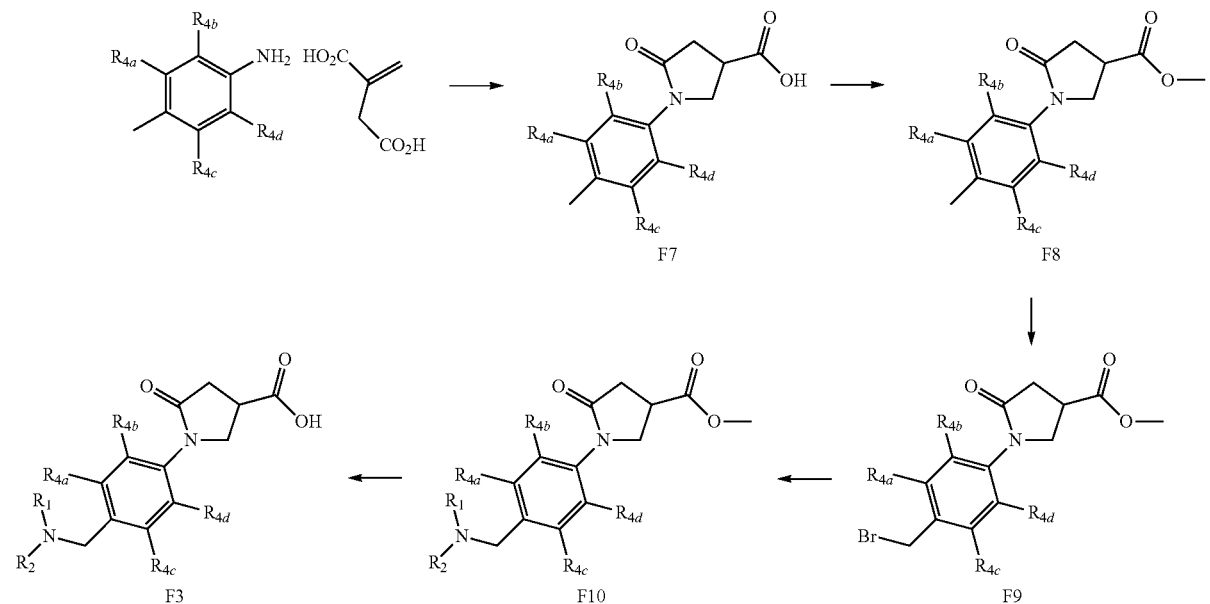

4-methyl aniline (optionally substituted) and itaconic acid can be reacted at elevated temperature either neat or in toluene to give the racemic pyrrolidinone acid F7.

Esterification of the pyrrolidinone acid F7 with MeOH and conc. H$_2$SO$_4$ gives the pyrrolidinone ester F8. Intermediate F8 can be brominated with NBS and benzoyl peroxide in refluxing CCl₄ to give the benzylic bromide F9. Intermediate F9 can be reacted with primary or secondary amines in the presence of a suitable base such as $K_2CO_3$ to give compounds of general formula F10. Compounds of formula F10 may be hydrolysed using by using LiOH in $H_2O$ to give the lithium carboxylate of F3 or with HCl in $H_2O$ to give the hydrochloride of F3.

An example of the method above is illustrated in Scheme 2:

removed under reduced pressure and the residue basified with saturated sodium bicarbonate solution and then diluted with $H_2O$. The resulting white solid was isolated by filtration, washed with $H_2O$ and dried under reduced pressure to afford the title compound (16.68 g).

LCMS method: Method 3, RT: 4.17 min, MI: 234 [M+1]

$^1$H NMR (500 MHz, DMSO-d₆) δ 7.51 (d, 2H), 7.17 (d, 2H), 4.05 (t, 1H), 4.03 (t, 1H), 3.94 (dd, 1H), 3.67 (s, 3H), 3.44 (m, 1H), 2.79 (dd, 1H), 2.70 (dd, 1H), 2.26 (s, 3H)

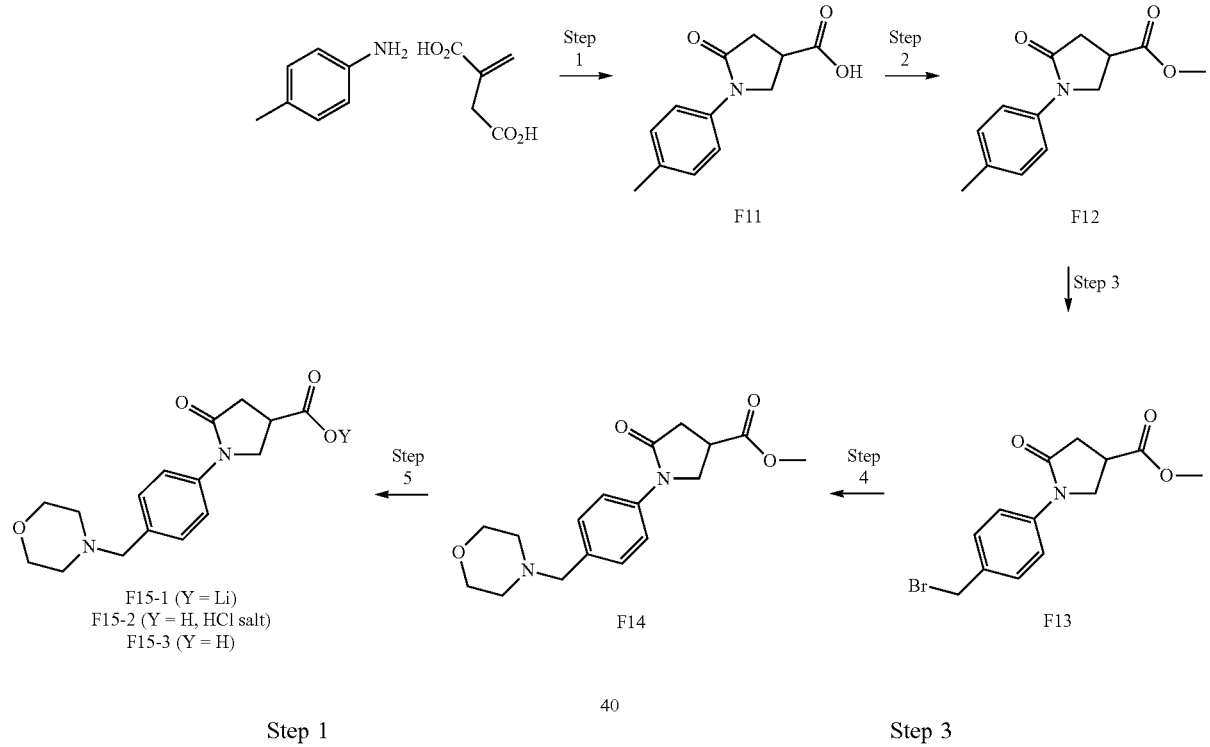

Scheme 2

Step 1

Synthesis of 5-oxo-1-(p-tolyl)pyrrolidine-3-carboxylic acid (F11)

Itaconic acid (12.14 g, 93.318 mmol) and p-toluidine (10.0 g, 93.318 mmol) were added to a flask which was fitted with a reflux condenser and toluene (100 mL) was added. The reaction mixture was heated to 120° C. for 3 hours then cooled to room temperature and stirred for 2 hours. The precipitate which formed was isolated by filtration, washed with toluene and dried to afford the title compound (19.48 g).

LCMS method: Method 3, RT: 1.35 min, MI: 220 [M+1]

$^1$H NMR (500 MHz, DMSO-d₆) δ 12.95 (s, 1H), 7.70 (d, 2H), 7.36 (d, 2H), 4.21 (t, 1H), 4.13 (m, 1H), 3.51 (m, 1H), 2.95 (dd, 1H), 2.86 (dd, 1H), 2.69 (s, 3H)

Step 2

Synthesis of methyl 5-oxo-1-(p-tolyl)pyrrolidine-3-carboxylate (F12)

5-Oxo-1-p-tolyl-pyrrolidine-3-carboxylic acid (19.48 g, 88.83 mmol) was dissolved in DCM (150 mL) and MeOH (50 mL) then conc. $H_2SO_4$ (0.5 mL) was added. The mixture was heated at reflux for 18 hours. The volatiles were

Step 3

Synthesis of methyl 1-[4-(bromomethyl)phenyl]-5-oxo-pyrrolidine-3-carboxylate (F13)

5-Oxo-1-p-tolyl-pyrrolidine-3-carboxylic acid methyl ester (0.87 g, 3.730 mmol), NBS (730 mg, 4.1030 mmol) and benzoyl peroxide (90 mg, 0.373 mmol) were suspended in CCl₄ (25 mL) and heated at reflux for 4 hours. The reaction mixture was allowed to cool to room temperature and concentrated under reduced pressure. The residue was dissolved in EtOAc and washed with saturated sodium bicarbonate solution and brine and dried using a phase separation cartridge. The EtOAc was removed under reduced pressure to give a dark red oil which was purified by flash column chromatography using a gradient of 0-40% EtOAc/cyclohexane. The relevant fractions were combined and dried under reduced pressure to afford the title compound (537 mg).

LCMS method: Method 3, RT: 4.13 min, MI: 312 [M+1]

$^1$H NMR (500 MHz, DMSO-d₆) δ 7.62 (d, 2H), 7.43 (d, 2H), 4.70 (s, 2H), 4.08 (m, 1H), 4.00 (m, 1H), 3.67 (s, 3H), 3.46 (m, 1H), 2.85 (dd, 1H), 2.76 (dd, 1H)

Step 4

Synthesis of methyl 1-[4-(morpholinomethyl)phenyl]-5-oxo-pyrrolidine-3-carboxylate (F14)

1-(4-Bromomethyl-phenyl)-5-oxo-pyrrolidine-3-carboxylic acid methyl ester (0.9 g, 2.883 mmol) was dissolved in ACN (15 mL) and treated with morpholine (377 μL, 4.325 mmol) and $K_2CO_3$ (1.193 g, 8.649 mmol). The mixture was stirred at room temperature for 10 minutes. The reaction mixture was filtered and the filtrate concentrated under reduced pressure to give a brown gum. The gum was dissolved in MeOH and acidified with a few drops of AcOH. The solution was loaded onto a 10 g SCX cartridge, washing first with MeOH and then eluting with 2M $NH_3$/MeOH. The second fraction was dried under reduced pressure to afford the title compound (0.563 g).

LCMS method: Method 3, RT: 3.66 min, MI: 319 [M+1]

$^1$H NMR (500 MHz, DMSO-$d_6$) δ 7.57 (d, 2H), 7.27 (d, 2H), 4.05 (t, 1H), 3.96 (dd, 1H), 3.67 (s, 3H), 3.55 (m, 4H), 3.48 (m, 1H), 3.41 (s, 2H), 2.80 (dd, 1H), 2.71 (dd, 1H), 2.31 (s, 4H)

Step 5

Synthesis of lithium; 1-[4-(morpholinomethyl)phenyl]-5-oxo-pyrrolidine-3-carboxylate (F15-1)

1-(4-Morpholin-4-ylmethyl-phenyl)-5-oxo-pyrrolidine-3-carboxylic acid methyl ester (0.2 g, 0.628 mmol) was dissolved in a mixture of $H_2O$ (2 mL) and THF (2 mL) then LiOH (15 mg, 0.628 mmol) was added. The mixture was stirred at room temperature for 1 hour then the mixture was concentrated under reduced pressure to afford the title compound (0.19 g).

LCMS method: Method 3, RT: 1.36 min, MI: 305 [M+1]

$^1$H NMR (500 MHz, DMSO-$d_6$) δ 7.57 (d, 2H), 7.27 (d, 2H), 4.05 (dd, 1H), 3.96 (dd, 1H), 3.67 (s, 3H), 3.54 (t, 4H), 3.45 (dd, 1H), 3.41 (s, 2H), 2.80 (dd, 1H), 2.71 (dd, 1H), 2.31 (br s, 4H)

Synthesis of 1-(4-morpholin-4-ylmethyl-phenyl)-5-oxo-pyrrolidine-3-carboxylic acid; hydrochloride (F15-2)

1-(4-Morpholin-4-ylmethyl-phenyl)-5-oxo-pyrrolidine-3-carboxylic acid methyl ester (4.38 g, 12.89 mmol) was dissolved in $H_2O$ (10 mL) and conc. HCl (10 mL) and the mixture was allowed to stand at room temperature for 48 hours. The volatiles were removed under reduced pressure and the residue azeotroped with toluene to afford the title compound (4.1 g).

LCMS method: Method 3, RT: 1.46 min, MI: molecular ion not observed $^1$H NMR (500 MHz, DMSO-$d_6$) δ 12.84 (br s, 1H), 11.11 (s, 1H), 7.79 (d, 2H), 7.64 (d, 2H), 4.34 (d, 2H), 4.11 (t, 1H), 4.03 (dd, 1H), 3.96 (d, 2H), 3.80 (t, 2H), 3.44-3.38 (m, 1H), 3.24 (d, 2H), 3.12-3.05 (m, 2H), 2.85 (dd, 1H), 2.75 (dd, 1H)

Synthesis of 1-(4-morpholin-4-ylmethyl-phenyl)-5-oxo-pyrrolidine-3-carboxylic acid (F15-3)

A mixture of 1-(4-morpholin-4-ylmethyl-phenyl)-5-oxo-pyrrolidine-3-carboxylic acid methyl ester (1.04 g, 3.26 mmol) and LiOH monohydrate (685 mg, 16.30 mmol) in THF (50 mL) and $H_2O$ (25 mL) was stirred at room temperature for 2 hours. The volatile were then removed under reduced pressure and the aqueous phase was adjusted to pH 7 with aqueous HCl (1M) and extracted with EtOAc. The aqueous phase was then loaded onto an SCX cartridge, washed with $H_2O$ then MeOH, then eluted with 2M $NH_3$/MeOH. The second fraction was concentrated under reduced pressure to afford the title compound (1.17 g).

$^1$H NMR (400 MHz, DMSO-$d_6$) δ 7.59 (d, 2H), 7.28 (d, 2H), 3.95 (d, 2H), 3.56 (m, 4H), 3.42 (s, 2H), 3.10 (m, 1H), 2.68 (m, 2H), 2.33 (m, 4H)

The following racemic intermediates (Table 1) were prepared using a similar method to that described for intermediates F15-1, F15-2 and F15-3 (Scheme 2):

TABLE 1

| Intermediate number | Structure | Data |
|---|---|---|
| F15-4 | 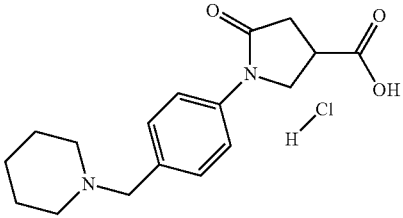 | LCMS method: Method 3, RT: 2.66 min, MI: 303 [M + 1] |
| F15-5 | 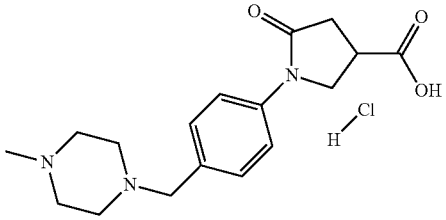 | LCMS method: Method 1, RT: 0.61 min, MI: 318 [M + 1] |

TABLE 1-continued

| Intermediate number | Structure | Data |
|---|---|---|
| F15-6 | 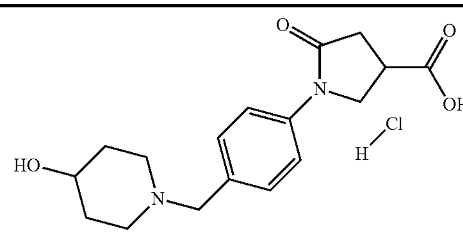 | LCMS method: Method 1, RT: 0.65 min, MI: 319 [M + 1] |
| F15-7 | 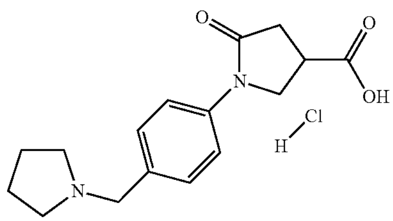 | LCMS method: Method 3, RT: 2.20 min, MI: 289 [M + 1] |
| F15-8 | 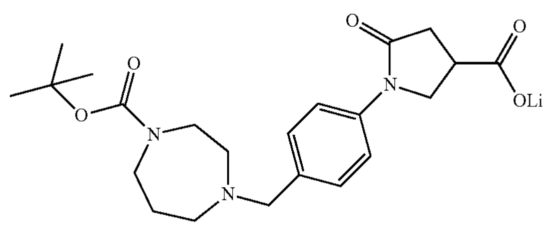 | LCMS method: Method 1, RT: 3.37 min, MI: 418 [M + 1] |
| F15-9 | 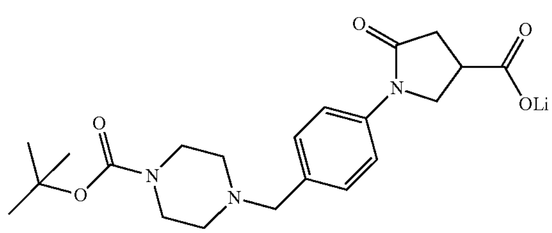 | LCMS method: Method 1, RT: 3.23 min, MI: 404 [M + 1] |
| F15-10 | 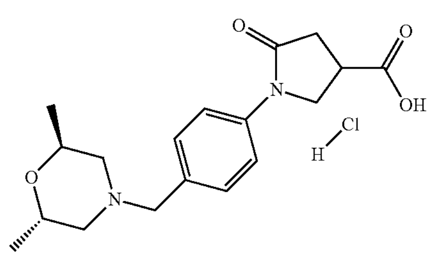 | LCMS method: Method 3, RT: 1.98 min, MI: 333 [M + 1] |

The following compounds (Table 2) were prepared by a similar method to that described in Scheme 2 starting from 2-fluoro-4-methyl-phenylamine:

TABLE 2

| Intermediate number | Structure | Data |
|---|---|---|
| F15-32 | 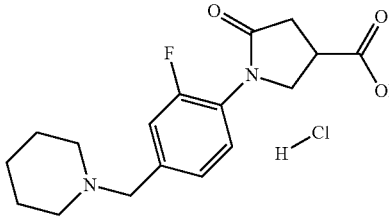 | LCMS method: Method 3, RT: 2.52 min, MI: 321 [M + 1] |
| F15-33 | 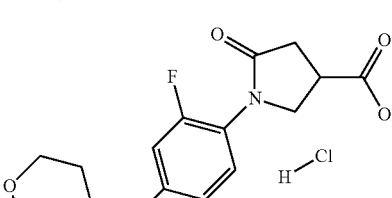 | LCMS method: Method 3, RT: 1.31 min, MI: 323 [M + 1] |
| F15-34 | 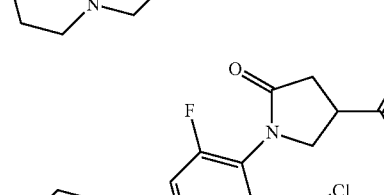 | LCMS method: Method 3, RT: 2.88 min, MI: 335 [M + 1] |

Synthesis of homochiral carboxypyrrolidinone intermediates such as F21 (Scheme 3)

Racemic intermediate F11 was resolved into the (S)-enantiomer by formation of a diastereomeric salt with (1R, 2R)-trans-1-amino-2-indanol to give F16. The salt F16 was then converted to the free chiral (S)-carboxylic acid F17 by partitioning between dilute aqueous HCl and EtOAc. Esterification of the pyrrolidinone acid F17 with MeOH and conc. $H_2SO_4$ gave the pyrrolidinone ester F18. Intermediate F18 was then brominated with NBS and benzoyl peroxide in refluxing $CCl_4$ to give the benzylic bromide F19. Intermediate F19 was reacted with morpholine in the presence of a suitable base such as $K_2CO_3$ to give F20. Compound F20 was hydrolysed with HCl in $H_2O$ to give the chiral carboxylic acid F21.

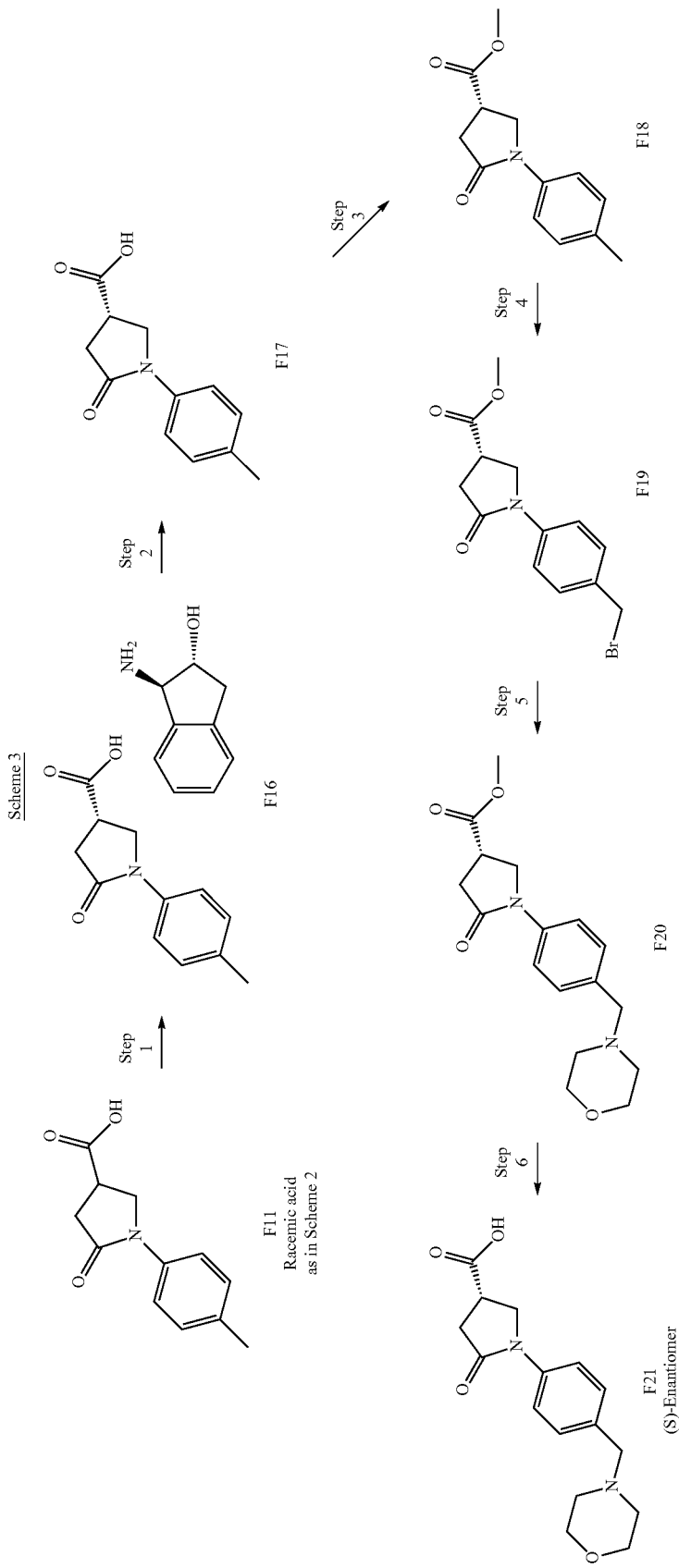

Synthesis of 3S)-1-[4-(morpholinomethyl)phenyl]-5-oxo-pyrrolidine-3-carboxylic acid (F21)

Steps 1 and 2

Synthesis of (3S)-5-oxo-1-(p-tolyl)pyrrolidine-3-carboxylic acid (F17)

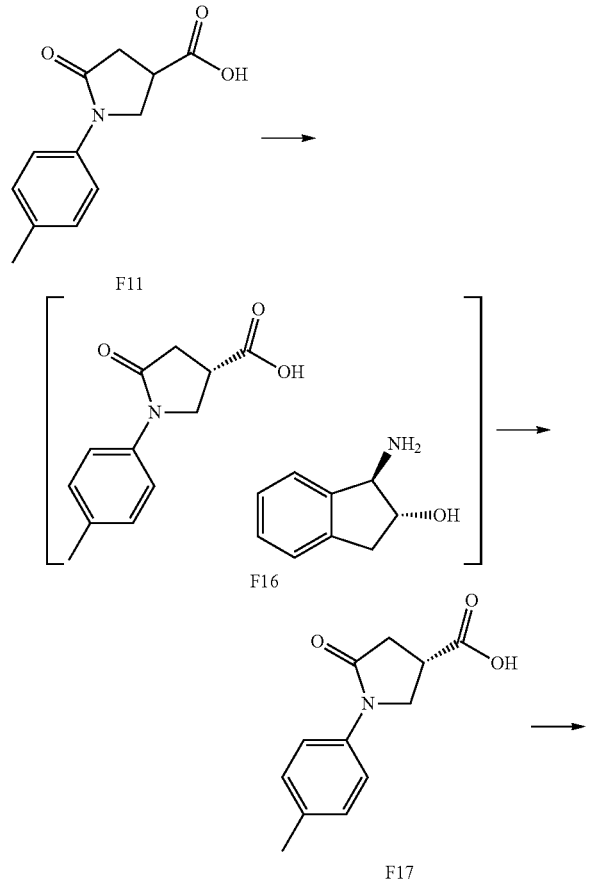

To a solution of 5-oxo-1-p-tolyl-pyrrolidine-3-carboxylic acid (5 g, 22.806 mmol) in 95:5 ACN: H$_2$O (200 mL) at 70° C. was quickly added a solution of (1R,2R)-1-aminoindan-2-ol in 95:5 ACN: H$_2$O (300 mL) at 70° C. with rapid stirring. The solution was allowed to slowly cool to room temperature, with stirring. The suspension was stirred for a further 1 hour at 25-28° C. before collecting the solid by filtration. The solid was washed with ACN (2×100 mL). The solid was partitioned between EtOAc (350 mL) and 2M HCl (100 mL), shaken and layers separated. The organic layer was washed with additional 2M HCl (50 mL), dried and evaporated to afford the title compound (2.22 g).

LCMS method: Method 5, RT: 3.17 min, MI: 220 [M+1]
$^1$H NMR (400 MHz, DMSO-d$_6$) δ 12.83 (br s, 1H), 7.56 (d, 2H), 7.21 (d, 2H), 4.05 (dd, 1H), 3.97 (dd, 1H), 3.41-3.33 (m, 1H), 2.80 (dd, 1H), 2.71 (dd, 1H), 2.31 (s, 3H)

Determination of d.e. using (1R,2R)-1-aminoindan-2-ol:

10 mg of the title compound was dissolved in DMF (0.5 mL) and treated with NEt$_3$ (8 μL, 0.0504 mmol). The resultant solution was treated with HBTU (20 mg, 0.0527 mmol) and stirred at room temperature for 60 minutes. A sample of the suspension was analysed by LCMS and the d.e. was determined as a surrogate measure of e.e.

LCMS method: Method 6, RT: 5.14 min and 5.42 min, ratio 99.72:0.28, MI: 351 [M+1], d.e. 99.4

Step 3

Synthesis of methyl (3S)-5-oxo-1-(p-tolyl)pyrrolidine-3-carboxylate (F18)

A solution of (3S)-5-oxo-1-(p-tolyl)pyrrolidine-3-carboxylic acid (6.406 g, 29.220 mmol) in MeOH (25 mL) and DCM (25 mL) was treated with conc. H$_2$SO$_4$ (5 mL) and stirred at reflux for 8 hours and then allowed to stand at room temperature for 16 hours. The solution was evaporated and the residue dissolved in DCM (200 mL). The solution was washed with saturated sodium bicarbonate solution, dried and evaporated to afford the title compound, which crystallised on standing and was dried under reduced pressure at 40° C. (6.83 g).

LCMS method: Method 5, RT: 3.74 min, MI: 234 [M+1]
$^1$H NMR (400 MHz, CDCl$_3$) δ 7.45 (dt, 2H), 7.18 (d, 2H), 4.10 (dd, 1H), 4.02 (dd, 1H), 3.78 (s, 3H), 3.41-3.32 (m, 1H), 2.96-2.82 (m, 2H), 2.33 (s, 3H)

Step 4

Synthesis of methyl (3S)-1-[4-(bromomethyl)phenyl]-5-oxo-pyrrolidine-3-carboxylate (F19)

Methyl (3S)-5-oxo-1-(p-tolyl)pyrrolidine-3-carboxylate (4.22 g, 18.07 mmol), NBS (5.95 g, 33.43 mmol) and benzoyl peroxide (43.77 mg, 0.1800 mmol) were suspended in CCl$_4$ (100 mL) and heated at reflux for 3 hours. The reaction mixture was cooled to room temperature, dissolved in DCM and washed with saturated aqueous sodium bicarbonate solution and brine, dried using a phase separation cartridge and concentrated under reduced pressure. The residue was dry-loaded onto silica and purified by silica flash column chromatography using a gradient of 0-40% EtOAc/cyclohexane. The relevant fractions were combined and dried under reduced pressure to give a brown oil. The residue was re-purified by silica flash column chromatography, dry loading from MeOH, using a gradient of 0-40% EtOAc/cyclohexane and the desired fractions were combined and dried under reduced pressure then triturated with Et$_2$O to afford the title compound (3.02 g).

LCMS method: Method 1, RT: 4.41 min, MI: 312 [M+1]
$^1$H NMR (500 MHz, DMSO-d$_6$) δ 7.64 (d, 2H), 7.44 (d, 2H), 4.70 (s, 2H), 4.07 (t, 1H), 3.98 (dd, 1H), 3.67 (s, 3H), 3.46 (m, 1H), 2.81 (dd, 1H), 2.72 (dd, 1H)

Step 5

Synthesis of methyl (3S)-1-[4-(morpholinomethyl)phenyl]-5-oxo-pyrrolidine-3-carboxylate (F20)

A solution of methyl (3S)-1-[4-(bromomethyl)phenyl]-5-oxo-pyrrolidine-3-carboxylate (8.41 g, 26.940 mmol) in ACN (150 mL) at 0° C. was treated with morpholine (2.60 mL, 29.630 mmol) and K$_2$CO$_3$ (7.46 g, 54.000 mmol). The reaction mixture was stirred at room temperature for 15 minutes and then filtered, washing with ACN. The filtrate was evaporated, adsorbed onto silica and further purified by column chromatography, eluting with 1 to 5% MeOH/DCM. All fractions containing the desired product were combined and evaporated to provide an orange oil that solidified with cooling and was further dried under reduced pressure for 4 hours to afford the title compound (3.32 g).

LCMS method: Method 5, RT: 0.67 min, MI: 319 [M+1]
¹H NMR (400 MHz, CDCl₃) δ 7.53 (d, 2H), 7.33 (d, 2H), 4.12 (dd, 1H), 4.03 (dd, 1H), 3.78 (s, 3H), 3.70 (t, 4H), 3.47 (s, 2H), 3.41-3.33 (m, 1H), 2.97-2.83 (m, 2H), 2.43 (t, 4H)

Step 6

Synthesis of (3S)-1-[4-(morpholinomethyl)phenyl]-5-oxo-pyrrolidine-3-carboxylic acid; hydrochloride (F21)

A solution of methyl (3S)-1-[4-(morpholinomethyl)phenyl]-5-oxo-pyrrolidine-3-carboxylate (3.327 g, 10.450 mmol) in aqueous HCl (30 mL, 2:1 H₂O:conc.HCl) was stirred at room temperature for 16 hours. The solution was evaporated and azeotroped from toluene and ACN to provide a yellow solid. The product was triturated in ACN for 3 hours at room temperature, cooled in an ice bath for 15 minutes and then collected by filtration. The solid was dried under reduced pressure to afford the title compound (3.255 g).

¹H NMR (400 MHz, DMSO-d₆) δ 12.88 (br s, 1H), 11.23 (s, 1H), 7.78 (d, 2H), 7.64 (d, 2H), 4.34 (d, 2H), 4.11 (t, 1H), 4.03 (dd, 1H), 3.97-3.94 (m, 2H), 3.81 (t, 2H), 3.44-3.37 (m, 1H), 3.24-3.21 (m, 2H), 3.12-3.05 (m, 2H), 2.85 (dd, 1H), 2.75 (dd, 1H)

The following chiral intermediates ((S)-enantiomers, Table 3) were prepared using a similar method to that described for intermediate F21 (Scheme 3):

TABLE 3

| Intermediate number | Structure | Data |
| --- | --- | --- |
| F21-1 | 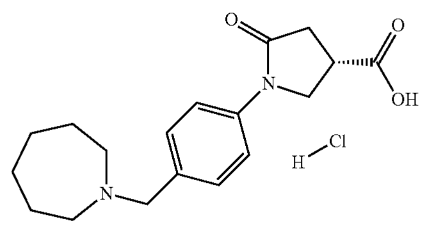 | LCMS method: Method 3, RT: 2.84 min, MI: 317 [M + 1] |
| F21-2 | 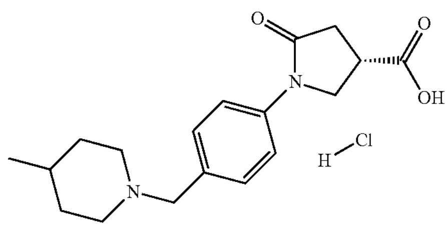 | LCMS method: Method 3, RT: 3.11 min, MI: 317 [M + 1] |
| F21-3 | 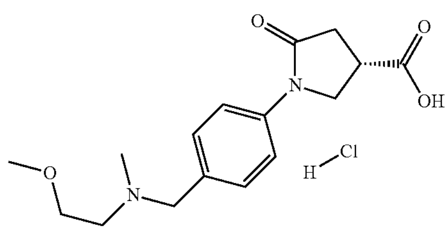 | LCMS method: Method 3, RT: 1.89 min, MI: 307 [M + 1] |
| F21-4 | 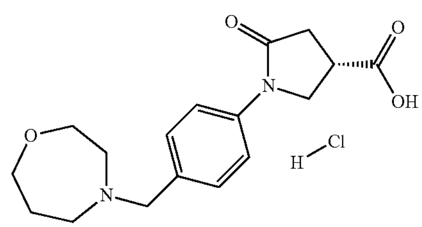 | LCMS method: Method 3, RT: 1.79 min, MI: 319 [M + 1] |
| F21-5 | 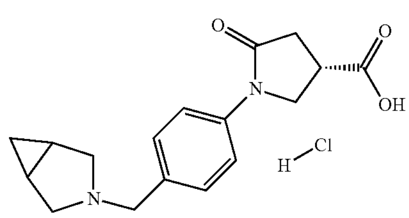 | LCMS method: Method 3, RT: 2.50 min, MI: 301 [M + 1] |

TABLE 3-continued

| Intermediate number | Structure | Data |
|---|---|---|
| F21-6 | 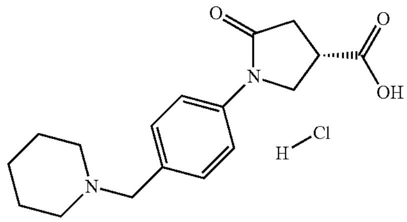 | LCMS method: Method 3, RT: 2.44 min, MI: 303 [M + 1] |
| F21-7 | 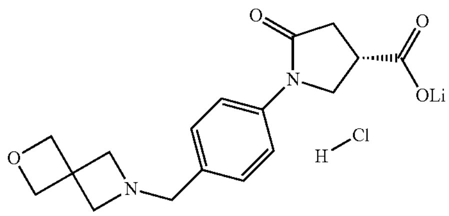 | LCMS method: Method 3, RT: 1.30 min, MI: 317 [M + 1] |
| F21-8 | 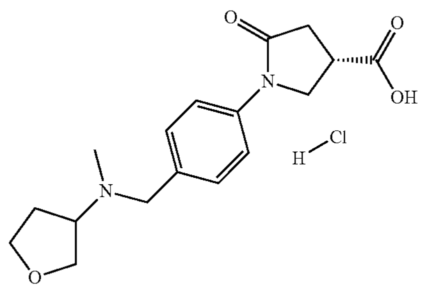 | LCMS method: Method 3, RT: 1.78 min, MI: 319 [M + 1] |
| F21-9 | 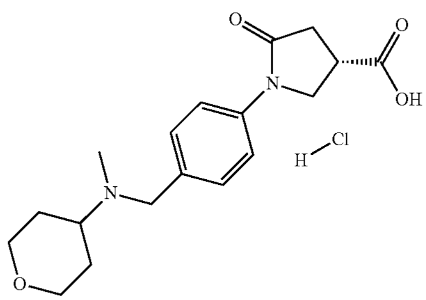 | LCMS method: Method 3, RT: 1.83 min, MI: 333 [M + 1] |
| F21-11 | 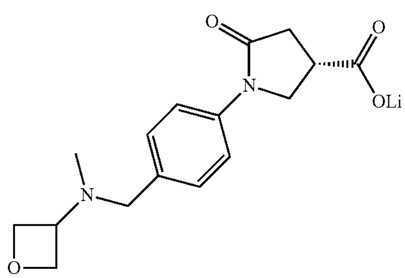 | LCMS method: Method 3, RT: 1.23 min, MI: 305 [M + 1] |
| F21-12 | 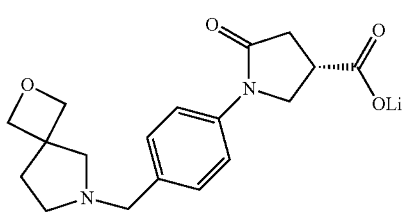 | LCMS method: Method 3, RT: 1.73 min, MI: 331 [M + 1] |

The corresponding (R)-enantiomers such as F22 (Table 4) were prepared by a similar method to that shown in Scheme 3 but substituting the (1R,2R)-1-amino-indan-2-ol in Step 1 with (1 S,2S)-1-amino-indan-2-ol (Table 4).

TABLE 4

| Intermediate number | Product | Data |
| --- | --- | --- |
| F22 | 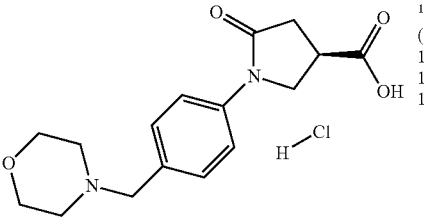 | $^1$H NMR (400 MHz, DMSO-$d_6$) δ 12.85 (br s, 1H), 11.19 (s, 1H), 7.75 (d, 2H), 7.61 (d, 2H), 4.30 (d, 2H), 4.07 (dd, 1H), 3.99 (dd, 1H), 3.93 (br d, 2H), 3.78 (t, 2H), 3.37 (m, 1H), 3.20 (d, 2H), 3.05 (m, 2H), 2.82 (dd, 1H), 2.72 (dd, 1H) |
| F22-1 | 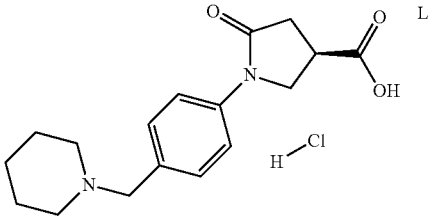 | LCMS method: Method 5, RT: 0.66 min, MI: 303 [M + 1] |

Synthesis of Aminopyrrolidinone Intermediates

Racemic 3-aminopyrrolidinone intermediates such as F27 were prepared by the method shown in Scheme 4:

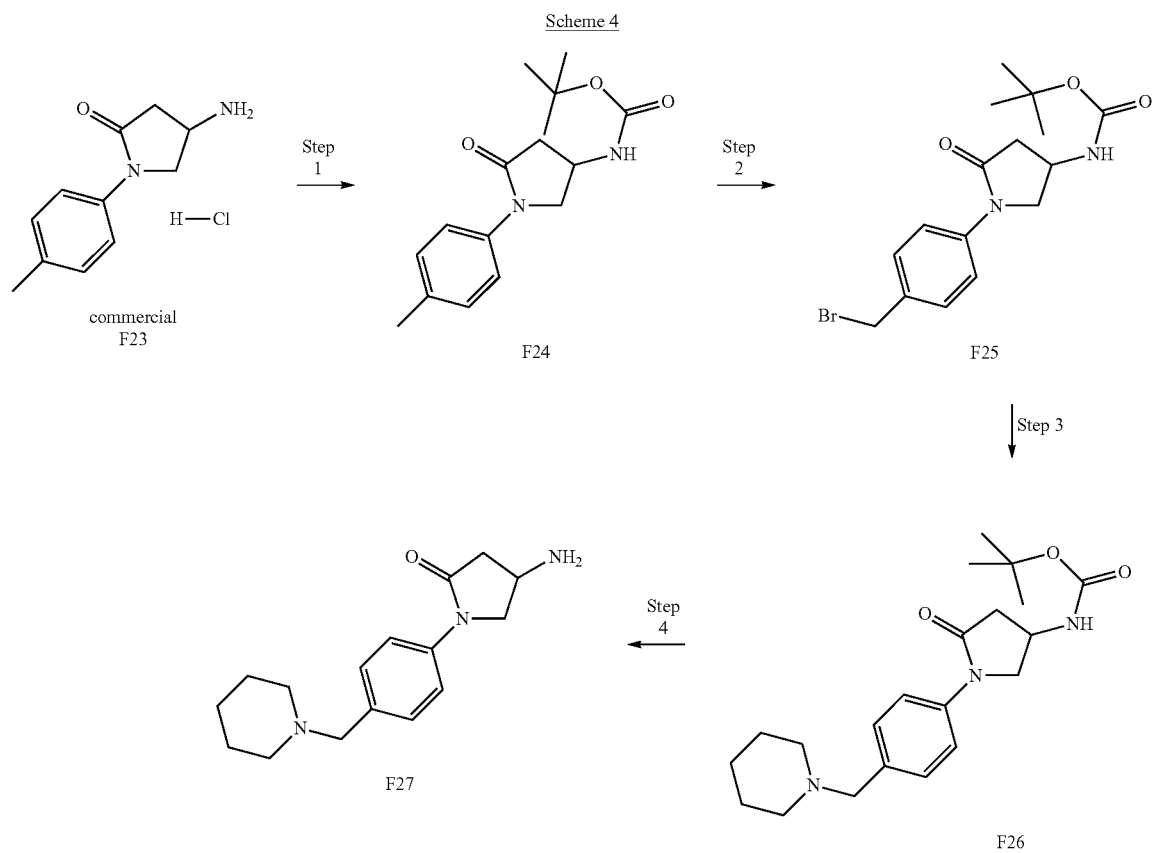

Scheme 4

Synthesis of 4-amino-1-[4-(piperidinomethyl)phenyl]pyrrolidin-2-one (F27)

Step 1

Synthesis of tert-butyl N-[5-oxo-1-(p-tolyl)pyrrolidin-3-yl]carbamate (F24)

To a mixture of commercially available 4-amino-1-p-tolyl-pyrrolidin-2-one hydrochloride (2.07 g, 9.13 mmol) and $NEt_3$ (2.53 mL, 18.26 mmol) in MeOH (80 mL) was added dropwise a solution of di-tert-butyl dicarbonate (2.19 g, 10.044 mmol) in MeOH (20 mL). The reaction mixture was stirred at room temperature for 2 hours. The solvent was then evaporated under reduced pressure and the residue dissolved in DCM. The organic layer was washed with aqueous $NH_4Cl$ solution, dried ($MgSO_4$), filtered, and solvent was evaporated under reduced pressure to afford the title compound (2.67 g).

$^1$H NMR (500 MHz, DMSO-$d_6$) δ 7.54 (dt, 2H), 7.46 (d, 1H), 7.20 (d, 2H), 4.21 (br s, 1H), 4.07 (dd, 1H), 3.61 (dd, 1H), 2.83 (dd, 1H), 2.44 (dd, 1H), 2.31 (s, 3H), 1.43 (s, 9H)

Step 2

Synthesis of tert-butyl N-[1-[4-(bromomethyl)phenyl]-5-oxo-pyrrolidin-3-yl]carbamate (F25)

(5-Oxo-1-p-tolyl-pyrrolidin-3-yl)-carbamic acid tert-butyl ester (1.00 g, 3.44 mmol), NBS (1.113 g, 6.37 mmol) and benzoyl peroxide (9 mg, 0.035 mmol) were suspended in $CCl_4$ (10 mL) and heated at reflux for 3 hours. After this time the reaction mixture was cooled to room temperature and concentrated under reduced pressure. The organic layer was washed with saturated aqueous NaCl solution, dried ($MgSO_4$), filtered and concentrated under reduced pressure. The residual material was purified by flash column chromatography eluting with EtOAc/cyclohexane (0-40%), to afford the title compound (0.57 g).

LCMS method: Method 1, RT: 5.13 min, MI: 371 [M+1]

Step 3

Synthesis of tert-butyl N-[1-[4-(piperidinomethyl)phenyl]-5-oxo-pyrrolidin-3-yl]carbamate (F26)

[1-(4-Bromomethyl-phenyl)-5-oxo-pyrrolidin-3-yl]-carbamic acid tert-butyl ester (0.57 g, 1.541 mmol) was dissolved in ACN (15 mL) and treated with piperidine (168 μL, 1.695 mmol) and $K_2CO_3$ (425 mg, 3.082 mmol). The mixture was stirred at room temperature for 16 hours. The reaction mixture was partitioned between $H_2O$ and DCM and the organic layer was isolated, dried ($MgSO_4$), filtered and concentrated under reduced pressure. The residue was purified by elution through a SCX cartridge, washing with MeOH then releasing the desired product using 7M $NH_3$/MeOH. The second fraction was concentrated under reduced pressure to afford the title compound (350 mg).

LCMS method: Method 1, RT: 2.35 min, MI: 374 [M+1]

$^1$H NMR (500 MHz, CDCl$_3$) δ 7.51 (d, 2H), 7.32 (d, 2H), 4.83 (br s, 1H), 4.41 (br s, 1H), 4.16 (dd, 1H), 3.71 (dd, 1H), 3.45 (s, 2H), 2.97 (dd, 1H), 2.47 (dd, 1H), 2.36 (br s, 4H), 1.56 (br s, 4H), 1.45 (br s, 11H)

Step 4

Synthesis of 4-amino-1-[4-(piperidinomethyl)phenyl]pyrrolidin-2-one; hydrochloride (F27)

To a solution of [5-oxo-1-(4-piperidin-1-ylmethyl-phenyl)-pyrrolidin-3-yl]-carbamic acid tert-butyl ester (350 mg, 0.937 mmol) in DCM (2.5 mL) was added 4M HCl in 1,4-dioxane (2.5 mL) and the mixture was stirred at room temperature for 1 hour. After this time the volatiles were removed under reduced pressure and the residue was azeotroped with toluene. The solid residue was then dissolved in DCM (2.5 mL) and treated with 4M HCl in 1,4-dioxane (2.5 mL). After stirring at room temperature for 1 hour the volatiles were removed under reduced pressure and the residue was azeotroped with toluene to afford the title compound (320 mg).

LCMS method: Method 3, RT: 3.61 min, MI: 277 [M+1]

$^1$H NMR (500 MHz, DMSO-$d_6$) δ 10.61 (br s, 1H), 8.60 (br s, 2H), 7.75 (d, 2H), 7.66 (d, 2H), 4.29-4.26 (m, 3H), 4.10 (br s, 1H), 3.89 (dd, 1H), 3.56 (br s, 5H), 3.28 (d, 2H), 3.07 (dd, 1H), 2.88-2.81 (m, 2H), 2.654 (dd, 1H)

The following racemic intermediates (Table 5) were prepared using a similar method to that described for intermediate F27 (Scheme 4):

TABLE 5

| Intermediate number | Product | Data |
|---|---|---|
| F27-1 | 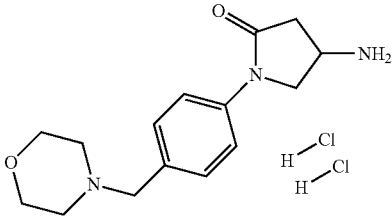 | LCMS method: Method 3, RT: 2.57 min, MI: 276 [M + 1] |

TABLE 5-continued

| Intermediate number | Product | Data |
|---|---|---|
| F27-2 | 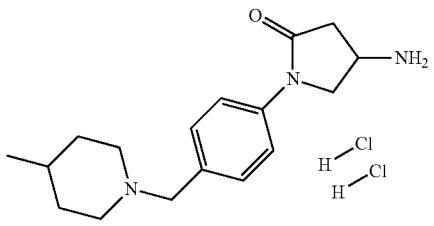 | LCMS method: Method 3, RT: 4.55 min, MI: 288 [M + 1] |
| F27-3 | 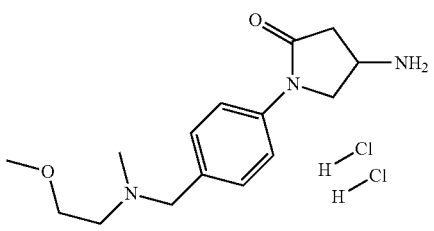 | LCMS method: Method 3, RT: 3.02 min, MI: 278 [M + 1] |
| F27-4 | 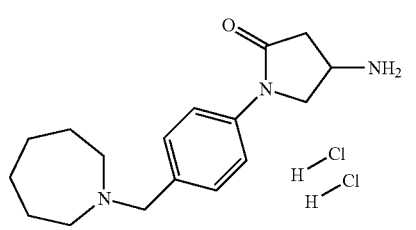 | LCMS method: Method 3, RT: 4.40 min, MI: 288 [M + 1] |
| F27-5 | 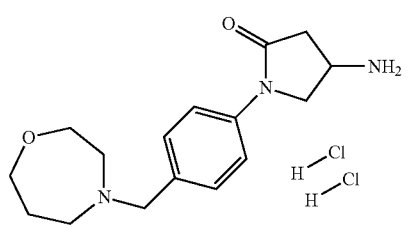 | LCMS method: Method 3, RT: 2.88 min, MI: 290 [M + 1] |
| F27-6 | 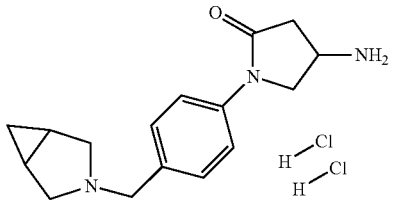 | LCMS method: Method 3, RT: 4.02 min, MI: 272 [M + 1] |

Homochiral aminopyrrolidinone intermediates ((R)-isomers) such as F32 were prepared by the method shown in Scheme 5, where intermediate F28 ((R)-enantiomer) was prepared in a similar manner to intermediate F17 ((S)-enantiomer, Scheme 3):

Scheme 5

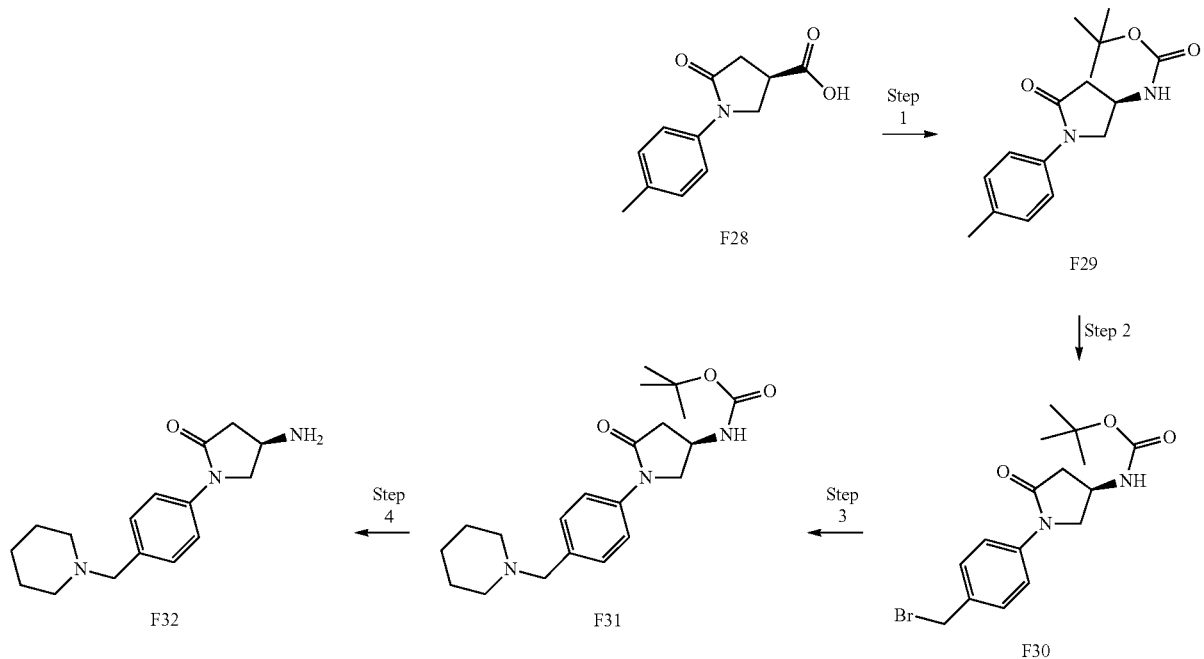

Step 1

Synthesis of tert-butyl N-[(3R)-5-oxo-1-(p-tolyl) pyrrolidin-3-yl]carbamate (F29)

Method A

A solution of (R)-5-oxo-1-p-tolyl-pyrrolidine-3-carboxylic acid (3.00 g, 13.686 mmol) in THF (60 mL) was treated with NMM (1.51 mL, 13.686 mmol). The reaction was then cooled to 00° C. and isobutyl chloroformate (1.80 mL, 13.686 mmol) was added. After stirring for 5 minutes, a solution of sodium azide (1.78 g, 27.37 mmol) in $H_2O$ (15 mL) was added while the temperature was maintained at 00° C. After stirring for 1 hour at 0° C., the suspension was diluted with 50 mL DCM and the organic layer was washed twice with saturated sodium bicarbonate solution and twice with brine. The organic layer was dried using a phase separation cartridge then concentrated under reduced pressure. The residue was re-dissolved in dry toluene (30 mL) and treated with ᵗBuOH and the mixture was stirred at 80° C. for 16 hours then allowed to cool to room temperature. A white crystalline precipitate was removed by filtration. The solvent was then removed under reduced pressure to afford a white solid, which was triturated in toluene, and the remaining white solid was again removed by filtration. The solvent was then removed under reduced pressure to afford the title compound (1.54 g).

LCMS method: Method 3, RT: 4.99 min, MI: 291 [M+1]

$^1$H NMR (500 MHz, DMSO-$d_6$) δ 7.49 (d, 2H), 7.41 (d, 1H), 7.15 (d, 2H), 4.17 (br s, 1H), 4.02 (dd, 1H), 3.56 (dd, 1H), 2.78 (dd, 1H), 2.39 (dd, 1H), 2.26 (s, 3H), 1.38 (s, 9H)

Determination of e.e.:

Column: Daicel Chiralpak OJ-H 250×4.6 mm, Mobile Phase: isocratic n-heptane/EtOH=60:40, e.e. 95.2%

Method B

To a solution of CDI (8.246 g, 50.903 mmol) in THF (170 mL) at room temperature was added (S)-5-oxo-1-p-tolyl-pyrrolidine-3-carboxylic acid (9.3 g, 42.419 mmol) and the mixture was stirred at room temperature for 1 hour. After this time the solution was then added to a stirred solution of 28% aqueous $NH_3$ solution (7.01 mL, 106.05 mmol) in THF (11 mL). After stirring for 30 minutes the reaction mixture was filtered to give a white precipitate. To a suspension of this material (9.04 g, 41.42 mmol) in a mixture of THF/$H_2O$ (1:1, 165 mL) at room temperature was added (diacetoxyiodo)benzene (20.01 g, 62.131 mmol) in one portion, maintaining the temperature at 20° C. After stirring for 5 hours the solution was diluted with DCM and washed with aqueous hydrogen chloride solution (0.2 M) then the aqueous layer was basified to pH 11 with aqueous NaOH solution (0.4 M), extracted with DCM, dried (MgSO₄) and dried under reduced pressure to give a pale tan solid. This material (5.88 g, 30.908 mmol) was dissolved in MeOH (165 mL) and treated with di-tert-butyl dicarbonate (10.12 g, 46.362 mmol) and the mixture was stirred at room temperature for 4 hours. After this time the reaction mixture was concentrated under reduced pressure, with the resulting residue partitioned between DCM and saturated aqueous NH₄Cl solution. The organic fraction was removed, washed with saturated aqueous NaCl solution, dried (MgSO₄), filtered and concentrated under reduced pressure. The resulting solid was suspended in cyclohexane/Et₂O (1:1) and filtered, then washed with further equivalents of cyclohexane/Et₂O (1:1) and dried under reduced pressure to afford the title compound (7.76 g).

Analytical data is identical to that reported above in Method A.

Step 2

Synthesis of tert-butyl N-[(3R)-1-[4-(bromomethyl) phenyl]-5-oxo-pyrrolidin-3-yl]carbamate (F30)

((R)-5-Oxo-1-p-tolyl-pyrrolidin-3-yl)-carbamic acid tert-butyl ester (1.54 g, 5.304 mmol), NBS (1.746 g, 9.812 mmol) and benzoyl peroxide (13 mg, 0.053 mmol) were suspended in CCl₄ (30 mL) and heated at reflux for 3.5 hours. The reaction mixture was cooled to room temperature and concentrated under reduced pressure. The residue was dissolved in EtOAc and washed three times with saturated sodium bicarbonate solution, then with H₂O and brine and dried using a phase separation cartridge. The organic layer was dry loaded onto silica and purified by flash column chromatography using a gradient of 0-40% EtOAc/cyclohexane. The relevant fractions were combined and dried under reduced pressure to afford the title compound (836 mg).

LCMS method: Method 1, RT: 5.19 min, MI: 369/371 [M+1]

¹H NMR (500 MHz, DMSO-d₆) δ 7.80 (d, 2H), 7.44 (d, 2H), 4.70 (s, 2H), 4.20 (br s, 1H), 4.06 (m, 1H), 3.61 (m, 1H), 2.80 (dd, 1H), 2.42 (dd, 1H), 1.38 (s, 9H)

Step 3

Synthesis of tert-butyl N-[(3R)-5-oxo-1-[4-(1-piperidylmethyl)phenyl]pyrrolidin-3-yl]carbamate (F31)

[(R)-1-(4-Bromomethyl-phenyl)-5-oxo-pyrrolidin-3-yl]-carbamic acid tert-butyl ester (0.418 g, 1.132 mmol) was dissolved in ACN (8 mL) and treated with piperidine (123 μL, 1.245 mmol) and K₂CO₃ (312 mg, 2.264 mmol). The mixture was stirred at room temperature for 1 hour then filtered (washing with ACN) and concentrated under reduced pressure. The residue was redissolved in MeOH and loaded onto a 1 g SCX cartridge, washing first with MeOH and then eluting with 2M NH₃/MeOH. The second fraction was concentrated under reduced pressure to afford the title compound (186 mg).

LCMS method: Method 3, RT: 5.29 min, MI: 374 [M+1]

¹H NMR (500 MHz, DMSO-d₆) δ 7.55 (d, 2H), 7.41 (d, 1H), 7.24 (d, 2H), 4.18 (s, 1H), 4.04 (m, 1H), 3.57 (dd, 1H), 3.36 (s, 2H), 2.79 (dd, 1H), 2.40 (dd, 1H), 2.27 (s, 4H), 1.46 (m, 4H), 1.38 (s, 11H)

Step 4

Synthesis of (4R)-4-amino-1-[4-(1-piperidylmethyl)phenyl]pyrrolidin-2-one; bis hydrochloride (F32)

To a solution of [(R)-5-oxo-1-(4-piperidin-1-ylmethyl-phenyl)-pyrrolidin-3-yl]-carbamic acid tert-butyl ester (275 mg, 0.736 mmol) in DCM (2 mL) was added 4M HCl/1,4-dioxane (2 mL) and the mixture was stirred at room temperature for 16 hours, after which time the volatiles were removed under reduced pressure to afford the title compound (237 mg).

LCMS method: Method 3, RT: 3.01 min, MI: 274 [M+1]

¹H NMR (500 MHz, DMSO-d₆) δ 10.35 (s, 1H), 8.46 (s, 3H), 7.70 (d, 2H), 7.60 (d, 2H), 4.24-4.21 (m, 3H), 4.04 (s, 1H), 3.82 (d, 1H), 3.24 (d, 2H), 3.02 (dd, 1H), 2.80 (m, 2H), 2.59 (dd, 1H), 1.76-1.66 (m, 5H), 1.33 (m, 1H)

The following chiral intermediates ((R)-isomers, Table 6) were prepared using a similar method to that described for intermediate F32 (Scheme 5):

TABLE 6

| Intermediate number | Product | Rearrangement method | Data |
|---|---|---|---|
| F32-1 | 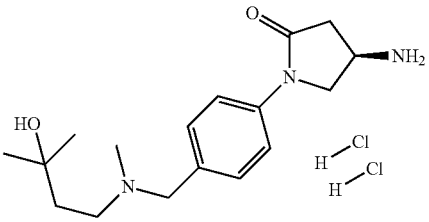 | B | LCMS method: Method 3, RT: 3.49 min, MI: 306 [M + 1] |
| F32-2 | 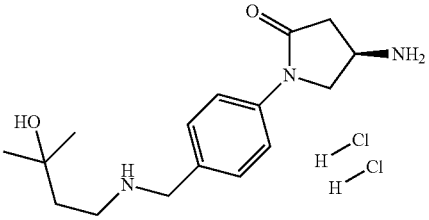 | B | LCMS method: Method 3, RT: 2.91 min, MI: 292 [M + 1] |
| F32-3 | 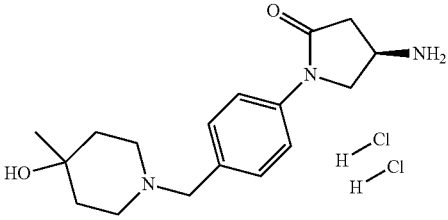 | B | LCMS method: Method 3, RT: 2.75 min, MI: 304 [M + 1] |

TABLE 6-continued
| Intermediate number | Product | Rearrangement method | Data |
|---|---|---|---|
| F32-4 | 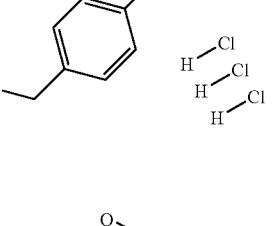 | B | LCMS method: Method 3, RT: 2.17 min, MI: 289 [M + 1] |
| F32-5 | 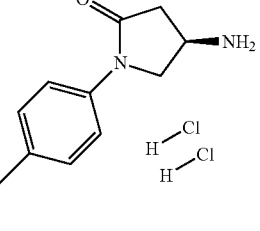 | B | LCMS method: Method 1, RT: 0.51 min, MI: 289 [M + 1] |
| F32-6 | 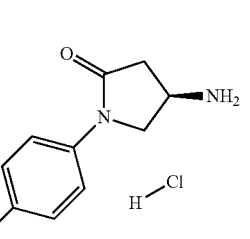 | B | LCMS method: Method 1, RT: 5.23 min, MI: 359 [M + 1] |
| F32-7 | 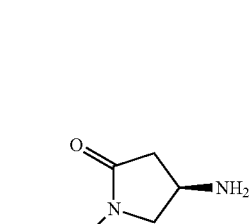 | A | LCMS method: Method 3, RT: 2.69 min, MI: 276 [M + 1] |
| F32-8 | 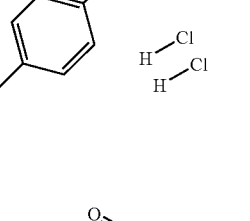 | A | LCMS method: Method 3, RT: 2.28 min, MI: 288 [M + 1] |
Homochiral aminopyrrolidinone intermediates ((S)-isomers) such as F36 were prepared by the method shown in Scheme 6:

Scheme 6

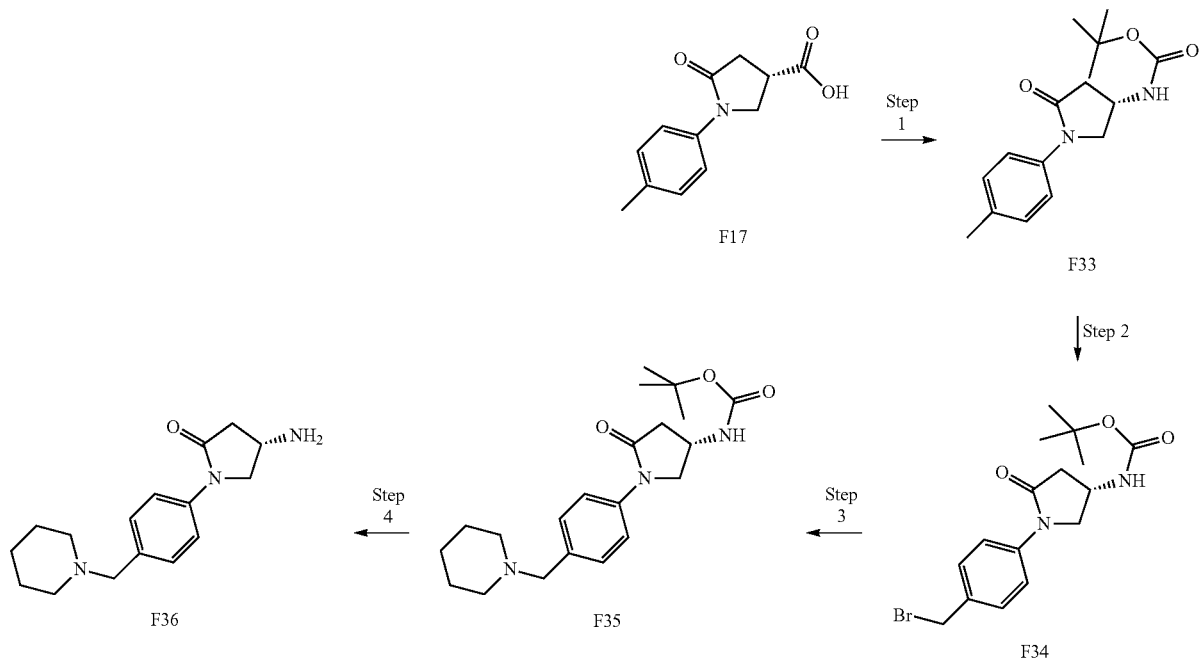

Step 1

Synthesis of tert-butyl N-[(3S)-5-oxo-1-(p-tolyl) pyrrolidin-3-yl]carbamate (F33)

Method A

A solution of (S)-5-oxo-1-p-tolyl-pyrrolidine-3-carboxylic acid (0.500 g, 2.281 mmol) in THF (10 mL) was treated with NMM (251 μL, 2.281 mmol). The reaction was then cooled to 0° C. and isobutyl chloroformate (300 μL, 2.281 mmol) was added. After stirring for 5 minutes, a solution of sodium azide (297 mg, 4.561 mmol) in $H_2O$ (2.5 mL) was added while the temperature was maintained at 00° C. After stirring for 1 hour at 0° C., the suspension was diluted with toluene (20 mL). The organic layer was washed twice with saturated sodium bicarbonate solution and twice with brine. The organic layer was dried using a phase separation cartridge then anhydrous $^tBuOH$ (50 mL) was added and the mixture stirred at 80° C. for 16 hours. The reaction mixture was then cooled to room temperature and a white crystalline precipitate was removed by filtration. The solvent was then removed under reduced pressure to give a white solid, which was triturated in toluene and the remaining white solid was removed by filtration. The solvent was removed under reduced pressure to afford the title compound (352 mg).

LCMS method: Method 3, RT: 4.90 min, MI: 291 [M+1]

$^1H$ NMR (500 MHz, DMSO-$d_6$) δ 7.48 (d, 2H), 7.40 (d, 1H), 7.14 (d, 2H), 4.17 (br s, 1H), 4.02 (dd, 1H), 3.55 (dd, 1H), 2.77 (dd, 1H), 2.38 (dd, 1H), 2.26 (s, 3H), 1.38 (s, 9H).

Determination of e.e.:

Column: Daicel Chiralpak OJ-H 250×4.6 mm, Mobile Phase: isocratic n-heptane/EtOH=60:40, e.e. 97.8%

Method B

To a solution of CDI (1.944 g, 12 mmol) in 2-MeTHF (40 mL) at room temperature was added (S)-5-oxo-1-p-tolyl-pyrrolidine-3-carboxylic acid (2.192 g, 10 mmol) and the mixture was stirred at room temperature for 1 hour. After this time the mixture was added to a stirred solution of 28% aqueous $NH_3$ solution in THF (5 mL). After stirring for 30 minutes the reaction mixture was filtered and the resulting white precipitate was washed with $H_2O$/THF 80:20. To a suspension of this material (2.06 g, 9.438 mmol) in a mixture of THF/$H_2O$ (1:1, 40 mL) at room temperature was added (diacetoxyiodo)benzene (3.952 g, 12.27 mmol) in one portion, maintaining the temperature at 20° C. After 150 minutes (diacetoxyiodo)benzene (0.608 g, 1.887 mmol) was added and the mixture stirred at room temperature for a further 18 hours. Then the solution was diluted with DCM and washed with aqueous hydrogen chloride solution (0.2 M) then the aqueous layer was basified to pH 11 with aqueous NaOH solution (0.4 M), extracted with DCM, dried ($MgSO_4$) and dried under reduced pressure. To a mixture of this material (0.9 g, 4.731 mmol) in MeOH (14 mL) was added dropwise a solution of di-tert-butyl dicarbonate (1.321 g, 5.204 mmol) in MeOH (5 mL). The reaction mixture was stirred at room temperature for 16 hours. After this time the solvent was removed under reduced pressure and the residue dissolved in DCM. The organic layer was washed with aqueous $NH_4Cl$ solution, dried (MgSO4), filtered and concentrated under reduced pressure to afford the title compound (1.12 g).

Analytical data is identical to that reported above in Method A.

Step 2

Synthesis of tert-butyl N-[(3S)-1-[4-(bromomethyl) phenyl]-5-oxo-pyrrolidin-3-yl]carbamate (F34)

((S)-5-Oxo-1-p-tolyl-pyrrolidin-3-yl)-carbamic acid tert-butyl ester (0.332 g, 1.143 mmol), NBS (376 mg, 2.115 mmol) and benzoyl peroxide (3 mg, 0.011 mmol) were suspended in $CCl_4$ (7 mL) and heated at reflux for 3 hours. The reaction mixture was cooled to room temperature and concentrated under reduced pressure. The residue was dissolved in EtOAc and washed with saturated sodium bicarbonate solution and brine and dried using a phase separation cartridge. The EtOAc was removed under reduced pressure and residue was dry loaded onto silica and purified by flash column chromatography using a gradient of 0-40% EtOAc/cyclohexane. The relevant fractions were combined and dried under reduced pressure to afford the title compound (190 mg).

LCMS method: Method 3, RT: 4.97 min, MI: 369/371 [M+1]

$^1$H NMR (500 MHz, DMSO-$d_6$) δ 7.81 (d, 2H), 7.43 (d, 2H), 4.70 (s, 2H), 4.20 (br s, 1H), 4.07 (m, 1H), 3.61 (m, 1H), 2.81 (m, 1H), 2.42 (m, 1H), 1.38 (s, 9H)

Step 3

Synthesis of tert-butyl N-[(3S)-5-oxo-1-[4-(1-piperidylmethyl)phenyl]pyrrolidin-3-yl]carbamate (F35)

[(S)-1-(4-Bromomethyl-phenyl)-5-oxo-pyrrolidin-3-yl]-carbamic acid tert-butyl ester (0.095 g, 0.257 mmol) was dissolved in ACN (2 mL) and treated with piperidine (28 µL, 0.283 mmol) and $K_2CO_3$ (71 mg, 0.515 mmol). The mixture was stirred at room temperature for 45 minutes then it was filtered, washed with ACN and concentrated under reduced pressure. The residue was redissolved in MeOH and loaded onto a 1 g SCX cartridge, washing first with MeOH and then eluting with 2M $NH_3$/MeOH. The second fraction was dried under reduced pressure to afford the title compound (68 mg).

LCMS method: Method 3, RT: 5.35 min, MI: 374 [M+1]

$^1$H NMR (500 MHz, DMSO-$d_6$) δ 7.54 (d, 2H), 7.41 (d, 1H), 7.24 (d, 2H), 4.18 (s, 1H), 4.04 (m, 1H), 3.57 (dd, 1H), 3.36 (s, 2H), 2.78 (dd, 1H), 2.39 (dd, 1H), 2.27 (s, 4H), 1.46 (m, 4H), 1.38 (s, 11H).

Step 4

Synthesis of (4S)-4-amino-1-[4-(1-piperidylmethyl)phenyl]pyrrolidin-2-one; bis hydrochloride (F36)

To a solution of [(S)-5-oxo-1-(4-piperidin-1-ylmethyl-phenyl)-pyrrolidin-3-yl]-carbamic acid tert-butyl ester (68 mg, 0.182 mmol) in DCM (1 mL) was added 4M HCl/1,4-dioxane (1 mL) and the mixture was stirred at room temperature for 16 hours, after which time the volatiles were removed under reduced pressure to afford the title compound (59 mg).

LCMS method: Method 3, RT: 4.09 min, MI: 274 [M+1]

$^1$H NMR (500 MHz, DMSO-$d_6$) δ 10.46 (s, 1H), 8.50 (s, 3H), 7.70 (d, 2H), 7.61 (d, 2H), 4.22 (m, 3H), 4.04 (s, 1H), 3.83 (dd, 1H), 3.22 (d, 2H), 3.01 (dd, 1H), 2.80 (m, 2H), 2.59 (dd, 1H), 1.75 (m, 4H), 1.67 (m, 1H), 1.33 (m, 1H)

The following chiral intermediates ((S)-isomers, Table 7) were prepared using a similar method to that described for intermediate F36 (Scheme 6):

TABLE 7

| Intermediate number | Structure | Rearrangement method | Data |
|---|---|---|---|
| F36-1 | 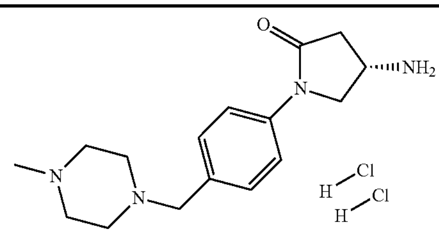 | B | LCMS method: Method 3, RT: 4.50 min, MI: 288 [M + 1] |
| F36-2 | 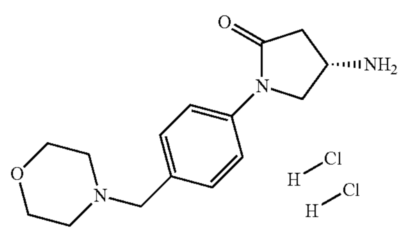 | A | LCMS method: Method 3, RT: 2.69 min, MI: 276 [M + 1] |

Synthesis of Aminoheterocycle Intermediates

Synthesis of aminoheterocycle intermediates of general formula F4 is described below:

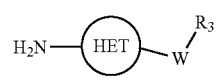

F4

Synthesis of Aminopyridazine Derivatives

Synthesis of 6-[2-(4-Fluoro-phenyl)-ethyl]-pyridazin-3-ylamine (F38)

Scheme 7

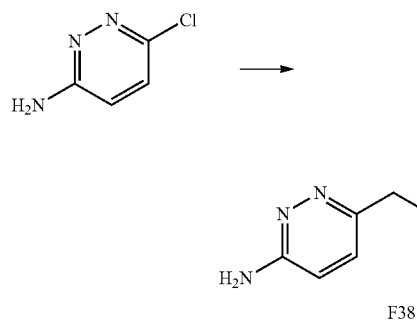

F38

A solution of bis(triphenylphosphine)nickel (II) dichloride (706 mg, 1.08 mmol) in anhydrous 1,4-dioxane (24 mL) was flushed with nitrogen for 5 minutes before dropwise addition of 1M diethyl zinc solution in hexane (32.4 mL, 32.4 mmol). The mixture was stirred at room temperature for 20 minutes, prior to addition of 4-fluorophenethyl bromide (4.4 mL, 32.3 mmol). The resulting mixture was heated at 65° C. for 5 hours. After this time, a suspension of 3-amino-6-chloropyridazine (0.70 g, 5.4 mmol) in warm 1,4-dioxane (16 mL) was added to the reaction mixture and it was stirred at 65° C. for 16 hours. MeOH (12 mL) was then added and the mixture was stirred for further 10 minutes. The reaction mixture was then cooled to room temperature and the suspension was passed through a pad of Celite™, washing with EtOAc. The filtrate was concentrated under reduced pressure and partitioned between 2M aqueous HCl solution and DCM. The aqueous layer was removed and the organic layer was washed twice with further 2M aqueous HCl solution. The combined aqueous portions were then back-extracted with DCM and basified with solid $K_2CO_3$. The aqueous phase was re-extracted with DCM, the organic layer passed through a phase separation cartridge and concentrated under reduced pressure, to afford the title compound (420 mg).

LCMS method: Method 3, RT: 3.95 min, MI: 218 [M+1]

$^1$H NMR (500 MHz, DMSO-$d_6$) δ 7.24 (m, 2H), 7.14-7.05 (m, 3H), 6.68 (d, 1H), 6.16 (s, 2H), 3.55 (s, 2H), 2.92 (m, 3H (over integrating))

The following intermediate (Table 8) was prepared using a similar method to that described for intermediate F38 (Scheme 7):

Synthesis of Aminothiadiazole Derivatives

Synthesis of 5-[2-(4-Chloro-phenyl)-ethyl]-[1,3,4]thiadiazol-2-ylamine (F40)

Scheme 8

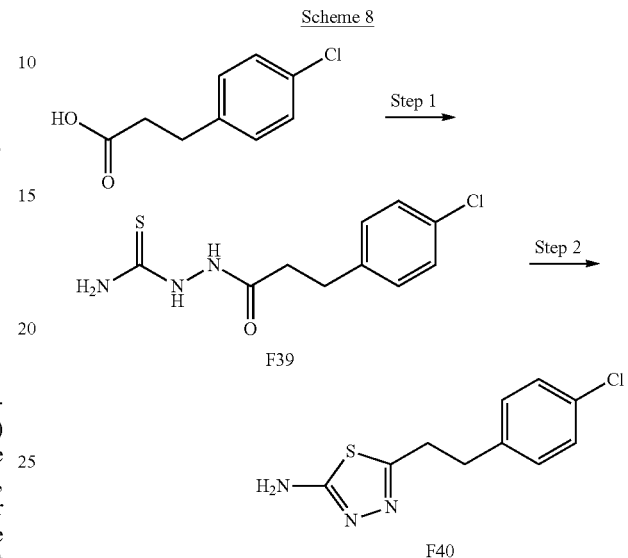

Step 1

Synthesis of 3-(4-chloro-phenyl)-propionic acid hydrazinecarbothioamide (F39)

To a solution of 3-(4-chloro-phenyl)-propionic acid (20 g, 108.3 mmol) in THF (500 mL) was added a few drops of anhydrous DMF and oxalyl chloride (18.6 mL, 216.7 mmol) and the mixture was stirred under nitrogen for 2 hours at room temperature The solvent was then removed under reduced pressure and the resulting oil was re-dissolved in anhydrous DMF (100 mL). The solution was added dropwise over 30 minutes to a solution of thiosemicarbazide (9.87 g, 108.3 mmol) and pyridine (8.74 mL, 108.3 mmol) in anhydrous THF (500 mL) at room temperature. Stirring was continued for 16 hours, and the mixture was poured onto iced water and the pH was adjusted to pH 9 with 2M aqueous NaOH solution. The resulting precipitate was isolated by suction filtration and washed with $H_2O$ to afford the title compound (25.887 g).

LCMS method: Method 2, RT: 2.92 min, MI: 258 [M+1]

TABLE 8

| Intermediate number | Structure | Data |
|---|---|---|
| F38-1 | H$_2$N-pyridazine-CH$_2$CH$_2$-phenyl | LCMS method: Method 5, RT: 2.08 min, MI: 200 [M + 1] |

Step 2

Synthesis of 5-[2-(4-chloro-phenyl)-ethyl]-[1,3,4] thiadiazol-2-ylamine (F40)

To a solution of 3-(4-chloro-phenyl)-propionic acid hydrazinecarbothioamide (25.9 g, 100.4 mmol) in toluene (300 mL) was added dropwise methane sulfonic acid (9.8 mL, 150.7 mmol). The reaction mixture was stirred at reflux for 1½ hours, after which time the solvent was evaporated under reduced pressure and the residue diluted with $H_2O$ and the pH was adjusted to pH 9 with 2M aqueous NaOH solution. The precipitate that formed was isolated by suction filtration, washed with $H_2O$ and dried under reduced pressure. The solid was dissolved in EtOAc and washed with saturated aqueous $NaHCO_3$ solution. The organic layer was washed with saturated aqueous NaCl solution, dried ($MgSO_4$) and concentrated under reduced pressure, to afford the title compound (6.6 g).

LCMS method: Method 2, RT: 3.31 min, MI: 240 [M+1]
$^1$H NMR (300 MHz, DMSO-$d_6$) δ 7.31 (d, 2H), 7.26 (d, 2H), 6.99 (s, 2H), 3.09 (t, 2H), 2.92 (t, 2H)

The following intermediates (Table 9) were prepared using a similar method to that described for intermediate F40 (Scheme 8):

TABLE 9

| Intermediate number | Structure | Data |
|---|---|---|
| F40-1 | 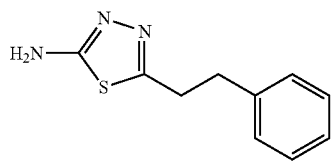 [SMILES: Nc1nnc(CCc2ccccc2)s1] | LCMS method: Method 2, RT: 2.81 min, MI: 206 [M + 1] |
| F40-2 | 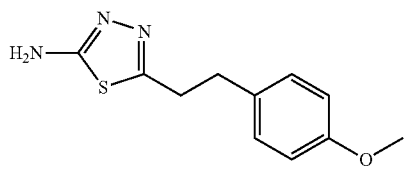 [SMILES: COc1ccc(CCc2nnc(N)s2)cc1] | LCMS method: Method 3, RT: 5.24 min, MI: 236 [M + 1] |
| F40-4 | 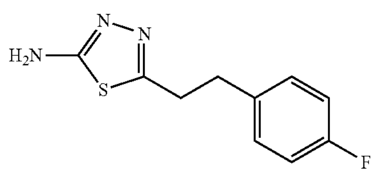 [SMILES: Nc1nnc(CCc2ccc(F)cc2)s1] | LCMS method: 1LCMS1, RT: 3.85 min, MI: 224 [M + 1] |
| F40-5 | 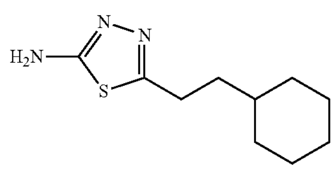 [SMILES: Nc1nnc(CCC2CCCCC2)s1] | LCMS method: Method 1, RT: 4.97 min, MI: 212 [M + 1] |
| F40-6 | 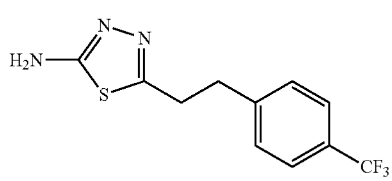 [SMILES: Nc1nnc(CCc2ccc(C(F)(F)F)cc2)s1] | LCMS method: Method 4, RT: 3.13 min, MI: 274 [M + 1] |
| F40-7 | 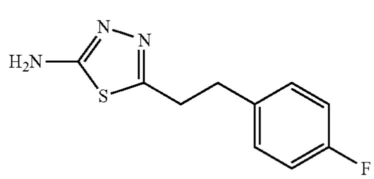 [SMILES: Nc1nnc(CCc2ccc(F)cc2)s1] | Commercially available |
| F40-8 | 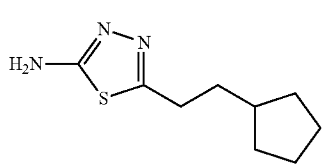 [SMILES: Nc1nnc(CCC2CCCC2)s1] | LCMS method: Method 1, RT: 4.52 min, MI: 198 [M + 1] |

TABLE 9-continued

| Intermediate number | Structure | Data |
|---|---|---|
| F40-9 | 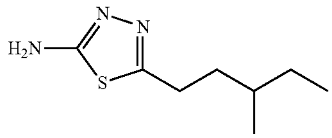 | LCMS method: Method 1, RT: 4.39 min, MI: 186 [M + 1] |
| F40-10 | 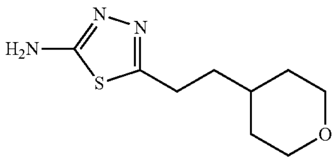 [SMILES: Nc1nnc(CCC2CCOCC2)s1] | LCMS method: Method 1, RT: 2.53 min, MI: 214 [M + 1] |
| F40-11 | 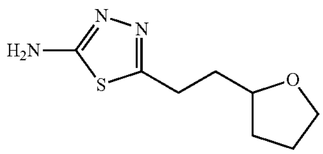 [SMILES: Nc1nnc(CCC2CCCO2)s1] | LCMS method: Method 1, RT: 2.59 min, MI: 200 [M + 1] |
| F40-12 | 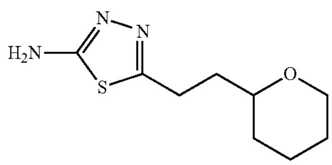 [SMILES: Nc1nnc(CCC2CCCCO2)s1] | LCMS method: Method 1, RT: 3.07 min, MI: 214 [M + 1] |

Synthesis of Aminoisoxazole Derivatives

Synthesis of 5-[2-(4-Chloro-phenyl)-ethyl]-isoxazol-3-ylamine (F43)

Scheme 9

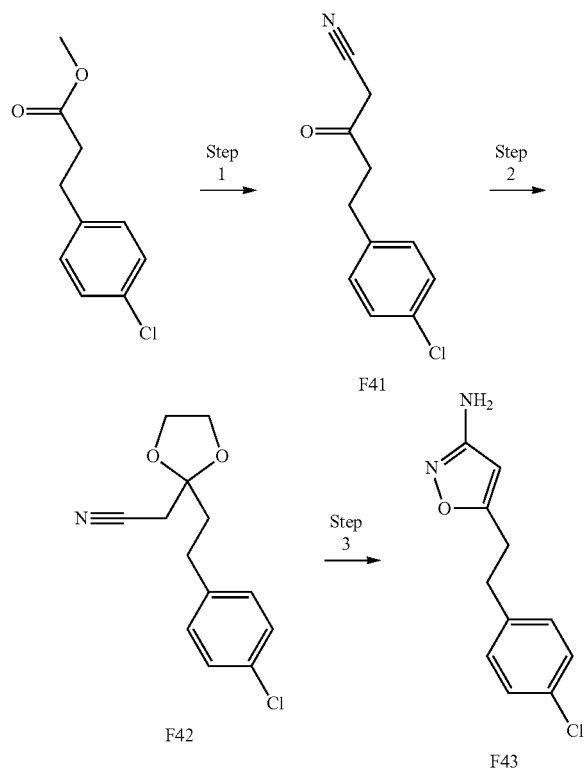

Step 1

Synthesis of 5-(4-chloro-phenyl)-3-oxo-pentanenitrile (F41)

To a suspension of NaH (60% in mineral oil, 1.67 g, 41.66 mmol) in anhydrous THF (27 mL) at 75° C., was added a mixture of 3-(4-chloro-phenyl)-propionic acid methyl ester (5.31 g, 26.71 mmol) and ACN (2.16 mL, 41.66 mmol) dropwise over 10 minutes. The resulting mixture was heated at 75° C. for a further 16 hours before the mixture was cooled to room temperature, and partitioned between EtOAc and $H_2O$. The aqueous layer was removed, acidified to pH 2 with 1M aqueous HCl solution and re-extracted with EtOAc. The organic layer was removed, dried ($MgSO_4$), filtered and concentrated under reduced pressure, to afford the title compound (2.009 g). The material was used without further purification.

$^1$H NMR (500 MHz, $CDCl_3$) δ 7.26 (m, 4H, overintegrating due to overlap with solvent peak), 7.13 (m, 2H), 3.41 (s, 1H), 2.93 (m, 4H), 2.66 (t, 1H)

Step 2

Synthesis of {2-[2-(4-chloro-phenyl)-ethyl]-[1,3] dioxolan-2-yl}-ACN (F42)

A mixture of 5-(4-chloro-phenyl)-3-oxo-pentanenitrile (2.10 g, 10.11 mmol), ethylene glycol (1.70 mL, 30.34 mmol) and TMS-Cl (3.83 mL, 30.34 mmol) in anhydrous DCM (50 mL) was heated at 40° C. for 16 hours. After this time the reaction mixture was diluted with EtOAc and partitioned with saturated aqueous $NaHCO_3$ solution. The organic layer was then washed with saturated aqueous NaCl solution, dried ($MgSO_4$), filtered and concentrated under reduced pressure. This material was purified by flash column chromatography, eluting with EtOAc/cyclohexane (0-40%) to afford the title compound (2.120 g).

¹H NMR (300 MHz, CDCl₃) δ 7.25 (m, 2H), 7.12 (m, 2H), 4.16 (m, 2H), 4.06 (m, 2H), 2.68 (m, 4H), 2.06 (m, 2H)

Step 3

Synthesis of 5-[2-(4-chloro-phenyl)-ethyl]-isoxazol-3-ylamine (F43)

To a stirred solution of NH₂OH.HCl (1.32 g, 35.05 mmol) in MeOH (15 mL) was added 7M NH₃/MeOH (6.02 mL, 42.11 mmol) and the reaction mixture was aged for 30 minutes at room temperature. 8-Hydroxyquinoline (134 mg, 0.84 mmol) was then added followed by a solution of {2-[2-(4-chloro-phenyl)-ethyl]-[1,3]dioxolan-2-yl}-ACN (2.12 g, 8.42 mmol) in MeOH (30 mL). The resulting mixture was heated at 70° C. for 16 hours, before being concentrated under reduced pressure and azeotroped with toluene (×3). The resulting solid was then dissolved in EtOH (10 mL) and acidified to pH 1 by addition of 37% HCl (1 mL). The mixture was submitted to microwave irradiation for 30 minutes at 120° C. The reaction mixture was then partitioned between DCM and saturated aqueous NaHCO₃ solution and the organic layer was removed, dried (MgSO₄), filtered and concentrated under reduced pressure. The resulting residue was purified by flash column chromatography, eluting with EtOAc/cyclohexane (0-40%) to afford the title compound (1.23 g).

¹H NMR (500 MHz, DMSO-d₆) δ 7.32 (m, 2H), 7.25 (m, 2H), 5.51 (s, 1H), 5.40 (s, 2H), 2.86 (m, 4H)

The following intermediate (Table 10) was prepared using a similar method to that described for intermediate F43 (Scheme 9):

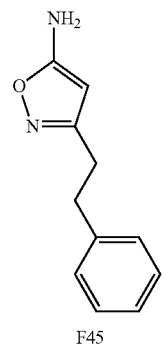

F45

Step 1

Synthesis of 3-oxo-5-phenyl-pentanenitrile (F44)

To a solution of 3-phenyl-propionic acid methyl ester (10.9 g, 66.56 mmol) and ACN (3.6 mL, 69.89 mmol) in toluene (50 mL) under nitrogen at 0° C., was added NaH (60% in mineral oil, 3.2 g, 79.87 mmol). The mixture was stirred at 0° C. for 30 minutes and then at reflux for 16 hours. The reaction mixture was concentrated under reduced pressure, and partitioned between EtOAc and H₂O. The aqueous phase was adjusted to pH 7 by dropwise addition of 2M aqueous HCl solution and the organic layer was separated. This was filtered through silicone-treated filter paper and concentrated under reduced pressure to afford a pale solid mass that was recrystallised from EtOAc to afford the title compound (3.8 g).

LCMS method: Method 5, RT: 4.03 min, MI: 172 [M−1]

TABLE 10

| Intermediate number | Structure | Data |
|---|---|---|
| F43-1 | H₂N—[isoxazole]—CH₂CH₂—[phenyl] | LCMS method: Method 5, RT: 3.76 min, MI: 189 [M + 1] |

Synthesis of 3-Phenethyl-isoxazol-5-ylamine (F45)

Scheme 10

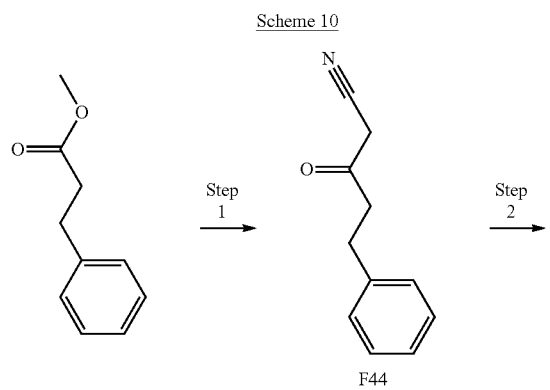

F44

Step 2

Synthesis of 3-phenethyl-isoxazol-5-ylamine (F45)

A mixture of 3-oxo-5-phenyl-pentanenitrile (0.69 g, 3.98 mmol), NaOH (192 mg, 4.77 mmol) and NH₂OH.HCl (331 mg, 4.77 mmol) in EtOH/H₂O (1:1, 10 mL) was submitted to microwave irradiation for 30 min at 100° C. The reaction mixture was then concentrated under reduced pressure and partitioned between H₂O and EtOAc. The aqueous phase was adjusted to pH 7 by dropwise addition of 2M aqueous HCl solution, and the organic layer was separated. The organic phase was filtered through silicone-treated filter paper and concentrated under reduced pressure. The residual material was purified by flash column chromatography, eluting with EtOAc/cyclohexane, (0-40%). The desired fractions were combined and concentrated under reduced pressure to afford the title compound (413 mg).

LCMS method: Method 5, RT: 3.76 min, MI: 189 [M+1]

The following intermediate (Table 11) was commercially available:

TABLE 11

| Intermediate number | Structure | Data |
|---|---|---|
| F46 | 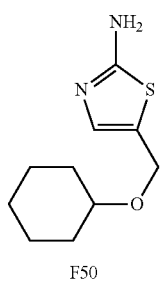 | Commercially available |

Synthesis of Aminothiazoles Derivatives

Synthesis of 5-Phenethyl-thiazol-2-ylamine (F48)

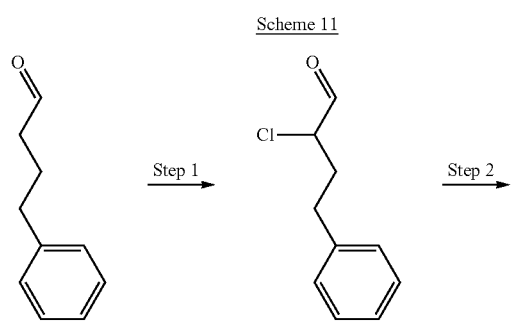

Scheme 11

F47

F48

Step 1

Synthesis of 2-chloro-4-phenyl-butyraldehyde (F47)

To a cooled solution of 4-phenyl-butyraldehyde (1.44 g, 9.70 mmol) in anhydrous DCM (60 mL) at 0° C. was added L-proline (223 mg, 1.94 mmol) and NCS (1.7 g, 12.61 mmol) consecutively. The resultant mixture was stirred at 0° C. for 2 hours and then allowed to warm to room temperature over 4 hours. The reaction mixture was then diluted with cyclohexane and filtered through Celite™, with the filtrate concentrated under reduced pressure to afford the title compound as a colourless oil (1.11 g), which was taken through to the subsequent step without any further purification or characterisation.

Step 2

Synthesis of 5-phenethyl-thiazol-2-ylamine (F48)

A mixture of 2-chloro-4-phenyl-butyraldehyde (1.77 g, 9.70 mmol) and thiourea (0.88 g, 11.64 mmol) in EtOH (60 mL) was stirred at 130° C. for 3 hours. The reaction mixture was then concentrated under reduced pressure, partitioned between H₂O and EtOAc, with the organic phase filtered through silicone-treated filter paper, concentrated under reduced pressure and purified by flash column chromatography, eluting with EtOAc/hexane (0-70%). The desired fractions were combined and concentrated under reduced pressure to afford the title compound (197 mg).

LCMS method: Method 5, RT: 2.23 min, MI: 205 [M+1]

Synthesis of 5-Cyclohexyloxymethyl-thiazol-2-ylamine (F50)

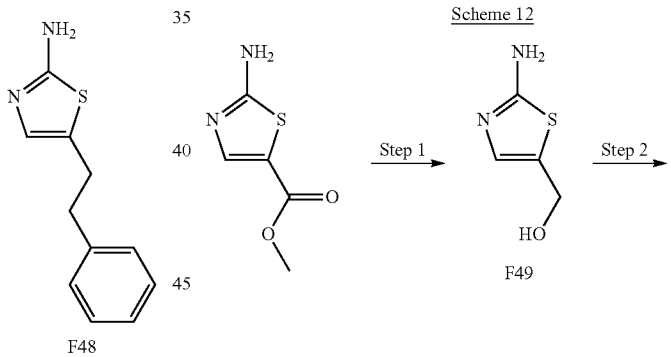

Scheme 12

F49

F50

Step 1

Synthesis of (2-amino-thiazol-5-yl)-methanol (F49)

A suspension of ethyl 2-amino-1,3-thiazole-5-carboxylate (1.72 g, 10 mmol) in anhydrous THF (100 mL) was cooled in an ice bath and treated with LiAlH$_4$ (0.76 g, 20 mmol) portionwise, under nitrogen. The reaction mixture was warmed to room temperature and stirred for 90 minutes. After this time, additional LiAlH$_4$ (0.76 g, 20 mmol) was added and the suspension was heated to reflux for 45 minutes. After this time, the suspension was cooled in an ice bath and cautiously treated with ice chips, followed by concentrated aqueous ammonium hydroxide solution (10 mL) and stirred for 60 hours. The orange suspension was filtered through Celite™, washing with MeOH. The filtrate was evaporated under reduced pressure, adsorbed onto silica and purified by flash column chromatography, eluting with MeOH/DCM (5-10%), with the desired fractions combined and concentrated under reduced pressure to afford the title compound (225 mg).

LCMS method: Method 5, RT: 0.55 min, MI: 131 [M+1]

Step 2

Synthesis of 5-cyclohexyloxymethyl-thiazol-2-ylamine (F50)

A solution of (2-amino-thiazol-5-yl)-methanol (225 mg, 1.73 mmol) and cyclohexanol (550 µL, 5.20 mmol) in nitromethane (17 mL) was treated with methanesulfonic acid (340 µL, 5.20 mmol) and heated to 80° C. for 4 hours. The solution was then cooled in a dry ice/acetone bath at −20° C. and treated with 2M NH$_3$/MeOH (2 mL). The reaction mixture was allowed to warm to room temperature and matured at room temperature for 16 hours. The mixture was evaporated, adsorbed onto silica and purified by column chromatography, eluting with MeOH/DCM (3-6%), with the desired fractions combined and evaporated to afford the title compound (184 mg).

LCMS method: Method 5, RT: 2.25 min, MI: 213 [M+1]

Synthesis of Aminopyrazole Derivatives

Synthesis of 5-[2-(4-Chloro-phenyl)-ethyl]-1H-pyrazol-3-ylamine (F51)

Scheme 13

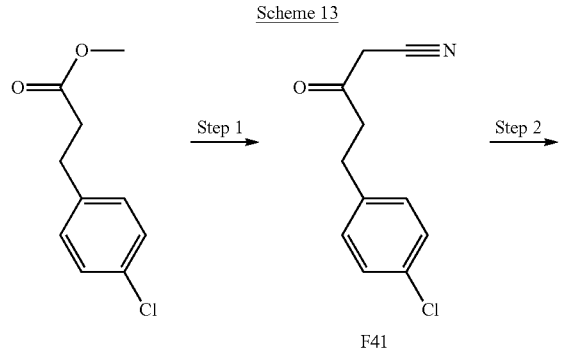

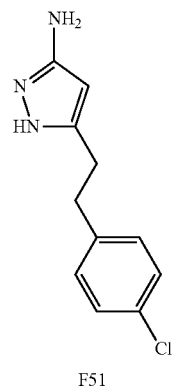

F51

Step 1

Synthesis of 5-(4-chloro-phenyl)-3-oxo-pentanenitrile (F41)

To a cooled solution of 3-(4-chloro-phenyl)-propionic acid methyl ester (12.5 g, 62.90 mmol) and anhydrous ACN (3.6 mL, 69.19 mmol) in anhydrous toluene (50 mL) under nitrogen at 0° C., was added NaH (60% in mineral oil, 3 g, 75.48 mmol) portionwise. The mixture was stirred at this temperature for 30 minutes and then at reflux for 16 hours. After this time, the reaction mixture was concentrated under reduced pressure and partitioned between H$_2$O and EtOAc. The aqueous phase was adjusted to pH 7 by dropwise addition of 2M aqueous HCl solution and then extracted with EtOAc. The organic phase was filtered through silicone-treated filter paper and concentrated under reduced pressure to afford the title compound (14.6 g). This material was used directly in the subsequent step without further purification or characterisation.

Step 2

Synthesis of 5-[2-(4-chloro-phenyl)-ethyl]-1H-pyrazol-3-ylamine (F51)

5-(4-Chloro-phenyl)-3-oxo-pentanenitrile (7.3 g, 35.15 mmol) was dissolved in EtOH (40 mL) and hydrazine hydrate (1.7 mL 35.15 mmol) was added. The reaction mixture was stirred at reflux for 16 hours after which time the solution was concentrated under reduced pressure and partitioned between H2O and EtOAc. The organic phase was filtered through silicone-treated filter paper, concentrated under reduced pressure and recrystallised from EtOAc to afford the title compound (1.07 g). The mother liquor was purified over silica gel using a gradient of EtOAc/hexane, 0-100%. Required product fractions were combined and concentrated under reduced pressure to afford the title compound (2.25 g). Both batches were combined to afford the title compound (3.32 g).

LCMS method: Method 5, RT: 2.51 min, MI: 222/224 [M+1]

The following intermediate (Table 12) was prepared using a similar method to that described for intermediate F51 (Scheme 13):

TABLE 12

| Intermediate number | Structure | Data |
|---|---|---|
| F51-1 | (structure shown) | LCMS method: Method 5, RT: 2.20 min, MI: 188 [M + 1] |

Synthesis of Methyl Aminopyrazole Derivatives

Synthesis of 5-[2-(4-Chloro-phenyl)-ethyl]-2-methyl-2H-pyrazol-3-ylamine (F54)

Scheme 14

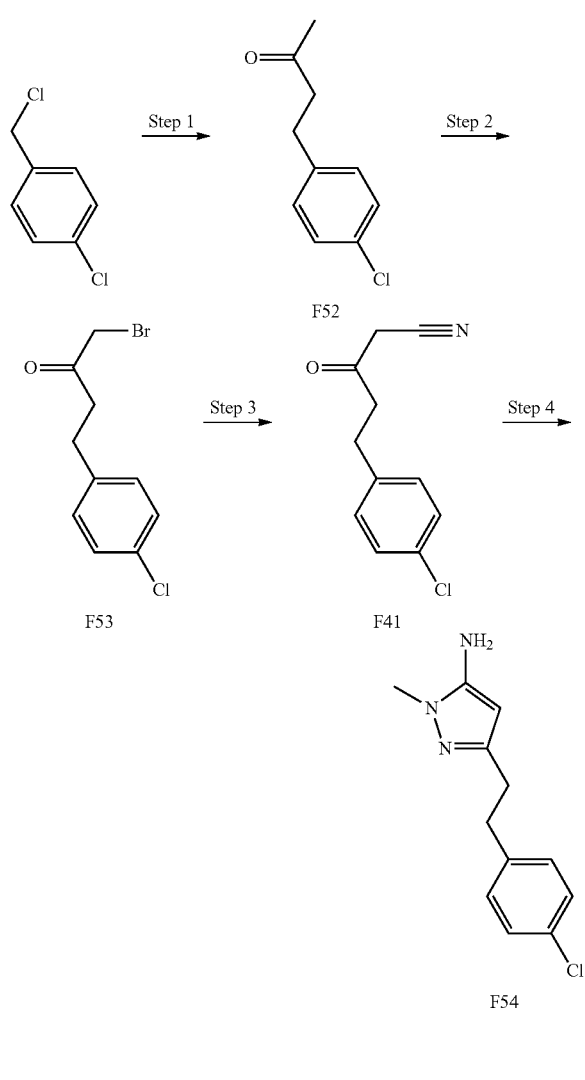

Step 1

Synthesis of 4-(4-chloro-phenyl)-butan-2-one (F52)

4-Chlorobenzyl chloride (8.05 g, 50 mmol), $K_2CO_3$ (6.9 g, 50 mmol) and acetylacetone (5.2 mL, 50 mmol) in EtOH (50 mL) were mixed and heated at reflux for 16 hours. After this time, the reaction mixture was concentrated under reduced pressure and partitioned between $H_2O$ and EtOAc; the organic phase separated, filtered through silicone-treated filter paper. The filtrate was concentrated under reduced pressure and purified by flash column chromatography, eluting with EtOAc/cyclohexane (0-40%). The desired fractions were combined, concentrated under reduced pressure to afford the title compound (3.2 g).

$^1$H NMR (400 MHz, $CDCl_3$) δ 7.24 (m, 2H), 7.11 (m, 2H), 2.86 (t, 2H), 2.74 (t, 2H), 2.14 (s, 3H)

Step 2

Synthesis of 1-bromo-4-(4-chloro-phenyl)-butan-2-one (F53)

A solution of bromine (453 μL, 8.85 mmol) in MeOH (10 mL) was added dropwise over 1 hour to a solution of 4-(4-chloro-phenyl)-butan-2-one (1.57 g, 8.60 mmol) in MeOH (10 mL) at 0° C. Once the orange-red colour of bromine had disappeared, $H_2O$ (40 mL) was added and the mixture stirred for 16 hours. After this time, the reaction mixture was concentrated under reduced pressure and partitioned between $H_2O$ and EtOAc. The organic phase was separated, filtered through silicone-treated filter paper and concentrated under reduced pressure. The residual material was purified by flash column chromatography, eluting with EtOAc/cyclohexane (0-10%), with the desired fractions combined and concentrated under reduced pressure to afford the title compound (2.17 g).

$^1$H NMR (400 MHz, $CDCl_3$) δ 7.25 (m, 2H), 7.12 (m, 2H), 3.84 (s, 2H), 2.99-2.89 (m, 4H)

Step 3

Synthesis of 5-(4-chloro-phenyl)-3-oxo-pentanenitrile (F41)

To a solution of 1-bromo-4-(4-chloro-phenyl)-butan-2-one (2.2 g 8.29 mmol) in EtOH (10 mL) was added a solution of potassium cyanide (810 mg, 12.44 mmol) in $H_2O$ (3 mL) and the resulting mixture was stirred at room temperature for 16 hours. After this time the reaction mixture was acidified to pH 5 by addition of 1M aqueous HCl solution (4 mL), stirred at room temperature for further 30 min, then concentrated under reduced pressure. The residual material was partitioned between EtOAc and $H_2O$ and the organic phase was separated, filtered through silicone-treated filter paper and concentrated under reduced pressure. This material was purified by flash column chromatography, eluting with EtOAc/cyclohexane (0-40%). The desired fractions were combined and concentrated under reduced pressure to afford the title compound (464 mg).

LCMS method: Method 5, RT: 4.44 min, MI: 206/208 [M−1]

Step 4

Synthesis of 5-[2-(4-chloro-phenyl)-ethyl]-2-methyl-2H-pyrazol-3-ylamine (F54)

A solution of 5-(4-chloro-phenyl)-3-oxo-pentanenitrile (0.30 g, 1.44 mmol) and methyl hydrazine (0.09 mL, 1.73 mmol) in MeOH (10 mL) was submitted to microwave irradiation at 120° C. for 45 minutes. After this time the reaction mixture was concentrated under reduced pressure and purified by flash column chromatography, eluting with EtOAc/cyclohexane (0-100%) then MeOH/DCM (0-20%). The desired fractions were combined and concentrated under reduced pressure to afford the title compound (210 mg).

LCMS method: Method 5, RT: 2.55 min, MI: 236 [M+1]

Amino Oxadiazole Derivative

The following intermediate (Table 13) was commercially available:

TABLE 13

| Intermediate number | Structure | Data |
|---|---|---|
| F54-1 | 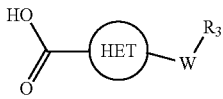 | Commercially available |

Synthesis of Carboxylic Acid Heterocycle Intermediates

Synthesis of carboxy-heterocycle intermediates of general formula F6 is described below:

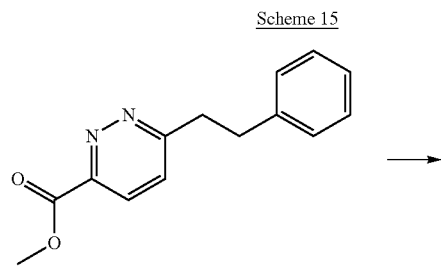

Synthesis of Carboxylic Acid Pyridazine Derivative

Synthesis of 6-Phenethyl-pyridazine-3-carboxylic acid (F55)

Scheme 15

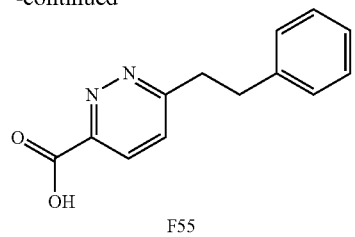

To a solution of 6-phenethyl-pyridazine-3-carboxylic acid methyl ester (242 mg, 1.0 mmol) in H$_2$O, THF and MeOH (1:1:1; 10 mL) was added LiOH (31 mg, 1.3 mmol) and the resulting mixture was stirred for 16 hours. After this time the reaction mixture was partitioned between H$_2$O and EtOAc and the organic fraction was removed. The aqueous layer was acidified to pH 2 and extracted with EtOAc and this organic fraction was separated and washed with brine, dried (MgSO$_4$), filtered and concentrated under reduced pressure to afford the title compound (204 mg), which was used in subsequent reactions without further purification.

LCMS method: Method 1, RT: 4.90 min, MI: 229 [M+1]

$^1$H NMR (500 MHz, DMSO-d$_6$) δ 13.73 (s, 1H), 8.07 (d, 1H), 7.73 (d, 1H), 7.26 (t, 2H), 7.22 (d, 2H), 7.17 (t, 1H), 3.31 (t, 2H) and 3.07 (t, 2H)

Synthesis of Carboxylic Acid Oxadiazole Derivative

Synthesis of Lithium 5-phenethyl-[1,3,4]oxadiazole-2-carboxylate (F58)

Scheme 16

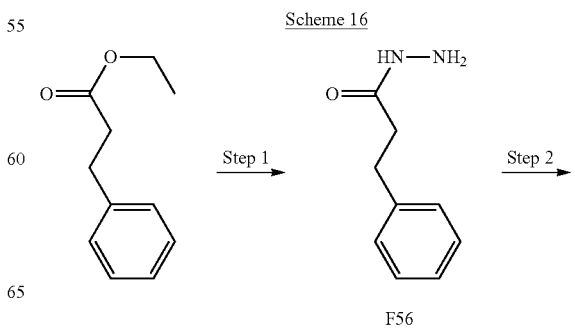

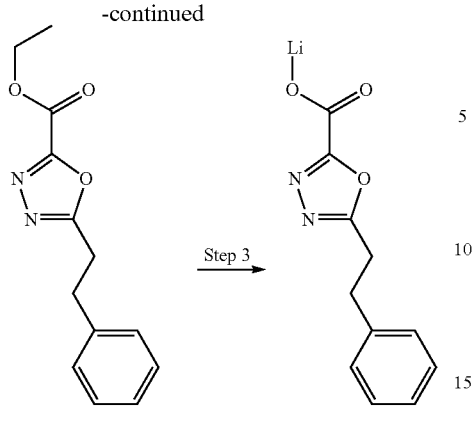

F57　　　　　　　　F58

Step 1

Synthesis of 3-phenyl-propionic acid hydrazide (F56)

To a solution of 3-phenyl-propionic acid ethyl ester (1.78 g, 10 mmol) in EtOH (20 mL) at room temperature was added aqueous hydrazine monohydrate (5.44 mL, 100 mmol) and the reaction mixture was stirred at room temperature for 60 hours, before being concentrated under reduced pressure. This material was partitioned between $H_2O$ and EtOAc and the organic layer was washed with brine, dried ($MgSO_4$), filtered and concentrated under reduced pressure to afford the title compound, which was used directly in the next step.

$^1$H NMR (500 MHz, $CDCl_3$) δ 7.30-7.22 (m, 2H), 7.21-7.18 (m, 3H), 6.80 (br s, 2H), 6.70 (br s, 1H), 2.97 (t, 2H), 2.45 (dd, 2H)

Step 2

Synthesis of 5-phenethyl-[1,3,4]oxadiazole-2-carboxylic acid ethyl ester (F57)

To a solution of 3-phenyl-propionic acid hydrazide (1.64 g, 10 mmol) and $NEt_3$ (4.16 mL, 30 mmol) in DCM (50 mL) at 0° C. was added dropwise ethyl chlorooxoacetate (1.12 mL, 10 mmol). The mixture was stirred and allowed to reach room temperature over 16 hours. After this time TsCl (1.91 g, 10 mmol) was added and the mixture was stirred for 24 hours at room temperature. After this time the reaction was diluted with DCM, washed with $H_2O$, saturated aqueous sodium bicarbonate solution and saturated aqueous NaCl solution, dried (MgSO4), filtered and concentrated under reduced pressure. Purification of the residual material was accomplished by flash column chromatography, eluting with EtOAc/cyclohexane (0-20%) to afford the title compound (1.19 g).

LCMS method: Method 1, RT: 4.73 min, MI: 247 [M+1]
$^1$H NMR (500 MHz, $CDCl_3$) δ 7.31 (t, 2H), 7.26-7.21 (m, 3H), 4.51 (q, 2H), 3.25 (dd, 2H), 3.17 (dd, 2H), 1.46 (t, 3H)

Step 3

Synthesis of lithium; 5-phenethyl-[1,3,4]oxadiazole-2-carboxylate (F58)

To a solution of 5-phenethyl-[1,3,4]oxadiazole-2-carboxylic acid ethyl ester (0.07 g, 0.28 mmol) in $H_2O$ and EtOH (1:2, 1.4 mL) was added LiOH (7 mg, 0.28 mmol) and the resulting mixture was stirred for 16 hours. The reaction mixture was then concentrated under reduced pressure and azeotroped with toluene (3×5 mL), to afford the title compound (60 mg).

$^1$H NMR (500 MHz, DMSO-$d_6$) δ 7.28-7.18 (m, 5H), 3.09 (t, 2H), 3.00 (t, 2H)

Synthesis of Carboxylic Acid Isoxazole Derivatives

Synthesis of 5-[2-(4-chlorophenyl)ethyl]isoxazole-3-carboxylic acid (F61)

Scheme 17

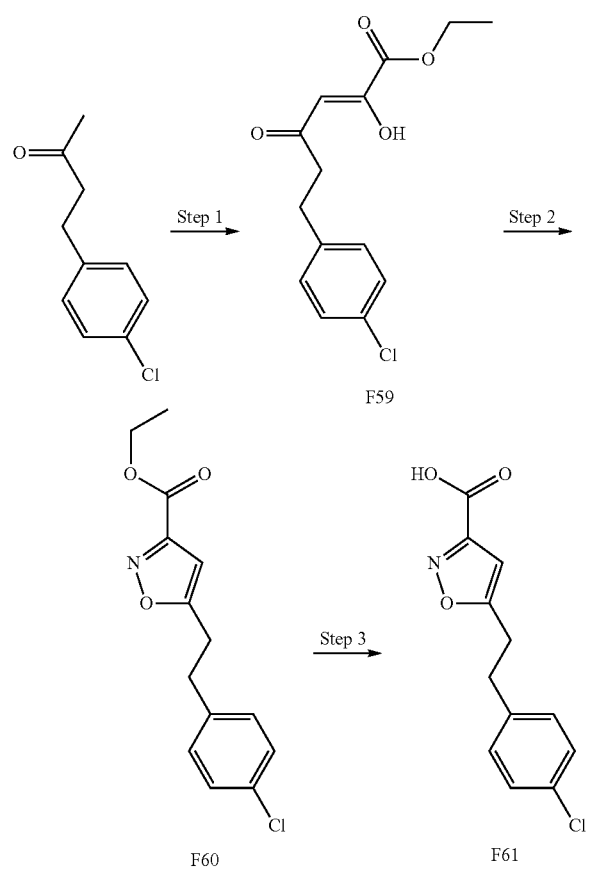

F59

F60　　　　　　　　F61

Step 1

Synthesis of (Z)-6-(4-chloro-phenyl)-2-hydroxy-4-oxo-hex-2-enoic acid ethyl ester (F59)

To a stirred solution of anhydrous EtOH (10 mL) at 0° C. under an atmosphere of nitrogen, was added NaH (60% in mineral oil, 1 g, 25 mmol) portionwise. 4-(4-Chlorophenyl)-2-butanone (4.57 g, 25 mmol) and diethyloxalate (3.38 mL, 25 mmol) were mixed together and then added to the chilled solution of sodium ethoxide. After 5 minutes stirring at this temperature the reaction mixture was allowed to warm to room temperature. After 10 minutes the reaction mixture solidified and anhydrous EtOH (8 mL) was added. After 16 hours stirring at room temperature, the reaction mixture was cooled to 0° C., quenched by addition of aqueous 1M HCl solution and extracted twice with EtOAc. The organic fractions were combined and washed with H₂O, dried (MgSO₄), filtered and concentrated under reduced pressure. Purification of the residual material was accomplished by flash column chromatography, eluting with DCM/cyclohexane (20-100%), to afford the title compound (5.91 g).

and concentrated under reduced pressure to afford the title compound (5.17 g).

¹H NMR (500 MHz, DMSO-d₆) δ 13.88 (s, 1H), 7.33 (m, 2H), 7.27 (m, 2H), 6.58 (s, 1H), 3.12 (t, 2H), 2.98 (t, 2H)

The following intermediates (Table 13) were prepared using a similar method to that described for intermediate F61 (Scheme 17):

TABLE 14

| Intermediate number | Structure | Data |
|---|---|---|
| F61-1 | HO-C(=O)-isoxazole-CH₂CH₂-Ph | ¹H NMR (500 MHz, CDCl₃) δ 7.31 (t, 3H), 7.23 (t, 1H), 7.18 (d, 2H), 6.40 (s, 1H), 3.15 (t, 2H), 3.05 (t, 2H) |
| F61-2 | HO-C(=O)-isoxazole-CH₂CH₂-C₆H₄-F | ¹H NMR (500 MHz, DMSO-d₆) δ 13.88 (s, 1H), 7.27 (m, 2H), 7.09 (m, 2H), 6.55 (s, 1H), 3.12 (t, 2H), 2.97 (t, 2H) |

¹H NMR (500 MHz, CDCl₃) δ 14.31 (br s, 1H), 7.25 (m, 2H), 7.13 (m, 2H), 6.34 (s, 1H), 4.34 (q, 2H), 2.95 (t, 2H), 2.80 (t, 2H), 1.37 (t, 3H)

Step 2

Synthesis of ethyl 5-[2-(4-chlorophenyl)ethyl]isoxazole-3-carboxylate (F60)

A solution of (Z)-6-(4-chloro-phenyl)-2-hydroxy-4-oxo-hex-2-enoic acid ethyl ester (5.91 g, 20.90 mmol) and NH₂OH.HCl (1.74 g, 25.09 mmol) in EtOH (70 mL) was heated at 80° C. for 2 hours. The reaction mixture was cooled to room temperature and the reaction was partitioned between EtOAc and saturated aqueous sodium bicarbonate solution. The organic fraction was separated, washed with brine, dried (MgSO₄), filtered and concentrated under reduced pressure. The residual material was purified by flash column chromatography, eluting with EtOAc/cyclohexane (0-30%) to afford the title compound (4.67 g).

¹H NMR (500 MHz, DMSO-d₆) δ 7.33 (m, 2H), 7.26 (m, 2H), 6.65 (s, 1H), 4.33 (q, 2H), 3.14 (t, 2H), 2.99 (t, 2H), 1.29 (t, 3H)

Step 3

Synthesis of 5-[2-(4-chlorophenyl)ethyl]isoxazole-3-carboxylic acid (F61)

A solution of ethyl 5-[2-(4-chlorophenyl)ethyl]isoxazole-3-carboxylate (5.85 g, 20.9 mmol) and LiOH (0.506 g, 21.11 mmol) in EtOH/H₂O (2:1, 42 mL) was stirred at room temperature for 16 hours. The aqueous layer was extracted with EtOAc and then acidified to pH 2 by dropwise addition of aqueous 1M HCl solution, and re-extracted with EtOAc. The organic fractions were combined then washed with saturated aqueous NaCl solution, dried (MgSO₄), filtered Synthesis of Carboxylic Acid Isoxazole Derivative Synthesis of 3-Phenethyl-isoxazole-5-carboxylic acid (F73)

Scheme 21

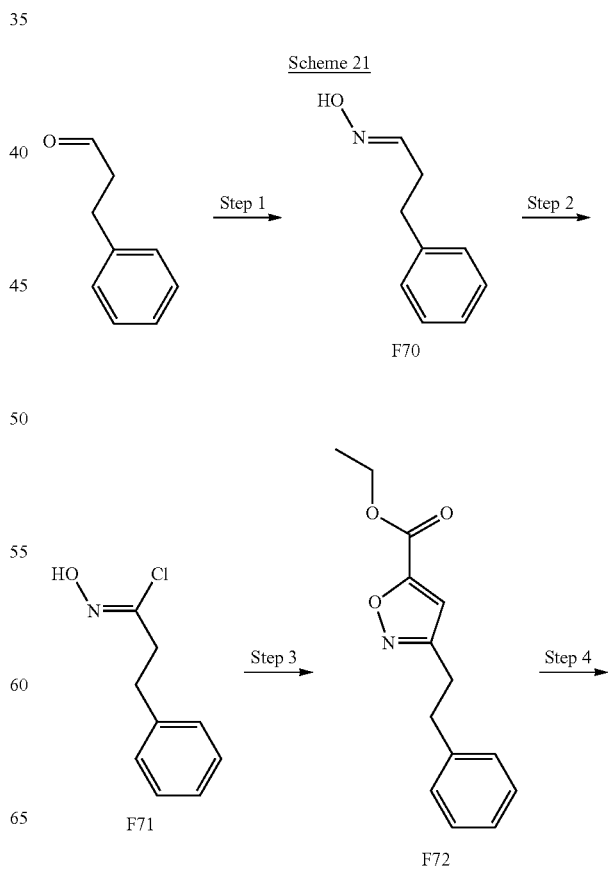

-continued

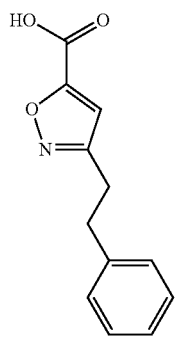

F73

Step 1

Synthesis of 3-phenylpropanal oxime (F70)

To a stirred solution of hydrocinnamaldehyde (2.68 g, 20 mmol) and NEt₃ (11.1 mL, 80 mmol) in DCM (50 mL) was added hyroxylamine hydrochloride (2.78 g, 40 mmol). The resulting suspension was stirred at room temperature for 16 hours then the reaction mixture was added to saturated aqueous sodium bicarbonate solution and extracted with DCM. The organic fractions were combined, dried (MgSO₄), filtered and concentrated under reduced pressure. Purification was accomplished by flash column chromatography, eluting with EtOAc/cyclohexane (0-20%) to afford the title compound (3.017 g).

¹H NMR (500 MHz, CDCl₃) [mixture of E and Z isomers in a ratio of 1.1:1.0]δ 7.78 (br s, 1H), 7.47 (t, 1H), 7.39 (br s, 1H), 7.30 (t, 4H), 7.21 (t, 6H), 6.76 (t, 1H), 2.83 (t, 4H), 2.72 (dt, 2H), 2.53 (dt, 2H)

Step 2

Synthesis of N-hydro-3-phenylpropimidoyl chloride (F71)

To a solution of 3-phenylpropanal oxime (3.02 g, 20.022 mmol) in DMF (40 mL) at 50° C. was added dropwise a solution of NCS (2.7 g, 20.2 mmol) in DMF (10 mL) over 30 minutes. After stirring for 1 hour at 50° C. the reaction was cooled to room temperature and stirred for 16 hours. After this time the reaction mixture was poured into ice-water (30 mL) and extracted twice with Et₂O. The combined organic extracts were washed with ice-water and saturated aqueous NaCl solution, dried (MgSO₄), filtered and concentrated under reduced pressure to afford the title compound (3.51 g) which was used in the next step without further purification or characterisation.

Step 3

Synthesis of 3-phenethyl-isoxazole-5-carboxylic acid ethyl ester (F72)

To a cooled solution of N-hydro-3-phenylpropimidoyl chloride (3.33 g, 18.11 mmol) and ethylpropiolate (1.8 mL, 18.11 mmol) in Et₂O (60 mL) at 0° C. was added NEt₃ (2.7 mL, 19.92 mmol) dropwise. After 2 hours the reaction mixture was filtered, washed with Et₂O and concentrated under reduced pressure. The residual material was purified by flash column chromatography, eluting with DCM/cyclohexane (0-75%) to afford the title compound (1.01 g).

LCMS method: Method 1, RT: 5.46 min, MI: 246 [M+1]

¹H NMR (500 MHz, CDCl₃) δ 7.30 (t, 2H), 7.24-7.19 (m, 3H), 6.70 (s, 1H), 4.41 (q, 2H), 3.07-3.00 (m, 2H), 1.40 (t, 3H)

Step 4

Synthesis of 3-phenethyl-isoxazole-5-carboxylic acid (F73)

To a solution of 3-phenethyl-isoxazole-5-carboxylic acid ethyl ester (1.01 g, 4.12 mmol) in H₂O/EtOH (1:2, 20 mL) was added LiOH (0.13 g, 5.36 mmol) and the resulting mixture was stirred for 16 hours. After this time the reaction mixture was partitioned between H₂O and EtOAc and the organic fraction removed. The aqueous layer was acidified to pH 2 and extracted with EtOAc. This organic fraction was washed with brine, dried (MgSO₄), filtered and concentrated under reduced pressure to afford the title compound (560 mg) which was used in subsequent reactions without further purification.

¹H NMR (500 MHz, DMSO-d₆) δ 14.22 (br s, 1H), 7.27 (t, 2H), 7.23 (d, 2H), 7.18 (t, 1H), 7.07 (s, 1H), 2.97 (br s, 4H)

Synthesis of Carboxylic Acid Thiazole Derivative

Synthesis of 5-Phenethyl-thiazole-2-carboxylic acid (F64)

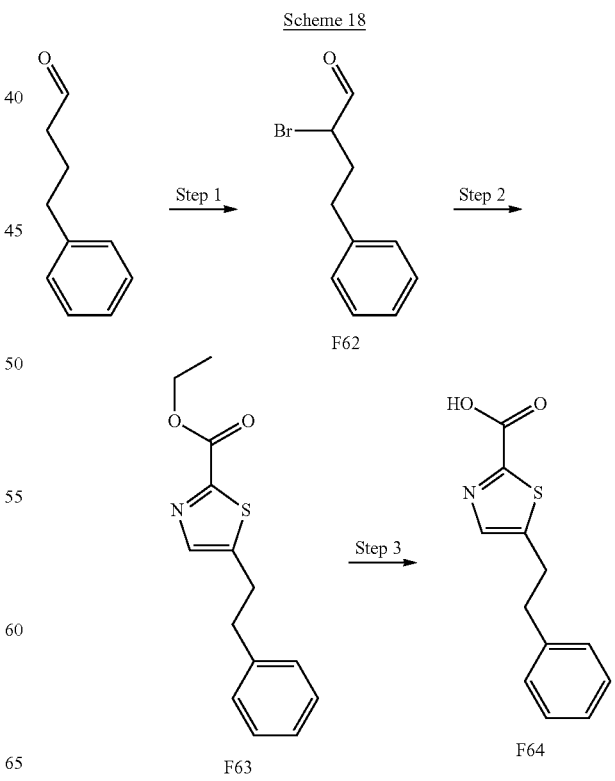

Scheme 18

Step 1

Synthesis of 2-bromo-4-phenyl-butyraldehyde (F62)

To a solution of 4-phenyl-butyraldehyde (1 g, 6.75 mmol) in anhydrous toluene (8.4 mL) was slowly added bromine (0.35 mL, 6.75 mmol) and the resulting solution was stirred at room temperature for 1 hour. Aqueous saturated NaHCO$_3$ solution was slowly added, followed by DCM. The organic layer was separated, dried (MgSO$_4$), filtered and evaporated under reduced pressure to give the title compound (1.53 g), which was used directly in the next step without further purification or characterisation.

Step 2

Synthesis of 5-phenethyl-thiazole-2-carboxylic acid ethyl ester (F63)

A solution of 2-bromo-4-phenyl-butyraldehyde (1.532 g, 6.75 mmol) and ethyl thiooxamate (0.9 g, 6.747 mmol) in EtOH (18 mL) was heated at reflux for 24 hours. After this time the reaction mixture was partitioned between H$_2$O and DCM and the organic layer was removed, washed with saturated aqueous NaCl solution, dried (MgSO$_4$), filtered and concentrated under reduced pressure. The residual material was purified by flash column chromatography, eluting with EtOAc/cyclohexane (0-25%), to afford the title compound (13.3 mg).

LCMS method: Method 1, RT: 5.48 min, MI: 262 [M+1]
$^1$H NMR (500 MHz, CDCl$_3$) δ 7.64 (s, 1H), 7.28 (t, 2H), 7.22 (t, 1H), 7.16 (d, 2H), 4.44 (q, 2H), 3.21 (t, 2H), 3.00 (t, 2H), 1.43 (t, 3H)

Step 3

Synthesis of 5-phenethyl-thiazole-2-carboxylic acid (F64)

To a solution of 5-phenethyl-thiazole-2-carboxylic acid ethyl ester (0.015 g, 0.06 mmol) in H$_2$O/THF/MeOH (0.6 mL, 1:1:1) was added LiOH (0.001 g, 0.06 mmol) and the resulting mixture was stirred for 16 hours. After this time the reaction mixture was partitioned between H$_2$O and DCM and the organic fraction removed. The aqueous layer was acidified to pH 2 by dropwise addition of aqueous 1M HCl solution and extracted with EtOAc. The organic fraction was washed with brine, dried (MgSO$_4$), filtered and concentrated under reduced pressure to afford the title compound (13 mg), which was used in subsequent reactions without further purification.

$^1$H NMR (500 MHz, CDCl$_3$) δ 7.64 (s, 1H), 7.32 (t, 2H), 7.24 (t, 1H), 7.16 (d, 2H), 3.23 (dd, 2H), 3.01 (dd, 2H)

2-Phenethyl-thiazole-5-carboxylic acid (F64-3)

Scheme 19

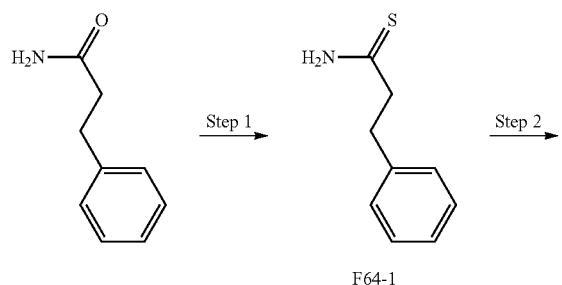

F64-1

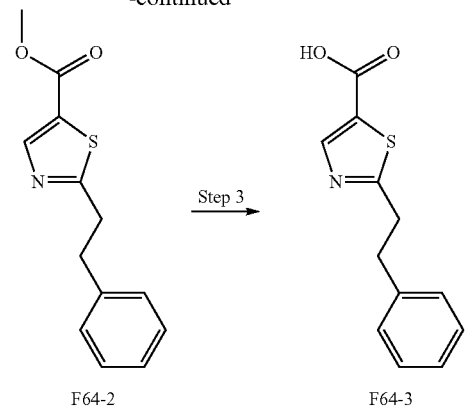

F64-2    F64-3

Step 1

Synthesis of 3-phenylpropanethioamide (F64-1)

DCM (20 mL) was added to a flask containing Lawesson's reagent (2.022 g, 5.00 mmol). 3-Phenylpropanamide (1.492 g, 10.00 mmol) was dissolved in DCM (20 mL), added to the suspension, and stirred at room temperature for 16 hours. The mixture was concentrated under reduced pressure and purified by column chromatography (DCM) to afford the title compound (1.07 g).

$^1$H NMR (500 MHz, CDCl$_3$) δ 7.30 (t, 2H), 7.24-7.21 (m, 3H), 3.12 (t, 2H), 2.95 (t, 2H)

Step 2

Synthesis of 2-phenethyl-thiazole-5-carboxylic acid methyl ester (F64-2)

A solution of 3-phenylpropanethioamide (1.049 g, 6.35 mmol) and ethyl 2-chloro-3-oxopropanoate (392 μL, 3.175 mmol) in DMF (6.4 mL) was heated at 95° C. for 48 hours. After this time, the reaction mixture was cooled to 0° C. and cold water (10 mL) was added. The reaction mixture was adjusted to pH 8 by slow addition of solid sodium bicarbonate and extracted with Et$_2$O, washed with water, saturated aqueous NaCl solution, dried (sodium sulfate), filtered and concentrated under reduced pressure. This material was purified by column chromatography, eluting with EtOAc/cyclohexane (0-25%). The desired fractions were combined and dried under reduced pressure then repurified by column chromatography (DCM/cyclohexane; 25-100%) to afford the title compound (0.036 g).

LCMS method: Method 1, RT: 5.36 min, MI: 248 [M+1]
$^1$H NMR (500 MHz, CDCl$_3$) δ 8.29 (s, 1H), 7.30 (t, 2H), 7.24-7.19 (m, 3H), 3.88 (s, 3H), 3.34 (dd, 2H), 3.13 (dd, 2H)

Synthesis of 2-phenethyl-thiazole-5-carboxylic acid (F64-3)

To a solution of 2-phenethyl-thiazole-5-carboxylic acid methyl ester (0.04 g) in water, tetrahydrofuran and methanol (1:1:1, 1.5 mL) was added lithium hydroxide (4 mg) and the resulting mixture was stirred at room temperature for 16 hours. After this time the reaction mixture was partitioned between water and dichloromethane and the organic fraction removed. The aqueous layer was acidified to pH 2 and extracted with EtOAc, with this organic fraction washed with brine, dried (MgSO$_4$), filtered and concentrated under reduced pressure to afford the title compound.

$^1$H NMR (500 MHz, CDCl$_3$) δ 8.39 (s, 1H), 7.30 (t, 2H), 7.23 (t, 1H), 7.21 (d, 2H), 3.39 (dd, 2H), 3.15 (dd, 2H)

Synthesis of Carboxylate Thiadiazole Derivatives

Synthesis of lithium; 5-[2-(4-chloro-phenyl)-ethyl]-[1,3,4]thiadiazole-2-carboxylate (F67)

Scheme 20

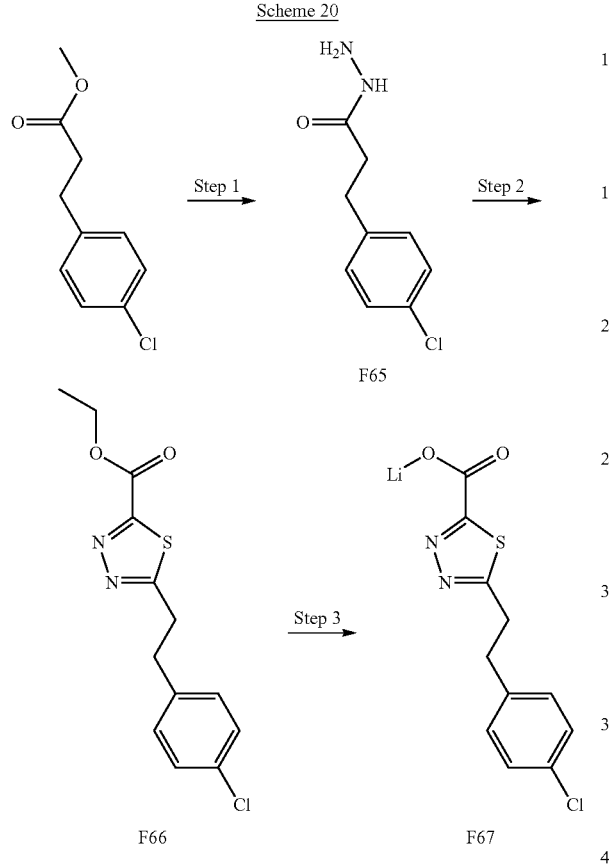

Step 1

Synthesis of 3-(4-chloro-phenyl)-propionic acid hydrazide (F65)

To a solution of methyl 3-(4-chlorophenyl)propanoate (16.14 g, 81.25 mmol) in EtOH (300 mL) was added hydrazine hydrate (40 mL, 812.50 mmol). The mixture was stirred for 4 hours at reflux, after which time the solvent was removed under reduced pressure and the residual material washed with cold Et$_2$O and filtered to afford the title compound (16 g).

LCMS method: Method 1, RT: 3.77 min, MI: 199 [M+1]
$^1$H NMR (500 MHz, DMSO-d$_6$) δ 8.94 (br s, 1H), 7.31 (d, 2H), 7.21 (d, 2H), 4.21 (br s, 2H), 2.78 (t, 2H), 2.29 (t, 2H)

Step 2

Synthesis of 5-[2-(4-chloro-phenyl)-ethyl]-[1,3,4]thiadiazole-2-carboxylic acid ethyl ester (F66)

To a mixture of 3-(4-chloro-phenyl)-propionic acid hydrazide (10 g, 50.34 mmol), NEt$_3$ (14.0 mL, 100.68 mmol) in anhydrous DCM (84 mL) was added ethyl chlorooxoacetate (5.9 mL, 52.86 mmol) over a period of 30 minutes at 0° C. The reaction mixture was warmed to room temperature and stirred for 2 hours. After this time the reaction was diluted with H$_2$O (10 mL) and the organic layer was washed with saturated aqueous sodium bicarbonate solution, dried (MgSO$_4$), filtered and concentrated under reduced pressure. To this residual material was added Lawesson's reagent (15.3 g, 37.75 mmol) and the mixture was dissolved in 2-MeTHF (50 mL) and heated at 60° C. for 16 hours. The solvent was then removed under reduced pressure and the residual material was partitioned between EtOAc and saturated aqueous NaHCO$_3$ solution. The organic layer was repeatedly washed with further amounts of saturated aqueous NaHCO$_3$ solution, dried (MgSO$_4$), filtered and concentrated under reduced pressure. The residual material was purified by flash column chromatography, eluting with EtOAc/cyclohexane (0-50%) to afford the title compound (8.4 g).

LCMS method: Method 1, RT: 5.36 min, MI: 297 [M+1]
$^1$H NMR (500 MHz, DMSO-d$_6$) δ 7.32 (d, 2H), 7.27 (d, 2H), 4.37 (q, 2H), 3.49 (t, 2H), 3.08 (t, 2H), 1.31 (t, 3H)

Step 3

Synthesis of lithium; 5-[2-(4-chloro-phenyl)-ethyl]-[1,3,4]thiadiazole-2-carboxylate (F67)

To a solution of 5-[2-(4-chloro-phenyl)-ethyl]-[1,3,4]thiadiazole-2-carboxylic acid ethyl ester (8.4 g, 28.30 mmol) in H$_2$O/THF (1:1, 180 mL) was added LiOH (0.75 g, 31.13 mmol) and the mixture was stirred at room temperature for 16 hours. After this time LiOH (0.38 g, 16.07 mmol) was added and the mixture was stirred at room temperature for 1 hour, then the reaction mixture was concentrated under reduced pressure, azeotroping three times with toluene to afford the title compound (8.685 g).

LCMS method: Method 3, RT: 2.94 min, MI: 269 [M+1]
$^1$H NMR (500 MHz, DMSO-d$_6$) δ 7.32 (d, 2H), 7.27 (d, 2H), 3.29 (t, 2H), 3.01 (t, 2H)

The following intermediates (Table 14) were prepared using a similar method to that described for intermediate F67 (Scheme 20):

TABLE 15

| Intermediate number | Structure | Data |
|---|---|---|
| F67-1 | 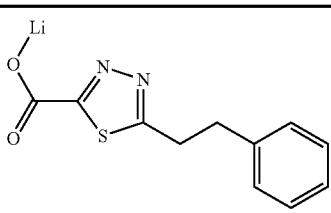 | $^1$H NMR (300 MHz, DMSO-d$_6$) δ 7.30-7.18 (m, 5H), 3.29 (dd, 2H), 3.00 (dd, 2H) |

TABLE 15-continued

| Intermediate number | Structure | Data |
|---|---|---|
| F67-2 | (Li salt of 5-[2-(4-fluorophenyl)ethyl]-1,3,4-thiadiazole-2-carboxylate) | LCMS method: Method 3, RT: 2.06 min, MI: 253 [M + 1] |
| F67-3 | (Li salt of 5-[2-(furan-2-yl)ethyl]-1,3,4-thiadiazole-2-carboxylate) | $^1$H NMR (500 MHz, DMSO-$d_6$) δ 7.52 (dd, 1H), 6.33 (dd, 1H), 6.13 (dd, 1H), 3.30 (dd, 2H), 3.04 (dd, 2H) |

Synthesis of lithium; 5-(4-chloro-benzylamino)-[1,3,4]thiadiazole-2-carboxylate (F69)

Scheme 21

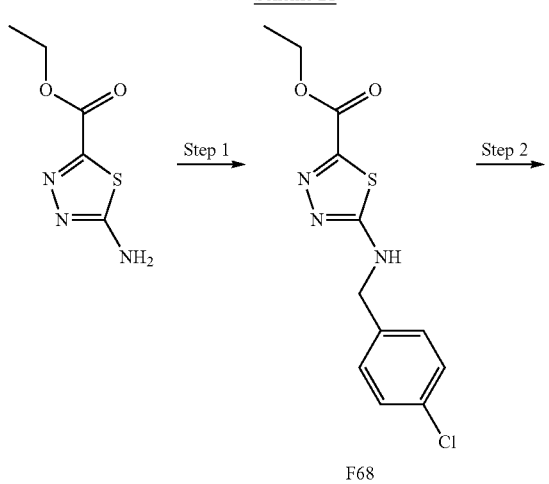

Step 1

Synthesis of 5-(4-chloro-benzylamino)-[1,3,4]thiadiazole-2-carboxylic acid ethyl ester (F68)

A suspension of 5-amino-[1,3,4]thiadiazole-2-carboxylic acid ethyl ester (0.30 g, 1.75 mmol), TFA (0.27 mL, 3.50 mmol), 4-chlorobenzaldehyde (0.27 g, 1.93 mmol) and sodium triacetoxyborohydride (0.45 g, 2.10 mmol) in isopropanol (3.5 mL) was stirred at room temperature for 2 hours and then at 70° C. for 16 hours. After this time the reaction mixture was concentrated under reduced pressure and purified by flash column chromatography, eluting with EtOAc/cyclohexane (0-50%) to afford the title compound (44 mg).

LCMS method: Method 3, RT: 4.81 min, MI: 298 [M+1]
$^1$H NMR (500 MHz, CDCl$_3$) δ 7.32 (d, 2H), 7.29 (d, 2H), 4.53 (s, 2H), 4.41 (q, 2H), 1.39 (t, 3H)

Step 2

Synthesis of lithium; 5-(4-chloro-benzylamino)-[1,3,4]thiadiazole-2-carboxylate (F69)

A suspension of 5-(4-chloro-benzylamino)-[1,3,4]thiadiazole-2-carboxylic acid ethyl ester (0.10 g, 0.34 mmol) and LiOH (0.02 g, 0.68 mmol) in EtOH/H$_2$O (2:1, 3.3 mL) was stirred at room temperature for 16 hours. The reaction mixture was then concentrated under reduced pressure and azeotroped three times with toluene to afford the title compound (95 mg).

$^1$H NMR (500 MHz, DMSO-$d_6$) δ 8.00 (t, 1H), 7.38 (d, 2H), 7.34 (d, 2H), 4.40 (d, 2H)

Synthesis of carboxylic acid pyrazole derivative

Synthesis of 5-Phenethyl-1H-pyrazole-3-carboxylic acid (F76)

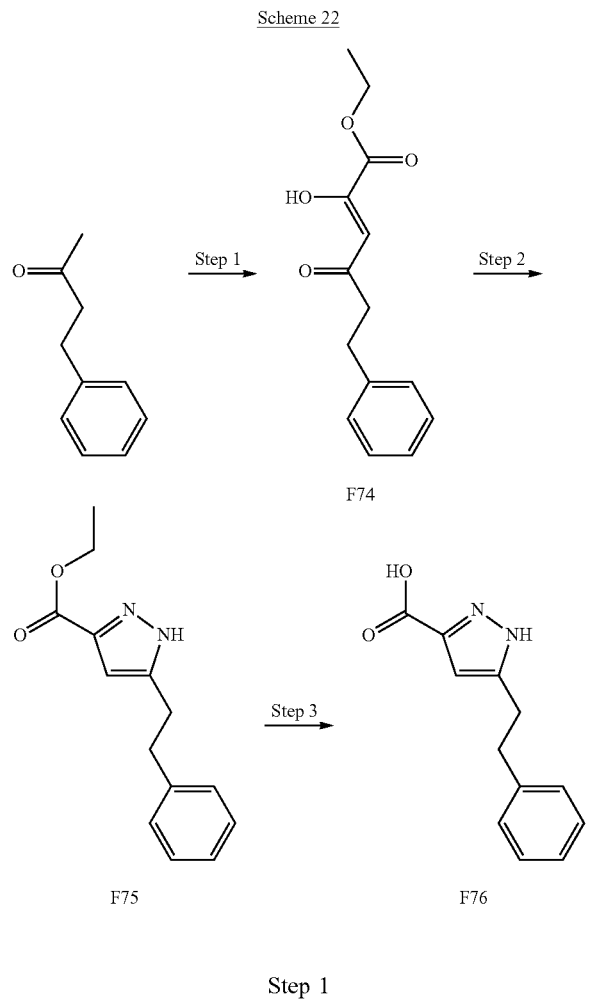

Scheme 22

F74

F75

F76

Step 1

Synthesis of (Z)-2-hydroxy-4-oxo-6-phenyl-hex-2-enoic acid ethyl ester (F74)

To a stirred solution of EtOH (1 mL) at 0° C. under an atmosphere of nitrogen was added NaH (60% in mineral oil, 131 mg, 3.266 mmol). Phenyl-4-butan-2-one (0.371 g, 2.5 mmol) and diethyloxalate (338 µL, 2.5 mmol) were mixed together and then added to the chilled solution of sodium ethoxide. After 5 minutes stirring at 0° C. the reaction mixture was warmed to room temperature. After 10 minutes the reaction mixture solidified and EtOH (2 mL) was added. After 16 hours stirring at room temperature, the reaction mixture was cooled to 0° C., and quenched with 1M HCl and extracted with DCM (×2). The organic fractions were combined and washed with H$_2$O, dried (MgSO$_4$), filtered and concentrated under reduced pressure. Purification by flash column chromatography, eluting with DCM/cyclohexane (1:1) afforded the title compound (244 mg).

$^1$H NMR (500 MHz, CDCl$_3$) δ 14.37 (br s, 1H), 7.31-7.26 (m, 2H), 7.22-7.19 (m, 3H), 6.35 (m, 1H), 4.34 (q, 2H), 2.98 (t, 2H), 2.82 (dd, 2H), 1.37 (t, 3H)

Step 2

Synthesis of 5-phenethyl-1H-pyrazole-3-carboxylic acid ethyl ester (F75)

To a solution of (Z)-2-hydroxy-4-oxo-6-phenyl-hex-2-enoic acid ethyl ester (0.122 mg, 0.491 mmol) in AcOH (1 mL) was added hydrazine monohydrate (24 µL, 0.496 mmol) and the reaction mixture was stirred at room temperature for 16 hours. After this time, the reaction mixture was diluted with EtOAc, and saturated aqueous sodium bicarbonate solution was added until evolution of gas ceased. The organic layer was separated and the aqueous layer was extracted with two further aliquots of EtOAc. The organic fractions were combined, dried (MgSO$_4$), filtered and concentrated under reduced pressure. Purification by silica gel column chromatography (MeOH/DCM, 0-5%) afforded the title compound (93 mg).

LCMS method: Method 1, RT: 5.33 min, MI: 245 [M+1]

$^1$H NMR (500 MHz, CDCl$_3$) δ 10.32 (br s, 1H), 7.31-7.26 (m, 2H), 7.23-7.17 (m, 3H), 6.62 (s, 1H), 4.37 (q, 2H), 3.01 (dd, 2H), 2.97 (dd, 2H), 1.38 (t, 3H)

Step 3

Synthesis of 5-phenethyl-1H-pyrazole-3-carboxylic acid (F76)

A solution of 5-phenethyl-1H-pyrazole-3-carboxylic acid ethyl ester (330 mg, 1.351 mmol) in aqueous 2M NaOH solution (10.1 mL, 20.265 mmol) and EtOH (10 mL, 1:1) was heated at 90° C. for 16 hours. After this time the reaction mixture was cooled to room temperature and was partitioned between H$_2$O and EtOAc. The organic fraction was removed and the aqueous layer was acidified to pH 2 and extracted with EtOAc. This organic fraction was washed with brine, dried (MgSO$_4$), filtered and concentrated under reduced pressure to afford the title compound (2:1 mixture of 1H and 2H isomers, 54 mg).

LCMS method: Method 1, RT: 4.67 min, MI: 217 [M+1]

$^1$H NMR (500 MHz, DMSO-d$_6$) δ 12.96 (br s, 0.65H), 12.48 (br s, 0.35H), 7.26 (t, 2H), 7.20 (d, 2H), 7.16 (t, 1H), 6.19 (s, 0.65H), 6.15 (s, 0.35H), 2.89 (br s, 4H)

EXAMPLE COMPOUNDS

Example compounds of formula F1 and F2 were prepared using the coupling methods described below (Coupling Methods A-G):

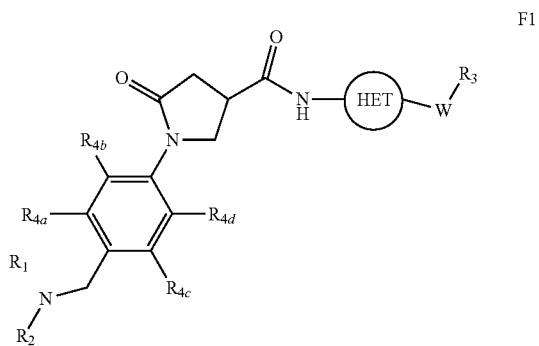

F1

-continued

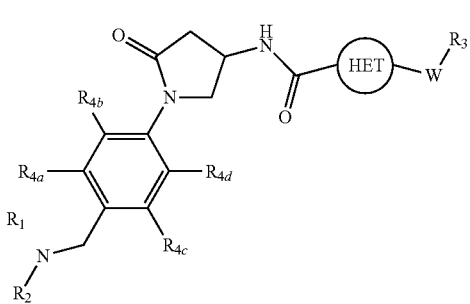

Coupling Method A (CM A) [HBTU]—Carboxylic Acid-Pyrrolidinone

Synthesis of 1-[4-(4-methyl-piperidin-1-ylmethyl)-phenyl]-5-oxo-pyrrolidine-3-carboxylic acid {5-[2-(4-chloro-phenyl)-ethyl]-[1,3,4]thiadiazol-2-yl}-amide (F95)

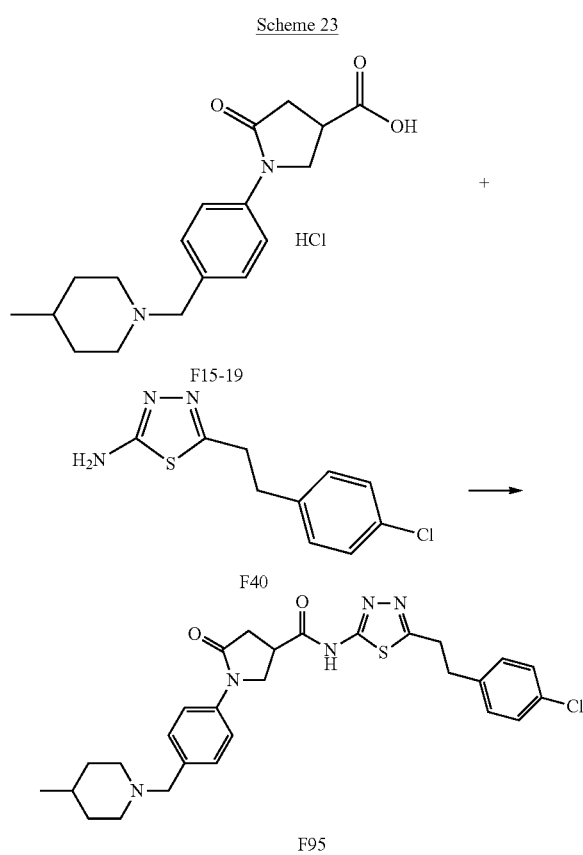

To a solution of 1-[4-(4-methyl-piperidin-1-ylmethyl)-phenyl]-5-oxo-pyrrolidine-3-carboxylic acid; hydrochloride (204 mg, 0.578 mmol) in DMA (15 mL) was added HBTU (549 mg, 1.45 mmol) and DIPEA (302 µL, 1.73 mmol). The resulting mixture was stirred at room temperature for 2 hours, before addition of 5-[2-(4-chloro-phenyl)-ethyl]-[1,3,4]thiadiazol-2-ylamine (69 mg, 0.289 mmol). The reaction mixture was stirred at room temperature for 16 hours. The reaction mixture was then diluted with DCM and washed with saturated aqueous NaHCO$_3$ solution and then H$_2$O. The organic fraction was passed through a phase separation cartridge and concentrated under reduced pressure. The residual material was purified by flash column chromatography, eluting with EtOAc (100%) then MeOH/DCM (0-10%) to afford the title compound (113 mg).

LCMS method: Method 1, RT: 3.54 min, MI: 538 [M+1]
$^1$H NMR (500 MHz, DMSO-d$_6$) δ 12.64 (br s, 1H), 7.55 (d, 2H), 7.32 (d, 2H), 7.27 (m, 4H), 4.07 (t, 1H), 3.98 (dd, 1H), 3.58 (m, 1H), 3.40 (s, 2H), 3.30 (t, 2H hidden partly by water peak), 3.02 (t, 2H), 2.83 (dd, 1H), 2.74 (m, 3H), 1.88 (br m, 2H), 1.53 (br d, 2H), 1.30 (br m, 1H), 1.09 (m, 2H), 0.86 (d, 3H)

Coupling-Method B (CM B) [HBTU]—Amino-Pyrrolidinone

Synthesis of 1-{4-[(S)-4-({5-[2-(4-chloro-phenyl)-ethyl]-[1,3,4]thiadiazole-2-carbonyl}-amino)-2-oxo-pyrrolidin-1-yl]-benzyl}-4-methyl-piperidine hydrochloride (F137)

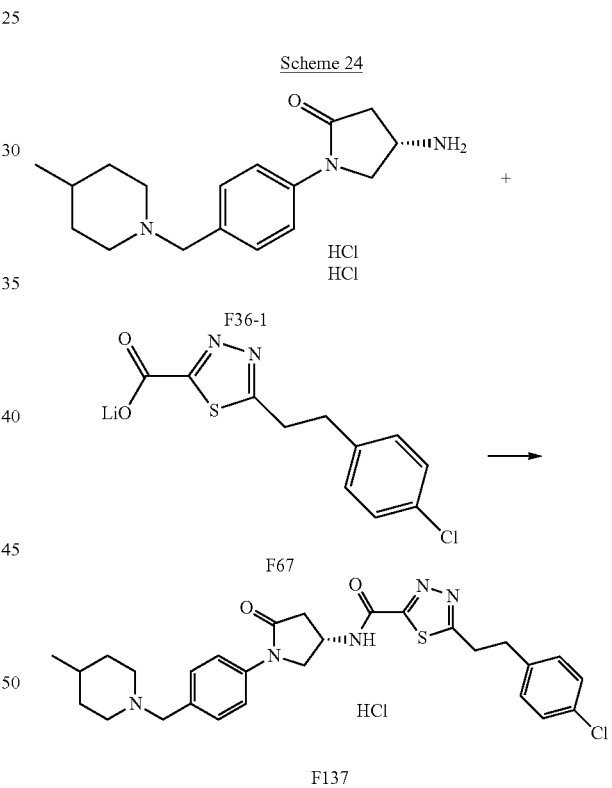

A solution of (S)-4-amino-1-[4-(4-methyl-piperidin-1-ylmethyl)-phenyl]-pyrrolidin-2-one; bis hydrochloride (90 mg, 0.25 mmol), lithium; 5-[2-(4-chloro-phenyl)-ethyl]-[1,3,4]thiadiazole-2-carboxylate (137 mg, 0.50 mmol), HBTU (190 mg, 0.50 mmol) and NMM (82 µL, 0.75 mmol) in DMF (5 mL) was stirred at room temperature for 48 hours. The reaction mixture was then concentrated under reduced pressure and the residue was purified by flash column chromatography, eluting with MeOH/DCM (0-20%). The desired fractions were combined and concentrated under reduced pressure then the residual material was partitioned between EtOAc and saturated aqueous NaHCO$_3$ solution. The organic fraction was washed with saturated aqueous NaCl solution, dried (MgSO₄), filtered and concentrated under reduced pressure. This material was stirred with 2M HCl in Et₂O for 1 hour. The solvent was removed under reduced pressure, and the residue was azeotroped three times with ether and dried under reduced pressure at 40° C. for 24 hours to afford the title compound (60 mg).

LCMS method: Method 1, RT: 3.48 min, MI: 538 [M+1]

¹H NMR (500 MHz, CDCl₃) δ 7.62 (d, 1H), 7.51 (d, 2H), 7.33 (d, 2H), 7.26 (s, 2H), 7.12 (d, 2H), 4.86 (br s, 1H), 4.29 (dd, 1H), 3.86 (dd, 1H), 3.46 (dd, 2H), 3.46 (s, 2H), 3.13 (dd, 2H), 3.09 (dd, 1H), 2.82 (br d, 2H), 2.69 (dd, 1H), 1.92 (t, 2H), 1.56 (s, 2H), 1.34 (br s, 1H), 1.27-1.22 (m, 2H), 0.91 (d, 3H)

Coupling-Method C (CM C) [EDC]

Synthesis of 5-phenethyl-1H-pyrazole-3-carboxylic acid [5-oxo-1-(4-piperidin-1-ylmethyl-phenyl)-pyrrolidin-3-yl]-amide hydrochloride (F204)

Scheme 25

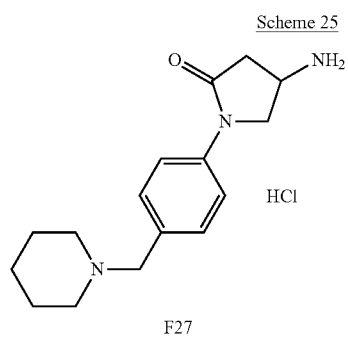

F27

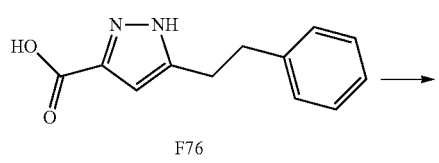

F76

-continued

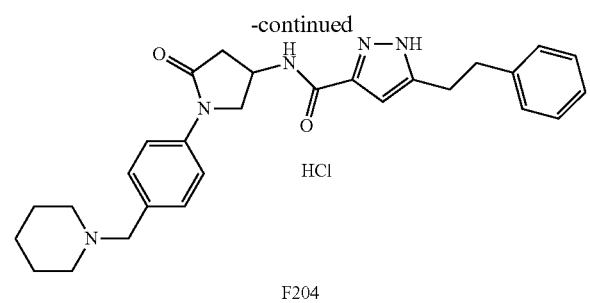

F204

A solution of 4-amino-1-(4-piperidin-1-ylmethyl-phenyl)-pyrrolidin-2-one; hydrochloride (87 mg, 0.25 mmol), 5-phenethyl-1H-pyrazole-3-carboxylic acid (54 mg, 0.25 mmol), HOBt (34 mg, 0.25 mmol), N-(3-dimethylaminopropyl)-N-ethylcarbodiimide hydrochloride (48 mg, 0.25 mmol) and NMM (82 μL, 0.75 mmol) in DMF (5 mL) was stirred at room temperature for 16 hours. Saturated aqueous NaCl solution was then added and the resulting precipitate was isolated via suction filtration. The resulting solid was dissolved in DCM, passed through a phase separation cartridge and concentrated under reduced pressure. Purification of the residual material was accomplished by flash column chromatography, eluting with MeOH/DCM (0-20%) and the desired fractions were combined and concentrated under reduced pressure. The residue was stirred with 2M HCl in Et₂O for 1 hour. The solvent was removed under reduced pressure and the residue was azeotroped with ether (×3) and dried under reduced pressure at 40° C. for 24 hours to give the title compound (56 mg).

LCMS method: Method 1, RT: 2.95 min, MI: 472 [M+1]

¹H NMR (300 MHz, CDCl₃) δ 7.54 (d, 2H), 7.37 (d, 2H), 7.32-7.18 (m, 3H), 7.14 (d, 2H), 6.61 (s, 1H), 4.88-4.78 (m, 2H), 4.24 (dd, 1H), 3.82 (dd, 1H), 3.59 (br s, 2H), 3.05 (dd, 1H), 3.01 (dd, 2H), 2.94 (dd, 2H), 2.63 (dd, 1H), 2.49 (br s, 4H), 1.78 (br s, 4H), 1.46 (br s, 2H)

Coupling-Method D (CM D) [Oxalyl Chloride]

Synthesis of 1-(4-morpholin-4-ylmethyl-phenyl)-5-oxo-pyrrolidine-3-carboxylic acid {6-[2-(4-fluorophenyl)-ethyl]-pyridazin-3-yl}-amide (F149)

Scheme 26

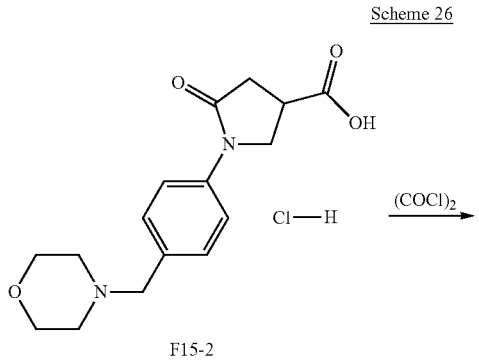

F15-2

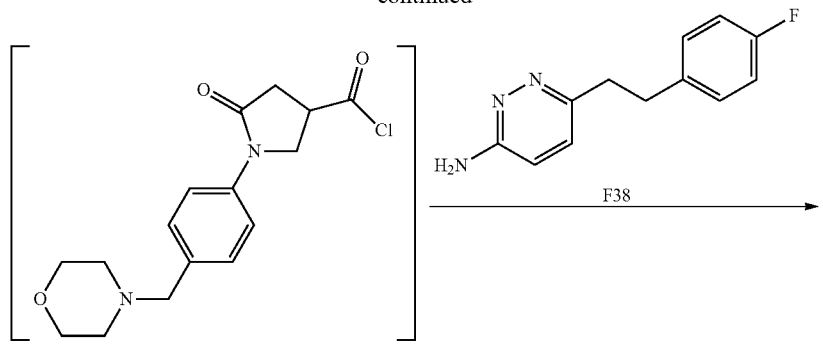

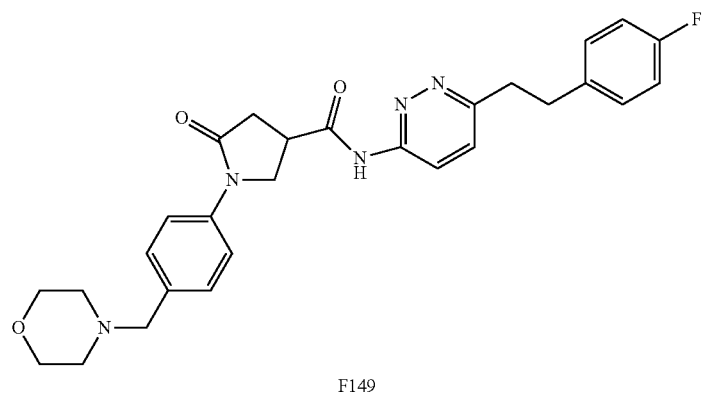

F149

1-(4-Morpholin-4-ylmethyl-phenyl)-5-oxo-pyrrolidine-3-carboxylic acid; hydrochloride (265 mg, 0.778 mmol) was dissolved in DCM (5 mL) and treated with DMF (0.0500 mL). Oxalyl chloride (200 µL, 2.33 mmol) was added dropwise and the mixture was stirred at room temperature for 3 hours. After this time the reaction mixture was concentrated under reduced pressure and the crude product was dissolved in DCM (5 mL) and treated with 6-[2-(4-fluoro-phenyl)-ethyl]-pyridazin-3-ylamine (169 mg, 0.778 mmol) and NEt$_3$ (323 µL, 2.33 mmol). The mixture was stirred at room temperature for 2 hours then the reaction mixture was partitioned between DCM and saturated aqueous sodium bicarbonate solution. The organic phase was passed through a phase separation cartridge and concentrated under reduced pressure. The residual material was dissolved in DCM and purified by flash column chromatography, eluting with MeOH/DCM (0-10%). The desired fractions were combined and concentrated under reduced pressure to afford the title compound (133 mg).

LCMS method: Method 1, RT: 3.11 min, MI: 504 [M+1]

$^1$H NMR (500 MHz, DMSO-d$_6$) δ 11.30 (s, 1H), 8.20 (d, 1H), 7.58 (m, 3H), 7.33-7.21 (m, 4H), 7.11-7.04 (m, 2H), 4.08 (t, 1H), 3.98 (dd, 1H), 3.61 (m, 1H), 3.54 (m, 4H), 3.41 (s, 2H), 3.14 (t, 2H), 2.99 (t, 2H), 2.82 (dd, 1H), 2.73 (dd, 1H), 2.31 (s, 4H).

Coupling Method E (CM E) [TBTU]

Synthesis of (S)-1-[4-(4-methyl-piperidin-1-ylmethyl)-phenyl]-5-oxo-pyrrolidine-3-carboxylic acid {5-[2-(4-chloro-phenyl)-ethyl]-[1,3,4]thiadiazol-2-yl}-amide (F92)

Scheme 27

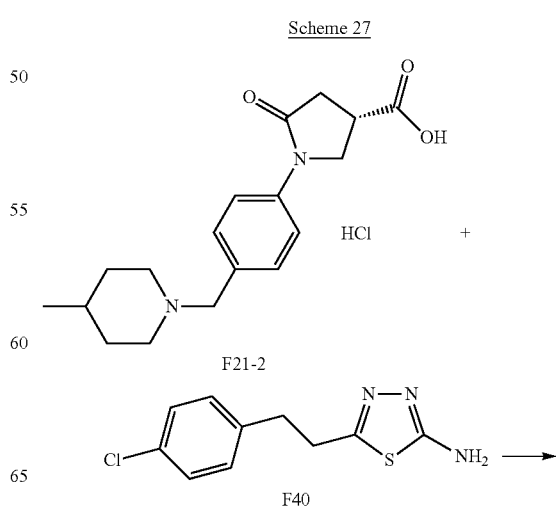

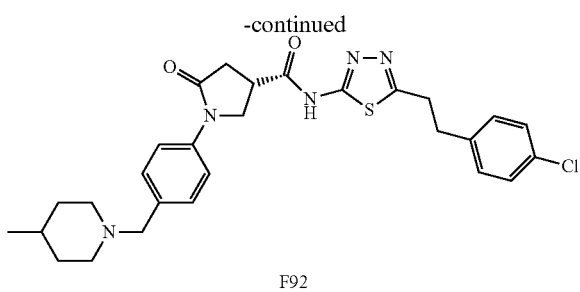

F92

To a solution of 5-[2-(4-chloro-phenyl)-ethyl]-[1,3,4]thiadiazol-2-ylamine (2.00 g, 8.34 mmol), (S)-1-[4-(4-methyl-piperidin-1-ylmethyl)-phenyl]-5-oxo-pyrrolidine-3-carboxylic acid; hydrochloride (4.22 g, 12.52 mmol) and NEt₃ (2.11 g, 20.85 mmol) in DMF (40 mL) was added TBTU (4.69 g, 14.61 mmol) and the mixture was stirred at room temperature for 5 hours. The reaction mixture was then diluted with DCM (100 mL) and washed with saturated aqueous NaHCO₃ solution (250 mL). The organic layer was removed and the aqueous layer was back-extracted with DCM (50 mL). The organic fractions were combined, dried (MgSO₄), filtered and concentrated under reduced pressure. The residual material was loaded onto silica gel and purified by flash column chromatography, eluting with MeOH/DCM (0-10%). The desired fractions were combined and concentrated under reduced pressure to afford the title compound (4.04 g).

LCMS method: Method 6, RT: 4.3 min, MI: 538/540 [M+1]

Coupling Method F (CM F) [Mixed Method]

Synthesis of (3S)—N-[6-[2-(4-fluorophenyl)ethyl]pyridazin-3-yl]-1-[4-(morpholinomethyl)phenyl]-5-oxo-pyrrolidine-3-carboxamide hydrochloride (F180)

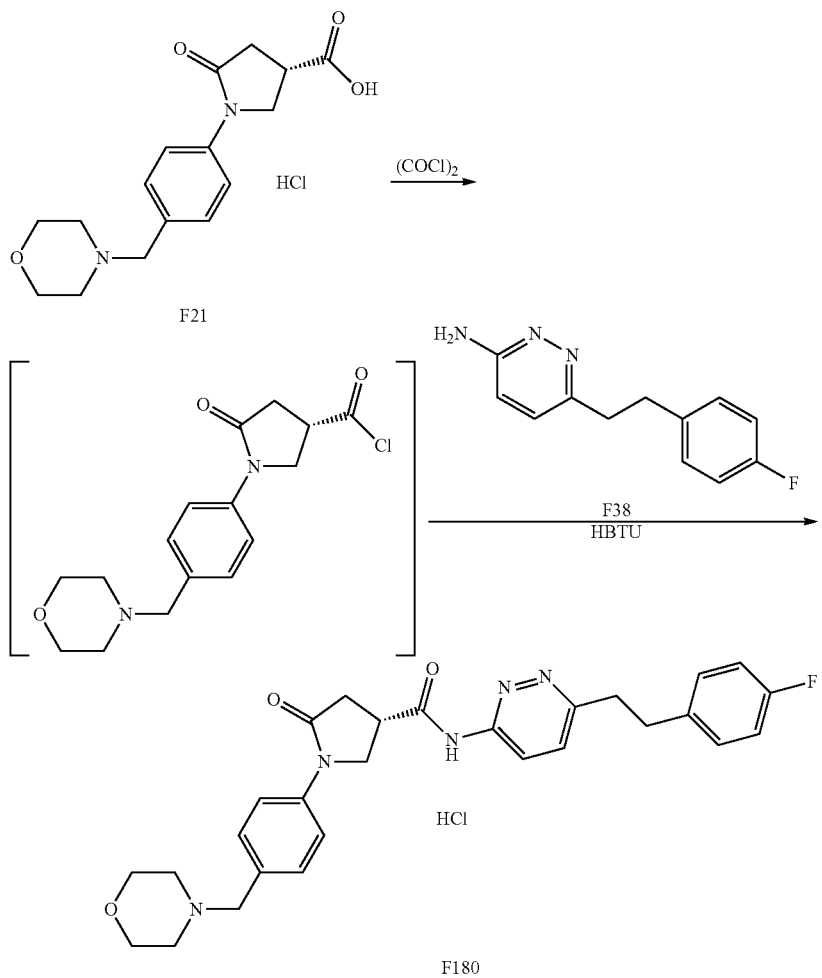

Scheme 28

(3S)-1-[4-(morpholinomethyl)phenyl]-5-oxo-pyrrolidine-3-carboxylic acid hydrochloride (0.15 g, 0.4400 mmol) was suspended in DCM (2 mL) and treated with DMF (0.0500 mL). Oxalyl chloride (0.11 mL, 1.32 mmol) was added dropwise and the mixture was stirred at room temperature for 3 hours. 1,4-Dioxane (1 mL) was then added followed by NEt₃ (120 μL, 0.880 mmol) and stirring was continued for 1 hour. After this time, the reaction mixture was concentrated under reduced pressure and the residual material was dissolved in DCM (2 mL) and treated with 6-[2-(4-fluorophenyl)ethyl]pyridazin-3-amine (0.1 g, 0.4400 mmol) and NEt₃ (0.18 mL, 1.32 mmol). The mixture was stirred at room temperature for 3 hours then HBTU (0.17 g, 0.440 mmol) was added and the mixture was stirred at room temperature for 16 hours. After this time, the mixture was partitioned between DCM and saturated aqueous sodium bicarbonate solution and the organic phase was removed, washed with H₂O and saturated aqueous NaCl solution, dried (MgSO₄), filtered and concentrated under reduced pressure. The residual material was purified by flash column chromatography, eluting with MeOH/DCM (0-10%) with the relevant fractions combined and concentrated under reduced pressure. The residual material was dissolved in DCM (1 mL) and treated with 2M HCl in Et₂O (1.0 mL, 0.440 mmol) and stirred at room temperature for 5 minutes. After this time, the volatiles were removed under reduced pressure and the solid was triturated with Et₂O and dried under reduced pressure to afford the title compound (115 mg).

LCMS method: Method 1, RT: 2.98 min, MI: 504 [M+1]

¹H NMR (500 MHz, DMSO-d₆) δ 11.38 (s, 1H), 10.97 (br s, 1H), 8.26 (d, 1H), 7.75 (d, 2H), 7.63 (d, 1H), 7.59 (d, 2H), 7.24 (m, 2H), 7.08 (m, 2H), 4.29 (d, 2H), 4.12 (t, 1H), 4.02 (dd, 1H), 3.92 (br d, 2H), 3.75 (br t, 2H), 3.64 (m, 1H), 3.20-3.15 (m, 4H), 3.08-2.99 (m, 4H), 2.88 (dd, 1H), 2.77 (dd, 1H)

Coupling Method G (CM G) [HBTU Plus NEt₃]

Synthesis of 5-oxo-1-(4-piperidin-1-ylmethyl-phenyl)-pyrrolidine-3-carboxylic acid [5-(3-methyl-pentyl)-[1,3,4]thiadiazol-2-yl]-amide; hydrochloride (F182)

A mixture of 5-oxo-1-(4-piperidin-1-ylmethyl-phenyl)-pyrrolidine-3-carboxylic acid; hydrochloride (0.100 g, 0.296 mmol) and 5-(3-methyl-pentyl)-[1,3,4]thiadiazol-2-ylamine (0.060 g, 0.326 mmol) in DMF (3 mL) was treated with NEt₃ (90 μL, 0.651 mmol) and HBTU (146 mg, 0.385 mmol) and stirred at room temperature for 16 hours. The solution was diluted with DCM, washed with saturated NaHCO₃, dried and concentrated under reduced pressure. The resultant DMF solution was added dropwise to a beaker containing ice-water (200 mL), with stirring. The mixture was stirred for 15 minutes then the precipitate was collected by filtration and washed with H₂O. The material was re-dissolved in DCM, washed with H₂O, dried and concentrated under reduced pressure. The residue was further dried under reduced pressure at 40° C. for 20 hours. This was then dissolved in DCM and treated with 2M HCl in Et₂O (2 mL). The mixture was stirred for 15 minutes then the volatiles were removed under reduced pressure and the residue was triturated in Et₂O and dried under reduced pressure at 40° C. for 16 hours to afford the title compound (72 mg).

LCMS method: Method 1, RT: 3.44 min, MI: 468 [M−1]

¹H NMR (500 MHz, DMSO-d₆) δ 12.71 (s, 1H), 10.12 (s, 1H), 7.73 (d, 2H), 7.55 (d, 2H), 4.21 (d, 2H), 4.11 (t, 1H), 4.02 (dd, 1H), 3.25 (d, 2H), 3.15 (s, 1H), 3.02-2.87 (m, 3H), 2.82-2.74 (m, 3H), 1.78-1.65 (m, 6H), 1.49 (m, 1H), 1.34 (m, 3H), 1.15 (m, 1H), 0.87 (d, 3H), 0.82 (t, 3H)

Coupling Method H (CM H) [HATU]

Synthesis of 1-(4-morpholin-4-ylmethyl-phenyl)-5-oxo-pyrrolidine-3-carboxylic acid [5-(4-fluoro-benzylsulfanyl)-[1,3,4]thiadiazol-2-yl]-amide (F154)

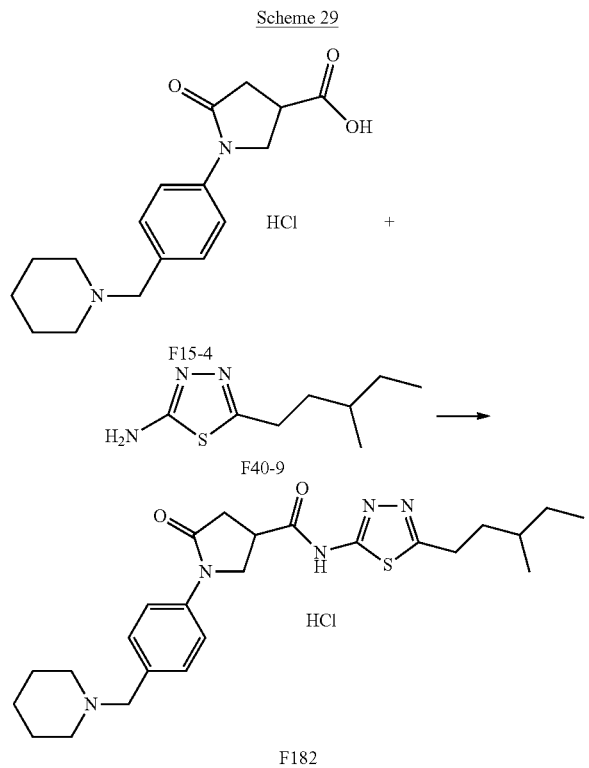

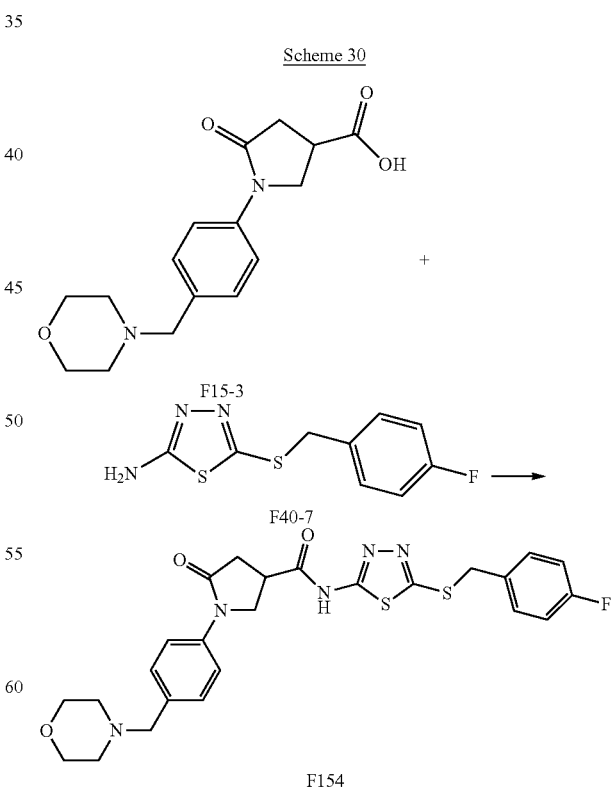

1-(4-Morpholin-4-ylmethyl-phenyl)-5-oxo-pyrrolidine-3-carboxylic acid (50 mg, 0.150 mmol) and HATU (113 mg,

121

0.300 mmol) were dissolved in DCM (10 mL) and treated with DIPEA (53 µL, 0.300 mmol) and the mixture was stirred at room temperature for 3 hours. 2-Amino-5-(4-fluorobenzylthio)-1,3,4-thiadiazole (43 mg, 0.180 mmol) and DIPEA (53 µL, 0.300 mmol) were then added and the mixture was stirred for 16 hours at room temperature. The reaction mixture was concentrated under reduced pressure and purified over silica gel using a gradient of 0-100% EtOAc/hexane and then 0-10% MeOH/DCM. The relevant fractions were combined and concentrated under reduced pressure then further purified by mass-directed preparative LCMS. The required fractions were combined and concentrated under reduced pressure to afford the title compound (4 mg).

LCMS method: Method 5, RT: 2.64 min, MI: 528 [M+1]

$^1$H NMR (400 MHz, CDCl$_3$) δ 7.55 (d, 2H), 7.29 (m, 4H), 6.96 (m, 2H), 4.33 (s, 2H), 4.22 (d, 2H), 3.83 (t, 1H), 3.71 (br m, 4H), 3.49 (br s, 2H), 3.07 (dd, 2H), 2.46 (br s, 4H)

Synthesis of Compounds Containing Amine Linkers

Compounds F216 and F181 were prepared as described below in Schemes 31 and 32:

Synthesis of 4-({5-[2-(4-Chloro-phenyl)-ethyl]-[1,3,4]thiadiazol-2-ylmethyl}-amino)-1-(4-morpholin-4-ylmethyl-phenyl)-pyrrolidin-2-one; hydrochloride (F183)

Scheme 31

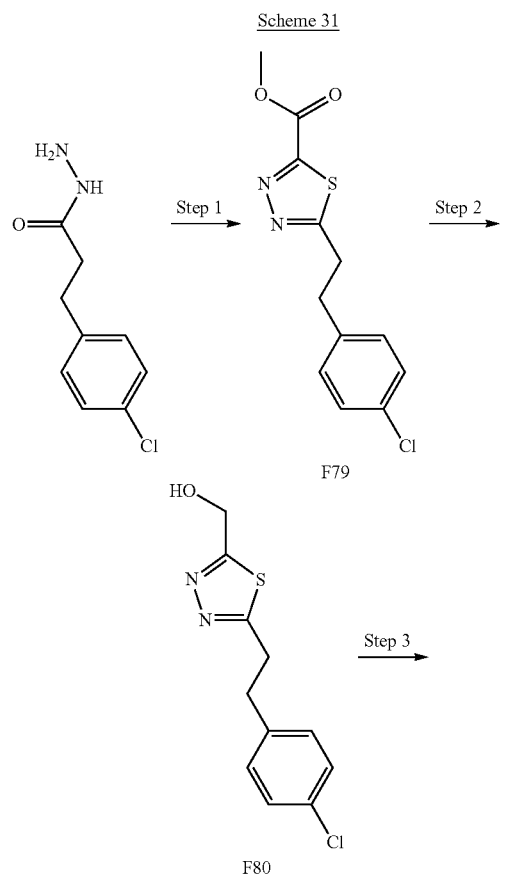

122

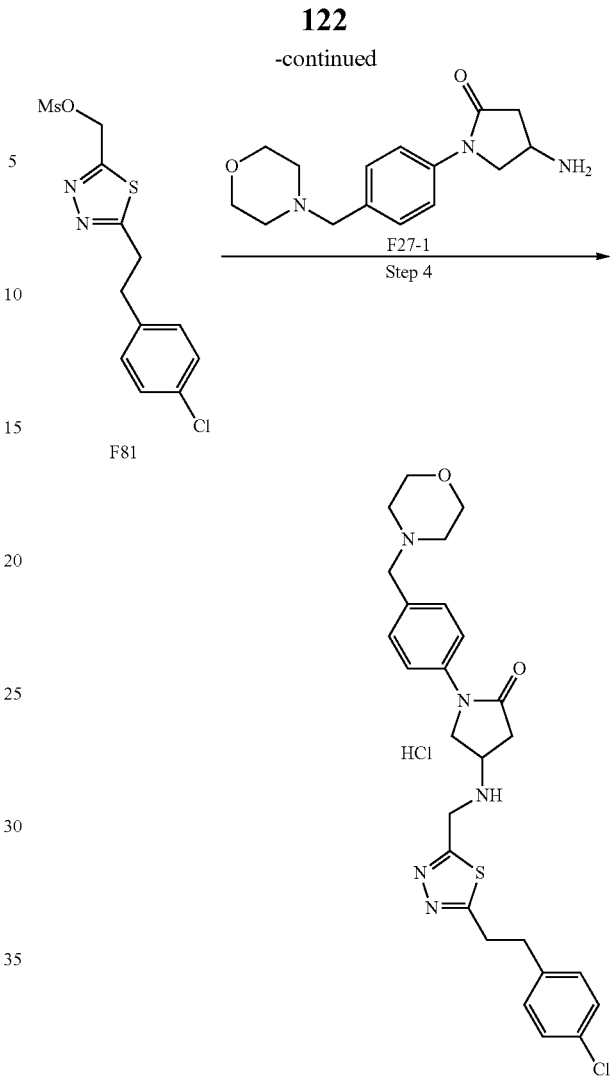

Step 1

Synthesis of 5-[2-(4-chloro-phenyl)-ethyl]-[1,3,4]thiadiazole-2-carboxylic acid methyl ester (F79)

To a mixture of 3-(4-chloro-phenyl)-propionic acid hydrazide (5 g, 25.2 mmol) and NEt$_3$ (7 mL, 50.4 mmol) in DCM (30 mL) was added methyl chlorooxoacetate (2.4 mL, 26.4 mmol) over 30 min at 0° C. The reaction mixture was warmed to room temperature and stirred for 2 hours. After this time, the reaction mixture was diluted with H$_2$O (5 mL) and the organic layer was separated, washed with saturated aqueous sodium bicarbonate solution (10 mL), dried (MgSO$_4$), filtered, and concentrated under reduced pressure. This residue was dissolved in anhydrous THF (25 mL) and to this solution was added Lawesson's reagent (7.9 g, 19.400 mmol) and the mixture was heated at 60° C. for 5 hours. After this time, the reaction mixture was concentrated under reduced pressure and the residual material was purified by flash column chromatography eluting with DCM/MeOH (0-10%) to afford the title compound (2.20 g).

LCMS method: Method 1, RT: 4.81 min, MI: 283 [M+1]

123

Step 2

Synthesis of {5-[2-(4-chloro-phenyl)-ethyl]-[1,3,4]thiadiazol-2-yl}-methanol (F80)

To a solution of 5-[2-(4-chloro-phenyl)-ethyl]-[1,3,4]thiadiazole-2-carboxylic acid methyl ester (2.01 g, 7.1 mmol) in EtOH (25 mL) was added sodium borohydride (537 mg, 14.2 mmol) portionwise at 0° C. The reaction mixture was warmed to room temperature and stirred for 2 hours. The reaction mixture was then concentrated under reduced pressure and the residue was partitioned between H$_2$O (50 mL) and DCM (50 mL). The organic layer was separated, washed with H$_2$O, dried (MgSO$_4$), filtered and concentrated under reduced pressure to afford the title compound (1.80 g).

LCMS method: Method 1, RT: 4.32 min, MI: 255 [M+1]

Step 3

Synthesis of [5-[2-(4-chlorophenyl)ethyl]-1,3,4-thiadiazol-2-yl]methyl methanesulfonate (F81)

To a mixture of {5-[2-(4-chloro-phenyl)-ethyl]-[1,3,4]thiadiazol-2-yl}-methanol (1.8 g, 7.05 mmol) and NEt$_3$ (3 mL, 21.15 mmol) in DCM (40 mL) at 0° C. was added methanesulfonyl chloride (1.2 mL, 15.4 mmol). The reaction mixture was stirred at 0° C. for 1 hour then H$_2$O was added and the organic layer was separated, washed with saturated aqueous NaHCO$_3$ solution, dried (MgSO$_4$), filtered and concentrated under reduced pressure to afford the title compound (1.20 g).

LCMS method: Method 1, RT: 4.48 min, MI: 333 [M+1]

Step 4

Synthesis of 4-({5-[2-(4-chloro-phenyl)-ethyl]-[1,3,4]thiadiazol-2-ylmethyl}-amino)-1-(4-morpholin-4-ylmethyl-phenyl)-pyrrolidin-2-one; hydrochloride (F183)

Coupling Method I (CM I) [Alkylation]
Amino-Pyrrolidinone

To a mixture of 4-amino-1-(4-morpholin-4-ylmethyl-phenyl)-pyrrolidin-2-one (290 mg, 1.04 mmol) and methanesulfonic acid 5-[2-(4-chloro-phenyl)-ethyl]-[1,3,4]thiadiazol-2-ylmethyl ester (380 mg, 1.14 mmol) in DMF (2 mL) was added NEt$_3$ (160 µl, 1.14 mmol). The mixture was stirred at room temperature for 16 hours. The reaction mixture was then diluted with DCM, washed with saturated NaHCO$_3$, dried (MgSO$_4$), filtered and concentrated under reduced pressure. The residual material was purified by flash column chromatography using a gradient of 0-90% DCM/MeOH and the desired fractions were combined and concentrated under reduced pressure. The material was then dissolved in DCM (5 mL) and treated with 2M HCl in Et$_2$O (2 mL). The volatiles were then evaporated under reduced pressure and triturated with Et$_2$O to afford the title compound (17 mg).

LCMS method: Method 4, RT: 2.07 min, MI: 512 [M+1]
$^1$H NMR (500 MHz, DMSO-d$_6$) δ 10.71 (br s, 1H), 9.80 (d, 1H), 7.76 (d, 2H), 7.57 (d, 2H), 7.34 (d, 2H), 7.29 (d, 2H), 4.68 (m, 1H), 4.30 (d, 2H), 4.18 (dd, 1H), 3.91 (m, 2H), 3.83 (dd, 1H), 3.71 (m, 2H), 3.47 (t, 2H), 3.18 (m, 2H), 3.05 (t, 2H), 3.02 (m, 1H), 2.95 (dd, 1H), 2.73 (dd, 1H)

124

Synthesis of 4-({5-[2-(4-Chloro-phenyl)-ethyl]-[1,3,4]thiadiazol-2-ylamino}-methyl)-1-(4-morpholin-4-ylmethyl-phenyl)-pyrrolidin-2-one (F153)

Scheme 32

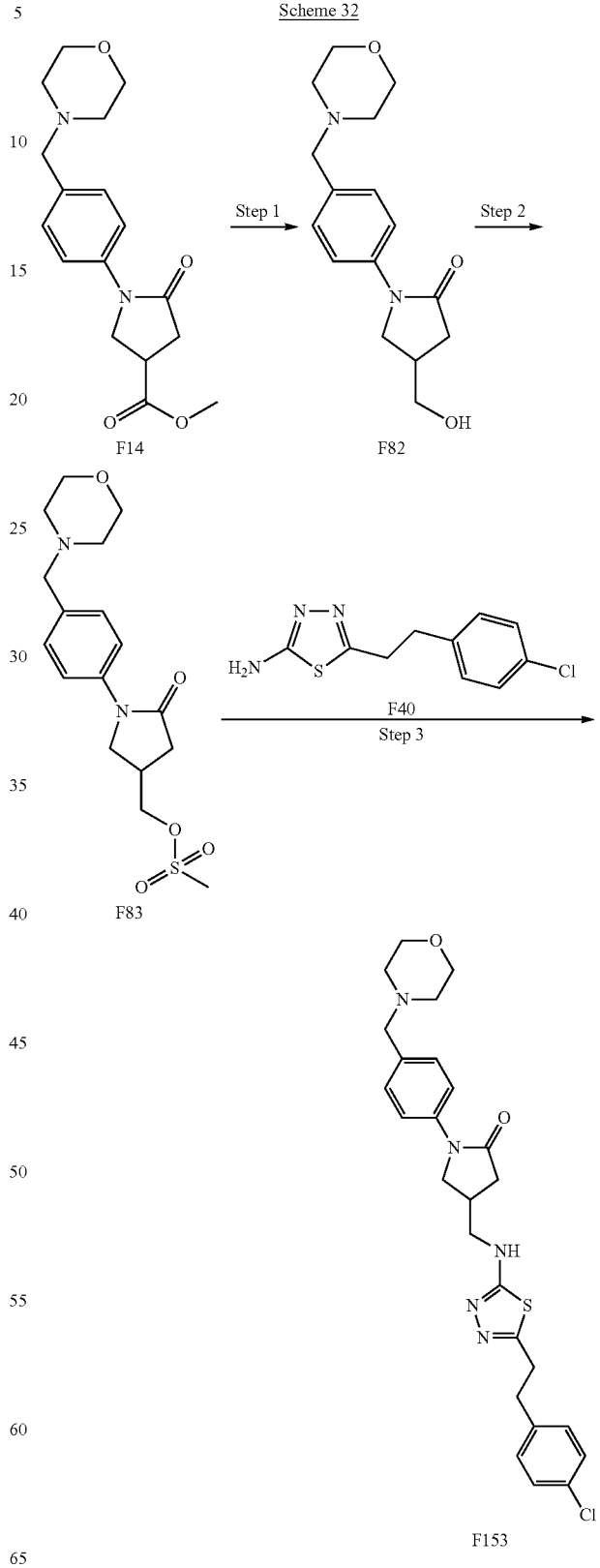

Step 1

Synthesis of 4-hydroxymethyl-1-(4-morpholin-4-ylmethyl-phenyl)-pyrrolidin-2-one (F82)

To a solution of 1-(4-morpholin-4-ylmethyl-phenyl)-5-oxo-pyrrolidine-3-carboxylic acid methylester (0.401 g, 1.258 mmol) in EtOH (5 mL) was added sodium borohydride (0.143 g, 3.774 mmol) at 0° C. The reaction mixture was warmed to room temperature and stirred for 1.75 hours. The reaction was quenched with $H_2O$ and stirred for 16 hours. A precipitate was removed by filtration and the filtrate was concentrated under reduced pressure. The crude material was purified using a 5 g SCX column, which was washed with MeOH and then 2M $NH_3$/MeOH. The second fraction was concentrated under reduced pressure to afford the title compound (250 mg).

$^1$H NMR (400 MHz, DMSO-$d_6$) δ 7.61 (m, 2H), 7.29 (m, 2H), 4.87 (t, 1H), 3.89 (dd, 1H), 3.61 (dd, 1H), 3.56 (t, 4H), 3.46-3.42 (m, 4H), 3.18 (d, 1H, underintegrating slightly), 2.60 (m, 1H), 2.33-2.26 (m, 5H)

Step 2

Synthesis of methanesulfonic acid 1-(4-morpholin-4-ylmethyl-phenyl)-5-oxo-pyrrolidin-3-ylmethyl ester (F83)

4-Hydroxymethyl-1-(4-morpholin-4-ylmethyl-phenyl)-pyrrolidin-2-one (0.976 g, 3.361 mmol) was dissolved in DCM (50 mL) and treated with $NEt_3$ (2.33 mL, 16.805 mmol). The mixture was cooled to 0° C. and methanesulfonyl chloride (0.399 mL, 5.042 mmol) was added under nitrogen. The reaction mixture was stirred at room temperature for 60 hours then aqueous saturated sodium bicarbonate solution (150 mL) was added. The aqueous phase was extracted three times with EtOAc (3×100 mL) then the combined organics were dried and concentrated under reduced pressure. The crude product was purified by flash column chromatography eluting with a gradient of 0-5% MeOH/DCM to afford the title compound (803 mg).

$^1$H NMR (400 MHz, DMSO-$d_6$) δ 7.60 (m, 2H), 7.30 (m, 2H), 4.30 (m, 2H), 3.97 (dd, 1H), 3.65 (dd, 1H), 3.56 (t, 4H), 3.42 (s, 2H), 3.23 (s 3H), 2.87 (m, 1H), 2.69 (dd, 1H), 2.41-2.32 (m, 5H)

Step 3

Synthesis of 4-({5-[2-(4-chloro-phenyl)-ethyl]-[1,3,4]thiadiazol-2-ylamino}-methyl)-1-(4-morpholin-4-ylmethyl-phenyl)-pyrrolidin-2-one (F153)

Coupling Method J (CM J) [Alkylation] Amino-Thiadiazole

A mixture of methanesulfonicacid1-(4-morpholin-4-ylmethyl-phenyl)-5-oxo-pyrrolidin-3-ylmethyl ester (500 mg, 1.36 mmol), 5-[2-(4-chloro-phenyl)-ethyl]-[1,3,4]thiadiazol-2-ylamine (293 mg, 1.22 mmol) and $K_2CO_3$ (281 mg, 2.04 mmol) in DMF (12 mL) was stirred at 80° C. for 16 hours and then at 100° C. for 3 hours. The reaction mixture was then cooled to room temperature, diluted with DCM (50 mL) and washed with $H_2O$ (2×50 mL). The organic phase was then dried (phase separation paper). Purification was carried out by mass-directed preparative LCMS and the desired fractions were dried under reduced pressure. The residue was purified using an SCX column, which was washed with MeOH and then the product eluted with 1M $NH_3$/MeOH. The second fraction was concentrated under reduced pressure to afford the title compound (40 mg).

LCMS method: Method 5, RT: 2.59 min, MI: 512 [M+1]
$^1$H NMR (400 MHz, DMSO-$d_6$) δ 7.78 (t, 1H), 7.59 (d, 2H), 7.35-7.28 (m, 6H), 3.94 (dd, 1H), 3.61 (dd, 1H), 3.56 (t, 4H), 3.43 (s, 2H), 3.37 (t, 2H), 3.12 (t, 2H), 2.94 (t, 2H), 2.79-2.72 (m, 1H), 2.69-2.63 (m, 1H), 2.36-2.31 (m, 5H)

Synthesis of Compounds Wherein One of $R_1$ or $R_2$ is $C(O)R_a$, Wherein $R_1$, $R_2$ and $R_a$ are as Defined Herein Above Compound F184 was prepared as described below in Scheme 33:

Synthesis of 1-Methyl-piperidine-4-carboxylic acid 4-(4-{5-[2-(4-chloro-phenyl)-ethyl]-[1,3,4]thiadiazol-2-ylcarbamoyl}-2-oxo-pyrrolidin-1-yl)-benzylamide (F184)

Scheme 33

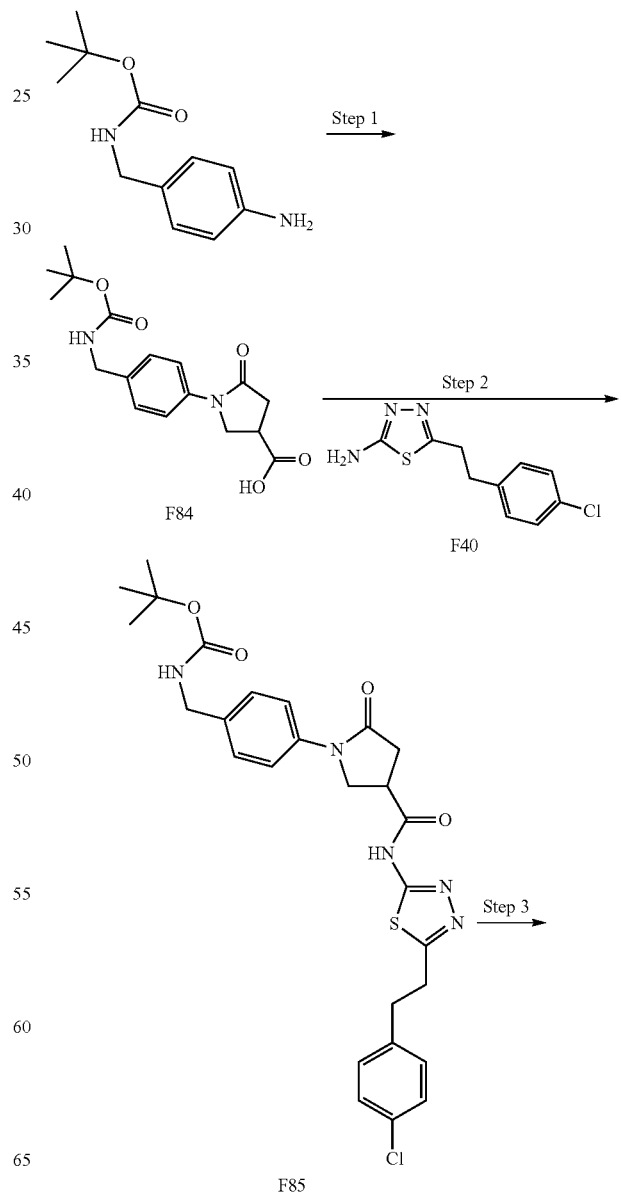

-continued

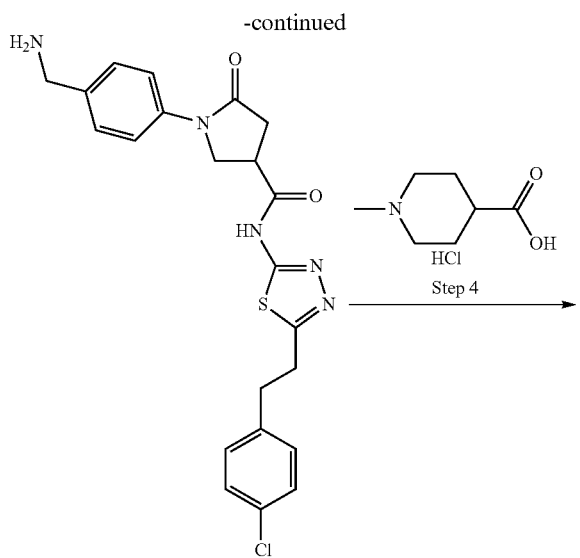

F203

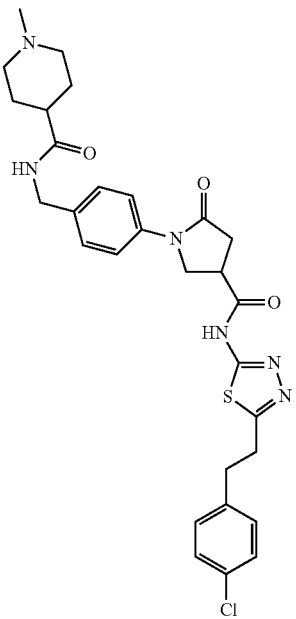

F184

Step 1

Synthesis of 1-[4-(tert-butoxycarbonylamino-methyl)-phenyl]-5-oxo-pyrrolidine-3-carboxylic acid (F84)

4[(N-Boc)aminomethyl]aniline (0.95 g, 4.274 mmol), itaconic acid (0.56 g, 4.304 mmol) and toluene (10 mL) were combined and heated to 100° C. for 4 hours then cooled to room temperature. MTBE (4 mL) was added and this mixture was stirred for 16 hours at room temperature. 1M NaOH solution (10 mL) was added and the layers were separated. The organic fraction was washed with 1M NaOH solution (10 mL) then the aqueous layers were combined and extracted with MTBE (20 mL). The aqueous layer was cooled in an ice bath and adjusted to pH 6 with conc.HCl, then to pH 4 with saturated sodium citrate solution. The resultant solid was isolated by filtration, washed with H$_2$O (2×2 mL) and dried under reduced pressure to afford the title compound (0.95 g).

LCMS method: Method 6, RT: 5.10 mg, MI: 333 [M−1]
$^1$H NMR (400 MHz, DMSO-d$_6$) δ 12.82 (br s, 1H), 7.58 (d, 2H), 7.38 (t, 1H), 7.23 (d, 2H), 4.09 (d, 2H), 4.03 (t, 1H), 3.95 (dd, 1H), 3.33 (m, 1H), 2.77 (dd, 1H), 2.69 (dd, 1H), 1.39 (s, 9H)

Step 2

Synthesis of [4-(4-{5-[2-(4-chloro-phenyl)-ethyl]-[1,3,4]thiadiazol-2-ylcarbamoyl}-2-oxo-pyrrolidin-1-yl)-benzyl]-carbamic acid tert-butyl ester (F85)

1-[4-(tert-Butoxycarbonylamino-methyl)-phenyl]-5-oxo-pyrrolidine-3-carboxylic acid (1.18 g, 3.529 mmol) was dissolved in DMA (20 mL) then HBTU (3.355 g, 8.823 mmol) and DIPEA (1.232 mL, 7.058 mmol) were added. The mixture was stirred at room temperature for 1 hour, then 5-[2-(4-chloro-phenyl)-ethyl]-[1,3,4]thiadiazol-2-ylamine (423 mg, 1.764 mmol) was added. The mixture was stirred for 16 hours at room temperature then NaHCO$_3$ was added and the resultant precipitate was isolated by filtration and washed with H$_2$O to afford the title compound (2.065 g).

LCMS method: Method 3, RT: 4.37 min, MI: 556 [M+1]

Step 3

Synthesis of 1-(4-aminomethyl-phenyl)-5-oxo-pyrrolidine-3-carboxylic acid {5-[2-(4-chloro-phenyl)-ethyl]-[1,3,4]thiadiazol-2-yl}-amide (F203)

[4-(4-{5-[2-(4-Chloro-phenyl)-ethyl]-[1,3,4]thiadiazol-2-ylcarbamoyl}-2-oxo-pyrrolidin-1-yl)-benzyl]-carbamic acid tert-butyl ester (2.00 g, 3.597 mmol) was dissolved in DCM (20 mL) and treated with 2M HCl/Et$_2$O (10 mL) and stirred at room temperature for 2 hours. 2M HCl/Et$_2$O (5 mL) was added and the reaction mixture stirred at room temperature for 16 hours. The resultant precipitate was isolated by filtration and washed with DCM and Et$_2$O. The solid was dissolved in a mixture of MeOH/DCM/DMSO and purified using an SCX cartridge, washing first with MeOH then eluting with 2M NH$_3$/MeOH. The second fraction was concentrated under reduced pressure then the material was purified by flash column chromatography using a gradient of 0-10% MeOH/DCM. The relevant fractions were combined and concentrated under reduced pressure (0.67 g). 50 mg of the residue was purified by mass-directed preparative LCMS to afford the title compound (30 mg).

LCMS method: Method 1, RT: 3.29 min, MI: 456 [M+1]
$^1$H NMR (500 MHz, DMSO-d$_6$) δ 8.31 (s, 1H), 7.62 (d, 2H), 7.39 (d, 2H), 7.33 (d, 2H), 7.28 (d, 2H), 4.06 (t, 1H), 4.00 (dd, 1H), 3.85 (s, 2H), 3.54 (m, 1H), 3.27 (t, 2H), 3.01 (t, 2H), 2.83 (dd, 1H), 2.75 (dd, 1H)

Step 4

Synthesis of 1-methyl-piperidine-4-carboxylic acid 4-(4-{5-[2-(4-chloro-phenyl)-ethyl]-[1,3,4]thiadiazol-2-ylcarbamoyl}-2-oxo-pyrrolidin-1-yl)-benzyl-amide (F184)

Coupling Method K (CM K) [HBTU]

To a solution of 1-methylpiperidine-4-carboxylic acid; hydrochloride (95 mg, 0.526 mmol) in DMA (5 mL) was added HBTU (200 mg, 0.526 mmol) and DIPEA (192 µL, 1.10 mmol). The reaction mixture was stirred at room temperature for 1 hour, then 1-(4-aminomethyl-phenyl)-5-oxo-pyrrolidine-3-carboxylic acid {5-[2-(4-chloro-phenyl)-ethyl]-[1,3,4]thiadiazol-2-yl}-amide (200 mg, 0.429 mmol) was added. The reaction mixture was stirred at room temperature for 16 hours then saturated NaHCO$_3$ solution was added and the resulting white precipitate was isolated by filtration. The precipitate was dissolved in H$_2$O, extracted with DCM, passed through a phase separation cartridge and concentrated under reduced pressure to afford the title compound (240 mg).

LCMS method: Method 1, RT: 3.52 min, MI: 581 [M+1]

$^1$H NMR (500 MHz, DMSO-d$_6$) δ 12.68 (s, 1H), 7.56 (d, 2H), 7.32 (d, 2H), 7.28 (d, 2H), 7.22 (d, 2H), 4.24 (d, 2H), 4.06 (dd, 1H), 3.97 (dd, 1H), 3.60 (m, 2H), 3.42 (br m, 2H), 3.30 (t, 2H under water peak), 3.13 (m, 2H), 3.02 (t, 2H), 2.84 (dd, 2H), 2.74 (s, 3H)

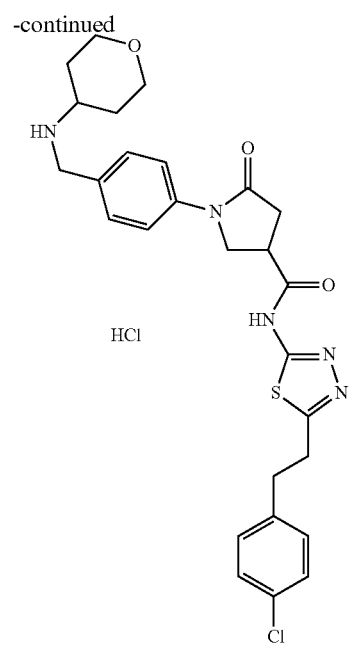

F105

Synthesis of Compounds Wherein One of R$_1$ or R$_2$ is H, Wherein R$_1$ and R$_2$ are as Defined Herein Above Compound F105 was prepared as described below in Scheme 34:

Step 1

Synthesis of 5-oxo-1-{4-[(tetrahydro-pyran-4-ylamino)-methyl]-phenyl}-pyrrolidine-3-carboxylic acid {5-[2-(4-chloro-phenyl)-ethyl]-[1,3,4]thiadiazol-2-yl}-amide; hydrochloride Starting from compound F203 as described in Scheme 33 above:

A vial was charged with 1-(4-aminomethyl-phenyl)-5-oxo-pyrrolidine-3-carboxylic acid {5-[2-(4-chloro-phenyl)-ethyl]-[1,3,4]thiadiazol-2-yl}-amide (0.199 g, 0.437 mmol), tetrahydro-4H-pyran-4-one (44 mg, 0.437 mmol), MP-CNBH$_3$ (2 mmol/g, 656 mg) and acetic acid (15 µL) in DCM (5 mL). The reactions were shaken overnight at room temperature. The resin was filtered off and the filtrate was purified by SCX, washing first with MeOH then eluting with 2M NH$_3$/MeOH. The second fraction was concentrated under reduced pressure. The residue was passed through a pad of silica, flushing with EtOAc then 10% MeOH/DCM and the volatiles were removed under reduced pressure to afford the title compound (145 mg).

LCMS method: Method 3, RT: 3.86 min, MI: 540 [M+1]

$^1$H NMR (500 MHz, DMSO-d$_6$) δ 7.68 (d, 2H), 7.51 (d, 2H), 7.33 (d, 2H), 7.29 (d, 2H), 4.08 (m, 3H), 4.02 (t, 1H), 3.90 (dd, 2H), 3.61 (m, 1H), 3.30 (m, 5H, hidden under water peak), 3.02 (t, 2H), 2.88 (dd, 1H), 2.76 (dd, 1H), 1.96 (br d, 2H), 1.59 (br m, 2H)

Scheme 34

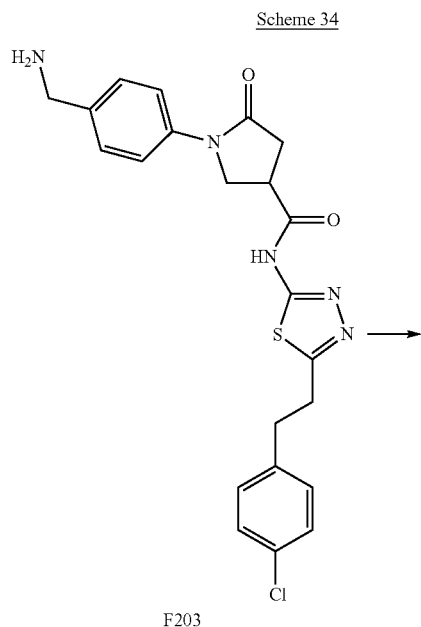

F203

Synthesis of the Pyrrolidine Core

Compounds F131 and F167 were prepared as described below in Schemes 35 and 36:

131

Synthesis of 5-[2-(4-Chloro-phenyl)-ethyl]-[1,3,4]thiadiazole-2-carboxylic acid [(R)-1-(4-morpholin-4-ylmethyl-phenyl)-pyrrolidin-3-yl]-amide (F131)

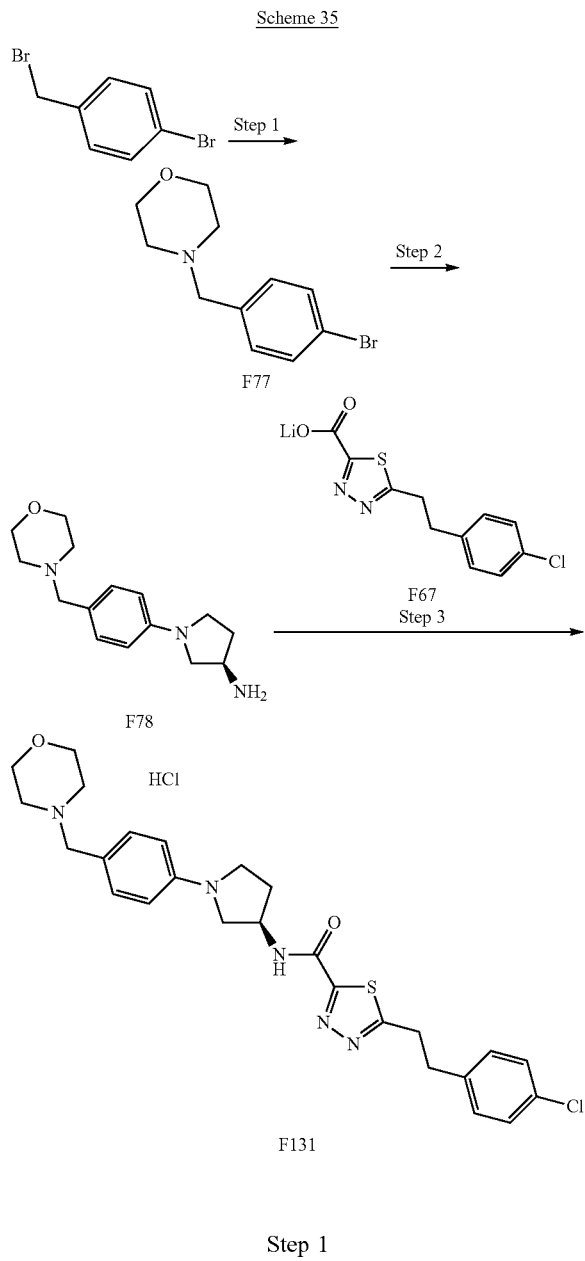

Step 1

Synthesis of 4-(4-bromo-benzyl)-morpholine (F77)

To a solution of 4-bromobenzyl bromide (15 g, 60 mmol) in EtOH (200 mL) was added morpholine (6 mL, 66 mmol) and K$_2$CO$_3$ (33 g, 238 mmol) and the mixture was stirred at reflux for 5 hours. The mixture was filtered and the solvent was evaporated under reduced pressure. The crude material was treated with Et$_2$O and the mixture was filtered. The solvent was evaporated under reduced pressure to afford the title compound (13 g).

LCMS method: Method 1, RT: 1.20 min, MI: 256/258 [M+1]

132

Step 2

Synthesis of (R)-1-(4-morpholin-4-ylmethyl-phenyl)-pyrrolidin-3-ylamine (F78)

A mixture of 4-(4-bromo-benzyl)-morpholine (460 mg, 1.8 mmol), (S)-(-)-3-(Boc-amino)pyrrolidine (502 mg, 2.7 mmol), K$_2$CO$_3$ (500 mg, 3.6 mmol), CuI (34 mg, 0.179 mmol) and L-proline (104 mg, 0.9 mmol) in DMSO (10 mL) was heated at 90° C. overnight. The reaction mixture was then partitioned between water and EtOAc. The organic layer was separated and the aqueous layer was extracted with EtOAc. The organic layer was washed with brine (10 mL), dried (MgSO$_4$), filtered and the solvent was evaporated under reduced pressure. The residue was purified by flash column chromatography (gradient of 0-10% MeOH in DCM). The residue was dissolved in 2 mL of TFA/DCM (1:2) and stirred at room temperature then the solvent was evaporated under reduced pressure.

LCMS method: Method 3, RT: 3.92 min, MI: 262 [M+1]

$^1$H NMR (500 MHz, DMSO-d$_6$) δ 7.05 (d, 2H), 6.43 (d, 2H), 3.53 (m, 4H), 3.36 (m, 1H), 3.29 (s, 2H), 3.19 (m, 1H), 2.86 (m, 1H), 2.27 (m, 4H), 2.06 (m, 1H), 1.69 (m, 1H)

Step 3

Synthesis of 5-[2-(4-chloro-phenyl)-ethyl]-[1,3,4]thiadiazole-2-carboxylic acid [(R)-1-(4-morpholin-4-ylmethyl-phenyl)-pyrrolidin-3-yl]-amide hydrochloride (F131)

A mixture of lithium; 5-[2-(4-chloro-phenyl)-ethyl]-[1,3,4]thiadiazole-2-carboxylate (193 mg, 0.074 mmol) and (R)-1-(4-morpholin-4-ylmethyl-phenyl)-pyrrolidin-3-ylamine (0.14 g, 0.542 mmol) in DMF 10 mL) was treated with triethylamine (174 μL 1.247 mmoL), followed by addition of HBTU (268 mg, 0.704 mmoL). The mixture was stirred at room temperature overnight. The solution was then diluted with DCM, washed with saturated aqueous NaHCO$_3$s solution, dried and the solvent was evaporated under reduced pressure. The residue was purified by flash column chromatography (gradient of 0-10% MeOH in DCM). The resulting compound was dissolved in DCM (5 mL) and treated with 2M HCl in Et$_2$O (2 mL). The volatiles were evaporated under reduced pressure and the residue was triturated in Et$_2$O to afford the title compound (65 mg).

LCMS method: Method 1, RT: 1.81 min, MI: 512 [M+1]

$^1$H NMR (500 MHz, DMSO-d$_6$) δ 10.67 (br s, 1H), 9.50 (d, 1H), 7.34 (m, 4H), 7.29 (d, 2H), 6.57 (d, 2H), 4.58 (m, 1H), 4.16 (d, 2H), 3.92 (m, 2H), 3.74 (dd, 2H), 3.58 (dd, 1H), 3.46 (t, 2H), 3.38 (m, 1H), 3.30 (m, 2H), 3.16 (m, 2H), 3.05 (t, 2H), 2.96 (m, 2H), 2.24 (m, 1H), 2.13 (m, 1H)

Synthesis of 5-[2-(4-Chloro-phenyl)-ethyl]-[1,3,4]thiadiazole-2-carboxylic acid [(S)-1-(4-morpholin-4-ylmethyl-phenyl)-pyrrolidin-3-yl]-amide (F167)

Scheme 36

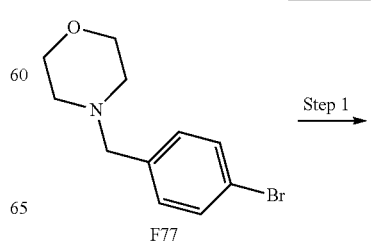

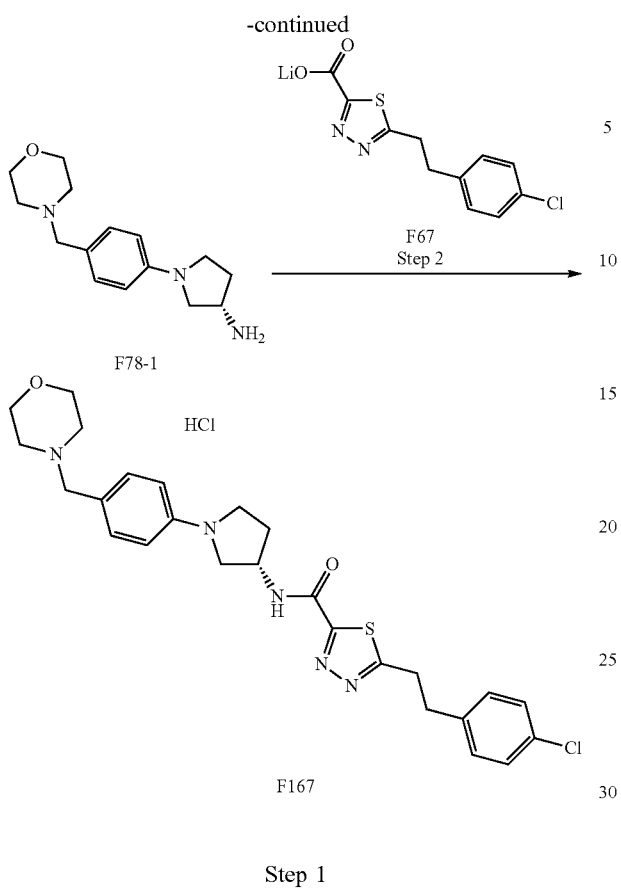

Step 1

Synthesis of (S)-1-(4-Morpholin-4-ylmethyl-phenyl)-pyrrolidin-3-ylamine (F78-1)

Starting from F77 as described above in Scheme 35:

A mixture of 4-(4-bromo-benzyl)-morpholine (460 mg, 1.8 mmol), (S)-(−)-3-(Boc-amino)pyrrolidine (502 mg, 2.7 mmol), $K_2CO_3$ (500 mg, 3.6 mmol), CuI (34 mg, 0.179 mmol) and L-proline (104 mg, 0.9 mmol) in DMSO (10 mL) was heated at 90° C. overnight. The reaction mixture was then partitioned between water and EtOAc. The organic layer was separated and the aqueous layer was extracted with EtOAc. The organic layer was washed with brine (10 mL), dried ($MgSO_4$), filtered and the solvent was evaporated under reduced pressure. The residue was dissolved in 4 mL of TFA/DCM (1:2). The solvent was then evaporated under reduced pressure and the residue was purified by flash column chromatography (gradient of 0-30% EtOAc in cyclohexane) to afford the title compound.

LCMS method: Method 3, RT: 3.92 min, MI: 262 [M+1]
$^1$H NMR (500 MHz, DMSO-$d_6$) δ 7.05 (d, 2H), 6.42 (d, 2H), 3.52 (m, 4H), 3.36 (m, 2H), 3.32 (t, 2H), 2.29 (t, 2H)

Step 2

Synthesis of 5-[2-(4-chloro-phenyl)-ethyl]-[1,3,4]thiadiazole-2-carboxylic acid [(S)-1-(4-morpholin-4-ylmethyl-phenyl)-pyrrolidin-3-yl]-amide (F167)

A mixture of lithium; 5-[2-(4-chloro-phenyl)-ethyl]-[1,3,4]thiadiazole-2-carboxylate (193 mg, 0.704 mmol) and (S)-1-(4-morpholin-4-ylmethyl-phenyl)-pyrrolidin-3-ylamine (0.14 g, 0.542 mmol) in DMF (10 mL) was treated with triethylamine (174 μL, 1.274 mmol), followed by addition of HBTU (268 mg, 0.704 mmol). The mixture was stirred at room temperature overnight. The solution was then diluted with DCM, washed with saturated aqueous $NaHCO_3$ solution, dried and the solvent was evaporated under reduced pressure. The residue was purified by flash column chromatography (gradient of 0-10% MeOH in DCM). The resulting compound was dissolved in DCM (5 mL) and treated with 2M HCl in $Et_2O$ (2 mL). The volatiles were evaporated under reduced pressure and the residue was triturated in $Et_2O$ to afford the title compound (65 mg).

LCMS method: Method 7, RT: 3.94 min, MI: 512 [M+1]
$^1$H NMR (500 MHz, DMSO-$d_6$) δ 10.91 (br s, 1H), 9.50 (d, 1H), 7.36 (m, 4H), 7.29 (d, 2H), 6.56 (d, 2H), 4.59 (m, 1H), 4.15 (d, 2H), 3.91 (m, 2H), 3.74 (t, 2H), 3.56 (dd, 1H), 3.46 (t, 2H), 3.38 (m, 1H), 3.28 (dd, 2H), 3.16 (m, 2H), 3.05 (t, 2H), 2.98 (m, 2H), 2.24 (m, 1H), 2.13 (m, 1H)

Synthesis of Compounds Wherein $R_1$ or $R_2$ are Linked to Form a Piperazine

Compound F160 was prepared as described below in Scheme 37:

Synthesis of 5-Oxo-1-(4-piperazin-1-ylmethyl-phenyl)-pyrrolidine-3-carboxylic acid {5-[2-(4-chlorophenyl)-ethyl]-[1,3,4]thiadiazol-2-yl}-amide; dihydrochloride (F160)

Scheme 37

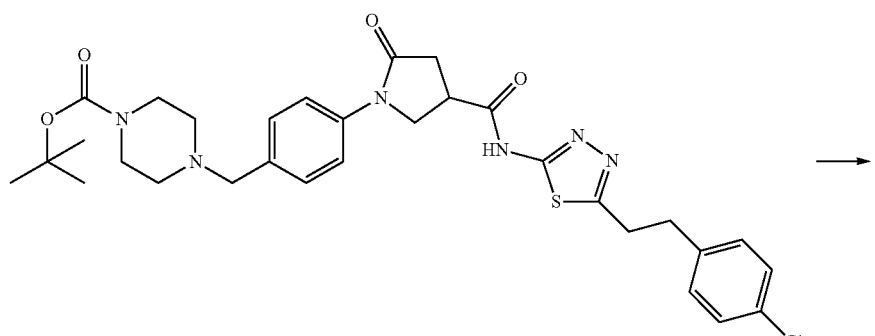

F157

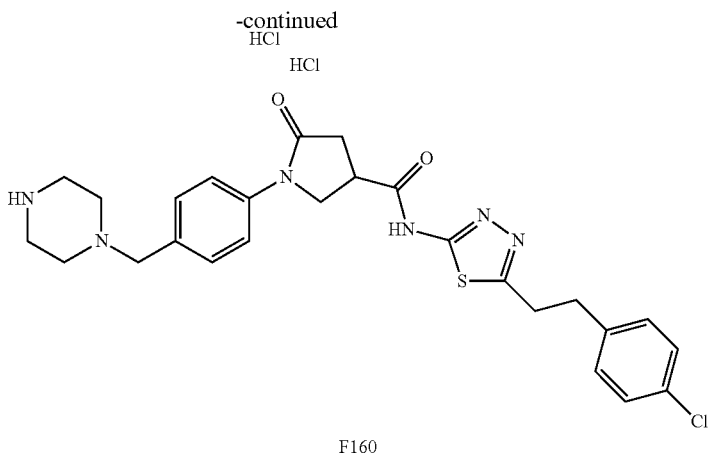

F160

4-[4-(4-{5-[2-(4-Chloro-phenyl)-ethyl]-[1,3,4]thiadiazol-2-ylcarbamoyl}-2-oxo-pyrrolidin-1-yl)-benzyl]-piperazine-1-carboxylic acid tert-butyl ester (20 mg, 0.032 mmol) was dissolved in DCM (0.5 mL) and treated with 4N HCl/1,4-dioxane (0.5 mL). A precipitate formed immediately so the volatiles were removed under reduced pressure, azeotroping with toluene, to afford the title compound (17 mg).

LCMS method: Method 1, RT: 3.31 min, MI: 525 [M+1]

Synthesis of Compounds Wherein $R_1$ or $R_2$ are Linked to Form a Homopiperazine Compound F156 was prepared as described below in Scheme 38:

Synthesis of 1-(4-[1,4]Diazepan-1-ylmethyl-phenyl)-5-oxo-pyrrolidine-3-carboxylic acid {5-[2-(4-chloro-phenyl)-ethyl]-[1,3,4]thiadiazol-2-yl}-amide; dihydrochloride (F156)

Scheme 38

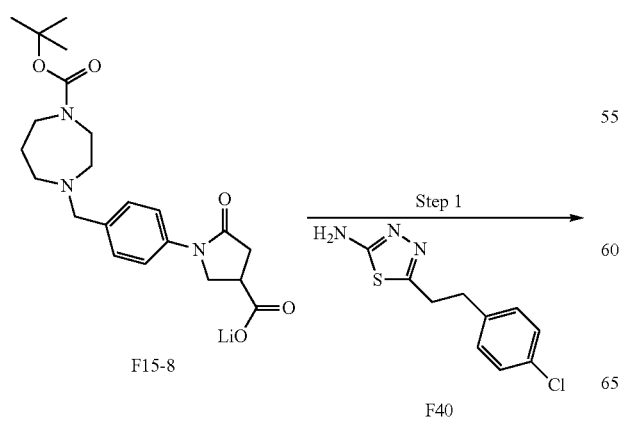

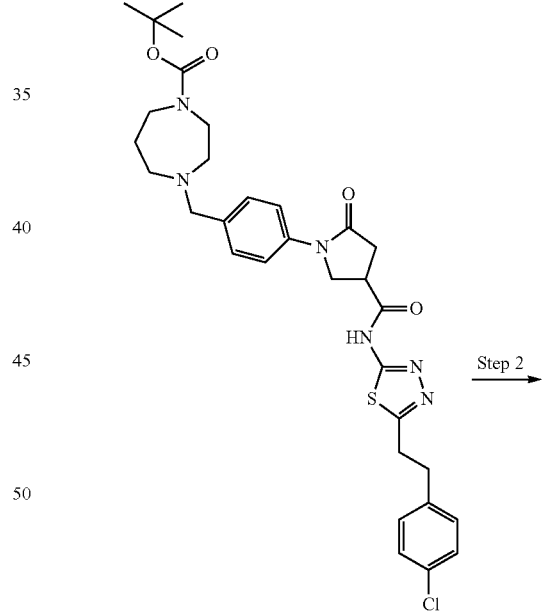

F86

-continued

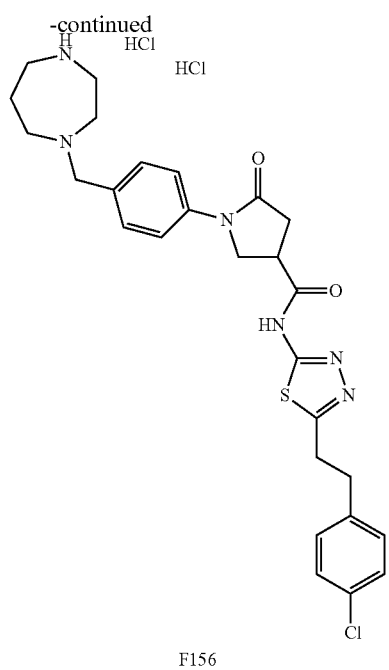

F156

Step 1

Synthesis of 4-[4-(4-{5-[2-(4-chloro-phenyl)-ethyl]-[1,3,4]thiadiazol-2-ylcarbamoyl}-2-oxo-pyrrolidin-1-yl)-benzyl]-[1,4]diazepane-1-carboxylic acid tert-butyl ester (F86)

The title compound was synthesised according to Coupling Method A using these materials:

Lithium; 1-[4-(4-tert-butoxycarbonyl-[1,4]diazepan-1-yl-methyl)-phenyl]-5-oxo-pyrrolidine-3-carboxylate (249 mg, 0.287 mmol), DMA (5 mL), HBTU (0.56 g, 1.468 mmol), DIPEA (308 µL, 1.761 mmol) and 5-[2-(4-Chloro-phenyl)-ethyl]-[1,3,4]thiadiazol-2-ylamine (71 mg, 0.294 mmol).

LCMS method: Method 1, RT: 3.88 min, MI: 639 [M+1]

Step 2

Synthesis of 1-(4-[1,4]diazepan-1-ylmethyl-phenyl)-5-oxo-pyrrolidine-3-carboxylic acid {5-[2-(4-chloro-phenyl)-ethyl]-[1,3,4]thiadiazol-2-yl}-amide; dihydrochloride (F156)

4-[4-(4-{5-[2-(4-Chloro-phenyl)-ethyl]-[1,3,4]thiadiazol-2-ylcarbamoyl}-2-oxo-pyrrolidin-1-yl)-benzyl]-[1,4]diazepane-1-carboxylic acid tert-butyl ester (20 mg, 0.031 mmol) was dissolved in DCM (0.5 mL) and treated with 4N HCl/1,4-dioxane (0.5 mL). After stirring at room temperature for 30 minutes, the volatiles were removed under reduced pressure, then the residue was washed with Et$_2$O and concentrated again under reduced pressure to afford the title compound (33 mg).

LCMS method: Method 1, RT: 2.62 min, MI: 539 [M+1]

$^1$H NMR (500 MHz, DMSO-d$_6$) δ 11.76 (s, 1H), 9.88 (s, 1H), 9.52 (s, 1H), 8.13 (s, 1H), 7.72 (d, 2H), 7.65 (d, 2H), 7.33 (d, 2H), 7.28 (d, 2H), 4.34 (br d, 2H), 4.11 (t, 1H), 4.01 (dd, 1H), 3.62 (m, 3H), 3.52 (m, 2H), 3.30 (t, 2H), 3.17 (m, 2H), 3.02 (t, 2H), 2.89 (dd, 1H), 2.76 (dd, 1H), 2.15 (m, 2H).

The following examples (Table 16) were prepared using Coupling Methods A-K described above:

TABLE 16

| Ex no. | Structure | Salt | Coupling method | Intermediates | Characterisation LCMS data | NMR data |
|---|---|---|---|---|---|---|
| F87 | Chiral | HCl | CM A | F21-8, F40 | LCMS method: Method 1, RT: 3.31 min, MI: 540 [M + 1] | 1H NMR (500 MHz, DMSOd$_6$) δ 12.68 (s, 1H), 10.12 (d, 1H), 7.75 (d, 2H), 7.54 (dd, 1H), 7.31 (d, 2H), 7.26 (d, 2H), 4.34 (ddd, 2H), 4.21-4.08 (m, 3H), 4.03-3.95 (m, 3H), 3.59 (m, 2H), 3.29 (t, 2H), 3.01 (t, 2H), 2.89 (dd, 1H), 2.76 (dd, 1H), 2.55 (dd, 2H), 2.23 (m, 2H) |

TABLE 16-continued
| Ex no. | Structure | Salt | Coupling method | Intermediates | Characterisation LCMS data | NMR data |
|---|---|---|---|---|---|---|
| F88 | 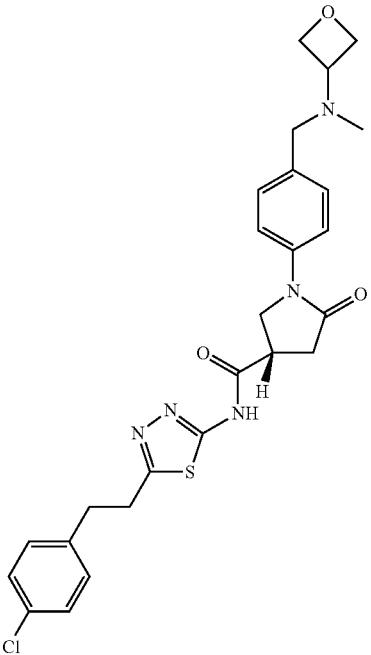 Chiral | — | CM A | F21-11, F40 | LCMS method: Method 1, RT: 3.40 min, MI: 526 [M + 1] | 1H NMR (500 MHz, DMSO-d<sub>6</sub>) δ 12.66 (s, 1H), 7.58 (m, 2H), 7.32 (m, 2H), 7.28 (m, 4H), 4.49 (t, 2H), 4.41 (t, 2H), 4.08 (dd, 1H), 4.00 (dd, 1H), 3.57 (m, 2H), 3.29 (m, 4H), 3.02 (t, 2H), 2.85 (dd, 1H), 2.74 (dd, 1H), 1.93 (s, 3H) |
| F89 | 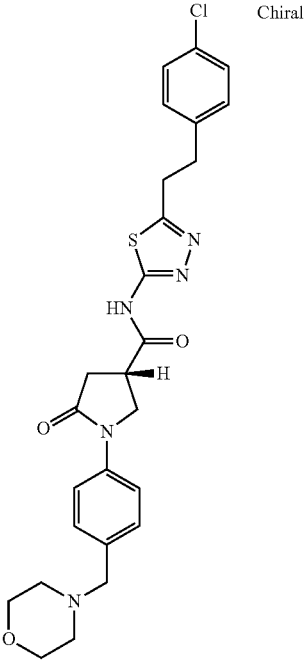 [SMILES: O=C(Nc1nnc(CCc2ccc(Cl)cc2)s1)[C@H]1CC(=O)N(c2ccc(CN3CCOCC3)cc2)C1] Chiral | HCl | CM A | F21, F40 | LCMS method: Method 5, RT: 2.74 min, MI: 526 [M + 1] | 1H NMR (400 MHz, DMOS-d<sub>6</sub>) δ 12.74 (br s, 1H), 11.12 (br s, 1H), 7.74 (d, 2H), 7.61 (d, 2H), 7.34 (d, 2H), 7.29 (d, 2H), 4.30 (d, 2H), 4.12 (t, 1H), 4.01-4.05 (m, 1H), 3.80 (br s, 8H), 3.63 (m, 1H), 3.31 (t, 2H), 3.03 (t, 2H), 2.87-2.94 (m, 1H), 2.75-2.81 (m, 1H) |

TABLE 16-continued
| Ex no. | Structure | Salt | Coupling method | Intermediates | Characterisation | |
|---|---|---|---|---|---|---|
| | | | | | LCMS data | NMR data |
| F90 | 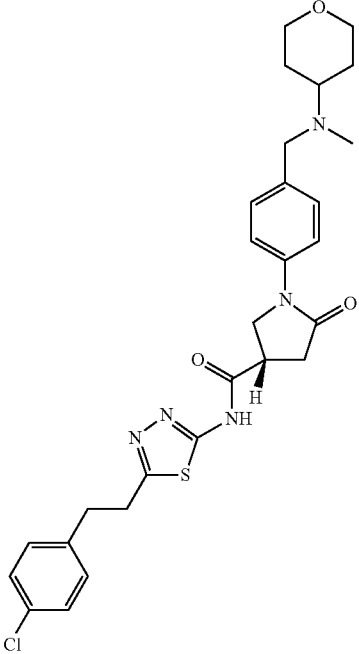 Chiral | HCl | CM A | F21-9, F40 | LCMS method: Method 1, RT: 3.35 min, MI: 554 [M + 1] | 1H NMR (500 MHz, DMSO-d$_6$) δ 12.69 (s, 1H), 9.92 (s, 1H), 7.75 (d, 2H), 7.57 (d, 2H), 7.33 (d, 2H), 7.27 (d, 2H), 4.44 (dd, 1H), 4.12 (m, 2H), 4.03 (m, 1H), 3.97 (m, 2H), 3.61 (m, 1H), 3.43 (m, 1H), 3.30 (m, 4H), 3.02 (t, 2H), 2.89 (dd, 1H), 2.77 (dd, 1H), 2.57 (d, 3H), 2.01 (m, 2H), 1.77 (m, 2H) |
| F91 | 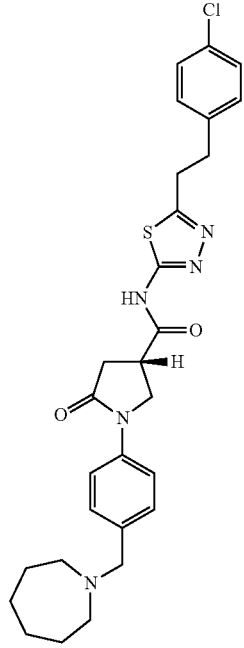 Chiral | HCl | CM A | F21-1, F40 | LCMS method: Method 1, RT: 4.06 min, MI: 538 [M + 1] | 1H NMR (500 MHz, DMSO-d$_6$) δ 12.71 (s, 1H), 10.46 (s, 1H), 7.71 (d, 2H), 7.61 (d, 2H), 7.31 (d, 2H), 7.27 (d, 2H), 4.25 (d, 2H), 4.10 (t, 1H), 4.01 (dd, 1H), 3.61 (m, 1H), 3.28 (m, 4H), 3.00 (m, 4H), 2.88 (dd, 1H), 2.75 (dd, 1H), 1.79 (m, 4H), 1.58 (m, 4H) |

TABLE 16-continued

| Ex no. | Structure | Salt | Coupling method | Intermediates | Characterisation | |
|---|---|---|---|---|---|---|
| | | | | | LCMS data | NMR data |
| F92 | Chiral | HCl | CM E | F21-2, F40 | LCMS method: Method 1, RT: 4.17 min, MI: 538 [M + 1] | 1H NMR (500 MHz, DMSO-d$_6$) δ 12.70 (s, 1H), 10.18 (s, 1H), 7.71 (d, 2H), 7.55 (d, 2H), 7.32 (d, 2H), 7.27 (d, 2H), 4.19 (d, 2H), 4.10 (t, 1H), 4.01 (dd, 1H), 3.61 (m, 1H), 3.30 (t, 2H), 3.24 (br d, 2H), 3.02 (t, 2H), 2.88 (dd, 1H), 2.81 (br d, 2H), 2.75 (dd, 1H), 1.75 (br d, 2H), 1.55 (br s, 1H), 1.42 (m, 2H), 0.87 (d, 3H) |
| F93 | Chiral | HCl | CM A | F21-6, F40 | LCMS method: Method 5, RT: 2.77 min, MI: 524/526 [M + 1] | 1H NMR (500 MHz, DMSO-d$_6$) δ 12.73 (br s, 1H), 10.08 (br s, 1H), 7.74 (d, 2H), 7.57 (d, 2H), 7.34 (d, 2H), 7.29 (d, 2H), 4.23 (d, 2H), 4.12 (m, 1H), 4.03 (m, 1H), 3.63 (m, 1H), 3.32 (t, 2H), 3.28 (m, 2H), 3.03 (t, 2H), 2.91 (m, 1H), 2.78 (m, 3H), 1.72 (m, 5H), 1.34 (m, 1H) |

TABLE 16-continued

| Ex no. | Structure | Salt | Coupling method | Intermediates | Characterisation | |
|---|---|---|---|---|---|---|
| | | | | | LCMS data | NMR data |
| F94 | Chiral | HCl | CM A | F21-3, F40 | LCMS method: Method 1, RT: 4.00 min, MI: 528 [M + 1] | 1H NMR (500 MHz, DMSO-d$_6$) δ 12.70 (s, 1H), 10.05 (s, 1H), 7.73 (d, 2H), 7.54 (d, 2H), 7.32 (d, 2H), 7.27 (d, 2H), 4.32 (dd, 1H), 4.22 (dd, 1H), 4.10 (t, 1H), 4.01 (dd, 1H), 3.69-3.58 (m, 3H), 3.31-3.22 (m, 6H), 3.14 (m, 1H), 3.02 (t, 2H), 2.88 (dd, 1H), 2.75 (dd, 1H), 2.67 (d, 3H) |
| F95 | 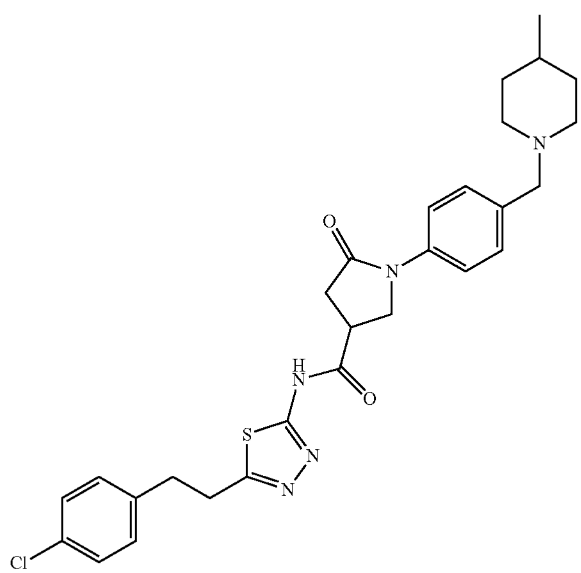 | HCl | CM A | F15-19, F40 | LCMS method: Method 1, RT: 3.63 min, MI: 538 [M + 1] | 1H NMR (500 MHz, DMSO-d$_6$) δ 12.68 (s, 1H), 9.69 (s, 1H), 7.72 (d, 2H), 7.51 (d, 2H), 7.31 (d, 2H), 7.26 (d, 2H), 4.20 (d, 2H), 4.10 (t, 1H), 3.99 (dd, 1H), 3.60 (m, 1H), 3.29 (m, 4H), 3.01 (t, 2H), 2.87 (m, 3H), 2.74 (dd, 1H), 1.73 (br d, 2H), 1.55 (br s, 1H), 1.33 (m, 2H), 0.87 (d, 3H) |

TABLE 16-continued
| Ex no. | Structure | Salt | Coupling method | Intermediates | LCMS data | NMR data |
|---|---|---|---|---|---|---|
| F96 | 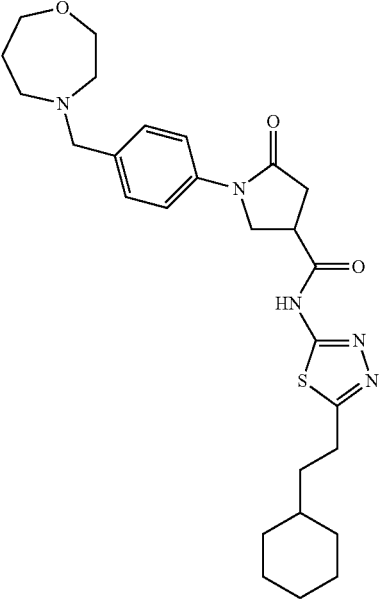 [SMILES: O=C(Nc1nnc(CCC2CCCCC2)s1)C1CC(=O)N(c2ccc(CN3CCCOCC3)cc2)C1] | HCl | CM A | F15-17, F40-5 | LCMS method: Method 1, RT: 3.89 min, MI: 512 [M + 1] | 1H NMR (500 MHz, DMSO-d₆) δ 12.70 (s, 1H), 10.77 (s, 1H), 7.72 (d, 2H), 7.61 (d, 2H), 4.33 (br d, 2H), 4.12 (t, 1H), 4.03 (m, 1H), 3.73-3.61 (m, 4H), 3.40 (m, 1H), 3.31 (m, 1H), 3.12 (m, 2H), 2.98 (t, 2H), 2.89 (dd, 1H), 2.76 (dd, 1H), 2.25 (m, 1H), 1.98 (m, 1H), 1.72-1.57 (m, 6H), 1.24-1.07 (m, 4H), 0.90 (m, 2H) (2H presumed under water peak) |
| F97 | 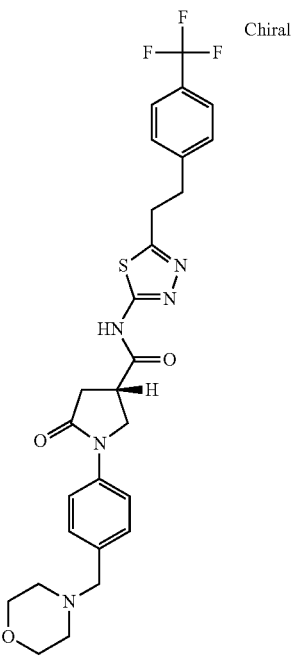 [SMILES: O=C(Nc1nnc(CCc2ccc(C(F)(F)F)cc2)s1)[C@H]1CC(=O)N(c2ccc(CN3CCOCC3)cc2)C1] | HCl | CM A | F21, F40-6 | LCMS method: Method 3, RT: 4.46 min, MI: 558 [M − 1] | 1H NMR (500 MHz, DMSO-d₆) δ 13.17 (s, 1H), 11.45 (s, 1H), 8.19 (d, 2H), 8.10 (d, 2H), 8.35 (d, 2H), 7.95 (d, 2H), 6.20 (s, 1H), 4.74 (m, 1H), 4.55 (t, 2H), 4.48 (t, 2H), 4.38 (d, 2H), 3.80 (t, 2H), 3.65-3.59 (m, 4H), 3.54 (m, 2H), 3.21 (m, 2H) |

TABLE 16-continued

| Ex no. | Structure | Salt | Coupling method | Intermediates | Characterisation | |
|---|---|---|---|---|---|---|
| | | | | | LCMS data | NMR data |
| F98 | 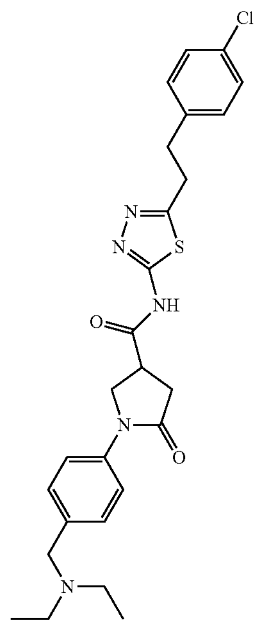 [SMILES: CCN(CC)Cc1ccc(N2CC(C(=O)Nc3nnc(CCc4ccc(Cl)cc4)s3)CC2=O)cc1] | — | CM A | F15-14, F40 | LCMS method: Method 1, RT: 3.46 min, MI: 512 [M + 1] | 1H NMR (500 MHz, DMSO-d$_6$) δ 7.55 (d, 2H), 7.32 (d, 2H), 7.29 (d, 2H), 7.27 (d, 2H), 4.07 (dd, 1H), 3.98 (dd, 1H), 3.58 (m, 1H), 3.49 (s, 2H), 3.30 (t, 2H, hidden partly by water peak), 3.02 (t, 2H), 2.83 (dd, 1H), 2.72 (dd, 1H), 2.43 (q, 4H), 0.96 (t, 6H) |
| F99 | 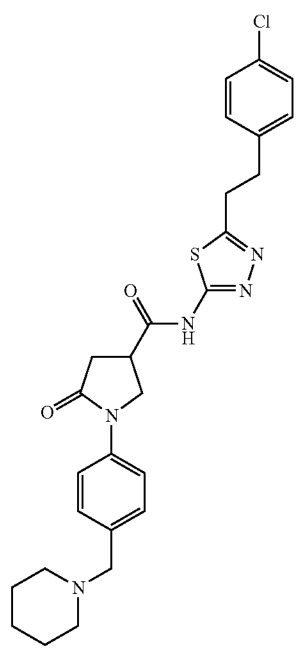 [SMILES: O=C(Nc1nnc(CCc2ccc(Cl)cc2)s1)C1CC(=O)N(c2ccc(CN3CCCCC3)cc2)C1] | HCl | CM A | F15-4, F40 | LCMS method: Method 1, RT: 3.44 min, MI: 524 [M + 1] | 1H NMR (500 MHz, DMSO-d$_6$) δ 12.69 (s, 1H), 9.76 (s, 1H), 7.72 (d, 2H), 7.52 (d, 2H), 7.32 (d, 2H), 7.27 (d, 2H), 4.22 (d, 2H), 4.10 (t, 1H), 4.01 (dd, 1H), 3.29 (t, 2H), 3.02 (t, 2H), 2.77 (dd, 1H), 2.68 (dd, 1H), 1.76 (br d, 2H), 1.65 (br d, 3H), 1.32 (m, 1H) (5H presumed under solvent peak) |

TABLE 16-continued

| Ex no. | Structure | Salt | Coupling method | Intermediates | LCMS data | NMR data |
|---|---|---|---|---|---|---|
| F100 | 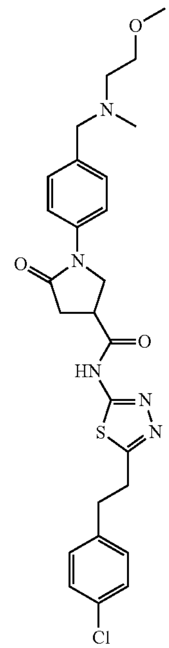 [SMILES: COCCN(C)Cc1ccc(N2CC(C(=O)Nc3nnc(CCc4ccc(Cl)cc4)s3)CC2=O)cc1] | HCl | CM A | F15-24, F40 | LCMS method: Method 1, RT: 3.39 min, MI: 528 [M + 1] | 1H NMR (500 MHz, DMSO-d$_6$) δ 12.70 (s, 1H), 10.09 (s, 1H), 7.72 (d, 2H), 7.53 (d, 2H), 7.31 (d, 2H), 7.26 (d, 2H), 4.31 (dd, 1H), 4.22 (dd, 1H), 4.10 (t, 1H), 4.01 (dd, 1H), 3.67 (t, 2H), 3.61 (m, 1H), 3.29 (t, 2H), 3.28 (s, 3H), 3.23 (m, 1H), 3.14 (m, 1H), 3.01 (t, 2H), 2.87 (dd, 1H), 2.74 (dd, 1H), 2.66 (d, 3H) |
| F101 | 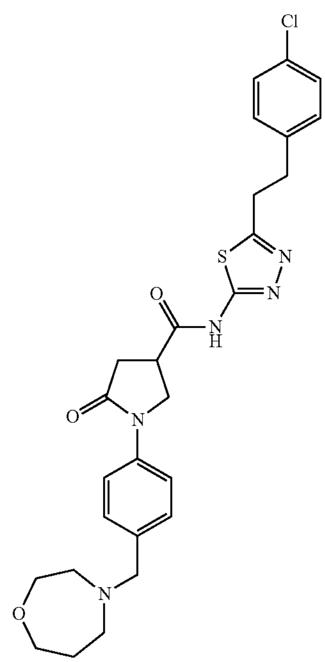 [SMILES: O=C(Nc1nnc(CCc2ccc(Cl)cc2)s1)C1CC(=O)N(c2ccc(CN3CCCOCC3)cc2)C1] | HCl | CM A | F15-17, F40 | LCMS method: Method 1, RT: 3.24 min, MI: 540 [M + 1] | 1H NMR (500 MHz, DMSO-d$_6$) δ 12.69 (s, 1H), 10.10 (s, 1H), 7.73 (d, 2H), 7.56 (d, 2H), 7.32 (d, 2H), 7.27 (d, 2H), 4.34 (d, 2H), 4.10 (t, 1H), 4.01 (dd, 1H), 3.83 (m, 1H), 3.74 (m, 3H), 3.67 (m, 1H), 3.60 (m, 1H), 3.43 (m, 1H), 3.30 (t, 2H), 3.15 (m, 2H), 3.02 (t, 2H), 2.88 (dd, 1H), 2.75 (dd, 1H), 2.15 (m, 1H), 2.01 (m, 1H) |

TABLE 16-continued
| Ex no. | Structure | Salt | Coupling method | Intermediates | Characterisation | |
|---|---|---|---|---|---|---|
| | | | | | LCMS data | NMR data |
| F102 | 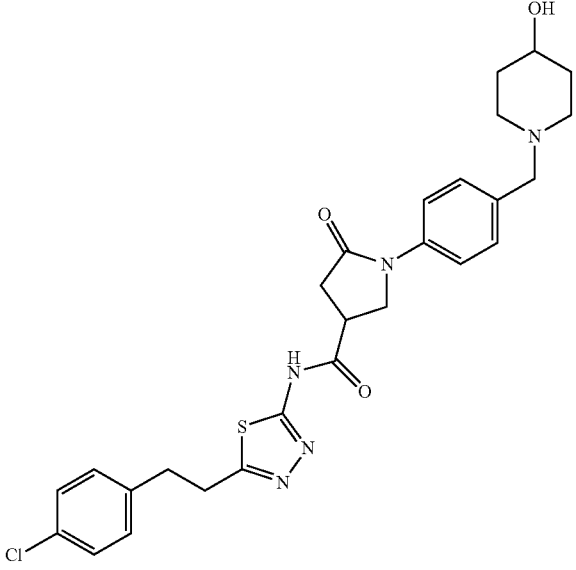 [SMILES: O=C(Nc1nnc(CCc2ccc(Cl)cc2)s1)C1CC(=O)N(c2ccc(CN3CCC(O)CC3)cc2)C1] | HCl | CM A | F15-6, F40 | LCMS method: Method 1, RT: 3.32 min, MI: 540 [M + 1] | 1H NMR (500 MHz, DMSO-d$_6$) δ 12.69 (s, 1H), 9.88 (s, 1H), 7.74 (d, 2H), 7.56 (d, 1H), 7.53 (d, 1H), 7.33 (d, 2H), 7.27 (d, 2H), 4.24 (dd, 1H), 4.10 (t, 1H), 4.02 (m, 1H), 3.30 (t, 2H), 3.10 (m, 2H), 3.02 (t, 2H), 2.88 (m, 2H), 2.76 (dd, 1H), 1.90 (m, 2H), 1.71 (m, 1H), 1.59 (m, 1H) (4H presumed under solvent peak) |
| F103 | 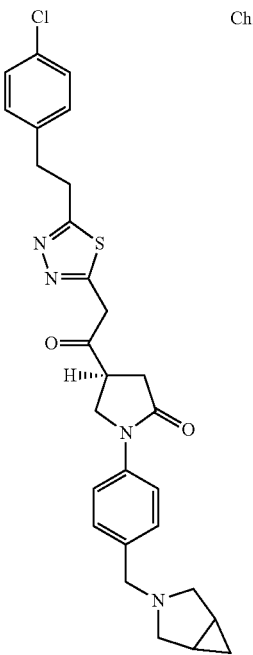 Chiral | HCl | CM A | F21-5, F40 | LCMS method: Method 1, RT: 4.22 min, MI: 522 [M + 1] | 1H NMR (500 MHz, DMSO-d$_6$) δ 12.69 (s, 1H), 10.07 (s, 1H), 7.70 (d, 2H), 7.55 (d, 2H), 7.32 (d, 2H), 7.27 (d, 2H), 4.28 (d, 2H), 4.09 (t, 1H), 4.01 (dd, 1H), 3.60 (m, 1H), 3.38-3.28 (m, 6H), 3.02 (t, 2H), 2.87 (dd, 1H), 2.75 (dd, 1H), 1.73 (br m, 2H), 0.87 (m, 1H), 0.62 (m, 1H) |

TABLE 16-continued

| Ex no. | Structure | Salt | Coupling method | Intermediates | LCMS data | NMR data |
|---|---|---|---|---|---|---|
| F104 | 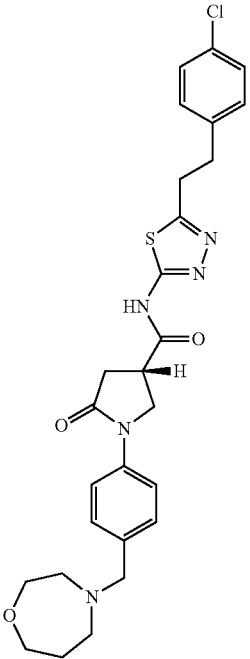 Chiral | HCl | CM A | F21-4, F40 | LCMS method: Method 1, RT: 4.41 min, MI: 540 [M + 1] | 1H NMR (500 MHz, DMOS-d$_6$) δ 12.68 (s, 1H), 10.00 (s, 1H), 7.73 (d, 2H), 7.54 (d, 2H), 7.31 (d, 2H), 7.26 (d, 2H), 4.34 (d, 2H), 4.09 (t, 1H), 4.01 (dd, 1H), 3.84-3.58 (m, 6H), 3.29 (t, 2H), 3.14 (m, 2H), 3.01 (t, 2H), 2.87 (dd, 1H), 2.74 (dd, 1H), 2.13 (m, 1H), 2.00 (m, 1H) |
| F105 | 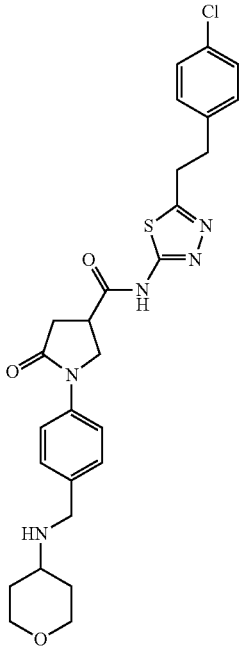 [SMILES: O=C(Nc1nnc(CCc2ccc(Cl)cc2)s1)C1CC(=O)N(c2ccc(CNC3CCOCC3)cc2)C1] | HCl | CM A | F84, F40 | LCMS method: Method 1, RT: 3.46 min, MI: 540 [M + 1] | 1H NMR (500 MHz, DMSO-d$_6$) δ 12.67 (s, 1H), 8.82 (s, 1H), 7.71 (d, 2H), 7.50 (d, 2H), 7.31 (d, 2H), 7.27 (d, 2H), 4.14 (br s, 1H), 4.09 (t, 1H), 4.00 (dd, 1H), 3.91 (br dd, 2H), 3.60 (m, 1H), 3.30 (t, 2H, partly hidden by water peak), 3.02 (t, 2H), 2.87 (dd, 1H), 2.75 (dd, 1H), 1.98 (br d, 2H), 1.56 (m, 2H) (4H presumed under solvent peak) |

TABLE 16-continued

| Ex no. | Structure | Salt | Coupling method | Intermediates | LCMS data | NMR data |
|---|---|---|---|---|---|---|
| F106 | (piperidinylmethyl-phenyl-pyrrolidinone-carboxamide-thiadiazole-ethyl-cyclohexyl structure) | HCl | CM A | F15-4, F40-5 | LCMS method: Method 1, RT: 3.81 min, MI: 494 [M − 1] | 1H NMR (500 MHz, DMSO-d$_6$) δ 12.69 (s, 1H), 7.75 (d, 2H), 7.54 (d, 2H), 4.23 (d, 2H), 4.12 (t, 1H), 4.03 (t, 1H), 3.6 (m, 2H), 3.28 (d, 2H), 2.98 (t, 2H), 2.6 (m, 2H), 2.73 (m, 4H), 1.77 (m, 2H), 1.72 (m, 6H), 1.57 (m, 2H), 1.32 (m, 1H), 1.23 (m, 1H), 1.13 (m, 2H), 0.90 (q, 2H) |
| F107 | (morpholinylmethyl-phenyl-pyrrolidinone-carboxamide-thiadiazole-ethyl-cyclohexyl structure) | — | CM A | F15-2, F40-8 | LCMS method: Method 1, RT: 3.56 min, MI: 482 [M + 1] | 1H NMR (500 MHz, DMSO-d$_6$) δ 7.59 (d, 2H), 7.29 (d, 2H), 4.08 (t, 1H), 3.99 (t, 1H), 3.58 (m, 5H), 3.41 (s, 2H), 3.95 (dd, 2H), 2.84 (dd, 1H), 2.82 (dd, 1H), 2.61 (br s, 4H), 1.74-1.68 (m, 6H), 1.46 (m, 1H), 1.45 (m, 2H), 1.10 (m, 2H) |

TABLE 16-continued
| Ex no. | Structure | Salt | Coupling method | Intermediates | Characterisation | |
|---|---|---|---|---|---|---|
| | | | | | LCMS data | NMR data |
| F108 | 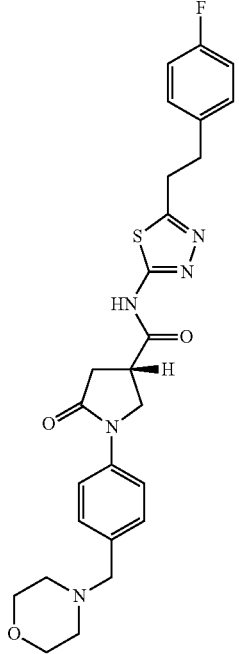 Chiral | HCl | CM A | F21, F40 | LCMS method: Method 3, RT: 4.00 min, MI: 508 [M − 1] | 1H NMR (500 MHz, DMSO-d$_6$) δ 12.70 (s, 1H), 7.74 (d, 2H), 7.58 (d, 2H), 7.28 (d, 2H), 7.09 (d, 2H), 4.29 (d, 2H), 4.12 (t, 1H), 4.01 (t, 1H), 3.93 (d, 2H), 3.29 (t, 2H), 3.20 (d, 2H), 3.01 (m, 4H), 2.89 (dd, 2H), 2.73 (dd, 2H), 2.67 (m, 1H) |
| F109 | 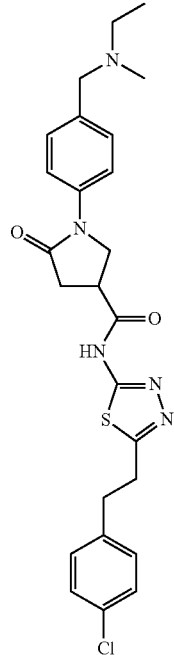 | — | CM A | F15-16, F40 | LCMS method: Method 1, RT: 3.52 min, MI: 512 [M + 1] | 1H NMR (500 MHz, DMSO-d$_6$) δ 12.61 (br s, 1H), 7.56 (d, 2H), 7.31 (d, 2H), 7.28 (d, 2H), 7.26 (d, 2H), 4.07 (dd, 1H), 3.98 (dd, 1H), 3.58 (m, 1H), 3.40 (s, 2H), 3.29 (t, 2H, hidden partly by water peak), 3.02 (t, 2H), 2.83 (dd, 1H), 2.73 (dd, 1H), 2.25 (t, 2H), 2.08 (s, 3H), 1.44 (sx, 2H), 0.83 (t, 3H) |

TABLE 16-continued

| Ex no. | Structure | Salt | Coupling method | Intermediates | Characterisation LCMS data | NMR data |
|---|---|---|---|---|---|---|
| F110 | 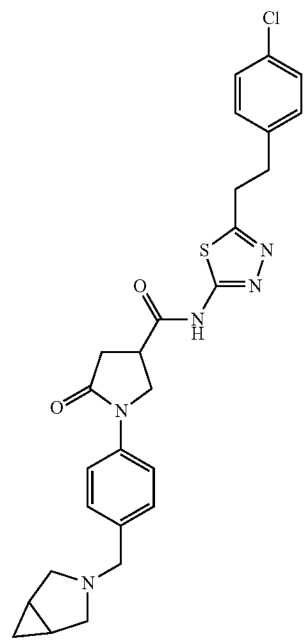 [SMILES: O=C(Nc1nnc(CCc2ccc(Cl)cc2)s1)C1CC(=O)N(c2ccc(CN3CC4CC4C3)cc2)C1] | HCl | CM A | F15-15, F40 | LCMS method: Method 1, RT: 3.48 min, MI: 522 [M + 1] | 1H NMR (500 MHz, DMSO-d$_6$) δ 12.68 (s, 1H), 9.81 (s, 1H), 7.71 (d, 2H), 7.53 (d, 2H), 7.32 (d, 2H), 7.27 (d, 2H), 4.29 (d, 2H), 4.10 (t, 1H), 4.01 (dd, 1H), 3.60 (m, 1H), 3.34 (m, 2H), 3.30 (t, 2H), 3.02 (t, 2H), 2.88 (dd, 1H), 2.75 (dd, 1H), 1.74 (br m, 2H), 0.81 (m, 1H), 0.65 (m, 1H) |
| F111 | 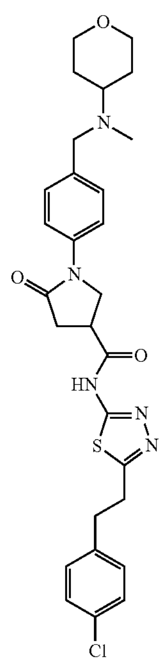 [SMILES: CN(Cc1ccc(N2CC(C(=O)Nc3nnc(CCc4ccc(Cl)cc4)s3)CC2=O)cc1)C1CCOCC1] | — | CM A | F15-18, F40 | LCMS method: Method 3, RT: 3.71 min, MI: 554 [M + 1] | 1H NMR (500 MHz, DMOS-d$_6$) δ 12.65 (br s, 1H), 7.55 (d, 2H), 7.32 (d, 2H), 7.27 (d, 4H), 4.07 (dd, 1H), 3.98 (dd, 1H), 3.87 (dd, 2H), 3.57 (m, 1H), 3.51 (s, 2H), 3.29 (t, 2H, hidden partly by water peak), 3.24 (dt, 2H), 3.02 (t, 2H), 2.83 (dd, 1H), 2.72 (dd, 1H), 2.56 (m, 1H), 2.07 (s, 3H), 1.66 (br d, 2H), 1.48 (dq, 2H) |

TABLE 16-continued

| Ex no. | Structure | Salt | Coupling method | Intermediates | LCMS data | NMR data |
|---|---|---|---|---|---|---|
| F112 | 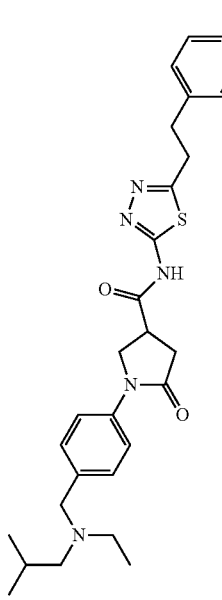 | HCl | CM A | F15-25, F40 | LCMS method: Method 1, RT: 3.57 min, MI: 540 [M + 1] | 1H NMR (500 MHz, DMOS-d<sub>6</sub>) δ 12.71 (s, 1H), 9.69 (s, 1H), 7.73 (d, 2H), 7.62 (d, 2H), 7.32 (m, 2H), 7.27 (d, 2H), 4.29 (dd, 1H), 4.23 (dd, 1H), 4.11 (t, 1H), 4.02 (m, 1H), 3.62 (m, 1H), 3.30 (t, 2H), 3.09 (m, 2H), 3.02 (t, 2H), 2.86 (m, 2H), 2.74 (m, 1H), 1.96 (m, 1H), 1.28 (t, 3H), (d, 3H), 0.86 (d, 3H) |
| F113 | 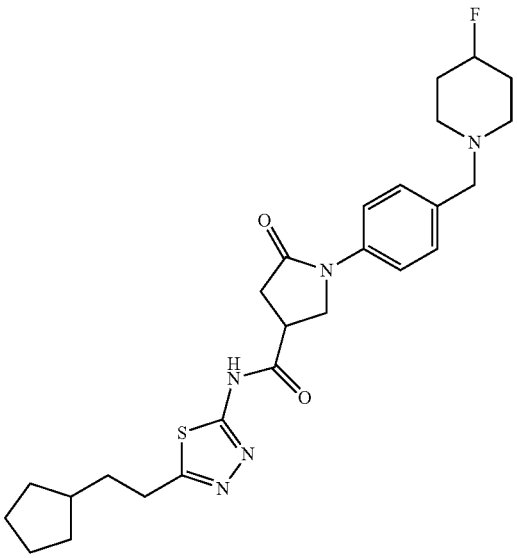 [SMILES: O=C(Nc1nnc(CCC2CCCC2)s1)C1CC(=O)N(c2ccc(CN3CCC(F)CC3)cc2)C1] | HCl | CM A | F15-29, F40-8 | LCMS method: Method 1, RT: 3.93 min, MI: 500 [M + 1] | 1H NMR (500 MHz, DMSO-d<sub>6</sub>) δ 12.71 (s, 1H), 10.76 (s, 1H), 7.71 (d, 2H), 7.59 (m, 2H), 5.02-4.73 (m, 1H), 4.25 (dd, 2H, overintegrates due to water peak), 4.11 (t, 1H, overintegrates due to water peak), 4.02 (dd, 1H, overintegrates due to water peak), 3.62 (m, 1H), 3.19 (m, 2H), 3.05 (m, 2H), 2.97 (t, 2H), 2.89 (m, 1H), 2.75 (dd, 1H), 2.21-1.92 (m, 4H), 1.79-1.67 (m, 5H), 1.56 (m, 2H), 1.46 (m, 2H), 1.10 (m, 2H) |

TABLE 16-continued

| Ex no. | Structure | Salt | Coupling method | Intermediates | Characterisation | |
|---|---|---|---|---|---|---|
| | | | | | LCMS data | NMR data |
| F114 | 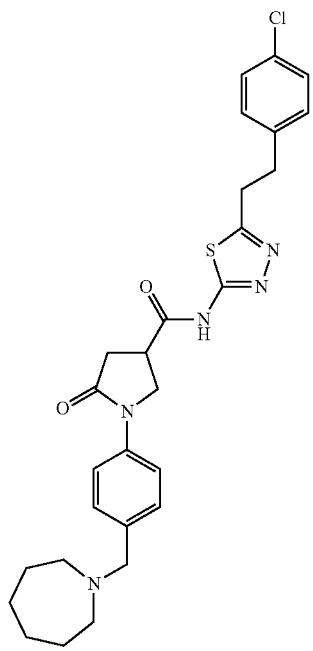 [SMILES: O=C(Nc1nnc(CCc2ccc(Cl)cc2)s1)C1CC(=O)N(c2ccc(CN3CCCCCC3)cc2)C1] | HCl | CM A | F15-13, F40 | LCMS Method: Method 1, RT: 3.61 min, MI: 538 [M + 1] | 1H NMR (500 MHz, DMSO-d$_6$) δ 12.68 (s, 1H), 9.59 (s, 1H), 7.72 (d, 2H), 7.53 (d, 2H), 7.31 (d, 2H), 7.26 (d, 2H), 4.28 (d, 2H), 4.09 (t, 1H), 4.01 (dd, 1H), 3.60 (m, 1H), 3.29 (m, 4H), 3.01 (m, 4H), 2.92 (dd, 1H), 2.88 (dd, 1H), 1.81 (m, 2H), 1.71 (m, 2H), 1.59 (m, 4H) |
| F115 | 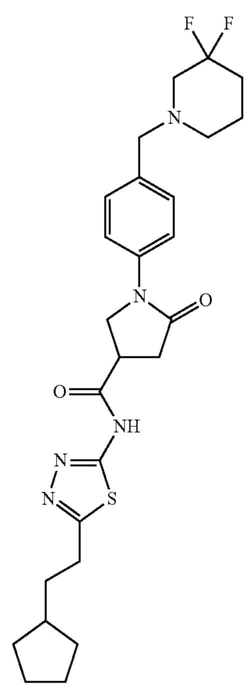 [SMILES: O=C(Nc1nnc(CCC2CCCC2)s1)C1CC(=O)N(c2ccc(CN3CCCC(F)(F)C3)cc2)C1] | HCl | CM A | F15-30, F40-8 | LCMS method: Method 1, RT: 4.90 min, MI: 518 [M + 1] | 1H NMR (500 MHz, DMSO-d$_6$) δ 12.73 (s, 1H), 11.16 (s, 1H), 7.74 (d, 2H), 7.58 (d, 2H), 4.33 (br s, 2H), 4.12 (t, 1H, overintegrates due to water peak), 4.02 (dd, 1H, overintegrates due to water peak), 3.63 (m, 1H), 3.37 (br s, 2H), 2.97 (t, 2H), 2.89 (dd, 1H), 2.76 (dd, 1H), 2.17 (m, 1H), 1.97 (m, 3H), 1.73 (m, 5H), 1.56 (m, 2H), 1.46 (m, 2H), 1.09 (m, 2H) |

TABLE 16-continued

| Ex no. | Structure | Salt | Coupling method | Intermediates | LCMS data | NMR data |
|---|---|---|---|---|---|---|
| F116 | 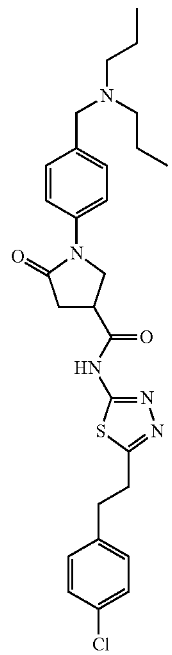 [SMILES: CCCN(CCC)Cc1ccc(N2CC(C(=O)Nc3nnc(CCc4ccc(Cl)cc4)s3)CC2=O)cc1] | HCl | CM A | F15-23, F40 | LCMS method: Method 1, RT: 3.74 min, MI: 540 [M + 1] | 1H NMR (500 MHz, DMSO-$d_6$) δ 12.70 (s, 1H), 10.06-9.69 (d, 1H), 7.74 (m, 2H), 7.56 (m, 2H), 7.32 (m, 2H), 7.27 (m, 2H), 4.26 (m, 2H), 4.11 (t, 1H), 4.02 (dd, 1H), 3.61 (m, 1H), 3.30 (t, 2H), 3.02 (t, 2H), 2.88 (m, 2H), 2.81 (m, 2H), 2.67 (d, 2H), 2.07 (m, 1H), 1.68 (m, 1H), 1.23 (t, 2H), 0.91 (m, 4H), 0.85 (t, 2H) |
| F117 | 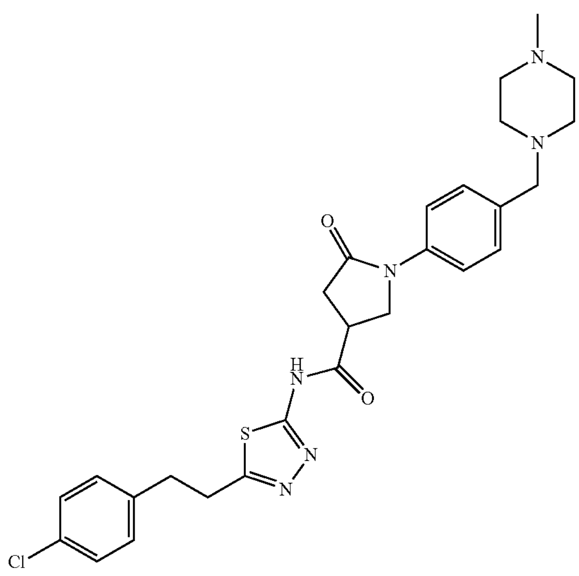 [SMILES: CN1CCN(Cc2ccc(N3CC(C(=O)Nc4nnc(CCc5ccc(Cl)cc5)s4)CC3=O)cc2)CC1] | Bis HCl | CM A | F15-5, F40 | LCMS method: Method 1, RT: 3.39 min, MI: 539 [M + 1] | 1H NMR (500 MHz, DMSO-$d_6$) δ 12.69 (s, 1H), 7.71 (br d, 2H), 7.57 (br s, 2H), 7.32 (d, 2H), 7.27 (d, 2H), 4.10 (t, 1H), 4.02 (dd, 1H), 3.59 (m, 2H), 3.30 (t, 2H), 3.02 (t, 2H), 2.88 (m, 1H), 2.78 (m, 4H) (8H presumed under solvent peak) |

TABLE 16-continued

| Ex no. | Structure | Salt | Coupling method | Intermediates | Characterisation LCMS data | NMR data |
|---|---|---|---|---|---|---|
| F118 | 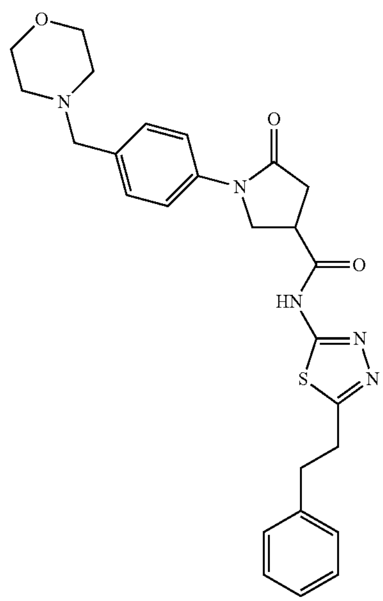 [SMILES: O=C(Nc1nnc(CCc2ccccc2)s1)C1CC(=O)N(c2ccc(CN3CCOCC3)cc2)C1] | — | CM A | F15-3, F48 | LCMS method: Method 5, RT: 2.73 min, MI: 491 [M + 1] | 1H NMR (400 MHz, CDCl$_3$) δ 12.58 (br s, 1H), 7.56 (d, 2H), 7.36 (d, 2H), 7.26 (td, 2H), 7.16 (td, 3H), 6.92 (s, 1H), 4.26 (dd, 1H), 3.98 (t, 1H), 3.71 (t, 4H), 3.49 (s, 2H), 3.36-3.45 (m, 1H), 3.10 (t, 2H), 3.01-3.07 (m, 1H), 2.95 (t, 2H), 2.82-2.89 (m, 1H), 2.44 (br s, 4H) |
| F119 | Chiral | HCl | CM A | F15-11, F40 | LCMS method: Method 3, RT: 3.48 min, MI: 554 [M + 1] | 1H NMR (500 MHz, DMSO-d$_6$) δ 12.70 (s, 1H), 11.13 (s, 1H), 7.74 (d, 2H), 7.57 (d, 2H), 7.34 (d, 2H), 7.27 (d, 2H), 4.25 (d, 2H), 4.11 (t, 1H), 4.01 (dd, 1H), 3.92 (m, 2H), 3.65 (m, 1H), 3.37 (t, 2H), 3.19 (d, 2H), 3.02 (t, 2H), 2.90 (dd, 1H, 2.75 (dd, 1H), 2.62 (m, 2H), 1.08 (d, 6H) |

TABLE 16-continued

| Ex no. | Structure | Salt | Coupling method | Intermediates | LCMS data | NMR data |
|---|---|---|---|---|---|---|
| F120 | 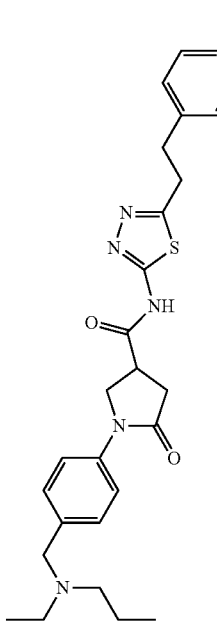 | HCl | CM A | F15-26, F40 | LCMS method: Method 1, RT: 3.73 min, MI: 540 [M + 1] | 1H NMR (500 MHz, DMSO-d$_6$) δ 12.71 (s, 1H), 10.22 (s, 1H), 7.73 (d, 2H), 7.58 (d, 2H), 7.32 (m, 2H), 7.27 (d, 2H), 4.26 (dd, 2H), 4.11 (t, 1H), 4.02 (dd, 1H), 3.61 (m, 1H), 3.30 (t, 2H), 3.02 (t, 2H), 2.96-2.86 (m, 5H), 2.77 (dd, 1H), 1.70 (m, 4H, overintegrates, should be 2H), 0.85 (t, 6H) |
| F121 | 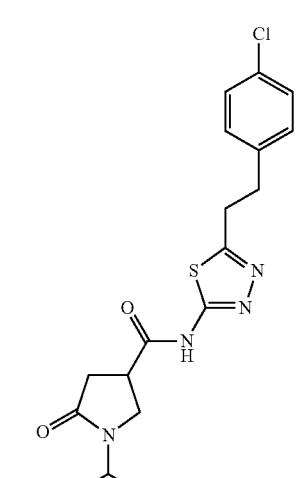 | HCl | CM A | F15-2, F40 | LCMS method: Method 1, RT: 4.4 min, MI: 526 [M + 1] | 1H NMR (500 MHz, CDCl$_3$) δ 12.7 (br s, 1H), 10.91 (br s, 1H), 7.73 (d, 2H), 7.58 (d, 2H), 7.35-7.26 (m, 4H), 4.29 (d, 2H), 4.13-4.07 (m, 1H, overlapping with water peak), 4.04-3.99 (m, 1H, overlapping with water peak), 3.94-3.88 (m, 2H), 3.77-3.69 (m, 2H), 3.65-3.58 (m, 1H), 3.30 (t, 2H), 3.22-3.16 (m, 2H), 3.09-2.98 (m, 4H), 2.93-2.85 (m, 1H), 2.80-2.73 (m, 1H) |

TABLE 16-continued

| Ex no. | Structure | Salt | Coupling method | Intermediates | Characterisation | |
|---|---|---|---|---|---|---|
| | | | | | LCMS data | NMR data |
| F122 | 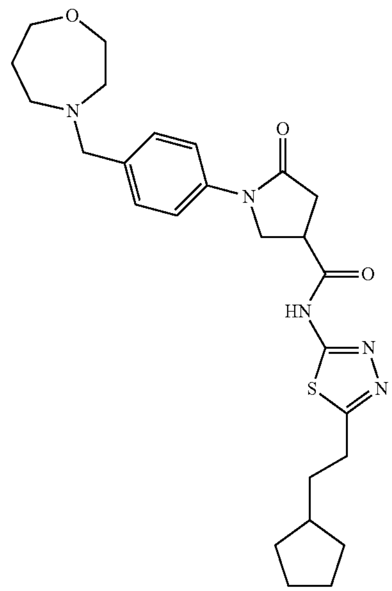 [SMILES: O=C(Nc1nnc(CCC2CCCC2)s1)C1CC(=O)N(c2ccc(CN3CCCOCC3)cc2)C1] | HCl | CM A | F15-17, F40-8 | LCMS method: Method 1, RT: 3.86 min, MI: 498 [M + 1] | 1H NMR (500 MHz, DMSO-d$_6$) δ 12.70 (s, 1H), 10.40 (s, 1H), 7.73 (d, 2H), 7.58 (d, 2H), 4.34 (d, 2H), 4.11 (t, 1H), 4.02 (dd, 1H), 3.85-3.60 (m, 9H, overintegrates, should be 5H), 3.42 (m, 1H), 3.32 (br d, 1H), 3.14 (m, 2H), 2.97 (t, 2H), 2.89 (dd, 1H), 2.75 (dd, 1H), 2.19 (m, 2H), 2.00 (m, 2H), 1.78-1.67 (m, 5H, overintegrates, should be 3H), 1.60-1.43 (m, 4H), 1.09 (m, 2H) |
| F123 | 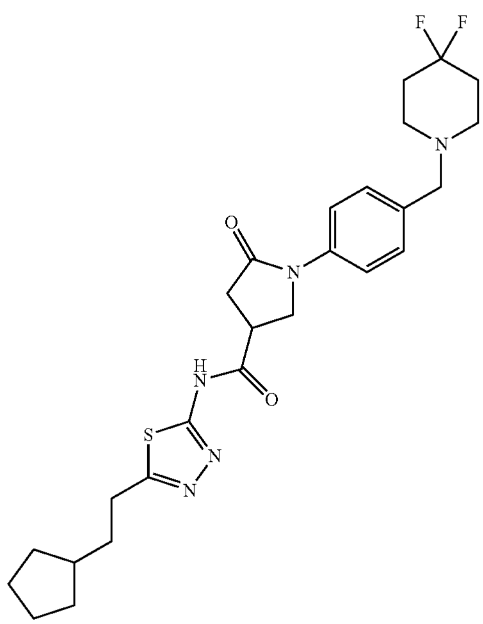 [SMILES: O=C(Nc1nnc(CCC2CCCC2)s1)C1CC(=O)N(c2ccc(CN3CCC(F)(F)CC3)cc2)C1] | HCl | CM A | F15-28, F40-8 | LCMS method: Method 1, RT: 4.31 min, MI: 518 [M + 1] | 1H NMR (500 MHz, DMSO-d$_6$) δ 12.70 (s, 1H), 10.91 (s, 1H), 7.73 (d, 2H), 7.57 (d, 2H), 4.34 (br s, 2H), 4.11 (t, 1H), 4.02 (dd, 1H), 3.40 (m, 2H), 3.11 (m, 2H), 2.97 (t, 2H), 2.89 (dd, 1H), 2.76 (dd, 1H), 2.31 (m, 2H), 1.73 (m, 5H), 1.56 (m, 2H), 1.47 (m, 2H), 1.09 (m, 2H), (2H presumed under water peak) |

TABLE 16-continued
| Ex no. | Structure | Salt | Coupling method | Intermediates | Characterisation LCMS data | NMR data |
|---|---|---|---|---|---|---|
| F124 | 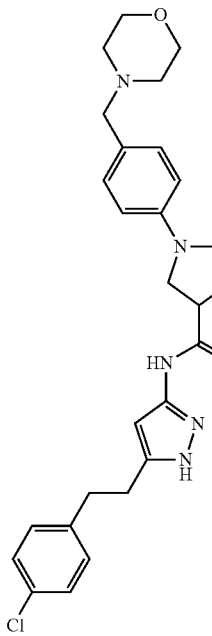 | — | CM A | F15-2, F51 | LCMS method: Method 5, RT: 265 min, MI: 499 [M + 1] | 1H NMR (500 MHz, DMSO-$d_6$) δ 12.10 (br s, 1H), 10.56 (s, 1H), 7.60 (d, 2H), 7.33 (d, 2H), 7.29 (d, 2H), 7.24 (d, 2H), 6.31 (s, 1H), 4.02 (m, 1H), 3.91 (m, 1H), 3.55 (m, 4H), 3.42 (m, 3H), 2.86 (m, 4H), 2.76 (m, 1H), 2.68 (m, 1H), 2.33 (m, 4H) |
| F125 | 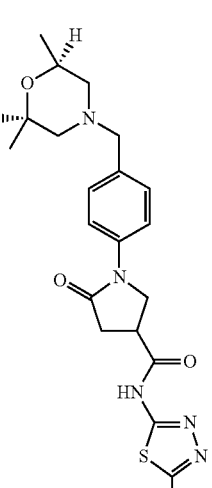 Chiral | HCl | CM A | F15-10, F40 | LCMS method: Method 1, RT: 3.64 min, MI: 554 [M + 1] | 1H NMR (500 MHz, DMSO-$d_6$) δ 12.69 (s, 1H), 9.69 (s, 1H), 7.77 (d, 2H), 7.54 (d, 2H), 7.33 (d, 2H), 7.29 (d, 2H), 4.30 (d, 2H), 4.24 (m, 1H), 4.08 (m, 1H), 3.98 (m, 2H), 3.67 (m, 2H), 3.47 (m, 2H), 3.30 (t, 2H, hidden partly by water peak), 3.08 (m, 2H), 3.02 (t, 1H), 2.91 (dd, 1H), 2.76 (dd, 1H), 1.32 (d, 3H), 1.08 (d, 3H) |

TABLE 16-continued

| Ex no. | Structure | Salt | Coupling method | Intermediates | Characterisation | |
|---|---|---|---|---|---|---|
| | | | | | LCMS data | NMR data |
| F126 | Chiral | HCl | CM A | F21-9, F38 | LCMS method: Method 1, RT: 3.00 min, MI: 532 [M + 1] | 1H NMR (500 MHz, DMSO-d$_6$) δ 11.37 (s, 1H), 10.10 (s, 1H), 8.24 (d, 1H), 7.76 (d, 2H), 7.60 (m, 3H), 7.24 (m, 2H), 7.07 (tt, 2H), 4.43 (dd, 1H), 4.13 (m, 2H), 4.02 (m, 1H), 3.97 (m, 2H), 3.64 (m, 1H), 3.44 (m, 1H), 3.30 (m, 2H), 3.16 (m, 2H), 3.00 (m, 2H), 2.88 (dd, 1H), 2.77 (dd, 1H), 2.56 (d, 3H), 2.06 (d, 1H), 1.84-1.71 (m, 2H) |
| F127 | 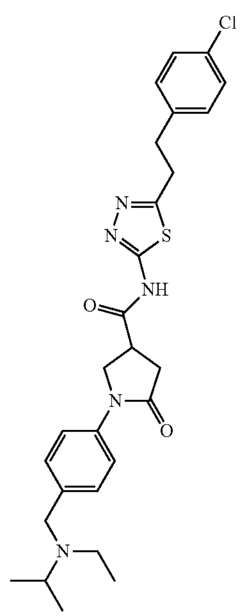 [SMILES: CCN(Cc1ccc(N2CC(C(=O)Nc3nnc(CCc4ccc(Cl)cc4)s3)CC2=O)cc1)C(C)C] | — | CM A | F15-20, F40 | LCMS method: Method 1, RT: 3.38 min, MI: 526 [M + 1] | 1H NMR (500 MHz, DMSO-d$_6$) δ 12.66 (br s, 1H), 7.53 (d, 2H), 7.30 (m, 6H), 4.07 (t, 1H), 3.98 (dd, 1H), 3.57 (m, 1H), 3.47 (s, 2H), 3.29 (t, 2H, hidden partly by water peak), 3.02 (t, 2H), 2.90 (m, 1H), 2.83 (dd, 1H), 2.72 (dd, 1H), 2.38 (m, 2H), 0.96 (d, 6H), 0.92 (t, 3H) |

TABLE 16-continued

| Ex no. | Structure | Salt | Coupling method | Intermediates | Characterisation | |
|---|---|---|---|---|---|---|
| | | | | | LCMS data | NMR data |

| F128 | (structure: 4-chlorophenethyl-1,3,4-thiadiazole-carboxamide-pyrrolidinone-phenyl-morpholinomethyl) | — | CM B | F27-1, F67 | LCMS method: Method 4, RT: 3.59 min, MI: 526 [M + 1] | 1H NMR (500 MHz, DMOS-d$_6$) δ 10.71 (br s, 1H), 9.80 (d, 1H), 7.76 (d, 2H), 7.57 (d, 2H), 7.34 (d, 2H), 7.29 (d, 2H), 4.68 (m, 1H), 4.30 (d, 2H), 4.18 (dd, 1H), 3.91 (m, 2H), 3.83 (dd, 1H), 3.71 (m, 2H), 3.47 (t, 2H), 3.18 (m, 2H), 3.05 (t, 2H), 3.02 (m, 1H), 2.95 (dd, 1H), 2.73 (dd, 1H) |
| F129 | (structure: 4-chlorophenethyl-1,3,4-thiadiazole-carboxamide-pyrrolidinone-phenyl-oxazepanylmethyl) | HCl | CM B | F27-5, F67 | LCMS method: Method 1, RT: 3.32 min, MI: 540 [M + 1] | 1H NMR (500 MHz, DMSO-d$_6$) δ 10.81 (br s, 1H), 9.79 (d, 1H), 7.74 (d, 2H), 7.62 (d, 2H), 7.34 (d, 2H), 7.27 (d, 2H), 4.68 (m, 1H), 4.33 (d, 2H), 4.18 (m, 1H), 3.82 (m, 2H), 3.55 (m, 2H), 3.48 (t, 2H), 3.30 (m, 2H), 3.08 (m, 2H), 2.8 (m, 1H), 2.7 (m, 1H), 2.26 (m, 1H), 1.9 (m, 1H), 1.26 (m, 2H), 0.8 (m, 1H) |

TABLE 16-continued

| Ex no. | Structure | Salt | Coupling method | Intermediates | Characterisation | |
|---|---|---|---|---|---|---|
| | | | | | LCMS data | NMR data |
| F130 | Chiral | HCl | CM B | F32-7, F67 | LCMS method: Method 3, RT: 5.14 min, MI: 526 [M + 1] | 1H NMR (500 MHz, DMSO-d$_6$) δ 10.34 (s, 1H), 9.79 (d, 1H), 7.76 (d, 2H), 7.53 (d, 2H), 7.33 (d, 2H), 7.29 (d, 2H), 4.69 (m, 1H), 4.30 (s, 2H), 4.18 (dd, 1H), 3.93 (d, 2H), 3.84 (dd, 1H), 3.66 (t, 2H), 3.47 (t, 2H), 3.19 (d, 2H, partly obscured by large water peak), 3.10-3.05 (m, 4H), 2.93 (dd, 1H), 2.70 (dd, 1H) |
| F131 | Chiral | HCl | CM B | F78, F67 | LCMS method: Method 1, RT: 1.81 min, MI: 512 [M + 1] | 1H NMR (500 MHz, DMSO-d$_6$) δ 10.67 (br s, 1H), 9.50 (d, 1H), 7.34 (m, 4H), 7.29 (d, 2H), 6.57 (d, 2H), 4.58 (m, 1H), 4.16 (d, 2H), 3.92 (m, 2H), 3.74 (dd, 2H), 3.58 (dd, 1H), 3.46 (t, 2H), 3.38 (m, 1H), 3.30 (m, 2H), 3.16 (m, 2H), 3.05 (t, 2H), 2.96 (m, 2H), 2.24 (m, 1H), 2.13 (m, 1H) |

TABLE 16-continued
| Ex no. | Structure | Salt | Coupling method | Intermediates | Characterisation LCMS data | NMR data |
|---|---|---|---|---|---|---|
| F132 | 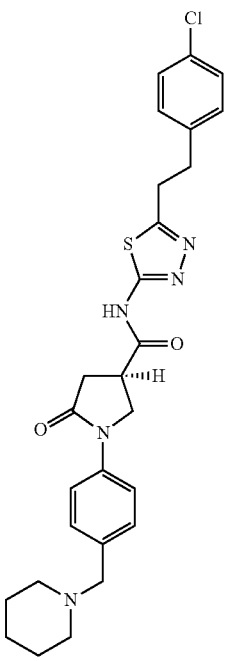 Chiral | HCl | CM B | F32, F67 | LCMS method: Method 3, RT: 5.82 min, MI: 524 [M + 1] | 1H NMR (500 MHz, DMSO-d$_6$) δ 9.79 (d, 1H), 9.64 (s, 1H), 7.75 (d, 2H), 7.52 (d, 2H), 7.33 (d, 2H), 7.28 (d, 2H), 4.69 (m, 1H), 4.23 (d, 2H), 4.19 (dd, 1H), 3.84 (m, 1H), 3.47 (t, 2H), 3.27 (br d, 2H), 3.07 (t, 2H), 2.94 (dd, 1H), 2.81 (m, 2H), 2.72 (dd, 1H), 1.78 (br d, 2H), 1.66 (m, 3H), 1.34 (m, 1H) |
| F133 | 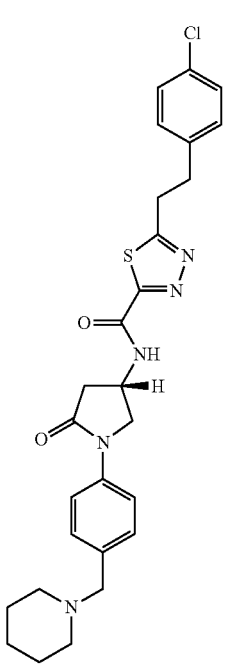 Chiral | HCl | CM B | F36, F67 | LCMS method: Method 3, RT: 5.81 min, MI: 524 [M + 1] | 1H NMR (500 MHz, DMSO-d$_6$) δ 9.79 (d, 1H), 9.67 (s, 1H, 7.74 (d, 2H), 7.52 (d, 2H), 7.33 (d, 2H), 7.28 (d, 2H), 4.69 (m, 1H), 4.23 (d, 2H), 4.19 (dd, 1H), 3.84 (m, 1H), 3.47 (t, 2H), 3.26 (br d, 2H), 3.07 (t, 2H), 2.94 (dd, 1H), 2.81 (m, 2H), 2.72 (dd, 1H), 1.78 (br d, 2H), 1.66 (m, 3H), 1.33 (m, 1H) |

TABLE 16-continued
| Ex no. | Structure | Salt | Coupling method | Intermediates | Characterisation LCMS data | NMR data |
|---|---|---|---|---|---|---|
| F134 | 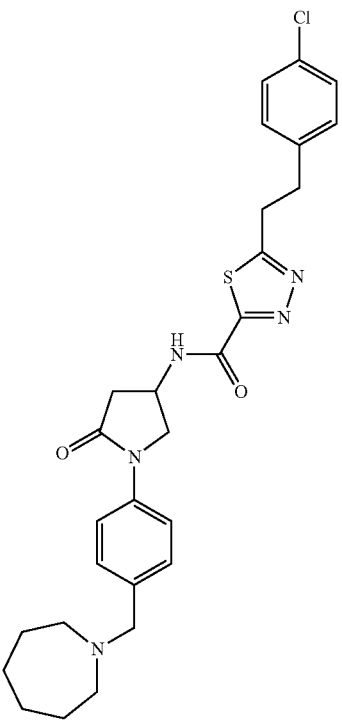 [SMILES: O=C(NC1CC(=O)N(c2ccc(CN3CCCCCC3)cc2)C1)c1nnc(CCc2ccc(Cl)cc2)s1] | HCl | CM B | F27-4, F67 | LCMS method: Method 1, RT: 3.48 min, MI: 538 [M + 1] | 1H NMR (500 MHz, DMSO-d) δ 10.32 (br s, 1H), 9.79 (d, 1H), 7.73 (d, 2H), 7.59 (d, 2H), 7.33 (d, 2H), 7.27 (d, 2H), 4.68 (br s, 1H), 1.74 (d, 2H), 4.18 (m, 2H), 3.85 (m, 1H), 3.46 (t, 2H), 3.06 (t, 2H), 2.96 (m, 2H), 1.79 (m, 3H), 1.62 (m, 2H), 1.53 (m, 2H), 1.26 (m, 2H), 0.84 (m, 2H) |
| F135 | 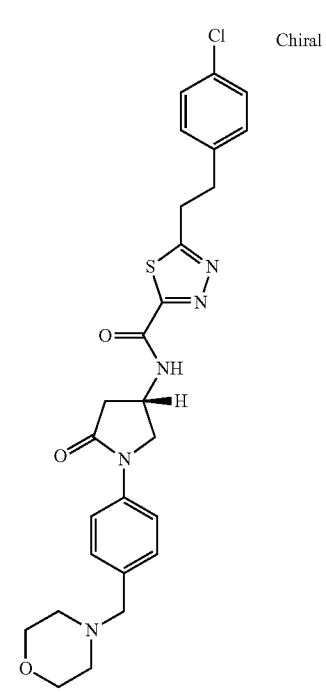 [SMILES: O=C(N[C@H]1CC(=O)N(c2ccc(CN3CCOCC3)cc2)C1)c1nnc(CCc2ccc(Cl)cc2)s1] Chiral | HCl | CM B | F36-2, F67 | LCMS method: Method 3, RT: 5.13 min, MI: 526 [M + 1] | 1H NMR (500 MHz, DMSO-d$_6$) δ 10.72 (s, 1H), 9.79 (d, 1H), 7.75 (d, 2H), 7.56 (d, 2H), 7.33 (d, 2H), 7.29 (d, 2H), 4.69 (m, 1H), 4.29 (d, 2H), 4.18 (dd, 1H), 3.92 (br d, 2H), 3.83 (dd, 1H), 3.71 (t, 2H), 3.47 (t, 2H), 3.20 (d, 2H), 3.09-3.02 (m, 4H), 2.93 (dd, 1H), 2.70 (dd, 1H) |

TABLE 16-continued

| Ex no. | Structure | Salt | Coupling method | Intermediates | Characterisation | |
|---|---|---|---|---|---|---|
| | | | | | LCMS data | NMR data |
| F136 | 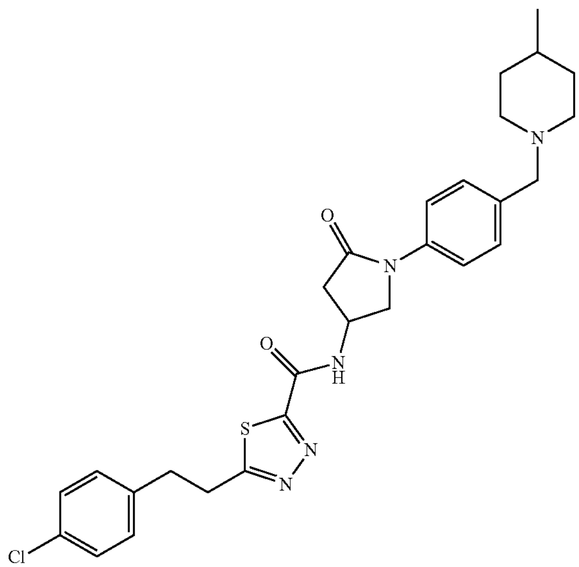 [SMILES: CC1CCN(Cc2ccc(N3CC(NC(=O)c4nnc(CCc5ccc(Cl)cc5)s4)CC3=O)cc2)CC1] | HCl | CM B | F27-2, F67 | LCMS method: Method 1, RT: 3.52 min, MI: 538 [M + 1] | 1H NMR (500 MHz, DMSO-$d_6$) δ 10.09 (br s, 1H), 9.80 (d, 1H), 7.74 (d, 2H), 7.58 (d, 2H), 7.32 (d, 2H), 7.25 (d, 2H), 4.69 (br s, 1H), 4.18 (m, 2H), 3.47 (t, 3H, underneath solvent), 3.27 (d, 2H), 3.07 (t, 2H), 2.92 (m, 2H), 2.82 (m, 2H), 1.76 (d, 2H), 1.40 (m, 2H), 0.86 (d, 2H) (3H presumed under solvent peak) |
| F137 | Chiral | HCl | CM B | F36-1, F67 | LCMS method: Method 1, RT: 3.48 min, MI: 538 [M + 1] | 1H NMR (500 MHz, CDCl$_3$) δ 7.62 (d, 1H), 7.51 (d, 2H), 7.33 (d, 2H), 7.26 (s, 2H), 7.12 (d, 2H), 4.86 (br s, 1H), 4.29 (dd, 1H), 3.86 (dd, 1H), 3.46 (dd, 2H), 3.46 (s, 2H), 3.13 (dd, 2H), 3.09 (dd, 1H), 2.82 (br d, 2H), 2.69 (dd, 1H), 1.92 (t, 2H), 1.56 (s, 2H), 1.34 (br s, 1H), 1.27-1.22 (m, 2H), 0.91 (d, 3H) |

TABLE 16-continued

| Ex no. | Structure | Salt | Coupling method | Intermediates | Characterisation | |
|---|---|---|---|---|---|---|
| | | | | | LCMS data | NMR data |
| F138 | Chiral | HCl | CM B | F32-8, F67 | LCMS method: Method 1, RT: 3.49 min, MI: 538 [M + 1] | 1H NMR (500 MHz, DMSO-d$_6$) δ 9.79 (s, 1H), 9.77 (s, 1H), 7.74 (d, 2H), 7.52 (d, 2H), 7.33 (d, 2H), 7.33 (d, 2H), 7.28 (d, 2H), 4.69 (m, 1H), 4.22-4.16 (m, 3H), 3.84 (m, 1H), 3.47 (t, 2H), 3.27 (br d, 2H), 3.07 (t, 2H), 2.94 (dd, 1H), 2.84 (m, 2H), 2.71 (dd, 1H), 1.75 (br d, 2H), 1.56 (m, 1H), 1.36 (m, 2H), 0.86 (d, 3H) |
| F139 | 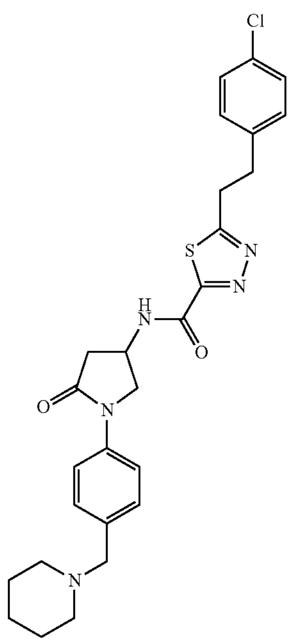 [SMILES: O=C(NC1CC(=O)N(c2ccc(CN3CCCCC3)cc2)C1)c1nnc(CCc2ccc(Cl)cc2)s1] | HCl | CM B | F27, F67 | LCMS method: Method 1, RT: 3.43 min, MI: 524 [M + 1] | 1H NMR (500 MHz, DMSO-d$_6$) δ 10.70 (br s, 1H), 9.80 (s, 1H), 7.72 (d, 2H), 7.60 (d, 2H), 7.33 (d, 2H), 7.27 (d, 2H), 4.68 (s, 1H), 4.20 (d, 2H), 3.94 (dd, 2H, underneath solvent), 3.46 (t, 2H), 3.23 (d, 2H), 3.06 (t, 2H), 2.96 (dd, 2H), 2.79 (m, 2H), 1.83-1.67 (m, 4H), 1.32 (m, 2H) |

TABLE 16-continued

| Ex no. | Structure | Salt | Coupling method | Intermediates | Characterisation | |
|---|---|---|---|---|---|---|
| | | | | | LCMS data | NMR data |
| F140 | 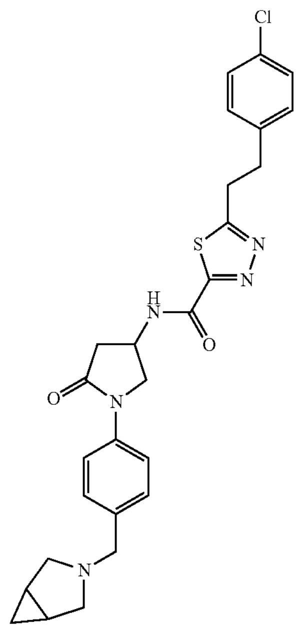 [SMILES: O=C(NC1CC(=O)N(c2ccc(CN3CC4CC4C3)cc2)C1)c1nnc(CCc2ccc(Cl)cc2)s1] | HCl | CM B | F27-6, F67 | LCMS method: Method 1, RT: 3.33 min, MI: 522 [M + 1] | 1H NMR (500 MHz, DMSO-d$_6$) δ 10.82 (br s, 1H), 9.80 (d, 1H), 7.70 (d, 2H), 7.62 (d, 2H), 7.33 (d, 2H), 7.27 (d, 2H), 4.69 (br s, 1H), 4.24 (d, 2H), 4.17 (m, 1H), 3.45 (t, 2H), 3.28 (m, 4H), 3.06 (t, 2H), 1.70 (m, 2H), 1.26 (m, 2H), 1.10 (m, 1H), 0.83 (m, 1H), 0.58 (m, 1H) |
| F141 | Chiral | HCl | CM B | F32-5, F67 | LCMS method: Method 1, RT: 3.89 min, MI: 537 [M + 1] | 1H NMR (500 MHz, CDCl$_3$) δ 7.73 (d, 1H), 7.54 (d, 2H), 7.33 (d, 2H), 7.26 (d, 2H), 7.12 (d, 2H), 5.85 (br s, 1H), 4.89-4.83 (m, 1H), 4.28 (dd, 1H), 3.86 (dd, 1H), 3.56 (s, 2H), 3.49-3.44 (m, 3H), 3.34 (br s, 2H), 3.16-3.07 (m, 5H), 2.71 (dd, 1H), 2.63 (t, 2H) |

TABLE 16-continued

| Ex no. | Structure | Salt | Coupling method | Intermediates | Characterisation | |
|---|---|---|---|---|---|---|
| | | | | | LCMS data | NMR data |
| F142 | 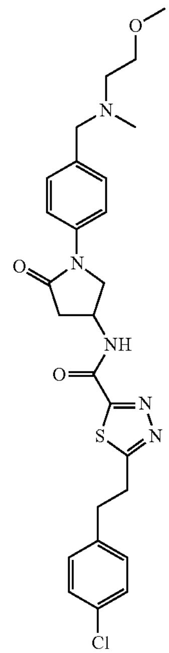 [SMILES: COCCN(C)Cc1ccc(N2CC(NC(=O)c3nnc(CCc4ccc(Cl)cc4)s3)CC2=O)cc1] | HCl | CM B | F27-3, F67 | LCMS method: Method 1, RT: 3.34 min, MI: 528 [M + 1] | 1H NMR (500 MHz, DMSO-$d_6$) δ 10.10 (br s, 1H), 9.80 (d, 1H), 7.75 (d, 2H), 7.55 (d, 2H), 7.34 (d, 2H), 7.27 (d, 2H), 4.69 (m, 1H), 4.33 (m, 1H), 4.23-4.12 (m, 2H), 3.83 (dd, 1H), 3.68 (t, 2H), 3.47 (t, 2H), 3.28 (s, 3H), 2.08 (t, 2H), 3.15 (m, 2H), 2.97-2.91 (m, 1H), 2.73 (m, 1H), 2.62 (br s, 3H) |
| F143 | Chiral | HCl | CM C | F32, F61 | LCMS method: Method 1, RT: 3.41 min, MI: 507 [M + 1] | 1H NMR (500 MHz, CDCl$_3$) δ 7.54 (d, 2H), 7.42 (d, 2H), 7.30 (d, 1H), 7.24 (d, 2H, 7.08 (d, 2H), 6.39 (s, 1H), 4.83 (m, 1H), 4.23 (dd, 1H), 3.82 (dd, 1H), 3.78 (br s, 2H), 3.08 (dd, 2H), 3.06 (dd, 1H), 2.98 (dd, 2H), 2.67 (dd, 1H), 2.66 (br s, 4H), 1.76 (br s, 4H), 1.50 (br s, 2H) |

TABLE 16-continued
| Ex no. | Structure | Salt | Coupling method | Intermediates | Characterisation LCMS data | NMR data |
|---|---|---|---|---|---|---|
| F144 | 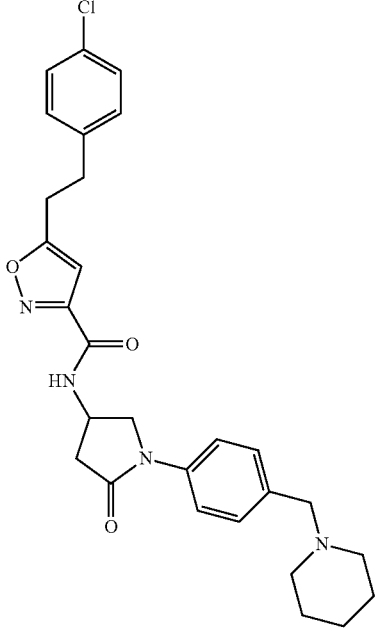 [SMILES: O=C(NC1CC(=O)N(c2ccc(CN3CCCCC3)cc2)C1)c1cc(CCc2ccc(Cl)cc2)on1] | HCl | CM C | F27, F61 | LCMS method: Method 1, RT: 3.48 min, MI: 507 [M + 1] | 1H NMR (500 MHz, CDCl$_3$) δ 7.54 (d, 2H), 7.42 (d, 2H), 7.30 (d, 1H), 7.24 (d, 2H), 7.08 (d, 2H), 6.39 (s, 1H), 4.83 (m, 1H), 4.23 (dd, 1H), 3.82 (dd, 1H), 3.78 (br s, 2H), 3.08 (dd, 2H), 3.06 (dd, 1H), 2.98 (dd, 2H), 2.67 (dd, 1H), 2.66 (br s, 4H), 1.76 (br s, 4H), 1.50 (br s, 2H) |
| F145 | 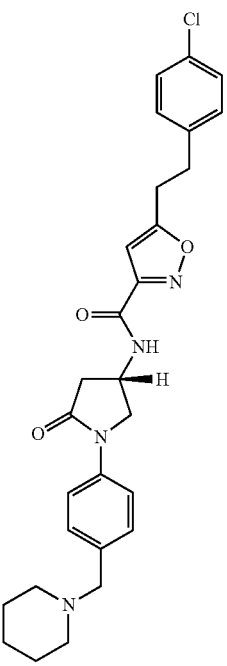 Chiral | HCl | CM C | F36, F61 | LCMS method: Method 1, RT: 3.42 min, MI: 507 [M + 1] | 1H NMR (500 MHz, CDCl$_3$) δ 7.54 (d, 2H), 7.42 (d, 2H), 7.30 (d, 1H), 7.24 (d, 2H), 7.08 (d, 2H), 6.39 (s, 1H), 4.83 (m, 1H), 4.23 (dd, 1H), 3.82 (dd, 1H), 3.78 (br s, 2H), 3.08 (dd, 2H), 3.06 (dd, 1H), 2.98 (dd, 2H), 2.67 (dd, 1H), 2.66 (br s, 4H), 1.76 (br s, 4H), 1.50 (br s, 2H) |

TABLE 16-continued
| Ex no. | Structure | Salt | Coupling method | Intermediates | Characterisation | |
|---|---|---|---|---|---|---|
| | | | | | LCMS data | NMR data |
| F146 | 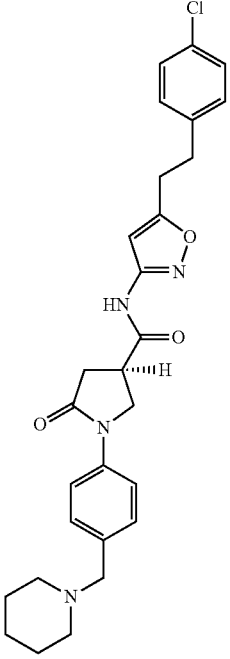 Chiral | HCl | CM D | F21-6, F43 | LCMS method: Method 1, RT: 3.55 min, MI: 507 [M + 1] | 1H NMR (500 MHz, CDCl₃) δ 9.26 (br s, 1H), 7.54 (d, 2H), 7.34 (d, 2H), 7.25 (d, 2H), 7.10 (d, 2H), 6.74 (s, 1H), 4.21 (dd, 1H), 4.06 (dd, 1H), 3.47 (s, 2H), 3.41 (dd, 1H), 3.04-2.90 (m, 6H), 2.38 (br s, 2H), 1.58 (br s, 6H), 1.43 (br s, 2H) |
| F147 | 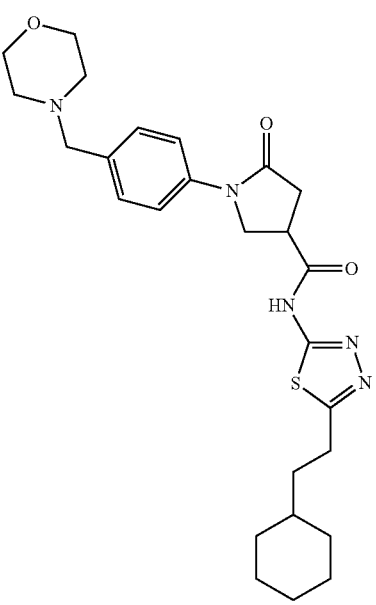 [SMILES: O=C(Nc1nnc(CCC2CCCCC2)s1)C1CC(=O)N(c2ccc(CN3CCOCC3)cc2)C1] | — | CM D | F15-2, F40-5 | LCMS method: Method 1, RT: 3.81 min, MI: 498 [M + 1] | 1H NMR (500 MHz, CDCl₃) δ 13.58 (br s, 1H), 7.57 (d, 2H), 7.33 (d, 2H), 4.34-4.19 (m, 2H), 4.00-3.90 (m, 1H), 3.77-3.65 (m, 4H), 3.47 (s, 2H), 3.14-2.98 (m, 4H), 2.49-2.38 (m, 4H), 1.79-1.59 (m, 6H), 1.37-1.08 (m, 5H), 1.00-0.86 (m, 2H) |

TABLE 16-continued

| Ex no. | Structure | Salt | Coupling method | Intermediates | Characterisation LCMS data | NMR data |
|---|---|---|---|---|---|---|
| F148 | Chiral | HCl | CM D | F21-8, F38 | LCMS method: Method 1, RT: 2.97 min, MI: 518 [M + 1] | 1H NMR (500 MHz, DMSO-d$_6$) δ 11.33 (s, 1H), 10.22 (br d, 1H), 8.21 (d, 1H), 7.77 (d, 2H), 7.57 (m, 3H), 7.24 (dd, 2H), 7.07 (t, 2H), 4.35 (m, 2H), 4.16 (m, 3H), 4.00 (m, 4H), 3.60 (m, 2H), 3.15 (t, 2H), 3.00 (t, 2H), 2.89 (dd, 1H), 2.77 (dd, 1H), 2.57 (dd, 2H), 2.25 (m, 2H) |
| F149 | 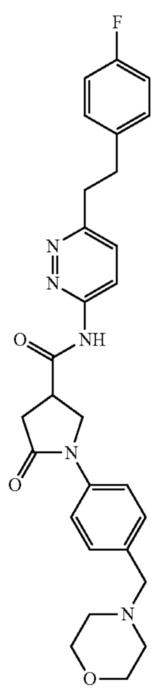 [SMILES: O=C(Nc1ccc(CCc2ccc(F)cc2)nn1)C1CC(=O)N(c2ccc(CN3CCOCC3)cc2)C1] | HCl | CM D | F15-2, F38 | LCMS method: Method 1, RT: 3.10 min, MI: 504 [M + 1] | 1H NMR (500 MHz, DMSO-d$_6$) δ 11.44 (s, 0.8H), 11.39 (s, 0.2H), 1.115 (br s, 1H), 8.28 (d, 0.8H), 8.22 (d, 0.2H), 7.79 (d, 0.2H), 7.73 (m, 1.8 H), 7.66 (d, 0.8H), 7.59 (m, 2H), 7.47 (d, 0.2H), 7.33 (m, 0.4H), 7.25 (m, 1.6H), 7.14-7.06 (m, 2H), 4.28 (d, 2H), 4.12 (t, 1H), 4.01 (dd, 1H), 3.89 (d, 2H), 3.76 (t, 2H), 3.65 (m, 1H), 3.18 (m, 4H), 3.07-2.99 (m, 4H), 2.87 (dd, 1H), 2.76 (dd, 1H) |

TABLE 16-continued

| Ex no. | Structure | Salt | Coupling method | Intermediates | Characterisation LCMS data | NMR data |
|---|---|---|---|---|---|---|
| F150 | (structure) | — | CM D | F15-2, F40-2 | LCMS method: Method 1, RT: 2.99 min, MI: 522 [M + 1] | 1H NMR (500 MHz, CDCl$_3$) δ 13.82 (br s, 1H), 7.58 (d, 2H), 7.33 (d, 2H), 7.09 (d, 2H), 6.81 (d, 2H), 4.30-4.20 (m, 2H), 3.94-3.85 (m, 1H), 3.77 (s, 3H), 3.73-3.65 (m, 4H), 3.46 (br s, 2H), 3.30 (t, 2H), 3.12-2.79 (m, 4H), 2.47-2.37 (br s, 4H) |
| F151 | (structure) | HCl | CM D | F15-7, F40 | LCMS method: Method 1, RT: 3.38 min, MI: 510 [M + 1] | 1H NMR (500 MHz, DMSO-d$_6$) δ 12.68 (s, 1H), 10.52 (s, 1H), 7.71 (d, 2H), 7.56 (d, 2H), 7.32 (d, 2H), 7.28 (d, 2H), 4.29 (d, 2H), 4.10 (t, 1H), 4.01 (m, 1H), 3.64 (m, 1H), 3.30 (br t, 4H), 3.02 (br t, 4H), 2.88 (dd, 1H), 2.77 (dd, 1H), 1.99 (br m, 2H), 1.86 (br m, 2H) |

TABLE 16-continued
| Ex no. | Structure | Salt | Coupling method | Intermediates | Characterisation | |
|---|---|---|---|---|---|---|
| | | | | | LCMS data | NMR data |
| F152 | 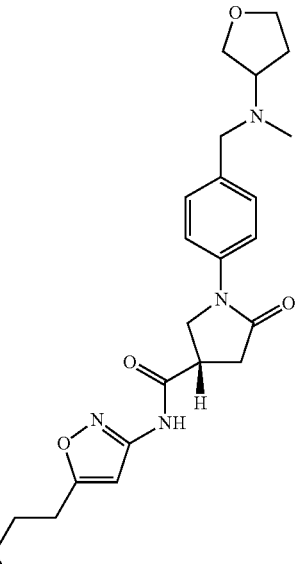 Chiral | HCl | CM F | F21-8, F43 | LCMS method: Method 1, RT: 3.42 min, MI: 523 [M + 1] | 1H NMR (500 MHz, DMOS-d$_6$) δ 11.21 (s, 1H), 10.36 (d, 1H), 7.75 (d, 2H), 7.56 (d, 2H), 7.33 (d, 2H), 7.27 (d, 2H), 6.62 (s, 1H), 4.35 (ddd, 1H), 4.17 (m, 2H), 4.08 (t, 1H), 3.97 (m, 3H), 3.73 (m, 1H), 3.61 (m, 2H), 3.04 (t, 2H), 2.94 (t, 2H), 2.84 (dd, 1H), 2.72 (dd, 1H), 2.55 (dd, 3H), 2.24 (m, 2H) |
| F153 | 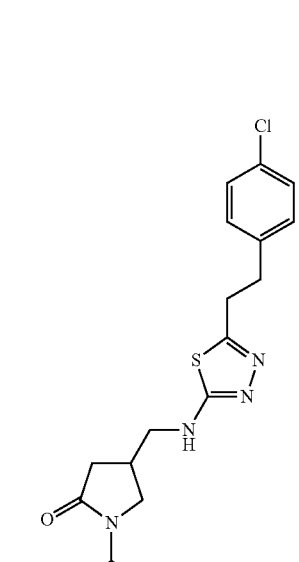 | — | CM J | F83, F40 | LCMS method: Method 5, RT: 2.59 min, MI: 512 [M + 1] | 1H NMR (400 MHz, DMSO-d$_6$) δ 7.78 (t, 1H), 7.59 (d, 2H), 7.35-7.28 (m, 6H), 3.94 (dd, 1H), 3.61 (dd, 1H), 3.56 (t, 4H), 3.43 (s, 2H), 3.37 (t, 2H), 3.12 (t, 2H), 2.94 (t, 2H), 2.79-2.72 (m, 1H), 2.69-2.63 (m, 1H), 2.36-2.31 (m, 5H) |

TABLE 16-continued

| Ex no. | Structure | Salt | Coupling method | Intermediates | Characterisation LCMS data | NMR data |
|---|---|---|---|---|---|---|
| F154 | 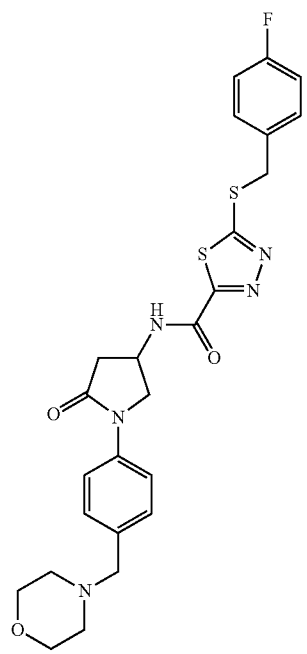 | — | CM H | F15-3, F40-7 | LCMS method: Method 5, RT: 2.64 min, MI: 528 [M + 1] | 1H NMR (400 MHz, CDCl$_3$) δ 7.54 (d, 2H), 7.26-7.34 (m, 4H), 6.96 (dt, 2H), 4.34 (s, 2H), 4.23 (d, 2H), 3.78-3.86 (m, 1H), 3.71 (br s, 4H), 3.48 (br s, 2H), 3.0-3.13 (m, 2H), 2.45 (br s, 4H) |
| F155 | Chiral | — | CM A | F21-11, F38 | LCMS method: Method 1, RT: 3.05 min, MI: 504 [M + 1] | 1H NMR (500 MHz, DMSO-d$_6$) δ 11.03 (s, 1H), 8.21 (d, 1H), 7.61 (d, 2H), 7.57 (d, 1H), 7.28 (d, 2H), 7.24 (m, 2H), 7.07 (tt, 2H), 4.50 (d, 2H), 4.41 (t, 2H), 4.09 (m, 1H), 3.99 (m, 1H), 3.62 (m, 1H), 3.55 (m, 1H), 3.29 (s, 2H), 3.15 (t, 2H), 3.00 (t, 2H), 2.84 (dd, 1H), 2.75 (dd, 1H), 1.94 (s, 3H) |

TABLE 16-continued

| Ex no. | Structure | Salt | Coupling method | Intermediates | Characterisation | |
|---|---|---|---|---|---|---|
| | | | | | LCMS data | NMR data |
| F156 | (structure with 4-chlorophenyl-ethyl-thiadiazole, pyrrolidinone, phenyl, diazepane) | Bis HCl | CM A | F15-8, F40 | LCMS method: Method 1, RT: 2.62 min, MI: 539 [M + 1] | 1H NMR (500 MHz, DMSO-$d_6$) δ 11.76 (s, 1H), 9.88 (s, 1H), 9.52 (s, 1H), 8.13 (s, 1H), 7.72 (d, 2H), 7.65 (d, 2H), 7.33 (d, 2H), 7.28 (d, 2H), 4.34 (br d, 2H), 4.11 (t, 1H), 4.01 (dd, 1H), 3.62 (m, 3H), 3.52 (m, 2H), 3.30 (t, 2H), 3.17 (m, 2H), 3.02 (t, 2H), 2.89 (dd, 1H), 2.76 (dd, 1H), 2.15 (m, 2H) |
| F157 | (structure with Boc-piperazine, benzyl, pyrrolidinone, thiadiazole, 4-chlorophenyl-ethyl) | — | CM A | F15-9, F40 | LCMS method: Method 1, RT: 3.98 min, MI: 625 [M + 1] | 1H NMR (500 MHz, DMSO-$d_6$) δ 7.59 (d, 2H), 7.33 (d, 2H), 7.29 (d, 4H), 4.07 (t, 1H), 3.98 (dd, 1H), 3.57 (m, 1H), 3.43 (s, 2H), 3.31 (t, 2H, hidden by water peak), 3.02 (t, 2H), 2.85 (dd, 1H), 2.74 (dd, 1H), 2.27 (m, 8H), 1.37 (s, 24H, overintegrating, should be 9H) |

TABLE 16-continued

| Ex no. | Structure | Salt | Coupling method | Intermediates | Characterisation LCMS data | NMR data |
|---|---|---|---|---|---|---|
| F158 | 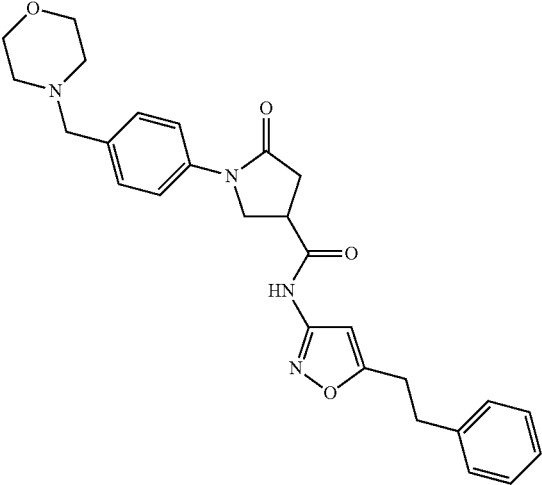 [SMILES: O=C(Nc1cc(CCc2ccccc2)on1)C1CC(=O)N(c2ccc(CN3CCOCC3)cc2)C1] | HCl | CM A | F15-2, F43-1 | LCMS method: Method 1, RT: 3.68 min, MI: 475 [M + 1] | 1H NMR (500 MHz, DMSO-d$_6$) δ 11.21 (s, 1H), 10.49 (s, 1H), 7.73 (d, 2H), 7.53 (d, 2H), 7.28-7.22 (m, 4H), 7.18 (m, 1H), 6.62 (s, 1H), 4.29 (br d, 2H), 4.06 (t, 1H), 3.94 (m, 3H), 3.68 (t, 2H), 3.49 (m, 1H), 3.19 (d, 2H), 3.04 (t, 4H), 2.94 (t, 2H), 2.83 (dd, 1H), 2.70 (dd, 1H) |
| F159 | 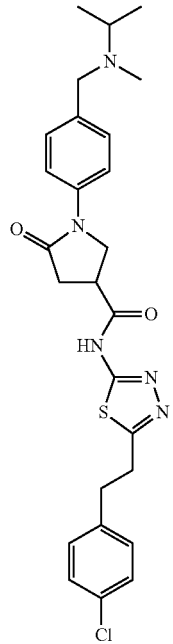 | — | CM A | F15-21, F40 | LCMS method: Method 1, RT: 3.47 min, MI: 512 [M + 1] | 1H NMR (500 MHz, DMSO-d$_6$) δ 12.67 (br s, 1H), 7.68 (br s, 2H), 7.44 (br s, 2H), 7.32 (d, 2H), 7.27 (d, 2H), 4.08 (m, 1H), 4.00 (dd, 1H), 3.59 (m, 1H), 3.30 (t, 2H, hidden partly by water peak), 3.02 (t, 2H), 2.86 (dd, 1H), 2.74 (dd, 1H), 1.16 (br s, 6H) (6H presumed under solvent peak) |

TABLE 16-continued

| Ex no. | Structure | Salt | Coupling method | Intermediates | Characterisation LCMS data | NMR data |
|---|---|---|---|---|---|---|
| F160 | (4-chlorophenethyl-thiadiazolyl)-carboxamide-oxopyrrolidinyl-phenyl-methyl-piperazine structure | Bis HCl | CM A | F15-9, F40 | LCMS method: Method 1, RT: 3.31 min, MI: 525 [M + 1] | — |
| F161 | Chiral (4-chlorophenethyl-thiadiazolyl)-carboxamide-(S)-oxopyrrolidinyl-phenyl-methyl-morpholine structure | HCl | CM A | F22, F40 | LCMS method: Method 5, RT: 2.67 min, MI: 525/528 [M + 1] | 1H NMR (500 MHz, DMSO-d$_6$) δ 12.74 (br s, 1H), 11.21 (br s, 1H), 7.74 (d, 2H), 7.62 (d, 2H), 7.34 (d, 2H), 7.29 (d, 2H), 4.30 (d, 2H), 4.12 (t, 1H), 4.03 (dd, 1H), 3.94-3.91 (br d, 2H), 3.78 (t, 2H), 3.63 (m, 1H), 3.31 (t, 2H), 3.20 (d, 2H), 3.10-3.01 (m, 4H), 2.90 (dd, 1H), 2.78 (dd, 1H) |

TABLE 16-continued

| Ex no. | Structure | Salt | Coupling method | Intermediates | Characterisation | |
|---|---|---|---|---|---|---|
| | | | | | LCMS data | NMR data |
| F162 | (structure) | — | CM A | F15-2, 38-1 | LCMS method: Method 5, RT: 2.46 min, MI: 486 [M + 1] | 1H NMR (400 MHz, DMSO-d$_6$) δ 11.37 (s, 1H), 8.26 (d, 1H), 7.64 (m, 3H), 7.34-7.21 (m, 7H), 4.13 (t, 1H), 4.03 (m, 1H), 3.66 (m, 1H), 3.59 (m, 4H), 3.46 (s, 2H), 3.20 (t, 1H), 3.04 (m, 2H), overintegrating due to water peak, should be 1H), 2.87 (dd, 2H, overintegrating due to water peak, should be 1H), 2.80 (m, 1H), 2.37 (s, 4H), 1.70 (d, 2H) |
| F163 | (structure, Chiral) | HCl | CM A | F22-1, F40 | LCMS method: Method 5, RT: 2.76 min, MI: 524/526 [M + 1] | 1H NMR (500 MHz, DMSO-d$_6$) δ 12.79 (br s, 1H), 10.89 (br s, 1H), 7.72 (d, 2H), 7.64 (d, 2H), 7.33 (d, 2H), 7.28 (d, 2H), 4.22 (d, 2H), 4.13 (m, 1H), 4.03 (m, 1H), 3.66 (m, 1H), 3.31 (t, 2H), 3.23 (m, 2H), 3.03 (t, 2H), 2.90 (m, 1H), 2.79 (m, 3H), 1.76 (m, 5H), 1.32 (m, 1H) |

TABLE 16-continued

| Ex no. | Structure | Salt | Coupling method | Intermediates | LCMS data | NMR data |
|---|---|---|---|---|---|---|
| F164 | Chiral | HCl | CM A | F21-6, F40-12 | LCMS method: Method 1, RT: 2.90 min, MI: 498 [M + 1] | 1H NMR (500 MHz, DMSO-d$_6$) δ 12.69 (s, 1H), 9.71 (s, 1H), 7.74 (d, 2H), 7.53 (d, 2H), 4.22 (d, 2H), 4.11 (dd, 1H), 4.03 (dd, 1H), 3.86 (dd, 1H), 3.62 (m, 1H), 3.31-3.20 (m, 4H), 3.07-2.96 (m, 2H), 2.90 (dd, 1H), 2.85-2.74 (m, 3H), 1.78 (m, 5H), 1.66 (m, 3H), 1.56 (d, 1H), 1.45-1.28 (m, 4H), 1.19 (m, 1H) |
| F165 | Chiral | HCl | CMA | F21, F40-12 | LCMS method: Method 3, RT: 1.96 min, MI: 498 [M −1] | 1H NMR (500 MHz, DMSO-d$_6$) δ 14.25 (s, 1H), 7.93 (d, 2H), 7.70 (d, 2H), 4.27 (m, 2H), 4.10 (m, 1H), 4.01 (m, 1H), 3.88 (m, 2H), 3.78 (m, 4H), 3.61 (m, 2H), 3.23-3.16 (m, 4H), 2.98 (m, 2H), 1.60 (m, 4H), 1.47 (m, 2H), 1.32-1.13 (m, 4H) |

TABLE 16-continued
| Ex no. | Structure | Salt | Coupling method | Intermediates | Characterisation LCMS data | NMR data |
|---|---|---|---|---|---|---|
| F166 | 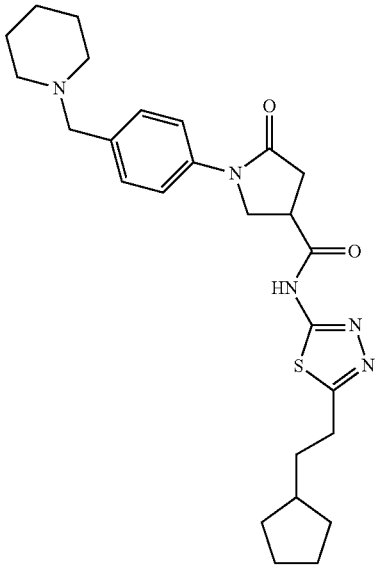 [SMILES: O=C(Nc1nnc(CCC2CCCC2)s1)C1CC(=O)N(c2ccc(CN3CCCCC3)cc2)C1] | — | CM A | F15-4, F40-8 | LCMS method: Method 1, RT: 3.62 min, MI: 480 [M − 1] | 1H NMR (500 MHz, DMSO-d$_6$) δ 7.57 (d, 2H), 7.27 (d, 2H), 4.07 (t, 1H), 3.99 (t, 1H), 3.54 (m, 1H), 3.37 (s, 2H), 2.96 (t, 2H), 2.82-2.77 (m, 2H), 2.49 (br s, 4H), 1.70-1.67 (m, 5H), 1.56 (m, 2H), 1.47 (m, 6H), 1.45 (m, 2H), 1.11 (m, 2H) |
| F167 | 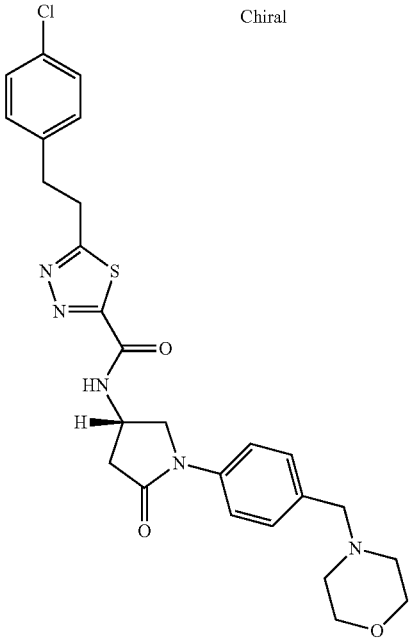 [SMILES: O=C(N[C@H]1CC(=O)N(c2ccc(CN3CCOCC3)cc2)C1)c1nnc(CCc2ccc(Cl)cc2)s1] Chiral | HCl | CM B | F78-1, F67 | LCMS method: Method 7, RT: 3.94 min, MI: 512 [M + 1] | 1H NMR (500 MHz, DMOS-d$_6$) δ 10.91 (br s, 1H), 9.50 (d, 1H), 7.36 (m, 4H), 7.29 (d, 2H), 6.56 (d, 2H), 4.59 (m, 1H), 4.15 (d, 2H), 3.91 (m, 2H), 3.74 (t, 2H), 3.56 (dd, 1H), 3.46 (t, 2H), 3.38 (m, 1H), 3.28 (dd, 2H), 3.16 (m, 2H), 3.05 (t, 2H), 2.98 (m, 2H), 2.24 (m, 1H), 2.13 (m, 1H) |

TABLE 16-continued

| Ex no. | Structure | Salt | Coupling method | Intermediates | Characterisation LCMS data | NMR data |
|---|---|---|---|---|---|---|
| F168 | 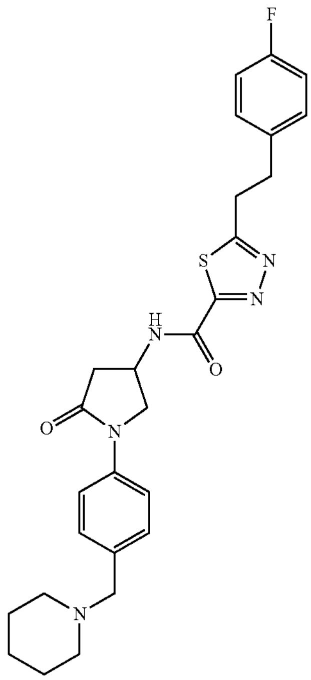 | HCl | CM B | F27, F67-2 | LCMS method: Method 1, RT: 3.01 min, MI: 508 [M + 1] | 1H NMR (500 MHz, DMSO-d$_6$) δ 9.79 (d, 1H), 9.53 (s, 1H), 7.75 (d, 2H), 7.51 (d, 2H), 7.29 (dd, 2H), 7.10 (t, 2H), 4.69 (m, 1H), 4.23 (d, 2H), 4.19 (dd, 1H), 3.83 (m, 1H), 3.46 (t, 2H), 3.27 (m, 2H), 3.06 (t, 2H), 2.94 (dd, 1H), 2.82 (m, 2H), 2.72 (dd, 1H), 1.79 (br d, 2H), 1.64 (m, 3H), 1.29 (m, 1H) |
| F169 | Chiral | HCl | CM B | F32-3, F67 | LCMS method: Method 1, RT: 3.29 min, MI: 554 [M + 1] | 1H NMR (500 MHz, CDCl$_3$) δ 7.73 (d, 1H), 7.52 (d, 2H), 7.34 (d, 2H), 7.26 (d, 2H), 7.12 (d, 2H), 4.88-4.82 (m, 1H), 4.27 (dd, 1H), 3.86 (dd, 1H), 3.54 (s, 2H), 3.46 (dd, 2H), 3.12 (dd, 2H), 3.09 (dd, 1H), 2.69 (dd, 1H), 2.58 (br s, 2H), 2.41 (br t, 2H), 1.69 (br m, 2H), 1.59 (br d, 2H), 1.24 (s, 3H) |

TABLE 16-continued

| Ex no. | Structure | Salt | Coupling method | Intermediates | Characterisation LCMS data | NMR data |
|---|---|---|---|---|---|---|
| F170 | Chiral | HCl | CM B | F32-2, F67 | LCMS method: Method 1, RT: 3.37 min, MI: 542 [M + 1] | 1H NMR (500 MHz, CDCl$_3$) δ 7.81 (d, 1H), 7.51 (d, 2H), 7.30 (d, 2H), 7.26 (d, 2H), 7.11 (d, 2H), 4.89-4.82 (m, 1H), 4.25 (dd, 1H), 3.86 (dd, 1H), 3.76 (s, 2H), 3.46 (t, 2H), 3.12 (t, 2H), 3.07 (dd, 1H), 2.91 (t, 2H), 6.38 (dd, 1H), 1.63 (t, 2H), 1.20 (s, 6H) |
| F171 | Chiral | HCl | CM B | F32-1, F67 | LCMS method: Method 1, RT: 3.36 min, MI: 556 [M + 1] | 1H NMR (500 MHz, CDCl$_3$) δ 7.73 (d, 1H), 7.54 (d, 2H), 7.31 (d, 2H), 7.26 (d, 2H), 7.12 (d, 2H), 4.89-4.83 (m, 1H), 4.26 (dd, 1H), 3.86 (dd, 1H), 3.58 (s, 2H), 3.46 (dd, 2H), 3.15 (dd, 2H), 3.09 (dd, 1H), 2.74 (t, 2H), 2.69 (dd, 1H), 2.72 (s, 3H), 1.67 (t, 2H), 1.17 (d, 6H) |

TABLE 16-continued
| Ex no. | Structure | Salt | Coupling method | Intermediates | Characterisation LCMS data | NMR data |
|---|---|---|---|---|---|---|
| F172 | 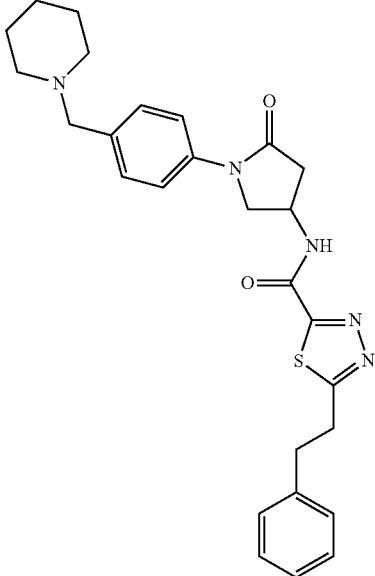 | HCl | CM B | F27, F67-1 | LCMS method: Method 1, RT: 2.98 min, MI: 490 [M + 1] | 1H NMR (500 MHz, CDCl₃) δ 7.83 (d, 1H), 7.50 (d, 2H), 7.33-7.28 (m, 4H), 7.24 (t, 1H), 7.18 (d, 2H), 4.85 (br s, 1H), 4.25 (dd, 1H), 3.85 (dd, 1H), 3.48 (dd, 2H), 3.46 (s, 2H), 3.13 (dd, 2H), 3.07 (dd, 1H), 2.71 (dd, 1H), 2.37 (br s, 4H), 1.56 (br s, 4H), 1.42 (br s, 2H) |
| F173 | 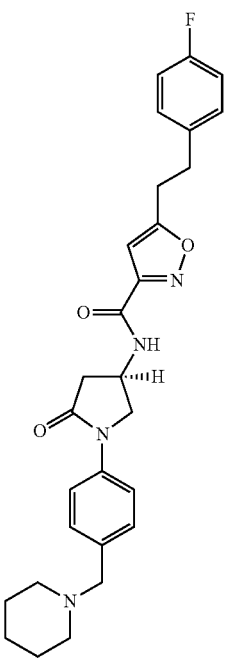 Chiral | HCl | CM C | F32, F61-2 | LCMS method: Method 1, RT: 3.22 min, MI: 491 [M + 1] | 1H NMR (500 MHz, CDCl₃) δ 7.56 (d, 2H), 7.44 (d, 2H), 7.21 (d, 1H), 7.12-7.09 (m, 2H), 6.98-6.95 (m, 2H), 6.39 (s, 1H), 4.86-4.81 (m, 1H), 4.25 (dd, 1H), 3.82 (dd, 1H), 3.68 (br s, 2H), 3.09 (dd, 2H), 3.05 (dd, 1H), 2.99 (t, 2H), 2.67 (dd, 1H), 2.58 (br s, 3H), 1.73 (br s, 4H), 1.49 (br s, 2H) |

TABLE 16-continued
| Ex no. | Structure | Salt | Coupling method | Intermediates | Characterisation | |
|---|---|---|---|---|---|---|
| | | | | | LCMS data | NMR data |
| F174 | 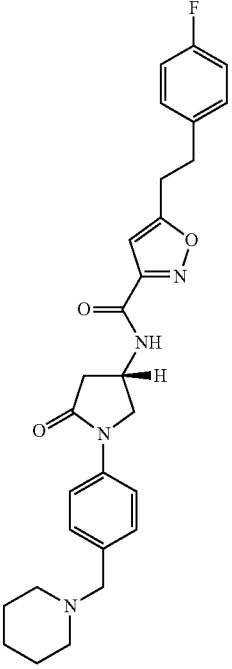 Chiral | HCl | CM C | F36, F61-2 | LCMS method: Method 1, RT: 3.18 min, MI: 491 [M + 1] | 1H NMR (500 MHz, CDCl₃) δ 7.51 (d, 2H), 7.33 (d, 2H), 7.11 (m, 2H), 6.97 (m, 2H), 6.39 (s, 1H), 4.83 (m, 1H), 4.27 (dd, 1H), 3.82 (dd, 1H), 3.45 (br s, 2H), 3.11-3.05 (m, 3H), 3.00 (t, 2H), 2.63 (dd, 1H), 2.36 (br s, 4H), 1.42 (br s, 2H) (4H presumed under water peak) |
| F175 | 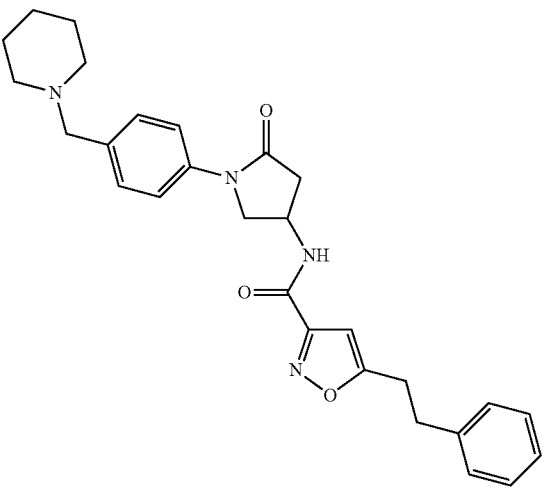 [SMILES: O=C(NC1CC(=O)N(c2ccc(CN3CCCCC3)cc2)C1)c1cc(CCc2ccccc2)on1] | HCl | CM C | F27, F61-1 | LCMS method: Method 1, RT: 3.17 min, MI: 473 [M + 1] | 1H NMR (500 MHz, CDCl₃) δ 7.52 (d, 2H), 7.34 (d, 2H), 7.29 (t, 2H), 7.22 (t, 1H), 7.16 (d, 2H), 7.14 (d, 1H), 6.40 (s, 1H), 4.83 (m, 1H), 4.26 (dd, 1H), 3.82 (dd, 1H), 3.49 (s, 2H), 3.11 (dd, 2H), 3.06 (dd, 1H), 3.03 (dd, 2H), 2.64 (dd, 1H), 2.40 (br s, 4H), 1.59 (br t, 4H), 1.43 (br s, 2H) |

TABLE 16-continued

| Ex no. | Structure | Salt | Coupling method | Intermediates | LCMS data | NMR data |
|---|---|---|---|---|---|---|
| F176 | 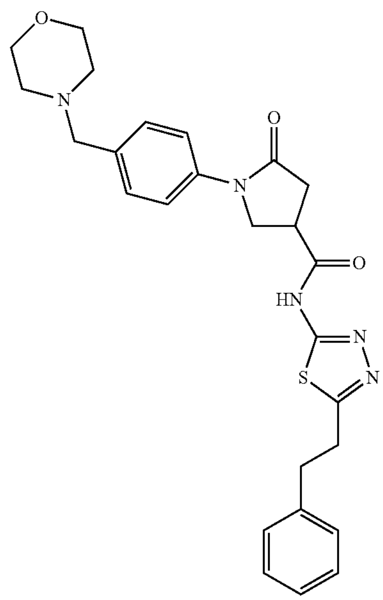 | HCl | CM D | F15-2, F40-1 | LCMS method: Method 1, RT: 3.00 min, MI: 492 [M + 1] | 1H NMR (500 MHz, CDCl$_3$) δ 12.68 (br s, 1H, 10.58 (br s, 1H), 7.77-7.72 (m, 2H), 7.57-7.54 (m, 2H), 7.31-7.16 (m, 5H), 4.30 (br d, 2H), 4.13-4.07 (m, 1H), 4.04-3.99 (m, 1H), 3.96-3.89 (m, 2H), 3.74-3.65 (m, 2H), 3.64-3.57 (m, 1H) overlapping with water peak), 3.30 (t, 2H), 3.23-3.17 (m, 2H), 3.10-2.99 (m, 4H), 2.92-2.84 (m, 1H), 2.80-2.73 (m, 1H) |
| F177 | 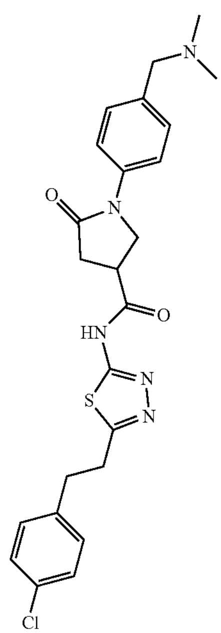 [SMILES: CN(C)Cc1ccc(N2CC(C(=O)Nc3nnc(CCc4ccc(Cl)cc4)s3)CC2=O)cc1] | — | CM D | F15-12, F40 | LCMS method: Method 1, RT: 3.22 min, MI: 484 [M + 1] | 1H NMR (500 MHz, DMSO-d$_6$) δ 12.53 (br s, 1H), 7.58 (d, 2H), 7.32 (d, 2H), 7.28 (d, 2H), 7.27 (d, 2H), 4.08 (t, 1H), 3.99 (dd, 1H), 3.58 (m, 1H), 3.37 (s, 2H), 3.30 (t, 2H hidden under water peak), 3.02 (t, 2H), 2.84 (dd, 1H), 2.73 (dd, 1H), 2.13 (s, 6H) |

TABLE 16-continued

| Ex no. | Structure | Salt | Coupling method | Intermediates | LCMS data | NMR data |
|---|---|---|---|---|---|---|
| F178 | Chiral | HCl | CM D | F21-6, F38 | LCMS method: Method 1, RT: 3.15 min, MI: 502 [M + 1] | 1H NMR (500 MHz, DMSO-d$_6$) δ 11.33 (s, 1H), 9.45 (s, 1H), 8.21 (d, 1H), 7.76 (d, 2H), 7.58 (d, 1H), 7.50 (d, 2H), 7.24 (m, 2H), 7.07 (m, 2H), 4.23 (d, 2H), 4.12 (t, 1H), 4.02 (dd, 1H), 3.64 (m, 1H), 3.28 (d, 2H), 3.15 (t, 2H), 3.00 (t, 2H), 2.91-2.75 (m, 4H), 1.79 (d, 2H), 1.68-1.58 (m, 4H) |
| F179 | 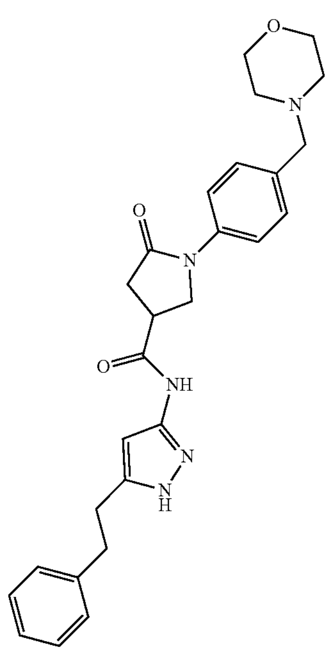 [SMILES: O=C(Nc1cc(CCc2ccccc2)[nH]n1)C1CC(=O)N(c2ccc(CN3CCOCC3)cc2)C1] | — | CM D | F15-3, F51-1 | LCMS method: Method 5, RT: 2.41 min, MI: 474 [M + 1] | 1H NMR (400 MHz, DMSO-d$_6$) δ 12.13 (br s, 1H), 10.58 (s, 1H), 7.60 (d, 2H), 7.17-7.31 (m, 7H), 6.33 (s, 1H), 4.03 (t, 1H), 3.91 (dd, 1H), 3.56 (t, 4H), 3.43 (s, 2H), 3.43-3.48 (m, 1H), 2.83-2.92 (m, 4H), 2.66-2.80 (m, 2H), 2.33 (br s, 4H) |

TABLE 16-continued

| Ex no. | Structure | Salt | Coupling method | Intermediates | LCMS data | NMR data |
|---|---|---|---|---|---|---|
| F180 | Chiral | HCl | CM F | F21, F38 | LCMS method: Method 1, RT: 2.98 min, MI: 504 [M + 1] | 1H NMR (500 MHz, DMSO-d$_6$) δ 11.38 (s, 1H), 10.97 (br s, 1H), 8.26 (d, 1H), 7.75 (d, 2H), 7.63 (d, 1H), 7.59 (d, 2H), 7.24 (m, 2H), 7.08 (m, 2H), 4.29 (d, 2H), 4.12 (t, 1H), 4.02 (dd, 1H), 3.92 (br d, 2H), 3.75 (br t, 2H), 3.64 (m, 1H), 3.20-3.15 (m, 4H), 3.08-2.99 (m, 4H), 2.88 (dd, 1H), 2.77 (dd, 1H) |
| F181 | 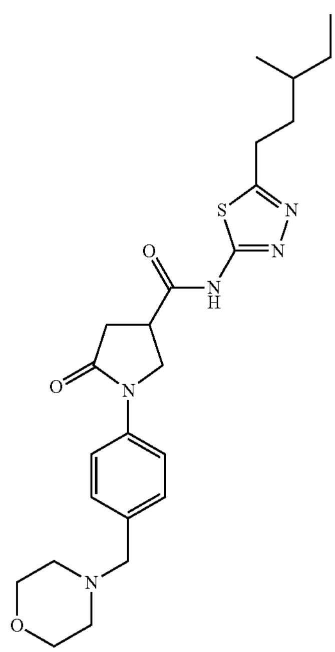 [SMILES: CCC(C)CCc1nnc(NC(=O)C2CC(=O)N(c3ccc(CN4CCOCC4)cc3)C2)s1] | HCl | CM G | F15-2, F40-9 | LCMS method: Method 1, RT: 3.38 min, MI: 494 [M − 1] | 1H NMR (500 MHz, DMSO-d$_6$) δ 12.70 (s, 1H), 7.75 (d, 2H), 7.56 (d, 2H), 4.30 (d, 2H), 4.11 (t, 1H), 4.03 (t, 1H), 3.91 (m, 2H), 3.22 (d, 2H), 3.07 (m, 2H), 2.99 (m, 1H), 2.89-2.74 (m, 2H), 2.62 (t, 2H), 2.34 (t, 2H), 1.69 (m, 1H), 1.51 (m, 1H), 1.35 (m, 2H), 1.15 (m, 1H), 0.88 (d, 3H), 0.81 (t, 3H) |

TABLE 16-continued

| Ex no. | Structure | Salt | Coupling method | Intermediates | Characterisation LCMS data | NMR data |
|---|---|---|---|---|---|---|
| F182 | 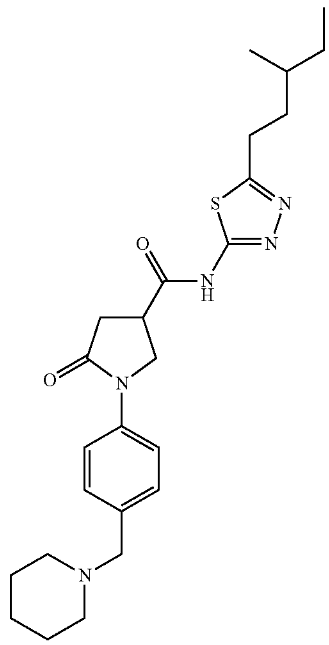 [SMILES: CCC(C)CCc1nnc(NC(=O)C2CC(=O)N(c3ccc(CN4CCCCC4)cc3)C2)s1] | HCl | CM G | F15-4, F40-9 | LCMS method: Method 1, RT: 3.44 min, MI: 468 [M − 1] | 1H NMR (500 MHz, DMSO-d$_6$) δ 12.72 (s, 1H), 7.73 (d, 2H), 7.57 (d, 2H), 4.20 (d, 2H), 4.11 (t, 1H), 4.02 (t, 1H), 3.38 (t, 1H), 3.24 (d, 2H), 3.15 (s, 2H), 3.01-2.80 (m, 2H), 2.74 (m, 2H), 1.78-1.85 (m, 6H), 1.49 (m, 1H), 1.34 (m, 2H), 1.15 (m, 1H), 1.08 (t, 1H), 0.87 (d, 3H), 0.82 (t, 3H) |
| F183 | 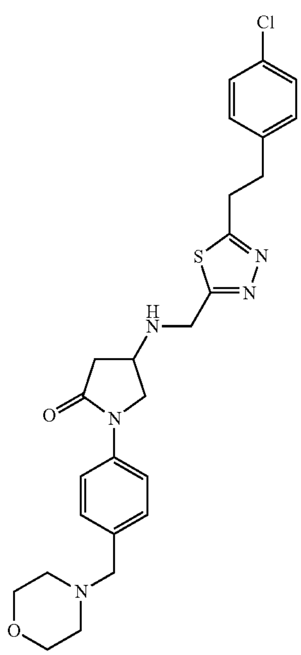 [SMILES: O=C1CC(NCc2nnc(CCc3ccc(Cl)cc3)s2)CN1c1ccc(CN2CCOCC2)cc1] | HCl | CM I | F27-1, F81 | LCMS method: Method 7, RT: 3.94 min, MI: 512 [M + 1] | 1H NMR (500 MHz, DMSO-d$_6$) δ 10.71 (br s, 1H), 9.80 (d, 1H), 7.76 (d, 2H), 7.57 (d, 2H), 7.34 (d, 2H), 7.29 (d, 2H), 4.80 (br s, 1H), 4.30 (d, 2H), 4.24-4.08 (m, 3H), 3.93 (d, 2H), 3.73 (t, 2H), 3.20 (d, 2H), 3.06 (m, 4H), 2.89 (m, 1H) (4H presumed under water peak) |

TABLE 16-continued

| Ex no. | Structure | Salt | Coupling method | Intermediates | Characterisation | |
|---|---|---|---|---|---|---|
| | | | | | LCMS data | NMR data |
| F184 | 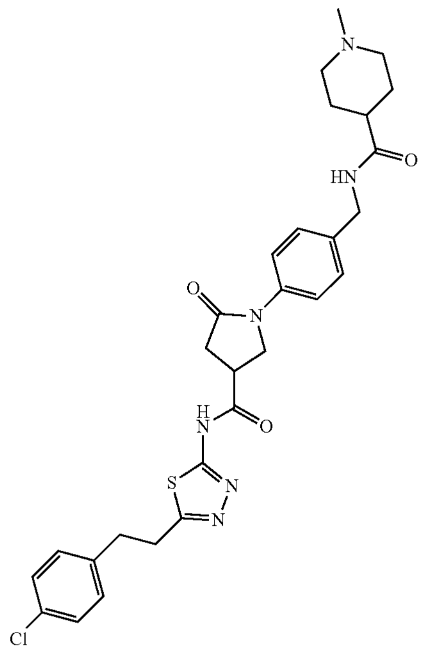 [SMILES: CN1CCC(C(=O)NCc2ccc(N3CC(C(=O)Nc4nnc(CCc5ccc(Cl)cc5)s4)CC3=O)cc2)CC1] | — | CM K | F84, F40 | LCMS method: Method 1, RT: 3.52 min, MI: 581 [M + 1] | 1H NMR (500 MHz, DMSO-d$_6$) δ 12.68 (s, 1H), 7.56 (d, 2H), 7.32 (d, 2H), 7.28 (d, 2H), 7.22 (d, 2H), 4.24 (d, 2H), 4.06 (dd, 1H), 3.97 (dd, 1H), 3.60 (m, 2H), 3.42 (br m, 2H), 3.30 (t, 2H, under water peak), 3.13 (m, 2H), 3.02 (t, 2H), 2.84 (dd, 2H), 2.74 (s, 3H) (5H presumed under solvent peak) |
| F186 | Chiral | HCl | CM A | F21, F40-11 | LCMS method: Method 3, RT: 1.96 min, MI: 484 [M − 1] | 1H NMR (500 MHz, DMSO-d$_6$ δ) 11.47 (s, 1H), 7.93 (d, 2H), 7.61 (d, 2H), 4.26 (m, 2H), 4.10 (m, 1H), 4.00 (m, 1H), 3.87 (m, 3H), 3.79 (m, 3H), 3.56 (m, 1H), 3.14 (m, 2H), 3.00 (m, 2H), 2.896 (m, 1H), 2.72 (m, 4H), 1.81 (m, 2H), 1.40 (m, 2H), 1.19 (m, 1H), 0.82 (m, 1H) |

TABLE 16-continued

| Ex no. | Structure | Salt | Coupling method | Intermediates | LCMS data | NMR data |
|---|---|---|---|---|---|---|
| F187 | 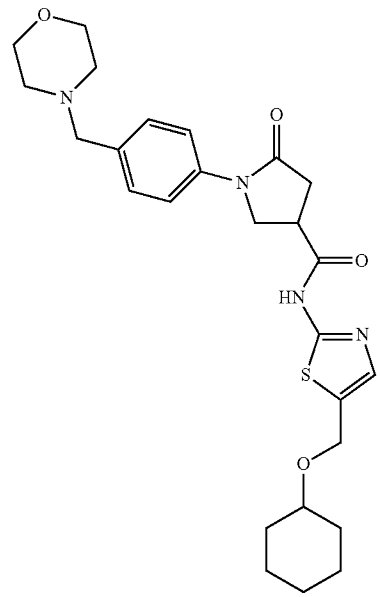 [SMILES: O=C(Nc1ncc(COC2CCCCC2)s1)C1CC(=O)N(c2ccc(CN3CCOCC3)cc2)C1] | — | CM A | F15-2, F50 | LCMS method: Method 5, RT: 2.65 min, MI: 499 [M + 1] | 1H NMR (500 MHz, DMSO-d$_6$) δ 7.52 (d, 2H), 7.32 (d, 2H), 7.26 (s, 1H), 4.65 (s, 2H), 4.25 (m, 1H), 4.03 (m, 1H), 3.69 (m, 4H), 3.50 (m, 1H), 3.47 (s, 2H), 3.37 (m, 1H), 3.05 (m, 1H), 2.91 (m, 1H), 2.43 (m, 4H), 1.87 (m, 2H), 1.71 (m, 2H), 1.51 (m, 1H), 1.27 (m, 5H) |
| F188 | 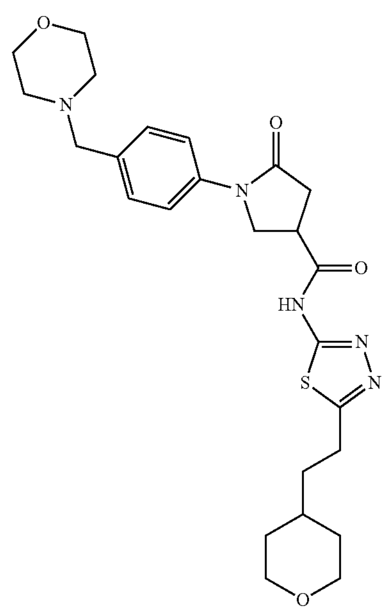 [SMILES: O=C(Nc1nnc(CCC2CCOCC2)s1)C1CC(=O)N(c2ccc(CN3CCOCC3)cc2)C1] | HCl | CM A | F15-2, F40-10 | LCMS method: Method 1, RT: 2.60 min, MI: 497 [M − 1] | 1H NMR (500 MHz, DMSO-d$_6$) δ 12.71 (s, 1H), 7.73 (d, 2H), 7.56 (d, 2H), 4.30 (d, 2H), 4.13 (t, 1H), 4.04 (dd, 1H), 3.93 (dd, 2H), 3.71 (dd, 2H), 3.25-3.19 (m, 4H), 3.06 (m, 1H), 3.00 (t, 4H), 2.91 (dd, 1H), 2.78 (dd, 1H), 2.62 (t, 1H), 1.65-1.48 (m, 4H), 1.48 (m, 1H), 1.31-1.03 (m, 2H) |

TABLE 16-continued

| Ex no. | Structure | Salt | Coupling method | Intermediates | Characterisation LCMS data | NMR data |
|---|---|---|---|---|---|---|
| F189 | 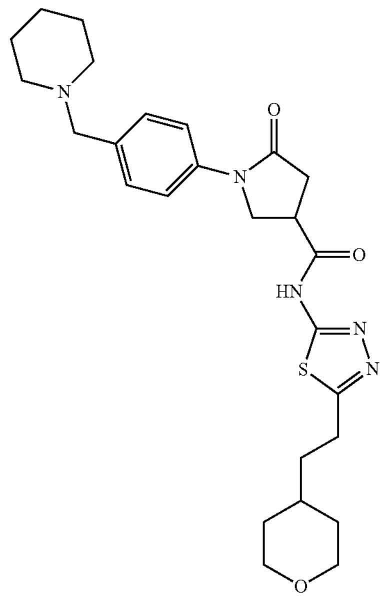 [SMILES: O=C(Nc1nnc(CCC2CCOCC2)s1)C1CC(=O)N(c2ccc(CN3CCCCC3)cc2)C1] | HCl | CM A | F15-4, F40-10 | LCMS method: Method 1, RT: 2.61 min, MI: 496/498 [M − 1] | 1H NMR (500 MHz, DMSO-d$_6$) δ 12.71 (s, 1H), 7.74 (d, 2H), 7.55 (d, 2H), 4.21 (d, 2H), 4.11 (t, 1H), 4.03 (t, 1H), 3.82 (dd, 2H), 3.27-2.33 (m, 5H), 2.99 (t, 2H), 2.93-2.72 (m, 5H), 1.77 (m, 2H), 1.57-1.44 (m, 6H), 1.37 (m, 1H), 1.36 (m, 1H), 1.13 (m, 2H) |
| F190 | Chiral | HCl | CM A | F21-6, F40-10 | LCMS method: Method 1, RT: 2.65 min, MI: 498 [M + 1] | 1H NMR (500 MHz, DMSO-d$_6$) δ 12.70 (s, 1H), 9.62 (s, 1H), 7.74 (d, 2H), 7.53 (d, 2H), 4.23 (d, 2H), 4.12 (dd, 1H), 4.03 (dd, 1H), 3.81 (dd, 2H), 3.62 (m, 1H), 3.37 (m, 1H), 3.29-3.20 (m, 4H), 3.00 (t, 2H), 2.90 (dd, 1H), 2.86-2.74 (m, 3H), 1.79 (d, 2H), 1.68-1.58 (m, 6H), 1.49 (m, 1H), 1.34 (m, 2H) |

TABLE 16-continued

| Ex no. | Structure | Salt | Coupling method | Intermediates | Characterisation LCMS data | NMR data |
|---|---|---|---|---|---|---|
| F191 | Chiral (piperidine-CH₂-phenyl-pyrrolidinone-C(=O)NH-thiadiazole-CH₂CH₂-tetrahydrofuran) | HCl | CM A | F21-6, F40-11 | LCMS method: Method 1, RT: 2.55 min, MI: 484 [M + 1] | 1H NMR (500 MHz, DMSO-d$_6$) δ 12.70 (s, 1H), 9.77 (s, 1H), 7.74 (d, 2H), 7.54 (d, 2H), 4.22 (d, 2H), 4.12 (dd, 1H), 4.02 (dd, 1H), 3.75 (m, 3H), 3.58 (m, 2H), 3.27 (d, 2H), 3.08-2.96 (m, 2H), 2.90 (dd, 1H), 2.84-2.74 (m, 3H), 1.94 (m, 1H), 1.87-1.76 (m, 5H), 1.66 (m, 3H), 1.43 (m, 1H), 1.33 (m, 1H) |
| F192 | (morpholine-CH₂-phenyl-pyrrolidinone-C(=O)NH-pyrazole-CH₂CH₂-4-chlorophenyl) | — | CM A | F15-3, F54 | LCMS method: Method 5, RT: 2.73 min, MI: 522/524 [M + 1] | 1H NMR (400 MHz, CDCl$_3$) δ 7.96 (br s, 1H), 7.54 (d, 2H), 7.34 (d, 2H), 7.26 (d, 2H), 7.09 (d, 2H), 6.55 (s, 1H), 4.23 (dd, 1H), 4.01 (t, 1H), 3.71 (t, 4H), 3.51 (s, 3H), 3.48 (br s, 2H), 3.26-3.34 (m, 1H), 3.00-3.06 (m, 1H), 2.83-2.95 (m, 5H), 2.44 (br s, 4H) |

TABLE 16-continued

| Ex no. | Structure | Salt | Coupling method | Intermediates | Characterisation LCMS data | NMR data |
|---|---|---|---|---|---|---|
| F193 | Chiral | HCl | CM B | F32-4, F67 | LCMS method: Method 1, RT: 3.25 min, MI: 537 [M + 1] | 1H NMR (500 MHz, CDCl$_3$) δ 7.98 (d, 1H), 7.48 (d, 2H), 7.30 (d, 2H), 7.25 (d, 2H), 7.10 (d, 2H), 4.89-4.82 (m, 1H), 4.24 (dd, 1H), 3.85 (dd, 1H), 3.46 (s, 2H), 3.45 (dd, 2H), 3.10 (dd, 2H), 3.05 (dd, 1H), 2.71 (dd, 1H), 2.45 (br s, 8H), 2.29 (s, 3H) |
| F194 | 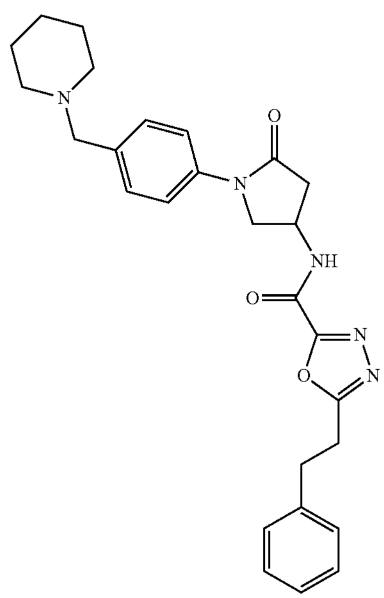 [SMILES: O=C(NC1CC(=O)N(c2ccc(CN3CCCCC3)cc2)C1)c1nnc(CCc2ccccc2)o1] | HCl | CM B | F27, F58 | LCMS method: Method 1, RT: 2.69 min, MI: 474 [M + 1] | 1H NMR (500 MHz, CDCl$_3$) δ 7.69 (d, 1H), 7.50 (d, 2H), 7.33 (d, 2H), 7.30 (dd, 2H), 7.23 (d, 1H), 7.20 (d, 2H), 4.88-4.85 (m, 1H), 4.26 (dd, 1H), 3.85 (dd, 1H), 3.55 (s, 2H), 3.24 (dd, 2H), 3.14 (dd, 2H), 3.08 (dd, 1H), 2.68 (dd, 1H), 2.47 (br s, 4H), 1.60 (br q, 4H), 1.43 (br s, 2H) |

TABLE 16-continued

| Ex no. | Structure | Salt | Coupling method | Intermediates | Characterisation | |
|---|---|---|---|---|---|---|
| | | | | | LCMS data | NMR data |
| F195 | 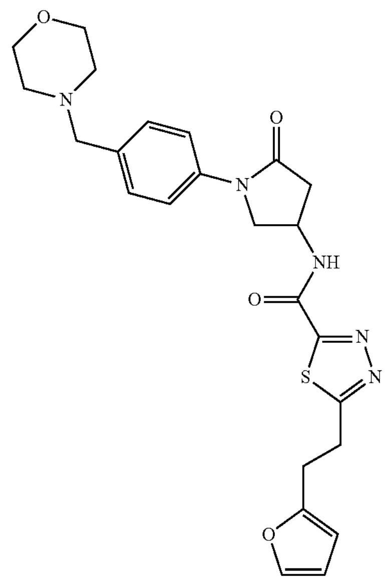 [SMILES: O=C(NC1CC(=O)N(c2ccc(CN3CCOCC3)cc2)C1)c1nnc(CCc2ccco2)s1] | HCl | CM B | F27, F67-3 | LCMS method: Method 1, RT: 2.69 min, MI: 480 [M + 1] | 1H NMR (500 MHz, CDCl$_3$) δ 7.84 (br d, 1H), 7.50 (d, 2H), 7.34-7.32 (m, 3H), 6.28 (dd, 1H), 6.05 (d, 1H), 4.87-4.84 (m, 1H), 4.25 (dd, 1H), 3.85 (dd, 1H), 3.51 (t, 2H), 3.48 (br s, 2H), 3.15 (t, 2H), 3.07 (dd, 1H), 2.71 (dd, 1H), 2.39 (br s, 4H), 1.58 (br s, 4H), 1.42 (br s, 2H) |
| F196 | 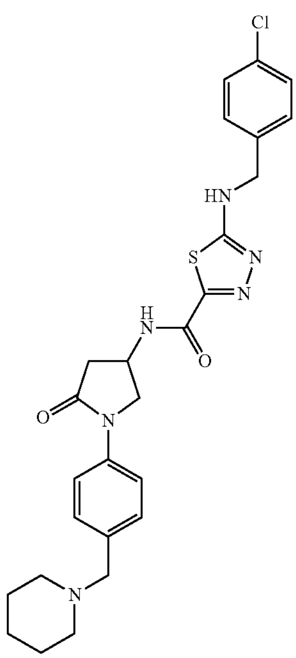 | HCl | CM B | F27, F69 | LCMS method: Method 1, RT: 5.56 min, MI: 525 [M + 1] | 1H NMR (500 MHz, CDCl$_3$) δ 9.17 (s, 1H), 8.31 (br s, 1H), 7.34 (d, 2H), 7.28 (d, 2H), 7.20 (m, 4H), 4.62 (br s, 1H), 4.48 (s, 2H), 4.19 (d, 1H), 3.86 (d, 1H), 3.81 (br s, 1H), 3.74 (d, 1H), 3.62 (br s, 2H), 2.95-2.88 (m, 1H), 2.69 (d, 1H), 2.65 (br s, 2H), 1.93 (br s, 6H) (2H presumed very broad aliphatic signals lost in baseline) |

TABLE 16-continued
| Ex no. | Structure | Salt | Coupling method | Intermediates | LCMS data | NMR data |
|---|---|---|---|---|---|---|
| F197 | 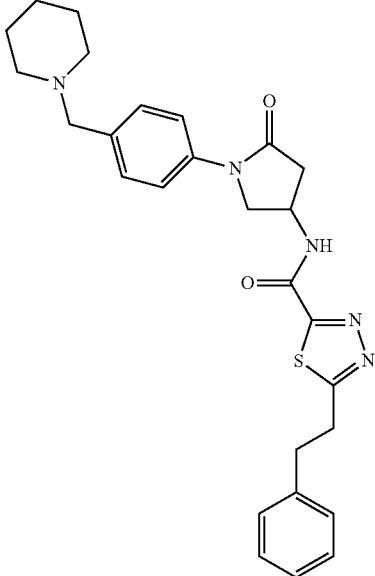 | HCl | CM C | F27, F64 | LCMS method: Method 1, RT: 3.37 min, MI: 489 [M + 1] | 1H NMR (500 MHz, CDCl₃) δ 7.53 (d, 2H), 7.45 (s, 1H), 7.35-7.23 (m, 4H), 7.22 (t, 1H), 7.15 (d, 2H), 4.87-4.80 (m, 1H), 4.27 (dd, 1H), 3.84 (dd, 1H), 3.49 (s, 2H), 3.20 (dd, 2H), 3.08 (dd, 1H), 2.99 (dd, 2H), 2.66 (dd, 1H), 2.47-2.33 (m, 4H), 1.42-1.40 (m, 4H), 1.31-1.25 (m, 2H) |
| F198 | 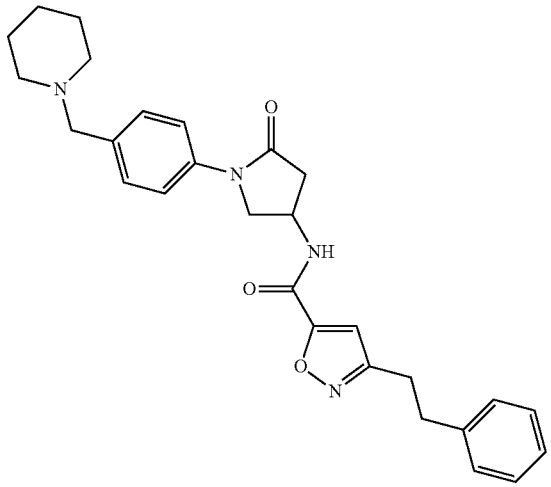 [SMILES: O=C(NC1CC(=O)N(c2ccc(CN3CCCCC3)cc2)C1)c1cc(CCc2ccccc2)no1] | HCl | CM C | F27, F73 | LCMS method: Method 1, RT: 3.06 min, MI: 473 [M + 1] | 1H NMR (300 MHz, DMSO-d₆) δ 9.68 (br s, 1H), 9.45 (d, 1H), 7.74 (d, 2H), 7.52 (d, 2H), 7.30-7.15 (m, 5H), 7.03 (s, 1H), 4.65 (m, 1H), 4.23-4.17 (m, 3H), 3.78 (dd, 1H), 3.26 (br d, 2H), 3.02-2.93 (m, 5H), 2.82-2.75 (m, 2H), 2.62 (dd, 1H), 1.82-1.58 (m, 4H), 1.38-1.22 (m, 2H) |

TABLE 16-continued
| Ex no. | Structure | Salt | Coupling method | Intermediates | LCMS data | NMR data |
|---|---|---|---|---|---|---|
| F199 | 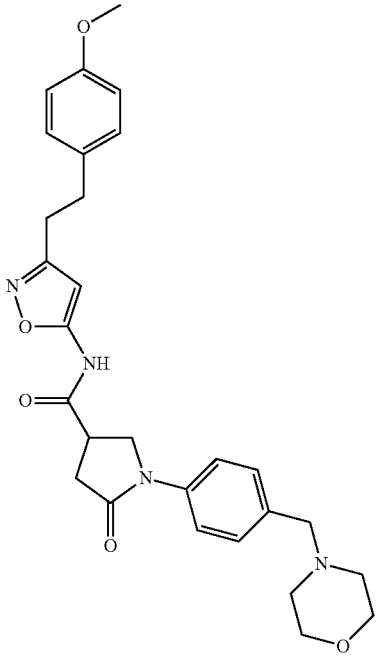 [SMILES: COc1ccc(CCc2cc(NC(=O)C3CC(=O)N(c4ccc(CN5CCOCC5)cc4)C3)on2)cc1] | — | CM D | F15-2, F46 | LCMS method: Method 1, RT: 3.11 min, MI: 505 [M + 1] | 1H NMR (500 MHz, CDCl$_3$) δ 9.82 (br s, 1H), 7.54-7.48 (m, 2H), 7.36-7.30 (m, 2H), 7.13-7.08 (m, 2H), 6.85-6.79 (m, 2H), 6.28 (s, 1H), 4.22-4.16 (m, 1H), 4.02-3.95 (m, 1H), 3.79-3.67 (m, 7H), 3.61-3.54 (m, 1H), 3.50-3.45 (m, 2H), 3.43-3.34 (m, 1H), 3.00-2.86 (m, 5H), 2.51-2.39 (m, 4H) |
| F200 | 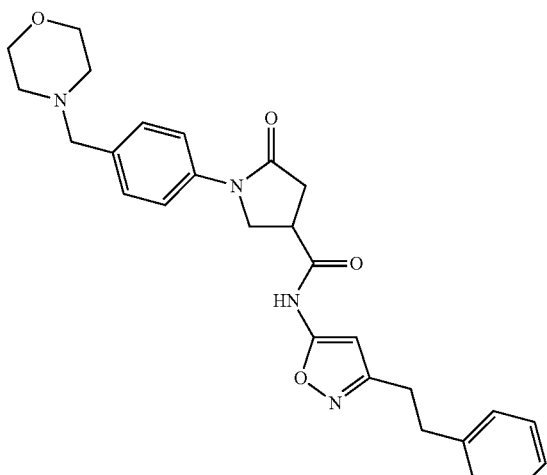 | HCl | CM D | F15-2, F45 | LCMS method: Method 1, RT: 3.20 min, MI: 475 [M + 1] | 1H NMR (300 MHz, DMSO-d$_6$) δ 11.89 (s, 1H), 10.76 (br s, 1H), 7.73 (d, 2H), 7.55 (d, 2H), 7.30-7.14 (m, 5H), 6.20 (s, 1H), 4.30 (br d, 2H), 4.09 (t, 1H), 4.02-3.90 (m, 3H), 3.71 (m, 2H), 3.51 (m, 1H), 3.21 (d, 2H), 3.11-3.02 (m, 3H), 2.94-2.70 (m, 5H) |

TABLE 16-continued

| Ex no. | Structure | Salt | Coupling method | Intermediates | LCMS data | NMR data |
|---|---|---|---|---|---|---|
| F201 | 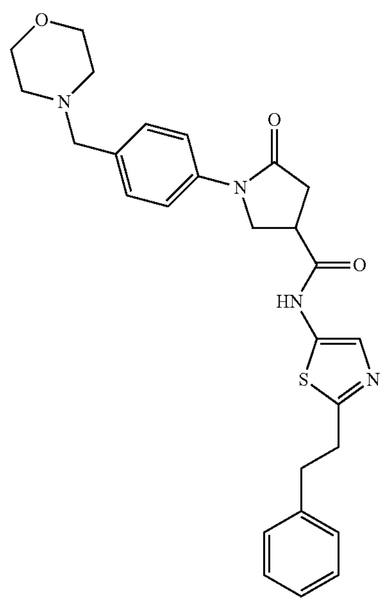 | HCO₂H | CM A | F15-3, F48 | LCMS method: Method 5, RT: 2.51 min, MI: 491 [M + 1] | 1H NMR (400 MHz, CDCl₃) δ 10.71 (br s, 1H), 7.51 (d, 2H), 7.34 (d, 2H), 7.31 (s, 1H), 7.28-7.24 (m, 2H), 7.19-7.16 (m, 3H), 4.19 (dd, 1H), 3.93 (t, 1H), 3.74 (t, 4H), 3.59 (s, 2H), 3.36-3.28 (m, 1H), 3.23 (t, 2H), 3.07 (t, 2H), 2.95 (dd, 1H), 2.78 (dd, 1H), 2.56 (br s, 4H) |
| F202 | 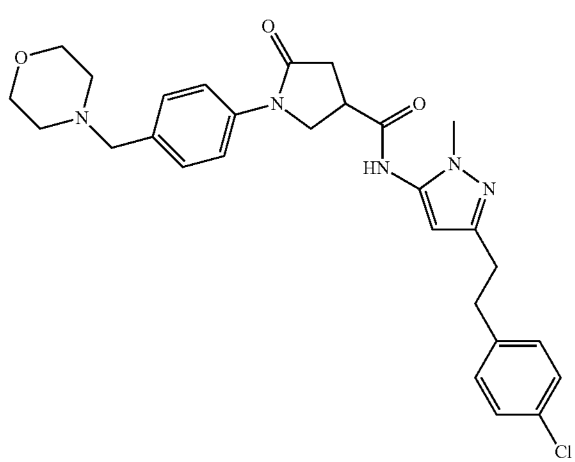 [SMILES: Cn1nc(CCc2ccc(Cl)cc2)cc1NC(=O)C1CC(=O)N(c2ccc(CN3CCOCC3)cc2)C1] | HCO₂H | CM A | F15-3, F54 | LCMS method: Method 5, RT: 2.69 min, MI: 522/524 [M + 1] | 1H NMR (400 MHz, CDCl₃) δ 7.68 (br s, 1H), 7.53 (d, 2H), 7.35 (d, 2H), 7.23 (d, 2H), 7.13 (d, 2H), 6.04 (s, 1H), 4.22 (t, 1H), 4.02 (t, 1H), 3.72 (t, 4H), 3.68 (s, 3H), 3.53 (s, 2H), 3.43-3.34 (m, 1H), 3.02-2.83 (m, 6H), 2.49 (br s, 4H) |

TABLE 16-continued

| Ex no. | Structure | Salt | Coupling method | Intermediates | LCMS data | NMR data |
|---|---|---|---|---|---|---|
| F203 | 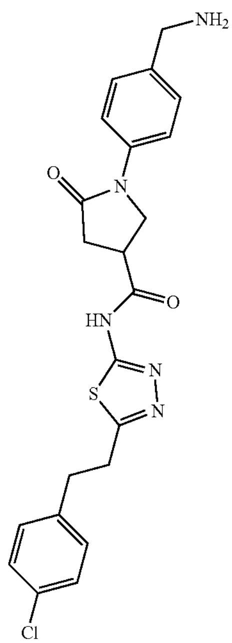 [SMILES: NCc1ccc(N2CC(C(=O)Nc3nnc(CCc4ccc(Cl)cc4)s3)CC2=O)cc1] | — | CM A | F84, F40 | LCMS method: Method 1, RT: 3.29 min, MI: 456 [M + 1] | 1H NMR (500 MHz, DMSO-d$_6$) δ 8.31 (s, 1H), 7.62 (d, 2H), 7.39 (d, 2H), 7.33 (d, 2H), 7.28 (d, 2H), 4.06 (t, 1H), 4.00 (dd, 1H), 3.85 (s, 2H), 3.54 (m, 1H), 3.27 (t, 2H), 3.01 (t, 2H), 2.83 (dd, 1H), 2.75 (dd, 1H) |
| F204 | 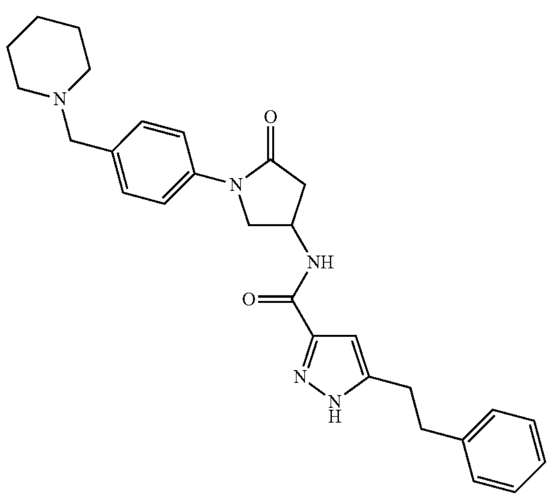 | HCl | CM C | F27, F76 | LCMS method: Method 1, RT: 2.95 min, MI: 472 [M + 1] | 1H NMR (300 MHz, CDCl$_3$) δ 7.54 (d, 2H), 7.37 (d, 2H), 7.32-7.18 (m, 3H), 7.14 (d, 2H), 6.61 (s, 1H), 4.88-4.78 (m, 2H), 4.24 (dd, 1H), 3.82 (dd, 1H), 3.59 (br s, 2H), 3.05 (dd, 1H), 3.01 (dd, 2H), 2.94 (dd, 2H), 2.63 (dd, 1H), 2.49 (br s, 4H), 1.78 (br s, 4H) 1.46 (br s, 2H) |

TABLE 16-continued
| Ex no. | Structure | Salt | Coupling method | Intermediates | LCMS data | NMR data |
|---|---|---|---|---|---|---|
| F205 | 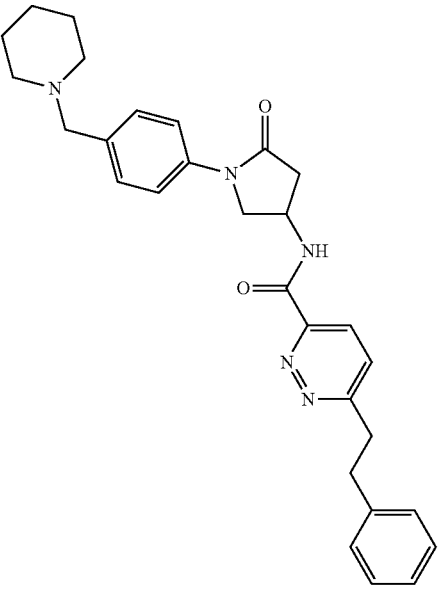 [SMILES: O=C(NC1CC(=O)N(c2ccc(CN3CCCCC3)cc2)C1)c1ccc(CCc2ccccc2)nn1] | HCl | CM C | F27, F55 | LCMS method: Method 1, RT: 2.92 min, MI: 484 [M + 1] | 1H NMR (500 MHz, CDCl$_3$) δ 8.49 (d, 1H), 8.12 (d, 1H), 7.53 (d, 2H), 7.35 (d, 2H), 7.33 (d, 1H), 7.27 (t, 2H), 7.20 (t, 1H), 7.15 (d, 2H), 4.92 (m, 1H), 4.32 (dd, 1H), 3.40 (s, 2H), 3.37 (dd, 2H), 3.14 (dd, 2H), 3.11 (dd, 1H), 2.72 (dd, 1H), 2.40 (br s, 4H), 1.59 (t, 4H), 1.43 (br s, 2H) |
| F206 | 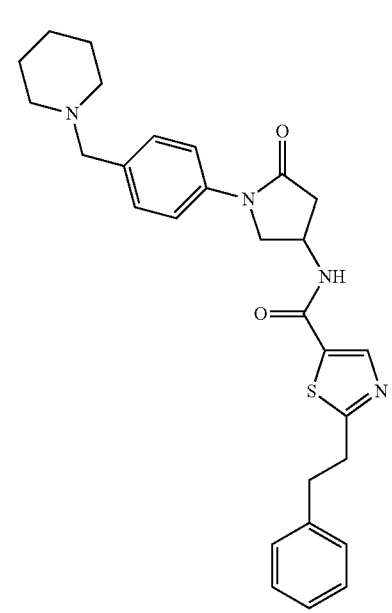 | HCl | CM C | F27, F64-3 | LCMS method: Method 1, RT: 3.14 min, MI: 489 [M + 1] | 1H NMR (500 MHz, CDCl$_3$) δ 8.18 (s, 1H), 7.62 (d, 1H), 7.44 (d, 2H), 7.29-7.18 (m, 8H), 4.81-4.76 (m, 1H), 4.20 (dd, 1H), 3.86 (dd, 1H), 3.41 (s, 1H), 3.30 (dd, 2H), 3.10 (dd, 2H), 3.01 (dd, 1H), 2.59 (dd, 1H), 2.33 (br s, 4H), 1.57-1.53 (m, 4H), 1.42-1.41 (m, 2H) |

TABLE 16-continued

| Ex no. | Structure | Salt | Coupling method | Intermediates | Characterisation LCMS data | NMR data |
|---|---|---|---|---|---|---|
| F207 | 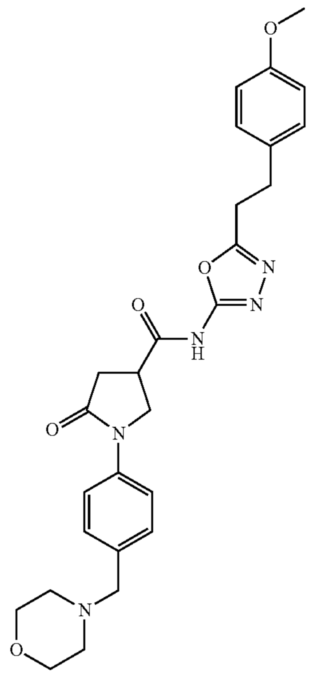 | — | CM D | F15-2, F54-1 | LCMS method: Method 1, RT: 2.48 min, MI: 506 [M + 1] | 1H NMR (500 MHz, CDCl₃) δ 7.56 (d, 2H), 7.33 (d, 2H), 7.12 (d, 2H), 6.83 (d, 2H), 4.22-4.11 (m, 2H), 3.77 (s, 3H), 3.72-3.68 (m, 5H), 3.47 (s, 2H), 3.12-2.99 (m, 5H), 2.48-2.43 (m, 5H) |
| F208 | 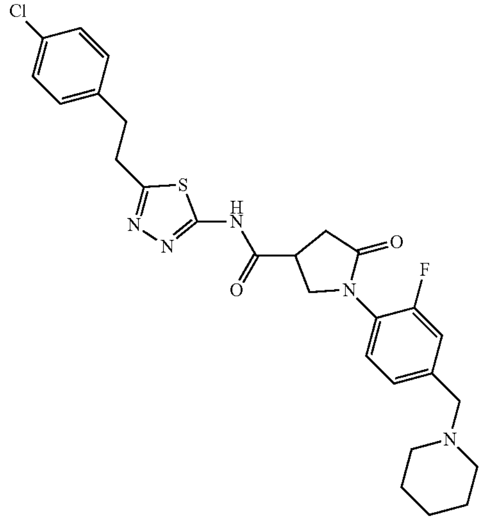 [SMILES: O=C(Nc1nnc(CCc2ccc(Cl)cc2)s1)C1CC(=O)N(c2ccc(CN3CCCCC3)cc2F)C1] | HCl | CM G | F15-32, F40 | LCMS method: Method 1, RT: 3.45 min, MI: 542 [M + 1] | 1H NMR (500 MHz, DMSO-d₆) δ 12.67 (s, 1H), 10.29 (s, 1H), 7.60 (d, 1H), 7.55 (t, 1H), 7.42 (d, 1H), 7.32 (d, 2H), 7.27 (d, 2H), 4.25 (d, 2H), 4.03 (t, 1H), 3.94 (dd, 1H), 3.66 (m, 1H), 3.31-3.26 (m, 4H), 3.02 (t, 2H), 2.81 (m, 3H), 2.70 (dd, 1H), 1.78-1.65 (m, 5H), 1.34 (m, 1H) |

TABLE 16-continued

| Ex no. | Structure | Salt | Coupling method | Intermediates | LCMS data | NMR data |
|---|---|---|---|---|---|---|
| F209 | 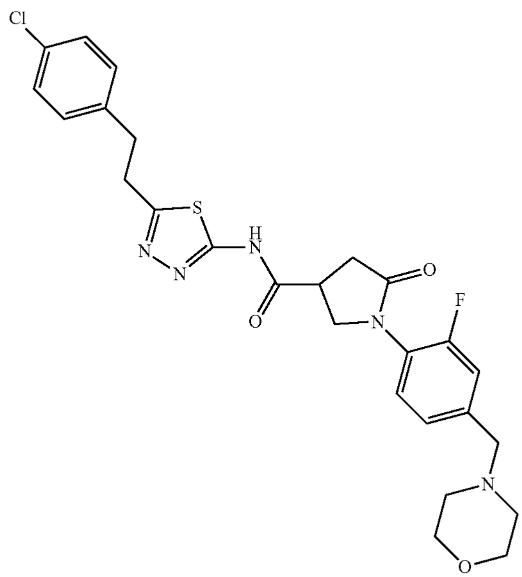 [SMILES: O=C(Nc1nnc(CCc2ccc(Cl)cc2)s1)C1CC(=O)N(c2ccc(CN3CCOCC3)cc2F)C1] | HCl | CM G | F15-33, F40 | LCMS method: Method 1, RT: 3.46 min, MI: 544 [M + 1] | 1H NMR (500 MHz, DMSO-d$_6$) δ 12.66 (s, 1H), 10.93 (s, 1H), 7.58 (m, 2H), 7.42 (d, 1H), 7.32 (d, 2H), 7.28 (d, 2H), 4.33 (d, 2H), 4.02 (t, 1H), 3.95-3.89 (m, 4H), 3.73 (t, 2H), 3.30 (t, 2H), 3.22 (d, 2H), 3.10-3.00 (m, 4H), 2.81 (dd, 1H), 2.71 (dd, 1H) |
| F210 | 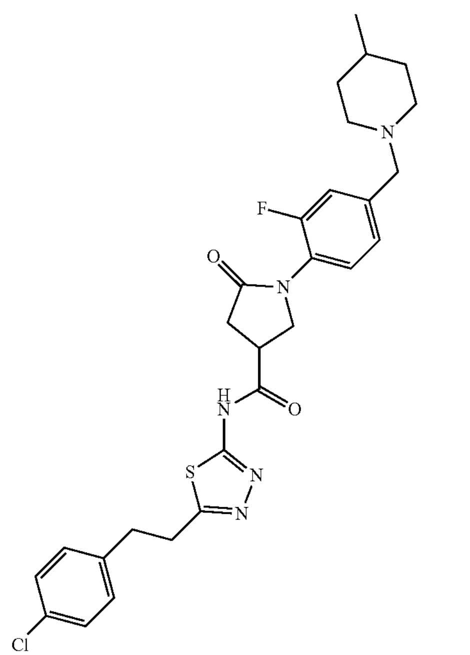 [SMILES: CC1CCN(Cc2ccc(N3CC(C(=O)Nc4nnc(CCc5ccc(Cl)cc5)s4)CC3=O)c(F)c2)CC1] | HCl | CM G | F15-34, F40 | LCMS method: Method 1, RT: 3.56 min, MI: 556 [M + 1] | 1H NMR (500 MHz, DMSO-d$_6$) δ 12.66 (s, 1H), 9.92 (s, 1H), 7.56 (m, 2H), 7.40 (d, 1H), 7.33 (d, 2H), 7.28 (d, 2H), 4.26 (d, 2H), 4.03 (t, 1H), 3.94 (dd, 1H), 3.66 (m, 1H), 3.30 (m, 4H), 3.03 (t, 2H), 2.92-2.79 (m, 3H), 2.71 (dd, 1H), 1.76 (d, 2H), 1.58 (m, 1H), 1.37 (m, 2H), 0.89 (d, 3H) |

TABLE 16-continued

| Ex no. | Structure | Salt | Coupling method | Intermediates | Characterisation | |
|---|---|---|---|---|---|---|
| | | | | | LCMS data | NMR data |
| F211 | 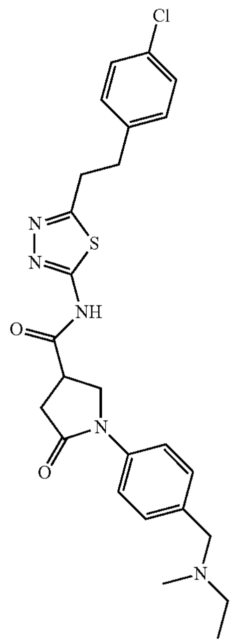 [SMILES: CCN(C)Cc1ccc(N2CC(C(=O)Nc3nnc(CCc4ccc(Cl)cc4)s3)CC2=O)cc1] | — | CM A | F15-22, F40 | LCMS method: Method 1, RT: 3.42 min, MI: 498 [M + 1] | 1H NMR (500 MHz, DMSO-d$_6$) δ 12.68 (br s, 1H), 7.71 (br s, 2H), 7.46 (br s, 2H), 7.32 (d, 2H), 7.27 (d, 2H), 4.08 (m, 1H), 4.01 (dd, 1H), 3.60 (m, 1H), 3.31 (t, 2H, partly hidden by water peak), 3.15 (d, 2H), 3.02 (t, 2H), 2.88 (dd, 1H), 2.75 (dd, 1H), 1.18 (br s, 3H) (5H presumed under solvent peak) |
| F212 | 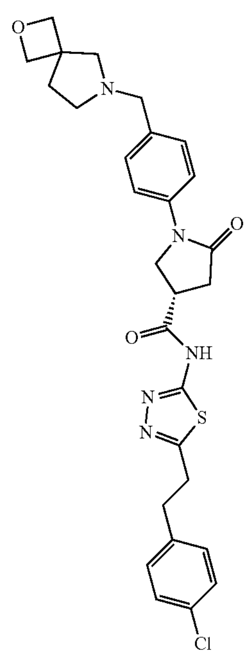 [SMILES: O=C(Nc1nnc(CCc2ccc(Cl)cc2)s1)[C@H]1CC(=O)N(c2ccc(CN3CCC4(COC4)C3)cc2)C1] | — | CM G | F21-12, F40 | LCMS method: Method 1, RT: 3.25 min, MI: 552 [M + 1] | 1H NMR (500 MHz, DMSO-d$_6$) δ 7.57 (m, 2H), 7.32 (m, 2H), 7.27 (m, 4H), 4.46 (d, 2H), 4.43 (d, 2H), 4.07 (m, 1H), 3.99 (dd, 1H), 3.57 (m, 1H), 3.50 (s, 2H), 3.29 (t, 2H, partly hidden by water peak), 3.02 (t, 2H), 2.84 (dd, 1H), 2.73 (dd, 1H), 2.68 (s, 2H), 2.41 (t, 2H), 2.02 (t, 2H) |

TABLE 16-continued

| Ex no. | Structure | Salt | Coupling method | Intermediates | Characterisation | |
|---|---|---|---|---|---|---|
| | | | | | LCMS data | NMR data |
| F213 | 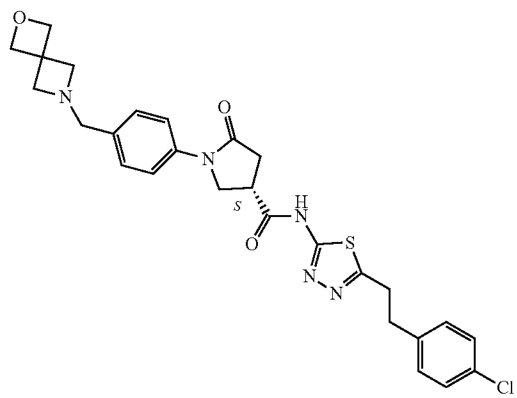 | — | CM B | F21-7, F40 | LCMS method: Method 3, RT: 4.08 min, MI: 538 [M + 1] | 1H NMR (500 MHz, CD₃OD) δ 7.56 (d, 2H), 7.29 (d, 2H), 7.24 (d, 2H), 7.19 (d, 2H), 4.71 (s, 4H), 4.13 (m, 2H), 3.63-3.56 (m, 3H), 3.44 (s, 4H), 3.30 (m, 5H, overintegrating due to solvent peak, should be 2H), 3.07 (t, 2H), 2.91 (dd, 2H) |
| F214 | 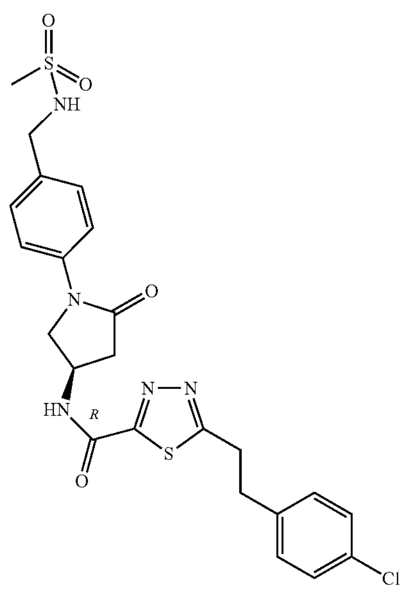 | — | CM B | F32-6, F67 | LCMS method: Method 1, RT: 4.83 min, MI: 534 [M + 1] | 1H NMR (500 MHz, CD₃OD) δ 7.61 (d, 2H), 7.40 (s, 2H), 7.26 (d, 2H), 7.21 (d, 2H), 4.29 (dd, 1H), 4.23 (s, 2H), 3.91 (dd, 1H), 3.49 (t, 2H), 3.13 (t, 2H), 3.04 (dd, 1H), 2.84 (s, 3H), 2.76 (dd, 1H) (1H missing, presumed under solvent peak) |
| F215 | 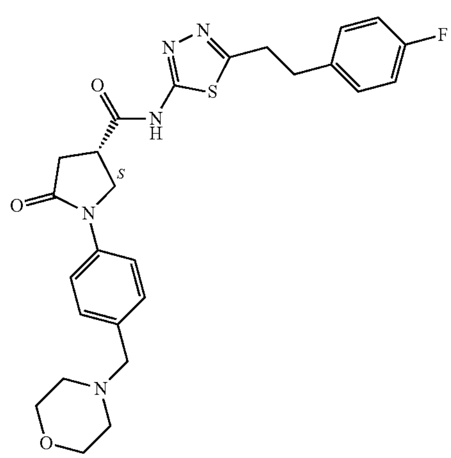 | HCl | CM G | F21, F40-4 | LCMS method: Method 3, RT: 4.00 min, MI: 508 [M − 1] | 1H NMR (500 MHz, DMSO-d₆) δ 12.70 (s, 1H), 7.74 (d, 2H), 7.58 (d, 2H), 7.28 (d, 2H), 7.09 (d, 2H), 4.29 (d, 2H), 4.12 (t, 1H), 4.01 (t, 1H), 3.93 (d, 2H), 3.29 (t, 2H), 3.20 (d, 2H), 3.01 (m, 4H), 2.89 (dd, 2H), 2.73 (dd, 2H), 2.67 (m, 1H) |

Autotaxin (ATX) Activity
Quanta Red Assay

Measuring ATX activity using an enzyme coupled Quanta Red assay (Thermo Scientific—Pierce Protein Research Products, Product #15159) was determined as follows. 8 µL human recombinant ATX (final concentration 0.8 µg/mL) in 1× Assay buffer containing 50 mM Tris-HCl (pH 8.0), 5 mM $CaCl_2$ was added to an opaque black flat-bottom 384-well plate (Corning, #3575) containing 2 µL test compound in 40% DMSO (4% final DMSO concentration). 10 µL of Quanta Red, Horseradish peroxidase (HRP), Choline Oxidase (CO), Rac-1-Palmitoyl-glycero-3-phosphocholine solution (final concentration 1:250 for Quanta Red, 0.5units/ml HRP, 0.5units/ml CO, 15 µM Rac-1-Palmitoyl-glycero-3-phosphocholine) in 1× assay buffer (as described previously) was added to each well to start the reaction and the plate was incubated at room temperature for 2 hours. The reaction was stopped after 2 hours with a 20 µL addition of Quanta Red Stop solution (1:20 dilution in distilled water). The above-described mixture with DMSO alone was used as a positive control whereas that with DMSO alone without ATX was taken as a negative control.

For each test compound, ten concentrations were measured covering a range of 6.1 nM to 120 µM to determine $IC_{50}$ values. The top concentration was decreased to 1.2 µM when a test compound's $IC_{50}$ value was evaluated in low nanomolar range. Fluorescence was determined in a BMG Labtech Pherastar plus plate reader (λ emission=540 nm, λ excitation=590 nm). Data were analysed using Excel fit software. $IC_{50}$ values were determined in duplicate.

TABLE 17

| | ATX activity (Quanta Red assay) | | | |
|---|---|---|---|---|
| EXAMPLE | STRUCTURE | NAME | SALT | AVERAGE IC50 (MEAN, µM) |
| F87 | 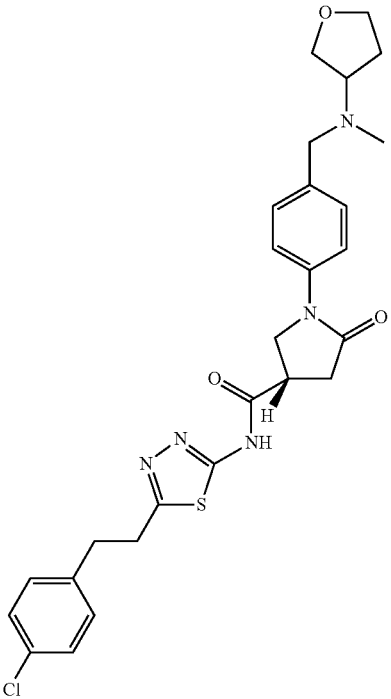 Chiral | (3S)-N-[5-[2-(4-chlorophenyl)ethyl]-1,3,4-thiadiazol-2-yl]-1-[4-[[methyl(tetrahydrofuran-3-yl)amino]methyl]phenyl]-5-oxo-pyrrolidine-3-carboxamide | HCl | 0.001 |

TABLE 17-continued
ATX activity (Quanta Red assay)
| EXAMPLE | STRUCTURE | NAME | SALT | AVERAGE IC50 (MEAN, μM) |
|---|---|---|---|---|
| F88 | 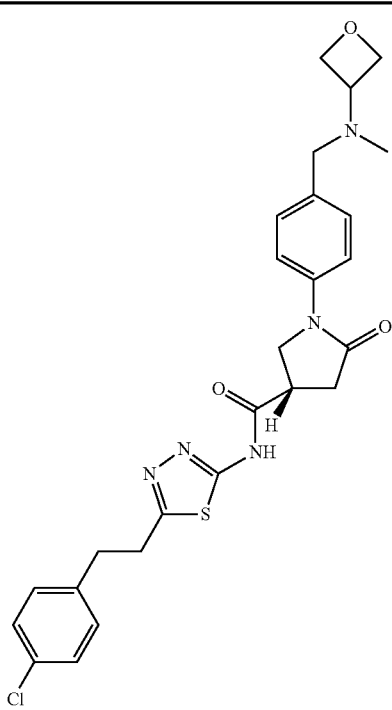 | (3S)-N-[5-[2-(4-chlorophenyl)ethyl]-1,3,4-thiadiazol-2-yl]-1-[4-[[methyl(oxetan-3-yl)amino]methyl]phenyl]-5-oxo-pyrrolidine-3-carboxamide | — | 0.001 |
| F89 | 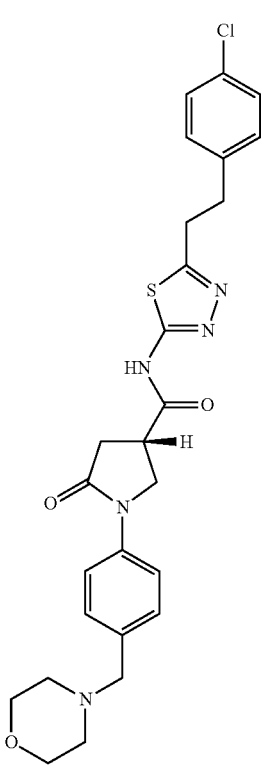 | (3S)-N-[5-[2-(4-chlorophenyl)ethyl]-1,3,4-thiadiazol-2-yl]-1-[4-(morpholinomethyl)phenyl]-5-oxo-pyrrolidine-3-carboxamide | HCl | 0.001 |

TABLE 17-continued
ATX activity (Quanta Red assay)
| EXAMPLE | STRUCTURE | NAME | SALT | AVERAGE IC50 (MEAN, μM) |
|---|---|---|---|---|
| F90 | 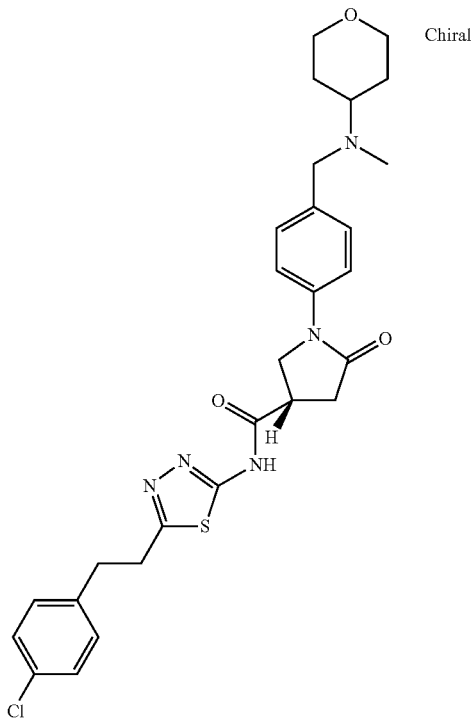 [SMILES: CN(Cc1ccc(N2C[C@@H](C(=O)Nc3nnc(CCc4ccc(Cl)cc4)s3)CC2=O)cc1)C1CCOCC1] | (3S)-N-[5-[2-(4-chlorophenyl)ethyl]-1,3,4-thiadiazol-2-yl]-1-[4-[[methyl(tetrahydropyran-4-yl)amino]methyl]phenyl]-5-oxo-pyrrolidine-3-carboxamide | HCl | 0.001 |
| F91 | 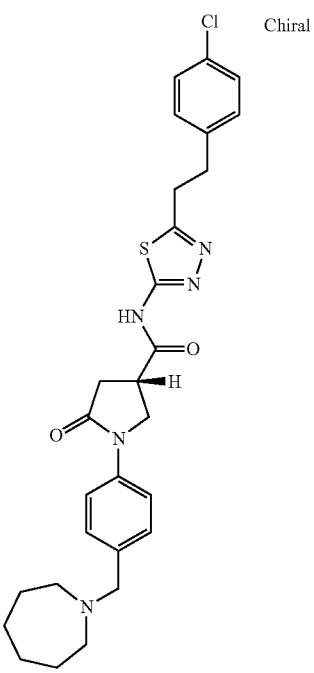 [SMILES: O=C(Nc1nnc(CCc2ccc(Cl)cc2)s1)[C@H]1CC(=O)N(c2ccc(CN3CCCCCC3)cc2)C1] | (3S)-1-[4-(azepan-1-ylmethyl)phenyl]-N-[5-[2-(4-chlorophenyl)ethyl]-1,3,4-thiadiazol-2-yl]-5-oxo-pyrrolidine-3-carboxamide | HCl | 0.001 |

TABLE 17-continued

| | ATX activity (Quanta Red assay) | | | |
|---|---|---|---|---|
| EXAMPLE | STRUCTURE | NAME | SALT | AVERAGE IC50 (MEAN, μM) |
| F92 | Chiral | (3S)-N-[5-[2-(4-chlorophenyl)ethyl]-1,3,4-thiadiazol-2-yl]-1-[4-[(4-methyl-1-piperidyl)methyl]phenyl]-5-oxo-pyrrolidine-3-carboxamide | HCl | 0.001 |
| F93 | Chiral | (3S)-N-[5-[2-(4-chlorophenyl)ethyl]-1,3,4-thiadiazol-2-yl]-5-oxo-1-[4-(1-piperidylmethyl)phenyl]pyrrolidine-3-carboxamide | HCl | 0.001 |

TABLE 17-continued

ATX activity (Quanta Red assay)

| EXAMPLE | STRUCTURE | NAME | SALT | AVERAGE IC50 (MEAN, μM) |
|---|---|---|---|---|
| F94 | Chiral | (3S)-N-[5-[2-(4-chlorophenyl)ethyl]-1,3,4-thiadiazol-2-yl]-1-[4-[[2-methoxyethyl(methyl)amino]methyl]phenyl]-5-oxo-pyrrolidine-3-carboxamide | HCl | 0.001 |
| F95 | 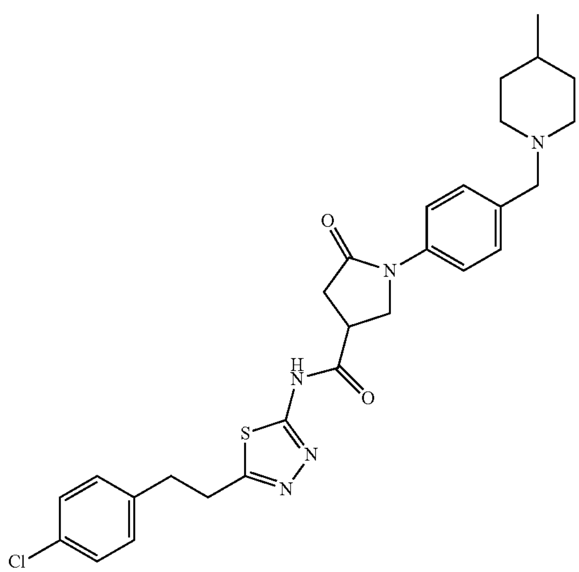 [SMILES: CC1CCN(Cc2ccc(N3CC(C(=O)Nc4nnc(CCc5ccc(Cl)cc5)s4)CC3=O)cc2)CC1] | N-[5-[2-(4-chlorophenyl)ethyl]-1,3,4-thiadiazol-2-yl]-1-[4-[(4-methyl-1-piperidyl)methyl]phenyl]-5-oxo-pyrrolidine-3-carboxamide | HCl | 0.002 |

TABLE 17-continued

ATX activity (Quanta Red assay)

| EXAMPLE | STRUCTURE | NAME | SALT | AVERAGE IC50 (MEAN, μM) |
|---|---|---|---|---|
| F96 | 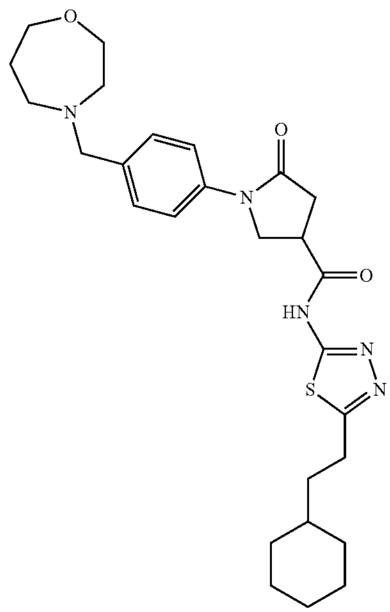 [SMILES: O=C(Nc1nnc(CCC2CCCCC2)s1)C1CC(=O)N(c2ccc(CN3CCCOCC3)cc2)C1] | N-[5-(2-cyclohexylethyl)-1,3,4-thiadiazol-2-yl]-1-[4-(1,4-oxazepan-4-ylmethyl)phenyl]-5-oxo-pyrrolidine-3-carboxamide | HCl | 0.002 |
| F97 | Chiral | (3S)-1-[4-(morpholinomethyl)phenyl]-5-oxo-N-[5-[2-[4-(trifluoromethyl)phenyl]ethyl]-1,3,4-thiadiazol-2-yl]pyrrolidine-3-carboxamide | HCl | 0.002 |

TABLE 17-continued

ATX activity (Quanta Red assay)

| EXAMPLE | STRUCTURE | NAME | SALT | AVERAGE IC50 (MEAN, μM) |
|---|---|---|---|---|
| F98 | 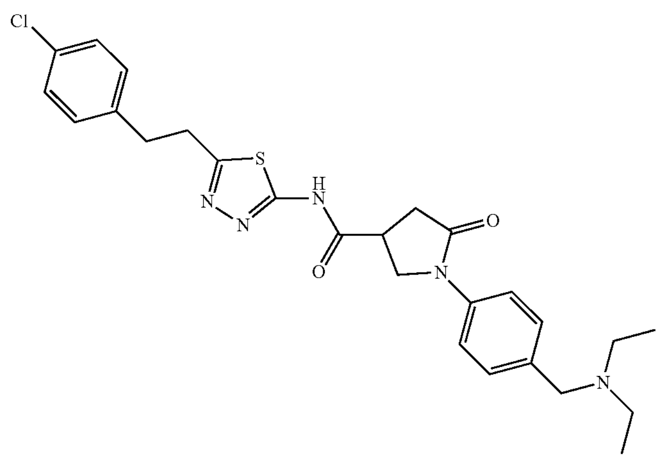 [SMILES: CCN(CC)Cc1ccc(N2CC(C(=O)Nc3nnc(CCc4ccc(Cl)cc4)s3)CC2=O)cc1] | N-[5-[2-(4-chlorophenyl)ethyl]-1,3,4-thiadiazol-2-yl]-1-[4-(diethylaminomethyl)phenyl]-5-oxo-pyrrolidine-3-carboxamide | — | 0.002 |
| F99 | 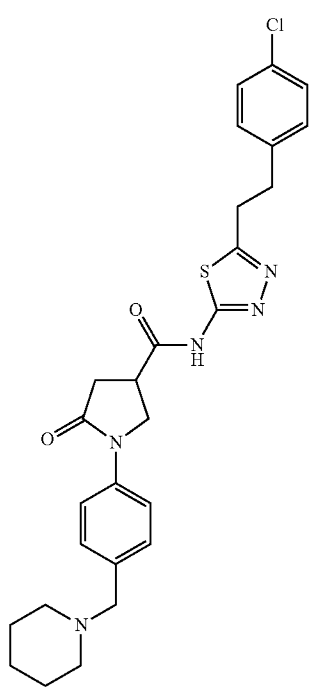 [SMILES: O=C(Nc1nnc(CCc2ccc(Cl)cc2)s1)C1CC(=O)N(c2ccc(CN3CCCCC3)cc2)C1] | N-[5-[2-(4-chlorophenyl)ethyl]-1,3,4-thiadiazol-2-yl]-5-oxo-1-[4-(1-piperidylmethyl)phenyl]pyrrolidine-3-carboxamide | HCl | 0.002 |

TABLE 17-continued

ATX activity (Quanta Red assay)

| EXAMPLE | STRUCTURE | NAME | SALT | AVERAGE IC50 (MEAN, μM) |
|---|---|---|---|---|
| F100 | 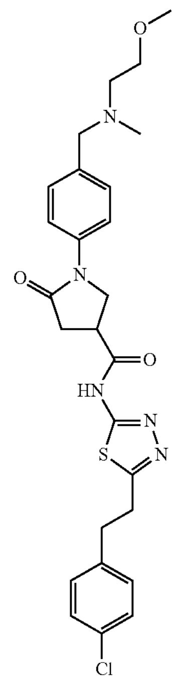 [SMILES: COCCN(C)Cc1ccc(N2CC(C(=O)Nc3nnc(CCc4ccc(Cl)cc4)s3)CC2=O)cc1] | N-[5-[2-(4-chlorophenyl)ethyl]-1,3,4-thiadiazol-2-yl]-1-[4-[[2-methoxyethyl(methyl)amino]methyl]phenyl]-5-oxo-pyrrolidine-3-carboxamide | HCl | 0.002 |
| F101 | 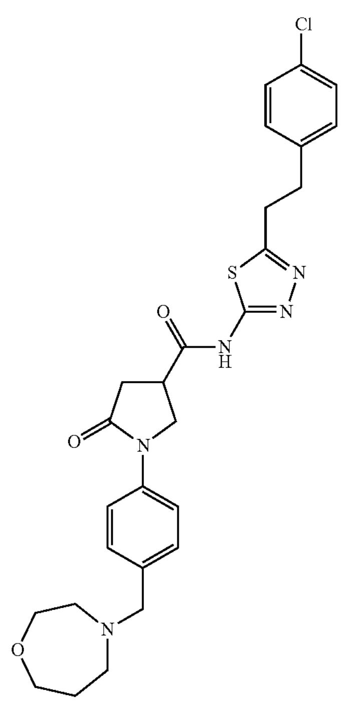 [SMILES: O=C(Nc1nnc(CCc2ccc(Cl)cc2)s1)C1CC(=O)N(c2ccc(CN3CCCOCC3)cc2)C1] | N-[5-[2-(4-chlorophenyl)ethyl]-1,3,4-thiadiazol-2-yl]-1-[4-(1,4-oxazepan-4-ylmethyl)phenyl]-5-oxo-pyrrolidine-3-carboxamide | HCl | 0.003 |

TABLE 17-continued
ATX activity (Quanta Red assay)
| EXAMPLE | STRUCTURE | NAME | SALT | AVERAGE IC50 (MEAN, μM) |
|---|---|---|---|---|
| F102 | 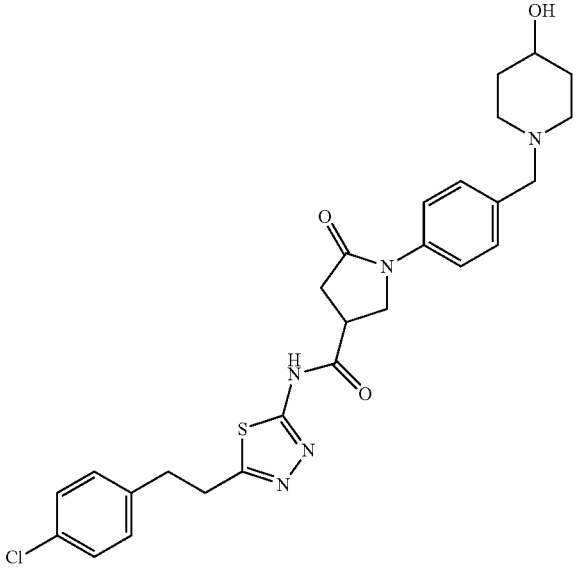 [SMILES: O=C(Nc1nnc(CCc2ccc(Cl)cc2)s1)C1CC(=O)N(c2ccc(CN3CCC(O)CC3)cc2)C1] | N-[5-[2-(4-chlorophenyl)ethyl]-1,3,4-thiadiazol-2-yl]-1-[4-[(4-hydroxy-1-piperidyl)methyl]phenyl]-5-oxo-pyrrolidine-3-carboxamide | HCl | 0.003 |
| F103 | 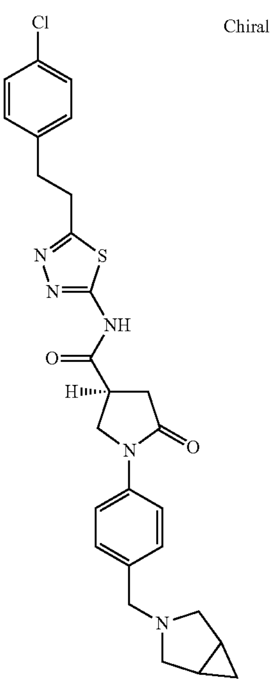 [SMILES: O=C(Nc1nnc(CCc2ccc(Cl)cc2)s1)[C@H]1CC(=O)N(c2ccc(CN3CC4CC4C3)cc2)C1] | (3S)-1-[4-(3-azabicyclo[3.1.0]hexan-3-ylmethyl)phenyl]-N-[5-[2-(4-chlorophenyl)ethyl]-1,3,4-thiadiazol-2-yl]-5-oxo-pyrrolidine-3-carboxamide | HCl | 0.003 |

TABLE 17-continued
| | ATX activity (Quanta Red assay) | | | |
|---|---|---|---|---|
| EXAMPLE | STRUCTURE | NAME | SALT | AVERAGE IC50 (MEAN, μM) |
| F104 | 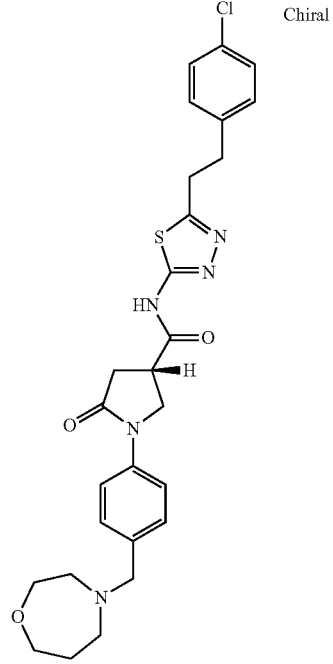 [SMILES: O=C(Nc1nnc(CCc2ccc(Cl)cc2)s1)[C@H]1CC(=O)N(c2ccc(CN3CCCOCC3)cc2)C1] | (3S)-N-[5-[2-(4-chlorophenyl)ethyl]-1,3,4-thiadiazol-2-yl]-1-[4-(1,4-oxazepan-4-ylmethyl)phenyl]-5-oxo-pyrrolidine-3-carboxamide | HCl | 0.003 |
| F105 | 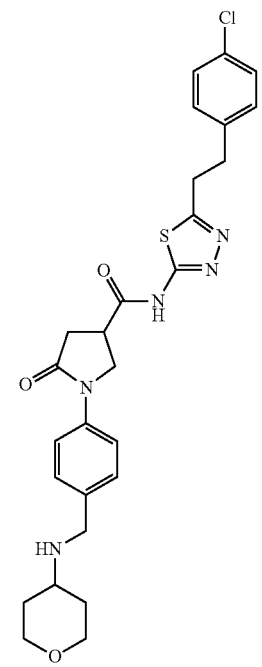 [SMILES: O=C(Nc1nnc(CCc2ccc(Cl)cc2)s1)C1CC(=O)N(c2ccc(CNC3CCOCC3)cc2)C1] | N-[5-[2-(4-chlorophenyl)ethyl]-1,3,4-thiadiazol-2-yl]-5-oxo-1-[4-[(tetrahydropyran-4-ylamino)methyl]phenyl]pyrrolidine-3-carboxamide | HCl | 0.003 |

TABLE 17-continued

ATX activity (Quanta Red assay)

| EXAMPLE | STRUCTURE | NAME | SALT | AVERAGE IC50 (MEAN, μM) |
|---|---|---|---|---|
| F106 | 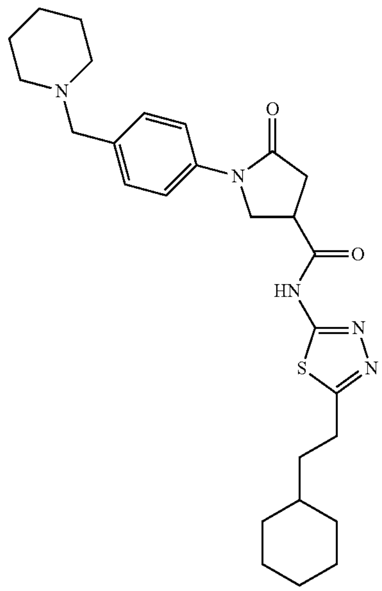 [SMILES: O=C(Nc1nnc(CCC2CCCCC2)s1)C1CC(=O)N(c2ccc(CN3CCCCC3)cc2)C1] | N-[5-(2-cyclohexylethyl)-1,3,4-thiadiazol-2-yl]-5-oxo-1-[4-(1-piperidylmethyl)phenyl]pyrrolidine-3-carboxamide | HCl | 0.003 |
| F107 | 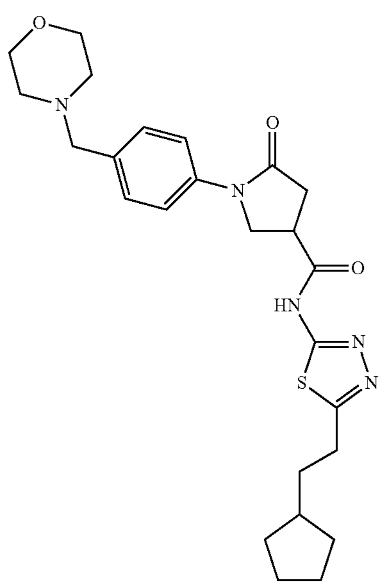 [SMILES: O=C(Nc1nnc(CCC2CCCC2)s1)C1CC(=O)N(c2ccc(CN3CCOCC3)cc2)C1] | N-[5-(2-cyclopentylethyl)-1,3,4-thiadiazol-2-yl]-1-[4-(morpholinomethyl)phenyl]-5-oxo-pyrrolidine-3-carboxamide | — | 0.003 |

TABLE 17-continued
ATX activity (Quanta Red assay)
| EXAMPLE | STRUCTURE | NAME | SALT | AVERAGE IC50 (MEAN, μM) |
|---|---|---|---|---|
| F108 | 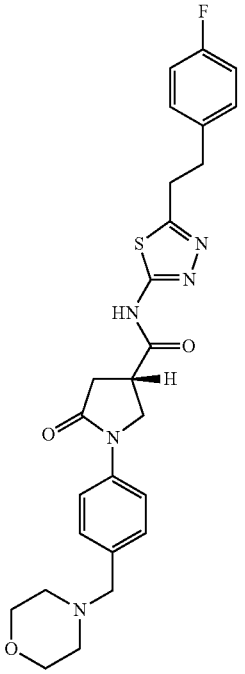 | (3S)-N-[5-[2-(4-fluorophenyl)ethyl]-1,3,4-thiadiazol-2-yl]-1-[4-(morpholinomethyl)phenyl]-5-oxo-pyrrolidine-3-carboxamide | HCl | 0.003 |
| F109 | 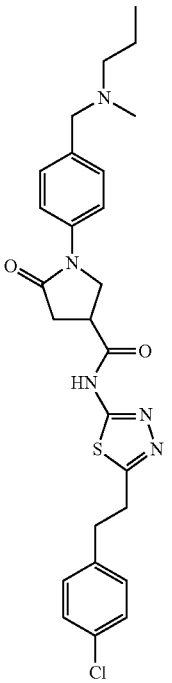 [SMILES: CCCN(C)Cc1ccc(N2CC(C(=O)Nc3nnc(CCc4ccc(Cl)cc4)s3)CC2=O)cc1] | N-[5-[2-(4-chlorophenyl)ethyl]-1,3,4-thiadiazol-2-yl]-1-[4-[[methyl)propyl)amino]methyl]phenyl]-5-oxo-pyrrolidine-3-carboxamide | — | 0.003 |

TABLE 17-continued

ATX activity (Quanta Red assay)

| EXAMPLE | STRUCTURE | NAME | SALT | AVERAGE IC50 (MEAN, μM) |
|---|---|---|---|---|
| F110 | 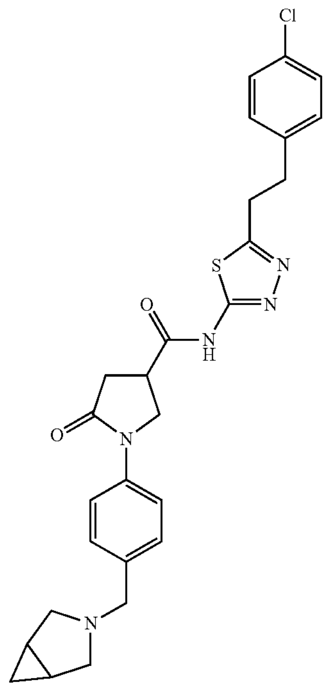 [SMILES: O=C(Nc1nnc(CCc2ccc(Cl)cc2)s1)C1CC(=O)N(c2ccc(CN3CC4CC4C3)cc2)C1] | 1-[4-(3-azabicyclo[3.1.0]hexan-3-ylmethyl)phenyl]-N-[5-[2-(4-chlorophenyl)ethyl]-1,3,4-thiadiazol-2-yl]-5-oxo-pyrrolidine-3-carboxamide | HCl | 0.003 |
| F111 | 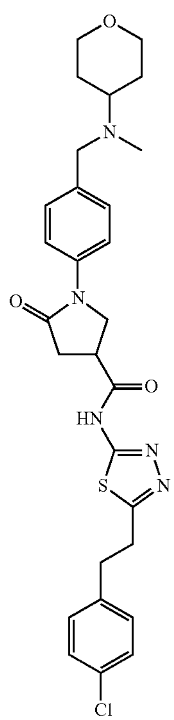 [SMILES: CN(Cc1ccc(N2CC(C(=O)Nc3nnc(CCc4ccc(Cl)cc4)s3)CC2=O)cc1)C1CCOCC1] | N-[5-[2-(4-chlorophenyl)ethyl]-1,3,4-thiadiazol-2-yl]-1-[4-[[methyl(tetrahydropyran-4-yl)amino]methyl]phenyl]-5-oxo-pyrrolidine-3-carboxamide | — | 0.003 |

TABLE 17-continued

ATX activity (Quanta Red assay)

| EX-AMPLE | STRUCTURE | NAME | SALT | AVERAGE IC50 (MEAN, μM) |
|---|---|---|---|---|
| F112 | 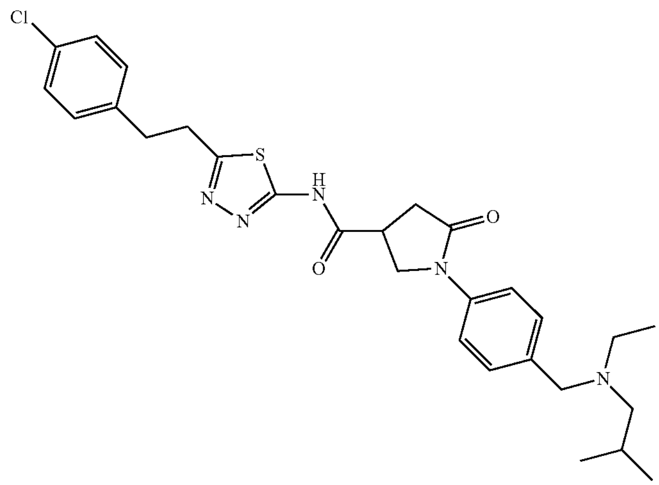 [SMILES: CCN(Cc1ccc(N2CC(C(=O)Nc3nnc(CCc4ccc(Cl)cc4)s3)CC2=O)cc1)CC(C)C] | N-[5-[2-(4-chlorophenyl)ethyl]-1,3,4-thiadiazol-2-yl]-1-[4-[[ethyl(isobutyl)amino]methyl]phenyl]-5-oxo-pyrrolidine-3-carboxamide | HCl | 0.003 |
| F113 | 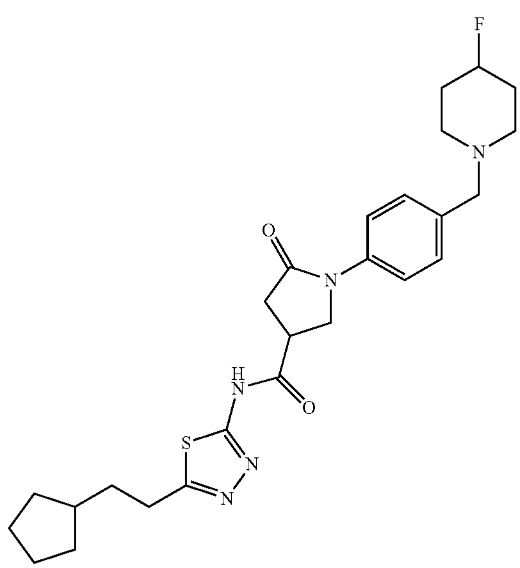 [SMILES: O=C(Nc1nnc(CCC2CCCC2)s1)C1CC(=O)N(c2ccc(CN3CCC(F)CC3)cc2)C1] | N-[5-(2-cyclopentylethyl)-1,3,4-thiadiazol-2-yl]-1-[4-[(4-fluoro-1-piperidyl)methyl]phenyl]-5-oxo-pyrrolidine-3-carboxamide | HCl | 0.003 |

TABLE 17-continued

| | ATX activity (Quanta Red assay) | | | |
|---|---|---|---|---|
| EXAMPLE | STRUCTURE | NAME | SALT | AVERAGE IC50 (MEAN, μM) |
| F114 | | 1-[4-(azepan-1-ylmethyl)phenyl]-N-[5-[2-(4-chlorophenyl)ethyl]-1,3,4-thiadiazol-2-yl]-5-oxo-pyrrolidine-3-carboxamide | HCl | 0.003 |
| F115 | | N-[5-(2-cyclopentylethyl)-1,3,4-thiadiazol-2-yl]-1-[4-[(3,3-difluoro-1-piperidyl)methyl]phenyl]-5-oxo-pyrrolidine-3-carboxamide | HCl | 0.003 |

TABLE 17-continued

ATX activity (Quanta Red assay)

| EXAMPLE | STRUCTURE | NAME | SALT | AVERAGE IC50 (MEAN, µM) |
|---|---|---|---|---|
| F116 | 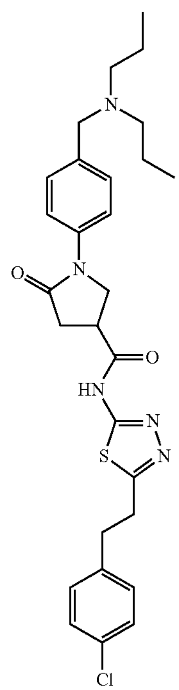 [SMILES: CCCN(CCC)Cc1ccc(N2CC(C(=O)Nc3nnc(CCc4ccc(Cl)cc4)s3)CC2=O)cc1] | N-[5-[2-(4-chlorophenyl)ethyl]-1,3,4-thiadiazol-2-yl]-1-[4-[(dipropylamino)methyl]phenyl]-5-oxo-pyrrolidine-3-carboxamide | HCl | 0.003 |
| F117 | 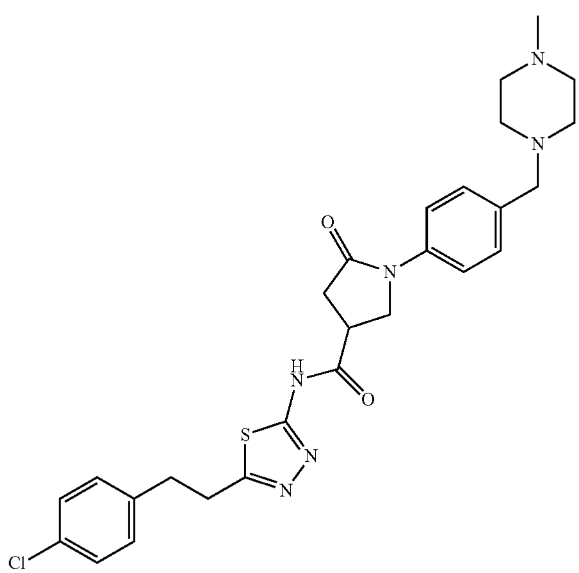 [SMILES: CN1CCN(Cc2ccc(N3CC(C(=O)Nc4nnc(CCc5ccc(Cl)cc5)s4)CC3=O)cc2)CC1] | N-[5-[2-(4-chlorophenyl)ethyl]-1,3,4-thiadiazol-2-yl]-1-[4-[(4-methylpiperazin-1-yl)methyl]phenyl]-5-oxo-pyrrolidine-3-carboxamide | Bis HCl | 0.004 |

TABLE 17-continued

ATX activity (Quanta Red assay)

| EXAMPLE | STRUCTURE | NAME | SALT | AVERAGE IC50 (MEAN, µM) |
|---|---|---|---|---|
| F118 | 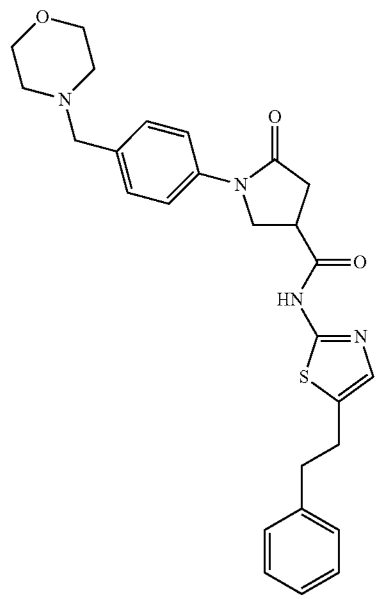 [SMILES: O=C(Nc1ncc(CCc2ccccc2)s1)C1CC(=O)N(c2ccc(CN3CCOCC3)cc2)C1] | 1-[4-(morpholinomethyl)phenyl]-5-oxo-N-[5-(2-phenylethyl)thiazol-2-yl]pyrrolidine-3-carboxamide | — | 0.004 |
| F119 | Chiral | N-[5-[2-(4-chlorophenyl)ethyl]-1,3,4-thiadiazol-2-yl]-1-[4-[[(2S,6R)-2,6-dimethylmorpholin-4-yl]methyl]phenyl]-5-oxo-pyrrolidine-3-carboxamide | HCl | 0.004 |

TABLE 17-continued

ATX activity (Quanta Red assay)

| EXAMPLE | STRUCTURE | NAME | SALT | AVERAGE IC50 (MEAN, μM) |
|---|---|---|---|---|
| F120 | 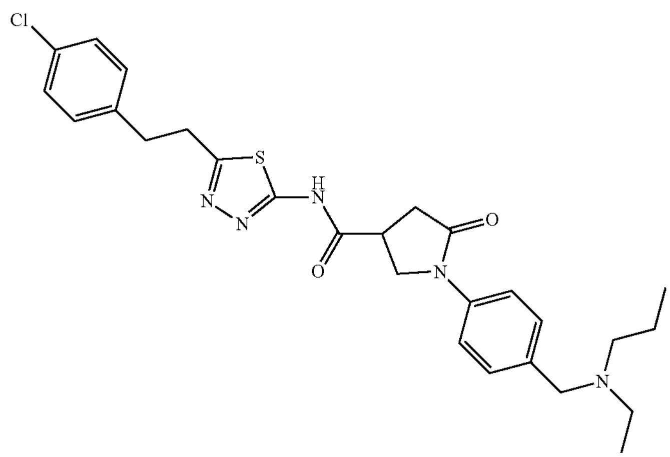 [SMILES: CCCN(CC)Cc1ccc(N2CC(C(=O)Nc3nnc(CCc4ccc(Cl)cc4)s3)CC2=O)cc1] | N-[5-[2-(4-chlorophenyl)ethyl]-1,3,4-thiadiazol-2-yl]-1-[4-[[ethyl(propyl)amino]methyl]phenyl]-5-oxo-pyrrolidine-3-carboxamide | HCl | 0.004 |
| F121 | 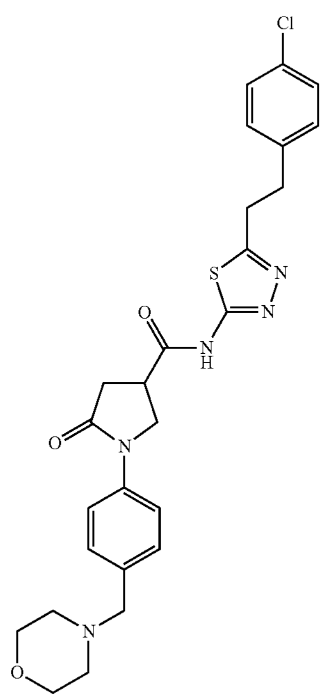 [SMILES: O=C(Nc1nnc(CCc2ccc(Cl)cc2)s1)C1CC(=O)N(c2ccc(CN3CCOCC3)cc2)C1] | N-[5-[2-(4-chlorophenyl)ethyl]-1,3,4-thiadiazol-2-yl]-1-[4-(morpholinomethyl)phenyl]-5-oxo-pyrrolidine-3-carboxamide | HCl | 0.004 |

TABLE 17-continued
ATX activity (Quanta Red assay)
| EX-AM-PLE | STRUCTURE | NAME | SALT | AVERAGE IC50 (MEAN, μM) |
|---|---|---|---|---|
| F122 | 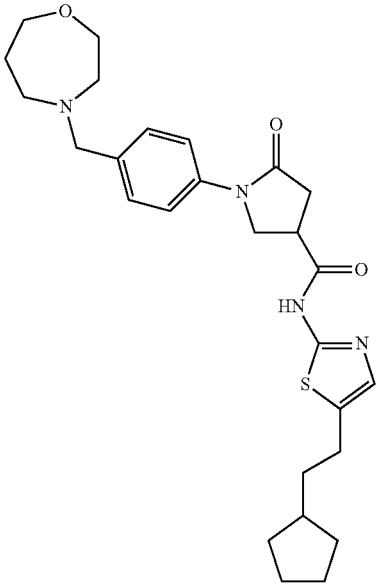 [SMILES: O=C(Nc1ncc(CCC2CCCC2)s1)C1CC(=O)N(c2ccc(CN3CCCOCC3)cc2)C1] | N-[5-(2-cyclopentylethyl)-1,3,4-thiadiazol-2-yl]-1-[4-(1,4-oxazepan-4-ylmethyl)phenyl]-5-oxo-pyrrolidine-3-carboxamide | HCl | 0.004 |
| F123 | 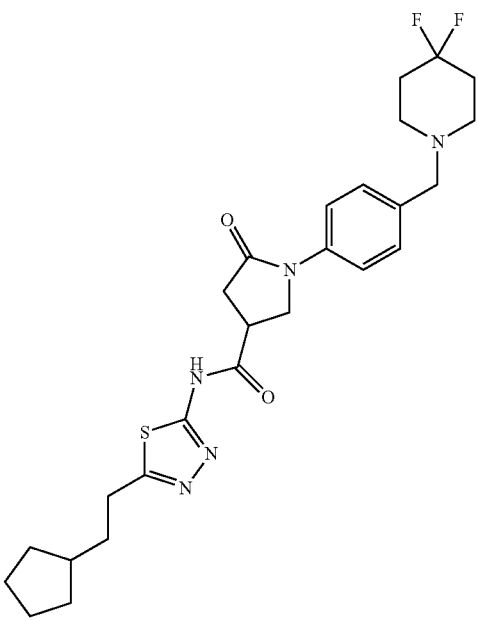 [SMILES: O=C(Nc1nnc(CCC2CCCC2)s1)C1CC(=O)N(c2ccc(CN3CCC(F)(F)CC3)cc2)C1] | N-[5-(2-cyclopentylethyl)-1,3,4-thiadiazol-2-yl]-1-[4-[(4,4-difluoro-1-piperidyl)methyl]phenyl]-5-oxo-pyrrolidine-3-carboxamide | HCl | 0.005 |

TABLE 17-continued

ATX activity (Quanta Red assay)

| EXAMPLE | STRUCTURE | NAME | SALT | AVERAGE IC50 (MEAN, μM) |
|---|---|---|---|---|
| F124 | 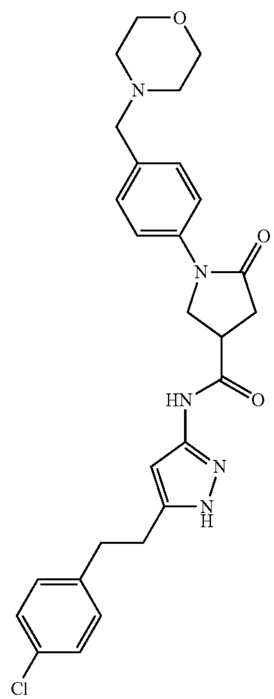 [SMILES: O=C(Nc1cc(CCc2ccc(Cl)cc2)[nH]n1)C1CC(=O)N(c2ccc(CN3CCOCC3)cc2)C1] | N-[3-[2-(4-chlorophenyl)ethyl]-1H-pyrazol-5-yl]-1-[4-(morpholinomethyl)phenyl]-5-oxo-pyrrolidine-3-carboxamide | — | 0.005 |
| F125 | Chiral | N-[5-[2-(4-chlorophenyl)ethyl]-1,3,4-thiadiazol-2-yl]-1-[4-[[(2S,6S)-2,6-dimethylmorpholin-4-yl]methyl]phenyl]-5-oxo-pyrrolidine-3-carboxamide | HCl | 0.008 |

TABLE 17-continued

ATX activity (Quanta Red assay)

| EXAMPLE | STRUCTURE | NAME | SALT | AVERAGE IC50 (MEAN, μM) |
|---|---|---|---|---|
| F126 | *(structure, Chiral)* | (3S)-N-[6-[2-(4-fluorophenyl)ethyl]pyridazin-3-yl]-1-[4-[[methyl(tetrahydropyran-4-yl)amino]methyl]phenyl]-5-oxo-pyrrolidine-3-carboxamide | HCl | 0.008 |
| F127 | *(structure)* | N-[5-[2-(4-chlorophenyl)ethyl]-1,3,4-thiadiazol-2-yl]-1-[4-[[ethyl(isopropyl)amino]methyl]phenyl]-5-oxo-pyrrolidine-3-carobxamide | — | 0.009 |

TABLE 17-continued

| | ATX activity (Quanta Red assay) | | | |
|---|---|---|---|---|
| EXAMPLE | STRUCTURE | NAME | SALT | AVERAGE IC50 (MEAN, μM) |
| F128 | | 5-[2-(4-chlorophenyl)ethyl]-N-[1-[4-(morpholinomethyl)phenyl]-5-oxo-pyrrolidine-3-yl]-1,3,4-thiadiazole-2-carboxamide | — | 0.001 |
| F129 | | 5-[2-(4-chlorophenyl)ethyl]-N-[1-[4-(1,4-oxazepan-4-ylmethyl)phenyl]-5-oxo-pyrrolidin-3-yl]-1,3,4-thiadiazole-2-carboxamide | HCl | 0.002 |

TABLE 17-continued

ATX activity (Quanta Red assay)

| EXAMPLE | STRUCTURE | NAME | SALT | AVERAGE IC50 (MEAN, μM) |
|---|---|---|---|---|
| F130 | Chiral | 5-[2-(4-chlorophenyl)ethyl]-N-[(3R)-1-[4-(morpholinomethyl)phenyl]-5-oxo-pyrrolidine-3-yl]-1,3,4-thiadiazole-2-carboxamide | HCl | 0.002 |
| F131 | Chiral | 5-[2-(4-chlorophenyl)ethyl]-N-[(3R)-1-[4-(morpholinomethyl)phenyl]pyrrolidine-3-yl]-1,3,4-thiadiazole-2-carboxamide | HCl | 0.002 |

TABLE 17-continued
| | ATX activity (Quanta Red assay) | | | |
|---|---|---|---|---|
| EXAMPLE | STRUCTURE | NAME | SALT | AVERAGE IC50 (MEAN, μM) |
| F132 | 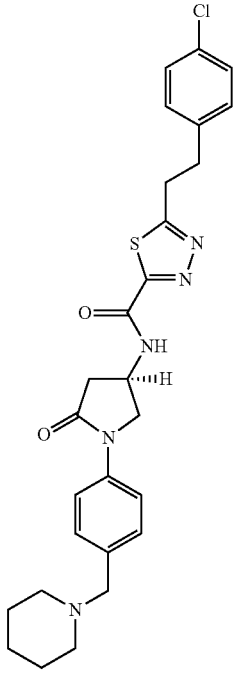 Chiral | 5-[2-(4-chlorophenyl)ethyl]-N-[(3R)-5-oxo-1-[4-(1-piperidylmethyl)phenyl]pyrrolidin-3-yl]-1,3,4-thiadiazole-2-carboxamide | HCl | 0.003 |
| F133 | 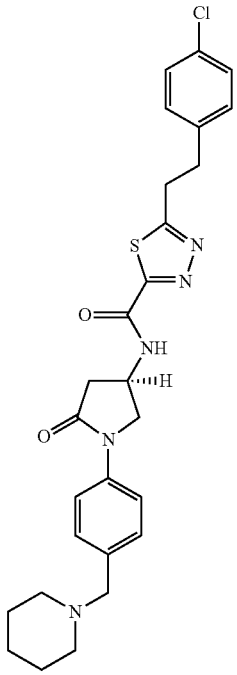 Chiral | 5-[2-(4-chlorophenyl)ethyl]-N-[(3S)-5-oxo-1-[4-(1-piperidylmethyl)phenyl]pyrrolidin-3-yl]-1,3,4-thiadiazole-2-carboxamide | HCl | 0.003 |

TABLE 17-continued

ATX activity (Quanta Red assay)

| EXAMPLE | STRUCTURE | NAME | SALT | AVERAGE IC50 (MEAN, μM) |
|---|---|---|---|---|
| F134 | 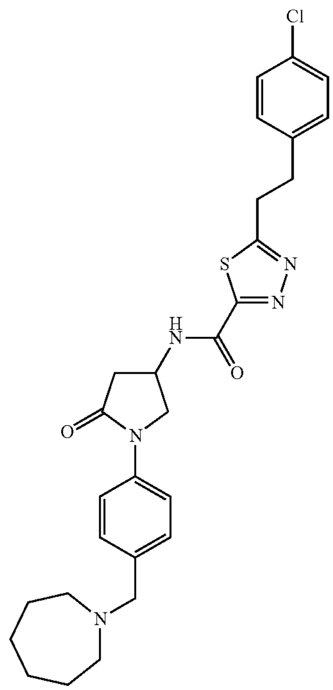 [SMILES: O=C(NC1CC(=O)N(c2ccc(CN3CCCCCC3)cc2)C1)c1nnc(CCc2ccc(Cl)cc2)s1] | N-[1-[4-(azepan-1-ylmethyl)phenyl]-5-oxo-pyrrolidin-3-yl]-5-[2-(4-chlorophenyl)ethyl]-1,3,4-thiadiazole-2-carboxamide | HCl | 0.003 |
| F135 | Chiral | 5-[2-(4-chlorophenyl)ethyl]-N-[(3S)-1-[4-(morpholinomethyl)phenyl]-5-oxo-pyrrolidin-3-yl]-1,3,4-thiadiazole-2-carboxamide | HCl | 0.003 |

TABLE 17-continued
| | ATX activity (Quanta Red assay) | | | |
|---|---|---|---|---|
| EXAMPLE | STRUCTURE | NAME | SALT | AVERAGE IC50 (MEAN, μM) |
| F136 | 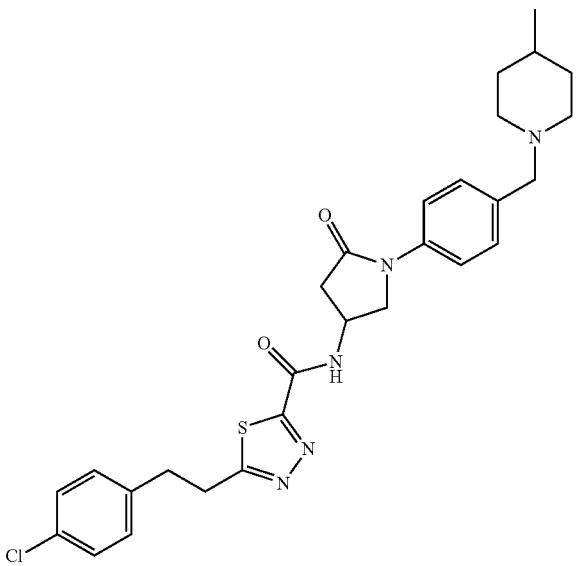 [SMILES: CC1CCN(Cc2ccc(N3CC(NC(=O)c4nnc(CCc5ccc(Cl)cc5)s4)CC3=O)cc2)CC1] | 5-[2-(4-chlorophenyl)ethyl]-N-[1-[4-[(4-methyl-1-piperidyl)methyl]phenyl]-5-oxo-pyrrolidin-3-yl]-1,3,4-thiadiazole-2-carboxamide | HCl | 0.004 |
| F137 | 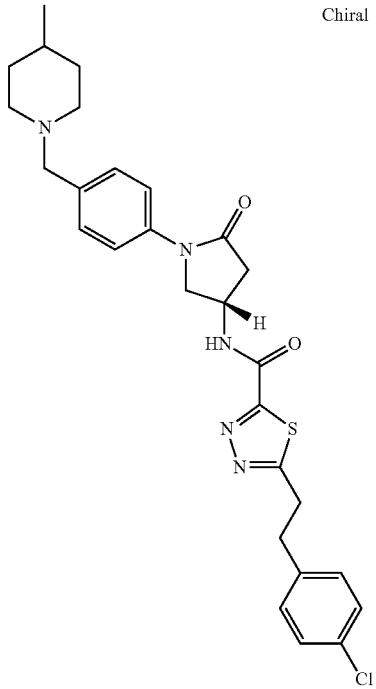 [SMILES: CC1CCN(Cc2ccc(N3C[C@@H](NC(=O)c4nnc(CCc5ccc(Cl)cc5)s4)CC3=O)cc2)CC1] Chiral | 5-[2-(4-chlorophenyl)ethyl]-N-[(3S)-1-[4-[(4-methyl-1-piperidyl)methyl]phenyl]-5-oxo-pyrrolidin-3-yl]-1,3,4-thiadiazole-2-carboxamide | HCl | 0.004 |

TABLE 17-continued
ATX activity (Quanta Red assay)
| EXAMPLE | STRUCTURE | NAME | SALT | AVERAGE IC50 (MEAN, μM) |
|---|---|---|---|---|
| F138 | 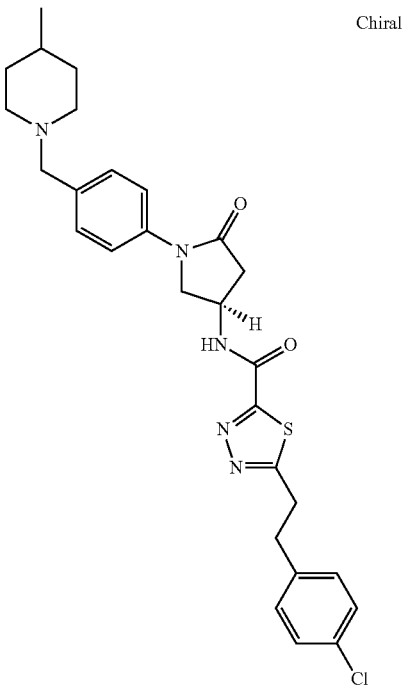 [SMILES: CC1CCN(Cc2ccc(N3C[C@H](NC(=O)c4nnc(CCc5ccc(Cl)cc5)s4)CC3=O)cc2)CC1] Chiral | 5-[2-(4-chlorophenyl)ethyl]-N-[(3R)-1-[4-[(4-methyl-1-piperidyl)methyl]phenyl]-5-oxo-pyrrolidin-3-yl]-1,3,4-thiadiazole-2-carboxamide | HCl | 0.005 |
| F139 | 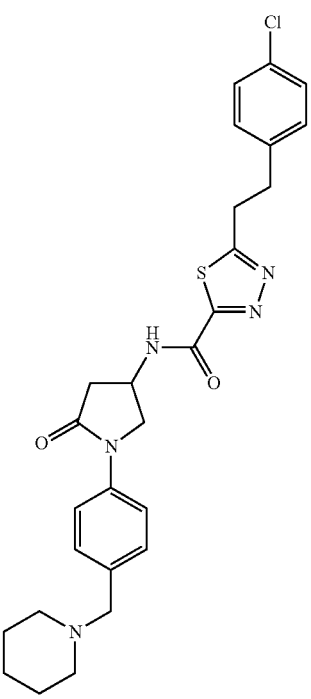 [SMILES: O=C(NC1CC(=O)N(c2ccc(CN3CCCCC3)cc2)C1)c1nnc(CCc2ccc(Cl)cc2)s1] | 5-[2-(4-chlorophenyl)ethyl]-N-[5-oxo-1-[4-(1-piperidylmethyl)phenyl]pyrrolidin-3-yl]-1,3,4-thiadiazole-2-carboxamide | HCl | 0.005 |

TABLE 17-continued
ATX activity (Quanta Red assay)
| EXAMPLE | STRUCTURE | NAME | SALT | AVERAGE IC50 (MEAN, μM) |
|---|---|---|---|---|
| F140 | 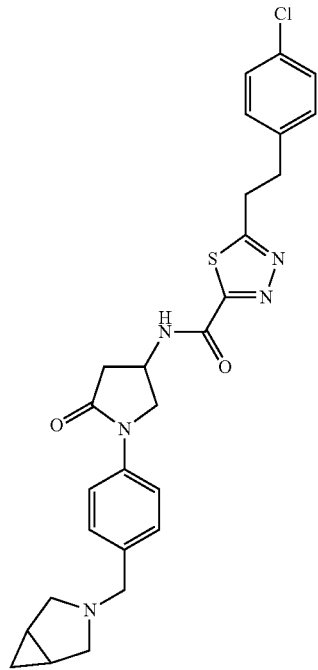 [SMILES: O=C(NC1CC(=O)N(c2ccc(CN3CC4CC4C3)cc2)C1)c1nnc(CCc2ccc(Cl)cc2)s1] | N-[1-[4-(3-azabicyclo[3.1.0]hexan-3-ylmethyl)phenyl]-5-oxo-pyrrolidin-3-yl]-5-[2-(4-chlorophenyl)ethyl]-1,3,4-thiadiazole-2-carboxamide | HCl | 0.005 |
| F141 | 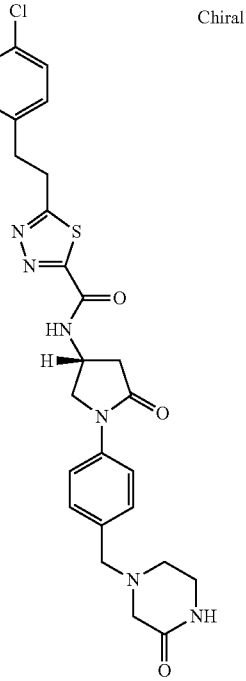 Chiral | 5-[2-(4-chlorophenyl)ethyl]-N-[(3R)-5-oxo-1-[4-[(3-oxopiperazin-1-yl)methyl]phenyl]pyrrolidin-3-yl]-1,3,4-thiadiazole-2-carboxamide | HCl | 0.008 |

TABLE 17-continued

ATX activity (Quanta Red assay)

| EXAMPLE | STRUCTURE | NAME | SALT | AVERAGE IC50 (MEAN, μM) |
|---|---|---|---|---|
| F142 | 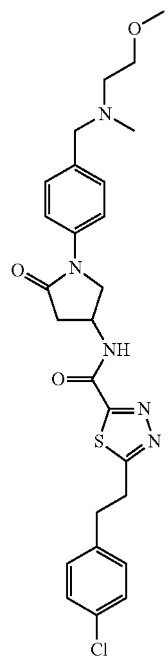 [SMILES: COCCN(C)Cc1ccc(N2CC(NC(=O)c3nnc(CCc4ccc(Cl)cc4)s3)CC2=O)cc1] | 5-[2-(4-chlorophenyl)ethyl]-N-[1-[4-[[2-methoxyethyl(methyl)amino]methyl]phenyl]-5-oxo-pyrrolidin-3-yl]-1,3,4-thiadiazole-2-carboxamide | HCl | 0.009 |
| F143 | Chiral | 5-[2-(4-chlorophenyl)ethyl]-N-[(3R)-5-oxo-1-[4-(1-piperidylmethyl)phenyl]pyrrolidin-3-yl]isoxazole-3-carboxamide | HCl | 0.002 |

TABLE 17-continued

ATX activity (Quanta Red assay)

| EXAMPLE | STRUCTURE | NAME | SALT | AVERAGE IC50 (MEAN, μM) |
|---|---|---|---|---|
| F144 | 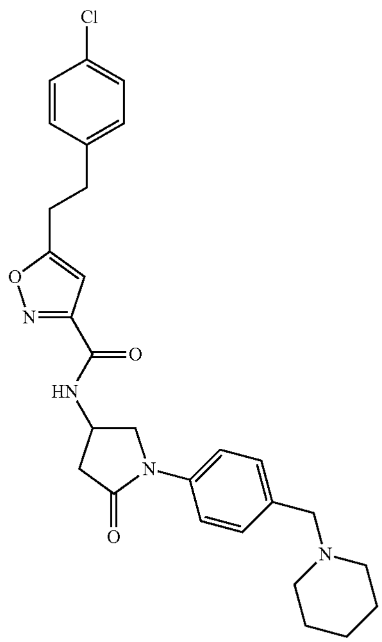 [SMILES: O=C(NC1CC(=O)N(c2ccc(CN3CCCCC3)cc2)C1)c1cc(CCc2ccc(Cl)cc2)on1] | 5-[2-(4-chlorophenyl)ethyl]-N-[5-oxo-1-[4-(1-piperidylmethyl)phenyl]pyrrolidin-3-yl]isoxazole-3-carboxamide | HCl | 0.002 |
| F145 | 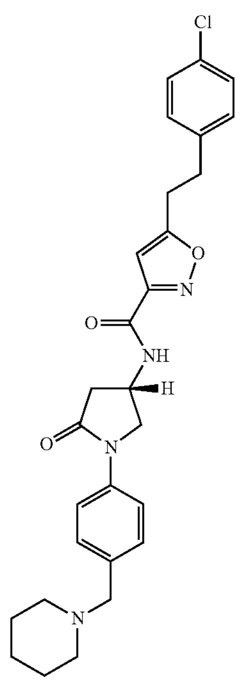 | 5-[2-(4-chlorophenyl)ethyl]-N-[(3S)-5-oxo-1-[4-(1-piperidylmethyl)phenyl]pyrrolidin-3-yl]isoxazole-3-carboxamide | HCl | 0.003 |

TABLE 17-continued
| | ATX activity (Quanta Red assay) | | | |
|---|---|---|---|---|
| EXAMPLE | STRUCTURE | NAME | SALT | AVERAGE IC50 (MEAN, μM) |
| F146 | 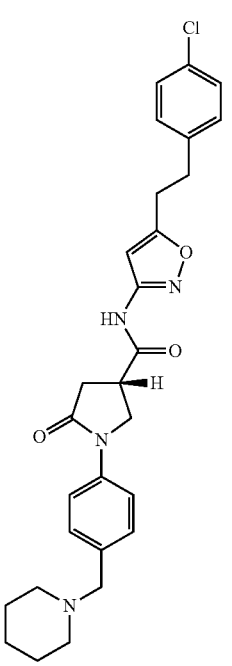 Chiral | (3S)-N-[5-[2-(4-chlorophenyyl)ethyl]isoxazol-3-yl]-5-oxo-1-[4-(1-piperidylmethyl)phenyl]pyrrolidine-3-carboxamide | HCl | 0.001 |
| F147 | 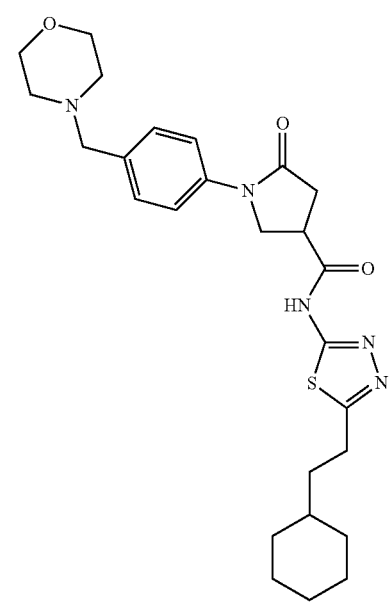 [SMILES: O=C(Nc1nnc(CCC2CCCCC2)s1)C1CC(=O)N(c2ccc(CN3CCOCC3)cc2)C1] | N-[5-(2-cyclohexylethyl)-1,3,4-thiadiazol-2-yl]-1-[4-(morpholinomethyl)phenyl]-5-oxo-pyrrolidine-3-carboxamide | — | 0.002 |

TABLE 17-continued

ATX activity (Quanta Red assay)

| EXAMPLE | STRUCTURE | NAME | SALT | AVERAGE IC50 (MEAN, μM) |
|---|---|---|---|---|
| F148 | Chiral | (3S)-N-[6-[2-(4-fluorophenyl)ethyl]pyridazin-3-yl]-1-[4-[[methyl(tetrahydrofuran-3-yl)amino]methyl]phenyl]-5-oxo-pyrrolidine-3-carboxamide | HCl | 0.006 |
| F149 | 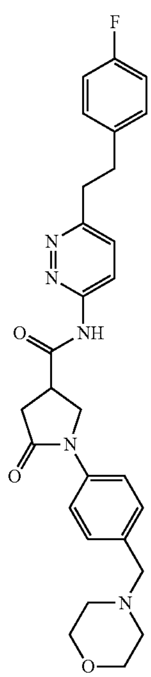 [SMILES: O=C(Nc1ccc(CCc2ccc(F)cc2)nn1)C1CC(=O)N(c2ccc(CN3CCOCC3)cc2)C1] | N-[6-[2-(4-fluorophenyl)ethyl]pyridazin-3-yl]-1-[4-(morpholinomethyl)phenyl]-5-oxo-pyrrolidine-3-carboxamide | HCl | 0.007 |

TABLE 17-continued
| | | ATX activity (Quanta Red assay) | | |
|---|---|---|---|---|
| EXAMPLE | STRUCTURE | NAME | SALT | AVERAGE IC50 (MEAN, μM) |
| F150 | 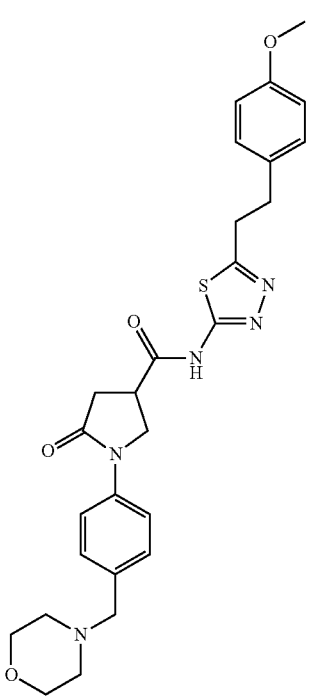 | N-[5-[2-(4-methoxyphenyl)ethyl]-1,3,4-thiadiazol-2-yl]-1-[4-(morpholinomethyl)phenyl]-5-oxo-pyrrolidine-3-carboxamide | — | 0.008 |
| F151 | 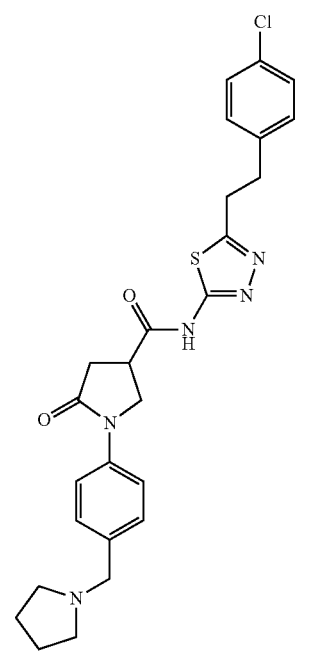 [SMILES: O=C(Nc1nnc(CCc2ccc(Cl)cc2)s1)C1CC(=O)N(c2ccc(CN3CCCC3)cc2)C1] | N-[5-[2-(4-chlorophenyl)ethyl]-1,3,4-thiadiazol-2-yl]-5-oxo-1-[4-(pyrrolidin-1-ylmethyl)phenyl]pyrrolidine-3-carboxamide | HCl | 0.009 |

TABLE 17-continued
| | ATX activity (Quanta Red assay) | | | |
|---|---|---|---|---|
| EXAMPLE | STRUCTURE | NAME | SALT | AVERAGE IC50 (MEAN, μM) |
| F152 | 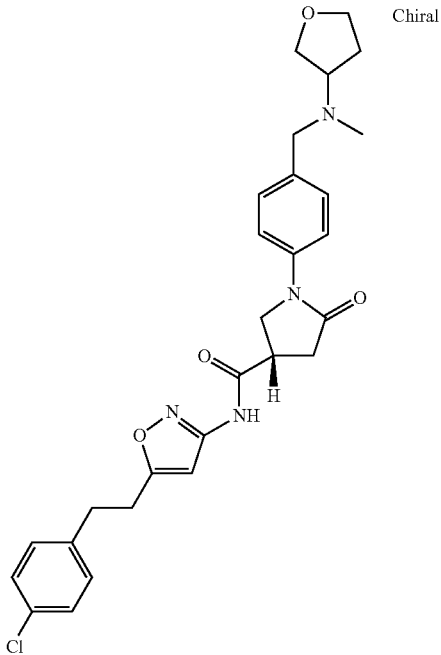 [SMILES: CN(Cc1ccc(N2C[C@@H](C(=O)Nc3cc(CCc4ccc(Cl)cc4)on3)CC2=O)cc1)C1CCOC1] Chiral | (3S)-N-[5-[2-(4-chlorophenyl)ethyl]isoxazol-3-yl]-1-[4-[[methyl(tetrahydrofuran-3-yl)amino]methyl]phenyl]-5-oxo-pyrrolidine-3-carboxamide | HCl | 0.002 |
| F153 | 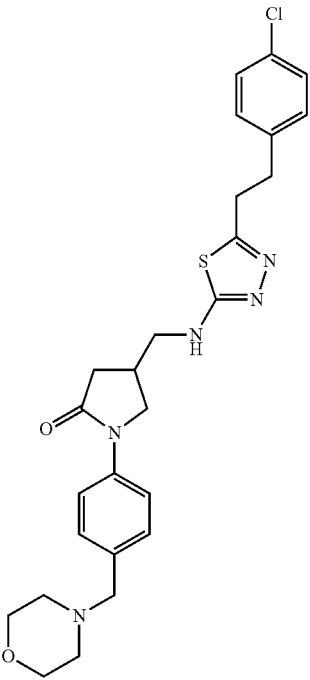 [SMILES: O=C1CC(CNc2nnc(CCc3ccc(Cl)cc3)s2)CN1c1ccc(CN2CCOCC2)cc1] | 4-[[[5-[2-(4-chlorophenyl)ethyl]-1,3,4-thiadiazol-2-yl]amino]methyl]-1-[4-(morpholinomethyl)phenyl]pyrrolidin-2-one | — | 0.002 |

TABLE 17-continued
| | ATX activity (Quanta Red assay) | | | |
|---|---|---|---|---|
| EXAMPLE | STRUCTURE | NAME | SALT | AVERAGE IC50 (MEAN, μM) |
| F154 | 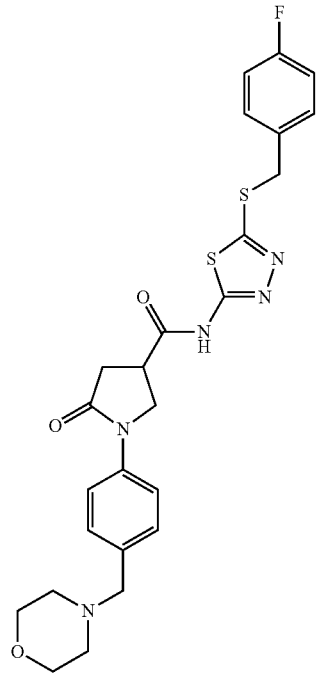 [SMILES: O=C(Nc1nnc(SCc2ccc(F)cc2)s1)C1CC(=O)N(c2ccc(CN3CCOCC3)cc2)C1] | N-[5-[(4-fluorophenyl)methylsulfanyl]-1,3,4-thiadiazol-2-yl]-1-[4-(morpholinomethyl)phenyl]-5-oxo-pyrrolidine-3-carboxamide | — | 0.003 |
| F155 | 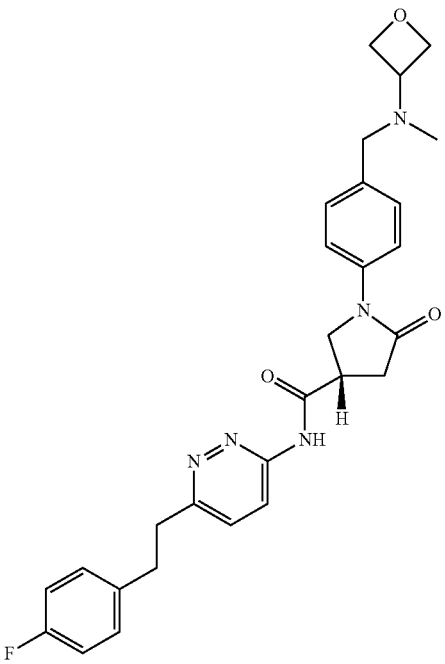 | (3S)-N-[6-[2-(4-fluorophenyl)ethyl]pyridazin-3-yl]-1-[4-[[methyl(oxetan-3-yl)amino]methyl]phenyl]-5-oxo-pyrrolidine-3-carboxamide | — | 0.011 |

TABLE 17-continued
| | ATX activity (Quanta Red assay) | | | |
|---|---|---|---|---|
| EXAMPLE | STRUCTURE | NAME | SALT | AVERAGE IC50 (MEAN, μM) |
| F156 | 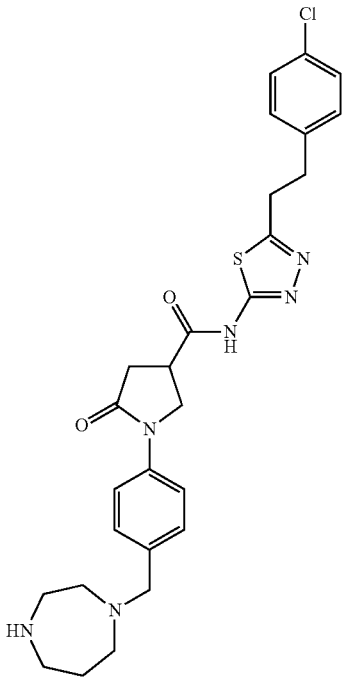 [SMILES: O=C(Nc1nnc(CCc2ccc(Cl)cc2)s1)C1CC(=O)N(c2ccc(CN3CCCNCC3)cc2)C1] | N-[5-[2-(4-chlorophenyl)ethyl]-1,3,4-thiadiazol-2-yl]-1-[4-(1,4-diazepan-1-ylmethyl)phenyl]-5-oxo-pyrrolidine-3-carboxamide | Bis HCl | 0.014 |
| F157 | 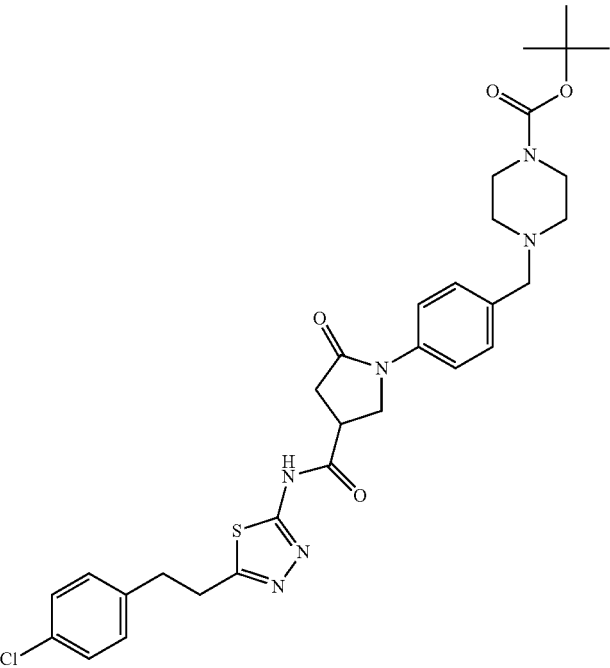 [SMILES: CC(C)(C)OC(=O)N1CCN(Cc2ccc(N3CC(C(=O)Nc4nnc(CCc5ccc(Cl)cc5)s4)CC3=O)cc2)CC1] | tert-butyl 4-[[4-[4-[[5-[2-(4-chlorophenyl)ethyl]-1,3,4-thiadiazol-2-yl]carbamoyl]-2-oxo-pyrrolidin-1-yl]phenyl]methyl]piperazine-1-carboxylate | — | 0.015 |

TABLE 17-continued

ATX activity (Quanta Red assay)

| EXAMPLE | STRUCTURE | NAME | SALT | AVERAGE IC50 (MEAN, μM) |
|---|---|---|---|---|
| F158 | 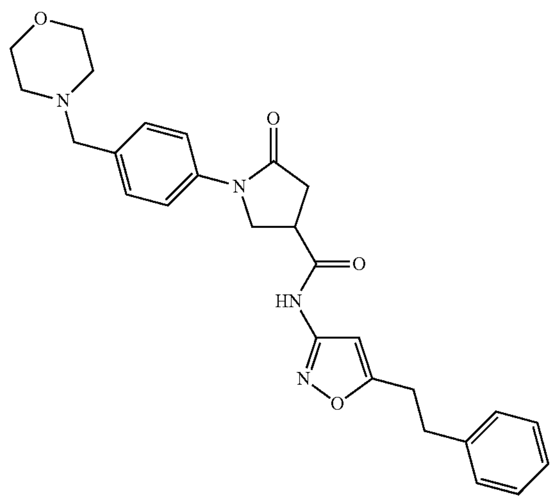 [SMILES: O=C(Nc1cc(CCc2ccccc2)on1)C1CC(=O)N(c2ccc(CN3CCOCC3)cc2)C1] | 1-[4-(morpholinomethyl)phenyl]-5-oxo-N-[5-(2-phenylethyl)isoxazol-3-yl]pyrrolidine-3-carboxamide | HCl | 0.017 |
| F159 | 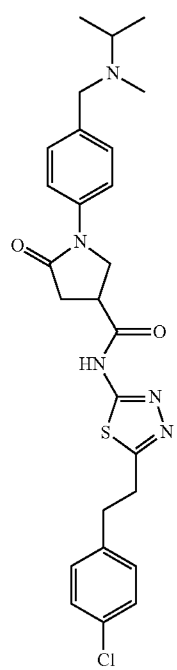 [SMILES: CC(C)N(C)Cc1ccc(N2CC(C(=O)Nc3nnc(CCc4ccc(Cl)cc4)s3)CC2=O)cc1] | N-[5-[2-(4-chlorophenyl)ethyl]-1,3,4-thiadiazol-2-yl]-1-[4-[[isopropyl(methyl)amino]methyl]phenyl]-5-oxo-pyrrolidine-3-carboxamide | — | 0.018 |

TABLE 17-continued
ATX activity (Quanta Red assay)
| EX-AMPLE | STRUCTURE | NAME | SALT | AVERAGE IC50 (MEAN, μM) |
|---|---|---|---|---|
| F160 | 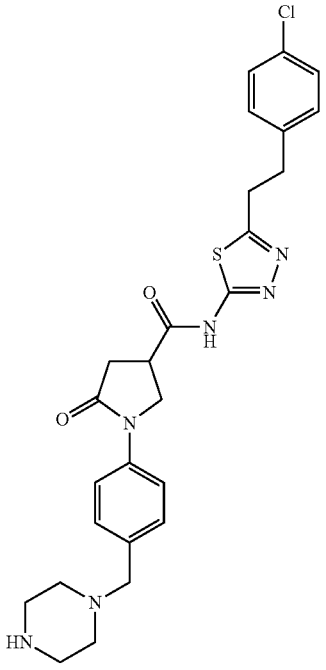 [SMILES: O=C(Nc1nnc(CCc2ccc(Cl)cc2)s1)C1CC(=O)N(c2ccc(CN3CCNCC3)cc2)C1] | N-[5-[2-(4-chlorophenyl)ethyl]-1,3,4-thiadiazol-2-yl]-5-oxo-1-[4-(piperazin-1-ylmethyl)phenyl]pyrrolidine-3-carboxamide | Bis HCl | 0.024 |
| F161 | 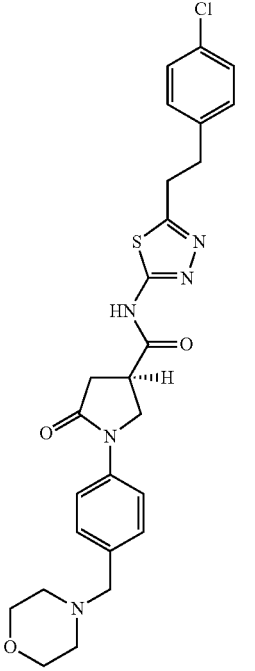 | (3R)-N-[5-[2-(4-chlorophenyl)ethyl]-1,3,4-thiadiazol-2-yl]-1-[4-(morpholinomethyl)phenyl]-5-oxo-pyrrolidine-3-carboxamide | HCl | 0.037 |

TABLE 17-continued
ATX activity (Quanta Red assay)
| EXAMPLE | STRUCTURE | NAME | SALT | AVERAGE IC50 (MEAN, μM) |
|---|---|---|---|---|
| F162 | 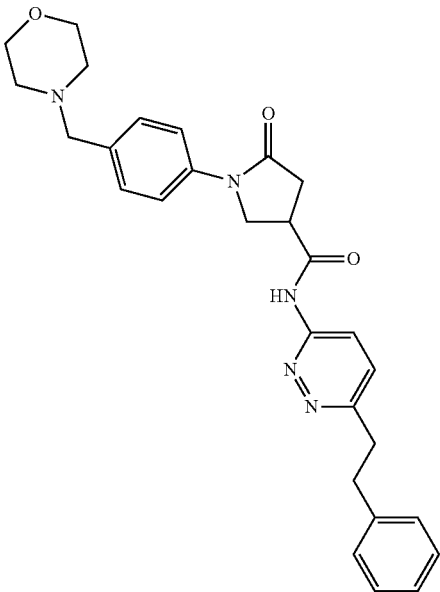 [SMILES: O=C(Nc1ccc(CCc2ccccc2)nn1)C1CC(=O)N(c2ccc(CN3CCOCC3)cc2)C1] | 1-[4-(morpholinomethyl)phenyl]-5-oxo-N-[6-(2-phenylethyl)pyridazin-3-yl]pyrrolidine-3-carboxamide | — | 0.037 |
| F163 | 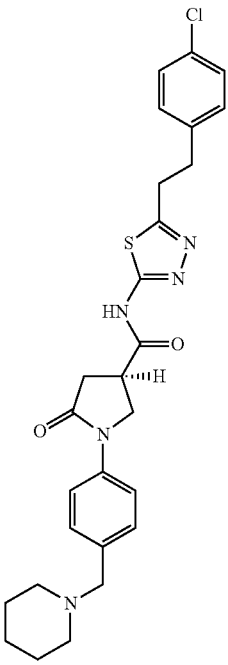 | (3R)-N-[5-[2-(4-chlorophenyl)ethyl]-1,3,4-thiadiazol-2-yl]-5-oxo-1-[4-(1-piperidylmethyl)phenyl]pyrrolidine-3-carboxamide | HCl | 0.049 |

TABLE 17-continued
ATX activity (Quanta Red assay)
| EXAMPLE | STRUCTURE | NAME | SALT | AVERAGE IC50 (MEAN, μM) |
|---|---|---|---|---|
| F164 | 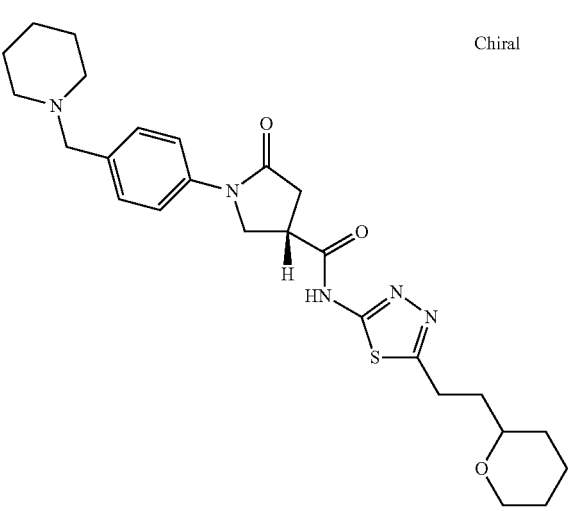 [SMILES: O=C(Nc1nnc(CCC2CCCCO2)s1)[C@H]1CC(=O)N(c2ccc(CN3CCCCC3)cc2)C1] Chiral | (3S)-5-oxo-1-[4-(1-piperidylmethyl)phenyl]-N-[5-(2-tetrahydropyran-2-ylethyl)-1,3,4-thiadiazol-2-yl]pyrrolidine-3-carboxamide | HCl | 0.070 |
| F165 | 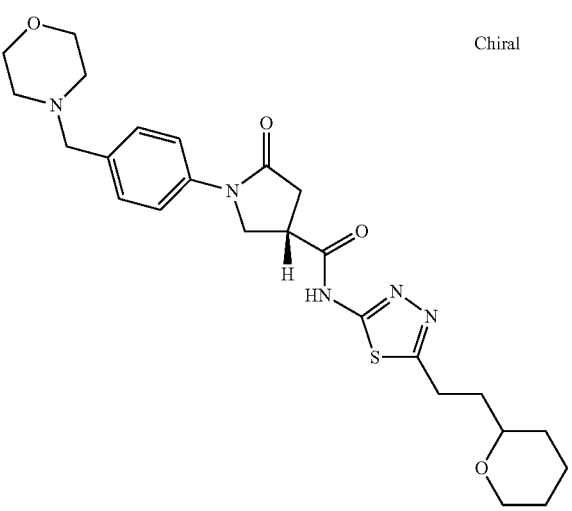 [SMILES: O=C(Nc1nnc(CCC2CCCCO2)s1)[C@H]1CC(=O)N(c2ccc(CN3CCOCC3)cc2)C1] Chiral | (3S)-1-[4-(morpholinomethyl)phenyl]-5-oxo-N-[5-(2-tetrahydropyran-2-ylethyl)-1,3,4-thiadiazol-2-yl]pyrrolidine-3-carboxamide | HCl | 0.095 |

TABLE 17-continued
ATX activity (Quanta Red assay)
| EXAMPLE | STRUCTURE | NAME | SALT | AVERAGE IC50 (MEAN, μM) |
|---|---|---|---|---|
| F166 | 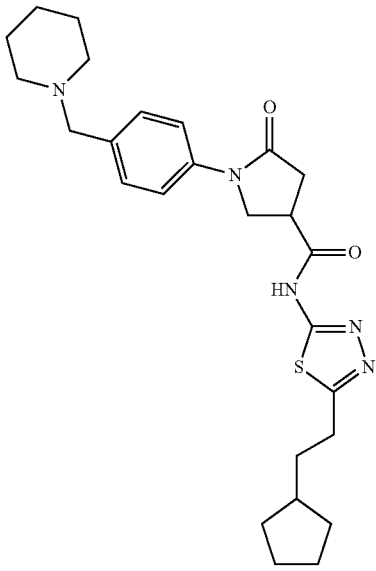 [SMILES: O=C(Nc1nnc(CCC2CCCC2)s1)C1CC(=O)N(c2ccc(CN3CCCCC3)cc2)C1] | N-[5-(2-cyclopentylethyl)-1,3,4-thiadiazol-2-yl]-5-oxo-1-[4-(1-piperidylmethyl)phenyl]pyrrolidine-3-carboxamide | — | 0.016 |
| F167 | 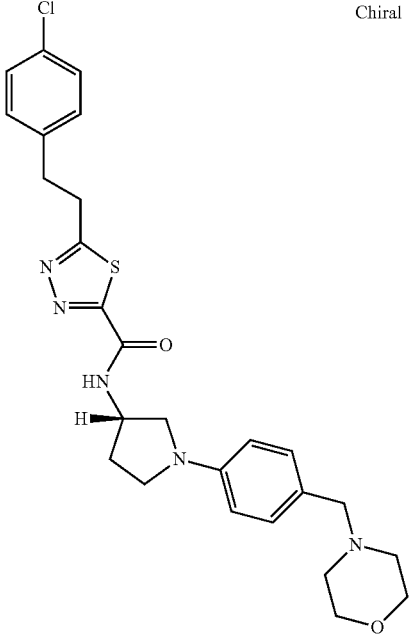 [SMILES: O=C(N[C@H]1CCN(c2ccc(CN3CCOCC3)cc2)C1)c1nnc(CCc2ccc(Cl)cc2)s1]  Chiral | 5-[2-(4-chlorophenyl)ethyl]-N-[(3S)-1-[4-(morpholinomethyl)phenyl]pyrrolidin-3-yl]-1,3,4-thiadiazole-2-carboxamide | HCl | 0.016 |

TABLE 17-continued

ATX activity (Quanta Red assay)

| EXAMPLE | STRUCTURE | NAME | SALT | AVERAGE IC50 (MEAN, μM) |
|---|---|---|---|---|
| F168 | 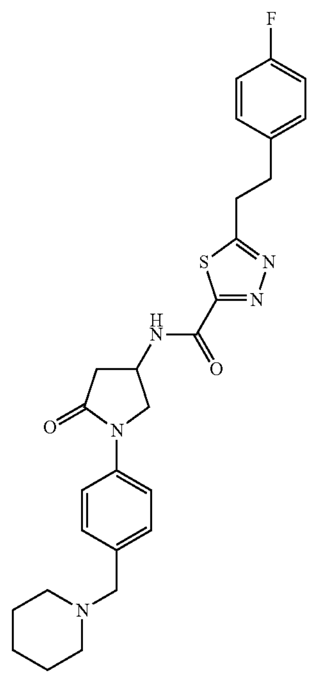 | 5-[2-(4-fluorophenyl)ethyl]-N-[5-oxo-1-[4-(1-piperidylmethyl)phenyl]pyrrolidin-3-yl]-1,3,4-thiadiazole-2-carboxamide | HCl | 0.017 |
| F169 | Chiral | 5-[2-(4-chlorophenyl)ethyl]-N-[(3R)-1-[4-[(4-hydroxy-4-methyl-1-piperidyl)methyl]phenyl]-5-oxo-pyrrolidin-3-yl]-1,3,4-thiadiazole-2-carboxamide | HCl | 0.022 |

TABLE 17-continued
| EXAMPLE | STRUCTURE | NAME | SALT | AVERAGE IC50 (MEAN, μM) |
|---|---|---|---|---|
| F170 | 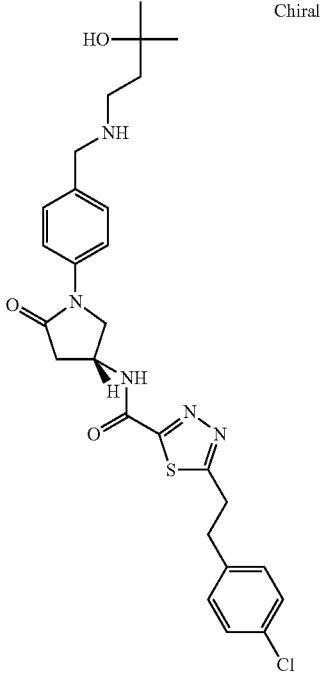 [SMILES: CC(C)(O)CCNCc1ccc(N2C[C@H](NC(=O)c3nnc(CCc4ccc(Cl)cc4)s3)CC2=O)cc1] Chiral | 5-[2-(4-chlorophenyl)ethyl]-N-[(3R)-1-[4-[[(3-hydroxy-3-methyl-butyl)amino]methyl]phenyl]-5-oxo-pyrrolidin-3-yl]-1,3,4-thiadiazole-2-carboxamide hydrochloride | HCl | 0.058 |
| F171 | 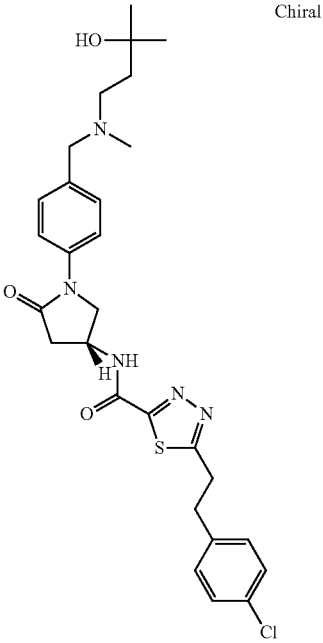 [SMILES: CN(CCC(C)(C)O)Cc1ccc(N2C[C@H](NC(=O)c3nnc(CCc4ccc(Cl)cc4)s3)CC2=O)cc1] Chiral | 5-[2-(4-chlorophenyl)ethyl]-N-[(3R)-1-[4-[[(3-hydroxy-3-methyl-butyl)-methyl-amino]methyl]phenyl]-5-oxo-pyrrolidin-3-yl]-1,3,4-thiadiazole-2-carboxamide | HCl | 0.058 |

TABLE 17-continued

ATX activity (Quanta Red assay)

| EXAMPLE | STRUCTURE | NAME | SALT | AVERAGE IC50 (MEAN, µM) |
|---|---|---|---|---|
| F172 | 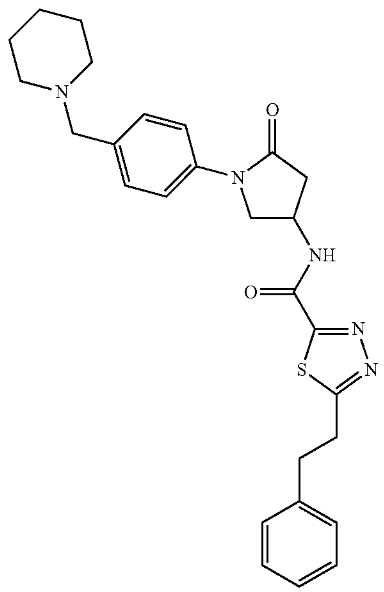 | N-[5-oxo-1-[4-(1-piperidylmethyl)phenyl]pyrrolidin-3-yl]-5-(2-phenylethyl)-1,3,4-thiadiazole-2-carboxamide | HCl | 0.076 |
| F173 | 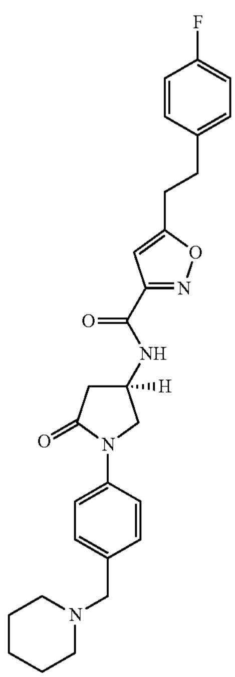 | 5-[2-(4-fluorophenyl)ethyl]-N-[(3R)-5-oxo-1-[4-(1-piperidylmethyl)phenyl]pyrrolidin-3-yl]isoxazole-3-carboxamide | HCl | 0.024 |

TABLE 17-continued
ATX activity (Quanta Red assay)
| EXAMPLE | STRUCTURE | NAME | SALT | AVERAGE IC50 (MEAN, μM) |
|---|---|---|---|---|
| F174 | 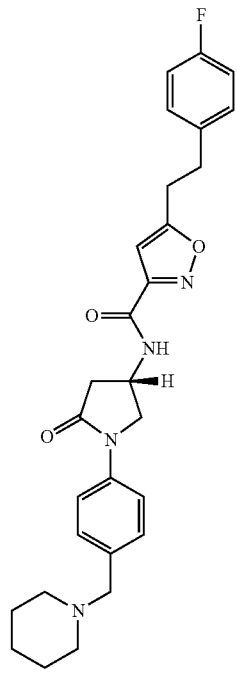 | 5-[2-(4-fluorophenyl)ethyl]-N-[(3S)-5-oxo-1-[4-(1-piperidylmethyl)phenyl]pyrrolidin-3-yl]isoxazole-3-carboxamide | HCl | 0.033 |
| F175 | 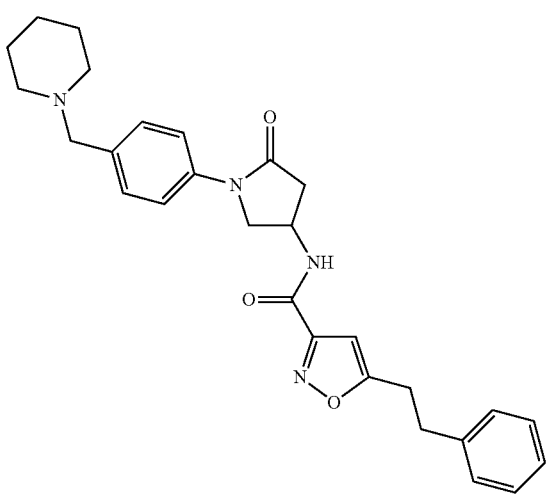 [SMILES: O=C(NC1CC(=O)N(c2ccc(CN3CCCCC3)cc2)C1)c1cc(CCc2ccccc2)on1] | N-[5-oxo-1-[4-(1-piperidylmethyl)phenyl]pyrrolidin-3-yl]-5-(2-phenylethyl)isoxazole-3-carboxamide | HCl | 0.047 |

TABLE 17-continued

ATX activity (Quanta Red assay)

| EXAMPLE | STRUCTURE | NAME | SALT | AVERAGE IC50 (MEAN, μM) |
|---|---|---|---|---|
| F176 | 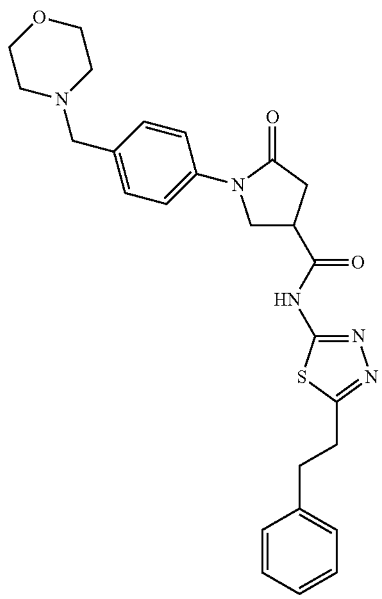 [SMILES: O=C(Nc1nnc(CCc2ccccc2)s1)C1CC(=O)N(c2ccc(CN3CCOCC3)cc2)C1] | 1-[4-(morpholinomethyl)phenyl]-5-oxo-N-[5-(2-phenylethyl)-1,3,4-thiadiazol-2-yl]pyrrolidine-3-carboxamide | HCl | 0.011 |
| F177 | 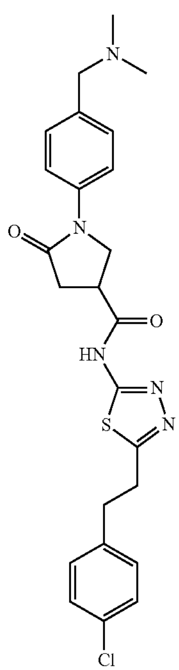 [SMILES: CN(C)Cc1ccc(N2CC(C(=O)Nc3nnc(CCc4ccc(Cl)cc4)s3)CC2=O)cc1] | N-[5-[2-(4-chlorophenyl)ethyl]-1,3,4-thiadiazol-2-yl]-1-[4-[(dimethylamino)methyl]phenyl]-5-oxo-pyrrolidine-3-carboxamide | — | 0.029 |

TABLE 17-continued

ATX activity (Quanta Red assay)

| EXAMPLE | STRUCTURE | NAME | SALT | AVERAGE IC50 (MEAN, µM) |
|---|---|---|---|---|
| F178 | Chiral | (3S)-N-[6-[2-(4-fluorophenyl)ethyl]pyridazin-3-yl]-5-oxo-1-[4-(1-piperidylmethyl)phenyl]pyrrolidine-3-carboxamide | HCl | 0.030 |
| F179 | 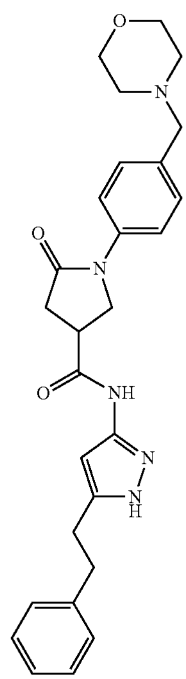 [SMILES: O=C(Nc1cc(CCc2ccccc2)[nH]n1)C1CC(=O)N(c2ccc(CN3CCOCC3)cc2)C1] | 1-[4-(morpholinomethyl)phenyl]-5-oxo-N-[5-(2-phenylethyl)-1H-pyrazol-3-yl]pyrrolidine-3-carboxamide | — | 0.038 |

| EXAMPLE | STRUCTURE | NAME | SALT | AVERAGE IC50 (MEAN, μM) |
|---|---|---|---|---|
| F180 | 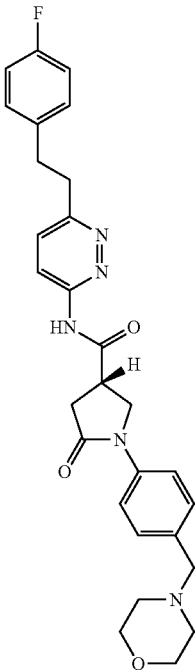 Chiral | (3S)-N-[6-[2-(4-fluorophenyl)ethyl]pyridazin-3-yl]-1-[4-(morpholinomethyl)phenyl]-5-oxo-pyrrolidine-3-carboxamide | HCl | 0.011 |
| F181 | 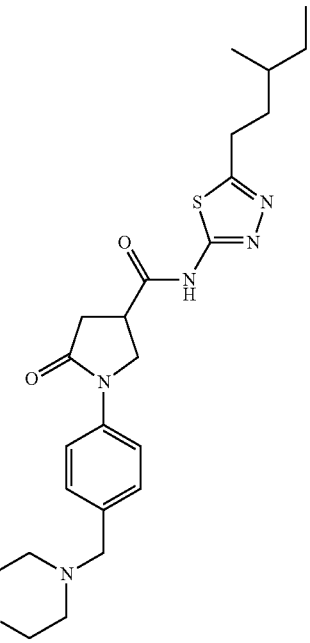 | N-[5-(3-methylpentyl)-1,3,4-thiadiazol-2-yl]-1-[4-(morpholinomethyl)phenyl]-5-oxo-pyrrolidine-3-carboxamide | HCl | 0.011 |

TABLE 17-continued

ATX activity (Quanta Red assay)

| EX-AM-PLE | STRUCTURE | NAME | SALT | AVERAGE IC50 (MEAN, µM) |
|---|---|---|---|---|
| F182 | 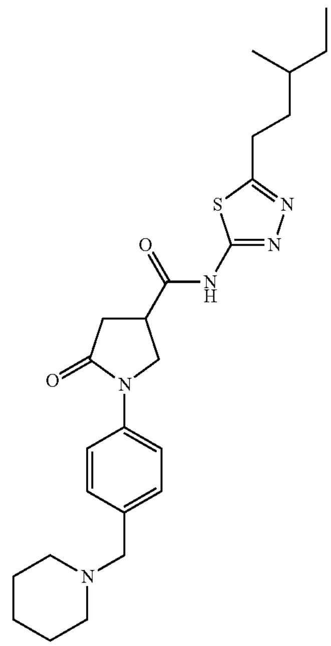 [SMILES: CCC(C)CCc1nnc(NC(=O)C2CC(=O)N(c3ccc(CN4CCCCC4)cc3)C2)s1] | N-[5-(3-methylpentyl)-1,3,4-thiadiazol-2-yl]-5-oxo-1-[4-(1-piperidylmethyl)phenyl]pyrrolidine-3-carboxamide | HCl | 0.021 |
| F183 | 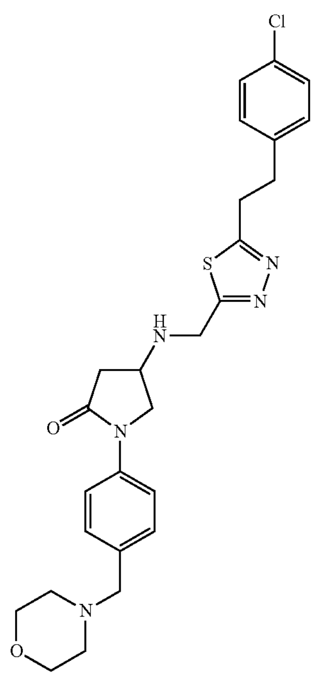 [SMILES: O=C1CC(NCc2nnc(CCc3ccc(Cl)cc3)s2)CN1c1ccc(CN2CCOCC2)cc1] | 4-[[5-[2-(4-chlorophenyl)ethyl]-1,3,4-thiadiazol-2-yl]methylamino]-1-[4-(morpholinomethyl)phenyl]pyrrolidin-2-one | HCl | 0.023 |

TABLE 17-continued

ATX activity (Quanta Red assay)

| EXAMPLE | STRUCTURE | NAME | SALT | AVERAGE IC50 (MEAN, μM) |
|---|---|---|---|---|
| F184 | 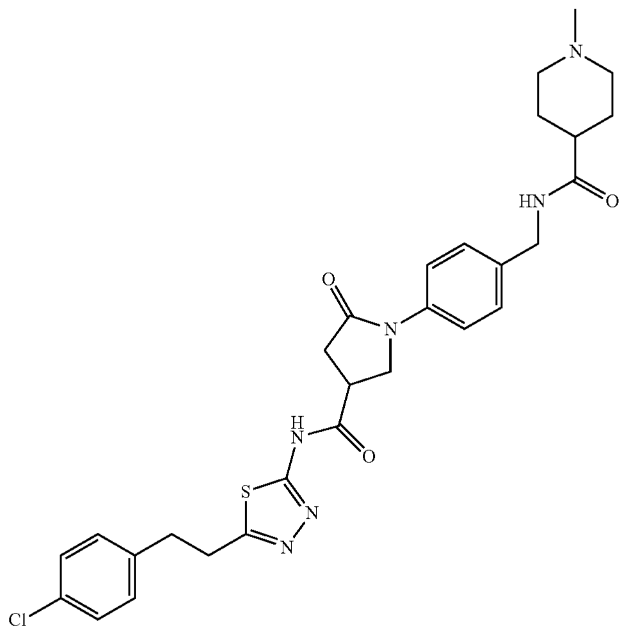 [SMILES: CN1CCC(C(=O)NCc2ccc(N3CC(C(=O)Nc4nnc(CCc5ccc(Cl)cc5)s4)CC3=O)cc2)CC1] | N-[[4-[4-[[5-[2-(4-chlorophenyl)ethyl]-1,3,4-thiadiazol-2-yl]carbamoyl]-2-oxo-pyrrolidin-1-yl]phenyl]methyl]-1-methyl-piperidine-4-carboxamide | — | 0.045 |
| F186 | Chiral | (3S)-1-[4-(morpholinomethyl)phenyl]-5-oxo-N-[5-(2-tetrahydrofuran-2-ylethyl)-1,3,4-thiadiazol-2-yl]pyrrolidine-3-carboxamide | HCl | 0.134 |

TABLE 17-continued
ATX activity (Quanta Red assay)
| EXAMPLE | STRUCTURE | NAME | SALT | AVERAGE IC50 (MEAN, μM) |
|---|---|---|---|---|
| F187 | 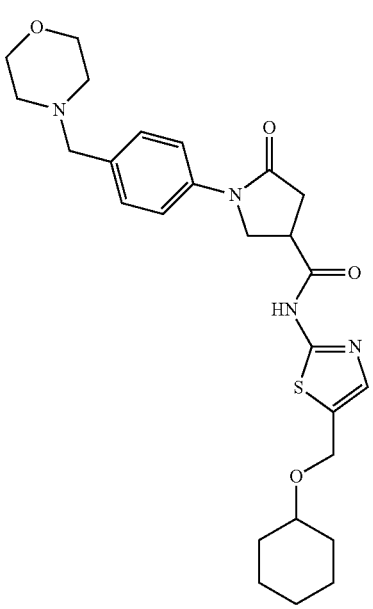 [SMILES: O=C(Nc1ncc(COC2CCCCC2)s1)C1CC(=O)N(c2ccc(CN3CCOCC3)cc2)C1] | N-[5-(cyclohexoxymethyl)thiazol-2-yl]-1-[4-(morpholinomethyl)phenyl]-5-oxo-pyrrolidine-3-carboxamide | — | 0.163 |
| F188 | 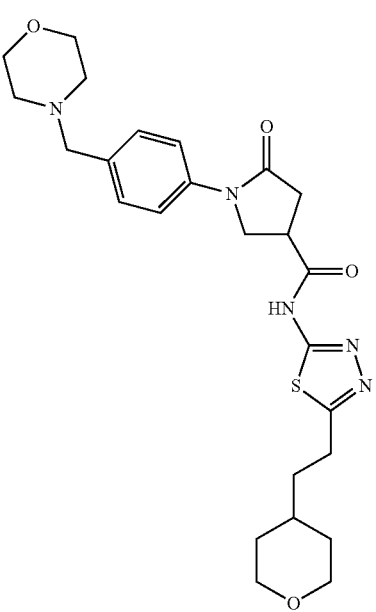 [SMILES: O=C(Nc1nnc(CCC2CCOCC2)s1)C1CC(=O)N(c2ccc(CN3CCOCC3)cc2)C1] | 1-[4-(morpholinomethyl)phenyl]-5-oxo-N-[5-(2-tetrahydropyran-4-ylethyl)-1,3,4-thiadiazol-2-yl]pyrrolidine-3-carboxamide | HCl | 0.358 |

TABLE 17-continued

ATX activity (Quanta Red assay)

| EXAMPLE | STRUCTURE | NAME | SALT | AVERAGE IC50 (MEAN, μM) |
|---|---|---|---|---|
| F189 | 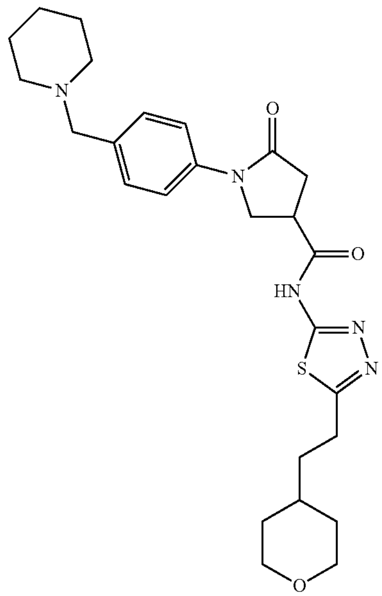 [SMILES: O=C(Nc1nnc(CCC2CCOCC2)s1)C1CC(=O)N(c2ccc(CN3CCCCC3)cc2)C1] | 5-oxo-1-[4-(1-piperidylmethyl)phenyl]-N-[5-(2-tetrahydropyran-4-ylethyl)-1,3,4-thiadiazol-2-yl]pyrrolidine-3-carboxamide | HCl | 0.487 |
| F190 | Chiral | (3S)-5-oxo-1-[4-(1-piperidylmethyl)phenyl]-N-[5-(2-tetrahydropyran-4-ylethyl)-1,3,4-thiadiazol-2-yl]pyrrolidine-3-carboxamide | HCl | 0.526 |

TABLE 17-continued

| | ATX activity (Quanta Red assay) | | | |
|---|---|---|---|---|
| EXAMPLE | STRUCTURE | NAME | SALT | AVERAGE IC50 (MEAN, µM) |
| F191 | Chiral | (3S)-5-oxo-1-[4-(1-piperidylmethyl)phenyl]-N-[5-(2-tetrahydrofuran-2-ylethyl)-1,3,4-thiadiazol-2-yl]pyrrolidine-3-carboxamide | HCl | 0.615 |
| F192 | | N-[5-[2-(4-chlorophenyl)ethyl]-1-methyl-pyrazol-3-yl]-1-[4-(morpholinomethyl)phenyl]-5-oxo-pyrrolidine-3-carboxamide | — | 0.773 |

TABLE 17-continued

ATX activity (Quanta Red assay)

| EXAMPLE | STRUCTURE | NAME | SALT | AVERAGE IC50 (MEAN, μM) |
|---|---|---|---|---|
| F193 | Chiral | 5-[2-(4-chlorophenyl)ethyl]-N-[(3R)-1-[4-[(4-methylpiperazin-1-yl)methyl]phenyl]-5-oxo-pyrrolidin-3-yl]-1,3,4-thiadiazole-2-carboxamide | HCl | 0.124 |
| F194 | 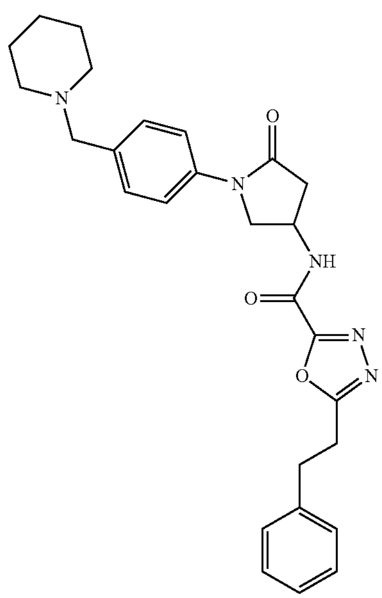 [SMILES: O=C(NC1CC(=O)N(c2ccc(CN3CCCCC3)cc2)C1)c1nnc(CCc2ccccc2)o1] | N-[5-oxo-1-[4-(1-piperidylmethyl)phenyl]pyrrolidin-3-yl]-5-(2-phenylethyl)-1,3,4-oxadiazole-2-carboxamide | HCl | 0.649 |

TABLE 17-continued
ATX activity (Quanta Red assay)
| EXAMPLE | STRUCTURE | NAME | SALT | AVERAGE IC50 (MEAN, μM) |
|---|---|---|---|---|
| F195 | 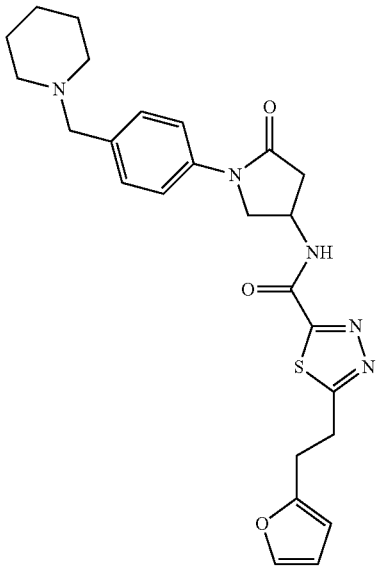 [SMILES: O=C(NC1CC(=O)N(c2ccc(CN3CCCCC3)cc2)C1)c1nnc(CCc2ccco2)s1] | 5-[2-(2-furyl)ethyl]-N-[5-oxo-1-[4-(1-piperidylmethyl)phenyl]pyrrolidin-3-yl]-1,3,4-thiadiazole-2-carboxamide | HCl | 0.766 |
| F196 | 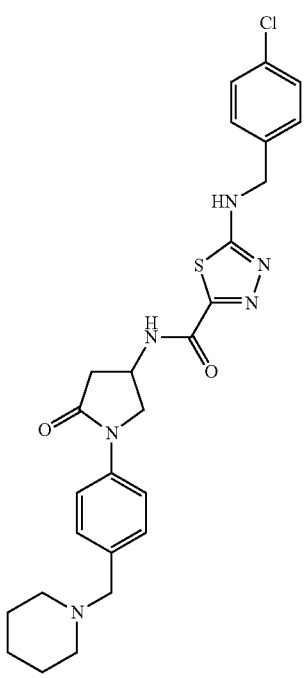 | 5-[(4-chlorophenyl)methyl-amino]-N-[5-oxo-1-[4-(1-piperidylmethyl)phenyl]pyrrolidin-3-yl]-1,3,4-thiadiazole-2-carboxamide | HCl | 0.103 |

TABLE 17-continued

| | ATX activity (Quanta Red assay) | | | |
|---|---|---|---|---|
| EXAMPLE | STRUCTURE | NAME | SALT | AVERAGE IC50 (MEAN, μM) |
| F197 | | N-[5-oxo-1-[4-(1-piperidylmethyl)phenyl]pyrrolidin-3-yl]-5-(2-phenylethyl)thiazole-2-carboxamide | HCl | 0.465 |
| F198 | | N-[5-oxo-1-[4-(1-piperidylmethyl)phenyl]pyrrolidin-3-yl]-3-(2-phenylethyl)isoxazole-5-carboxamide | HCl | 0.989 |

TABLE 17-continued

ATX activity (Quanta Red assay)

| EXAMPLE | STRUCTURE | NAME | SALT | AVERAGE IC50 (MEAN, μM) |
|---|---|---|---|---|
| F199 | 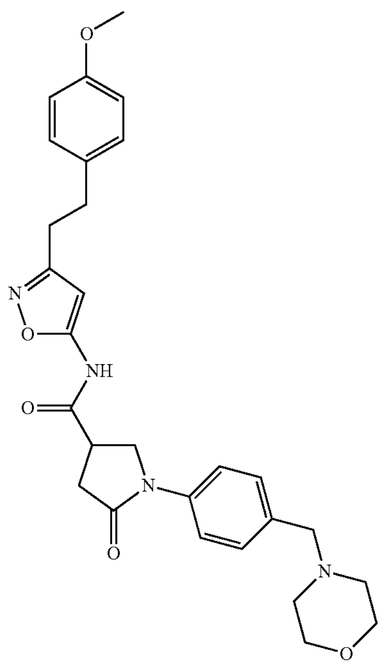 [SMILES: COc1ccc(CCc2cc(NC(=O)C3CC(=O)N(c4ccc(CN5CCOCC5)cc4)C3)on2)cc1] | N-[3-[2-(4-methoxyphenyl)ethyl]isoxazol-5-yl]-1-[4-(morpholinomethyl)phenyl]-5-oxo-pyrrolidine-3-carboxamide | — | 0.293 |
| F200 | 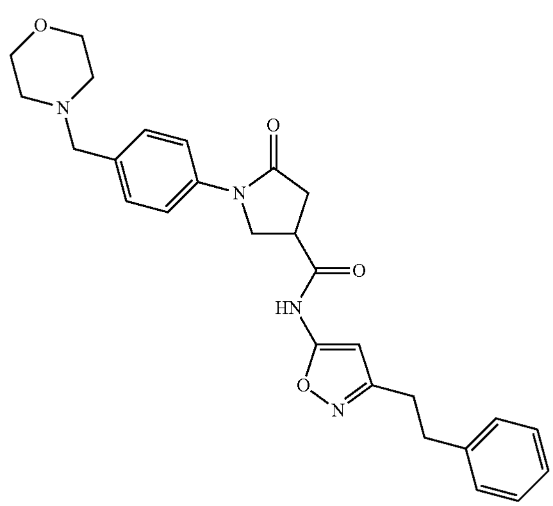 [SMILES: O=C(Nc1cc(CCc2ccccc2)no1)C1CC(=O)N(c2ccc(CN3CCOCC3)cc2)C1] | 1-[4-(morpholinomethyl)phenyl]-5-oxo-N-[3-(2-phenylethyl)isoxazol-5-yl]pyrrolidine-3-carboxamide | HCl | 0.760 |

TABLE 17-continued
ATX activity (Quanta Red assay)
| EXAMPLE | STRUCTURE | NAME | SALT | AVERAGE IC50 (MEAN, μM) |
|---|---|---|---|---|
| F201 | 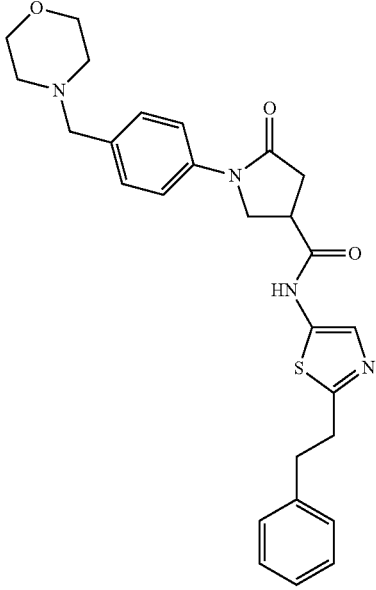 | 1-[4-(morpholinomethyl)phenyl]-5-oxo-N-[2-(2-phenylethyl)thiazol-5-yl]pyrrolidine-3-carboxamide | HCOOH | 1.0703 |
| F202 | 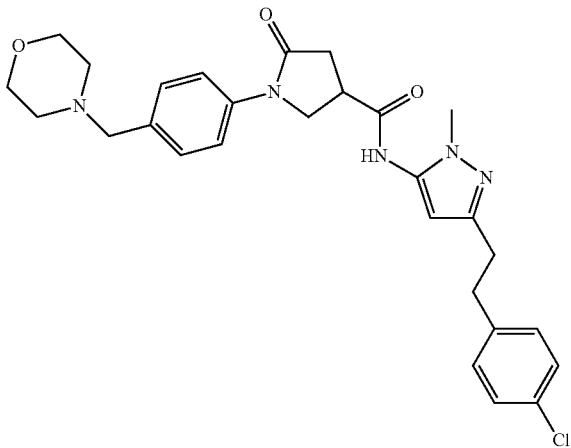 [SMILES: Cn1nc(CCc2ccc(Cl)cc2)cc1NC(=O)C1CC(=O)N(c2ccc(CN3CCOCC3)cc2)C1] | N-[5-[2-(4-chlorophenyl)ethyl]-2-methyl-pyrazol-3-yl]-1-[4-(morpholinomethyl)phenyl]-5-oxo-pyrrolidine-3-carboxamide | HCOOH | 1.5483 |

TABLE 17-continued

ATX activity (Quanta Red assay)

| EX-AM-PLE | STRUCTURE | NAME | SALT | AVERAGE IC50 (MEAN, μM) |
|---|---|---|---|---|
| F203 | 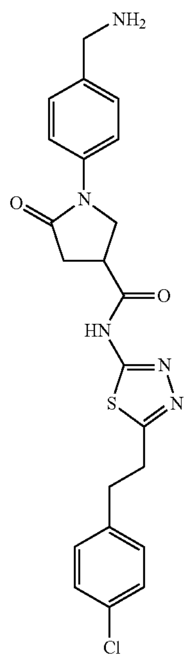 [SMILES: NCc1ccc(N2CC(C(=O)Nc3nnc(CCc4ccc(Cl)cc4)s3)CC2=O)cc1] | 1-[4-(aminomethyl)phenyl]-N-[5-[2-(4-chlorophenyl)ethyl]-1,3,4-thiadiazol-2-yl]-5-oxo-pyrrolidine-3-carboxamide | — | 0.385 |
| F204 | 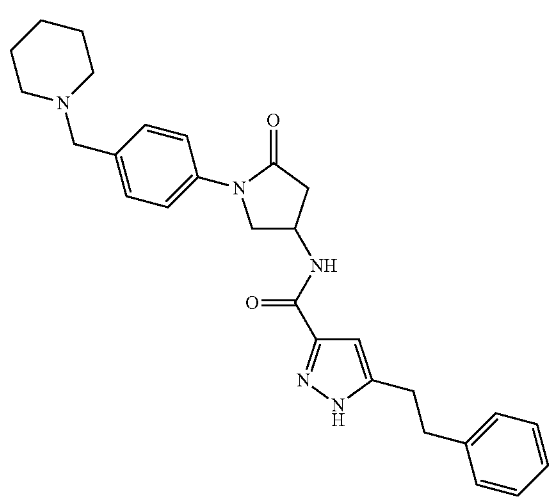 [SMILES: O=C(NC1CC(=O)N(c2ccc(CN3CCCCC3)cc2)C1)c1cc(CCc2ccccc2)[nH]n1] | N-[5-oxo-1-[4-(1-piperidylmethyl)phenyl]pyrrolidin-3-yl]-3-(2-phenylethyl)-1H-pyrazole-5-carboxamide | HCl | 1.0834 |

TABLE 17-continued

ATX activity (Quanta Red assay)

| EXAMPLE | STRUCTURE | NAME | SALT | AVERAGE IC50 (MEAN, μM) |
|---|---|---|---|---|
| F205 | 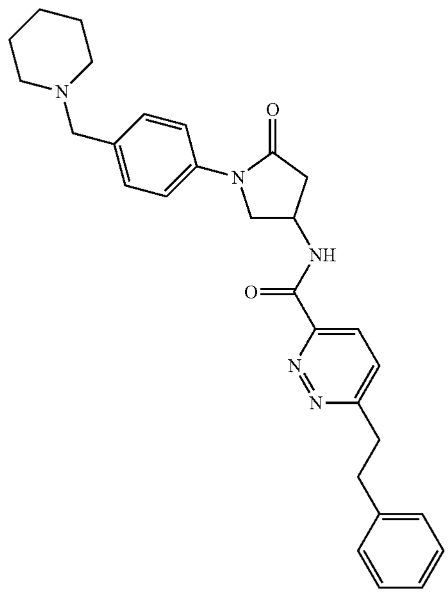 [SMILES: O=C(NC1CC(=O)N(c2ccc(CN3CCCCC3)cc2)C1)c1ccc(CCc2ccccc2)nn1] | N-[5-oxo-1-[4-(1-piperidylmethyl)phenyl]pyrrolidin-3-yl]-6-(2-phenylethyl)pyridazine-3-carboxamide | HCl | 7.0612 |
| F206 | 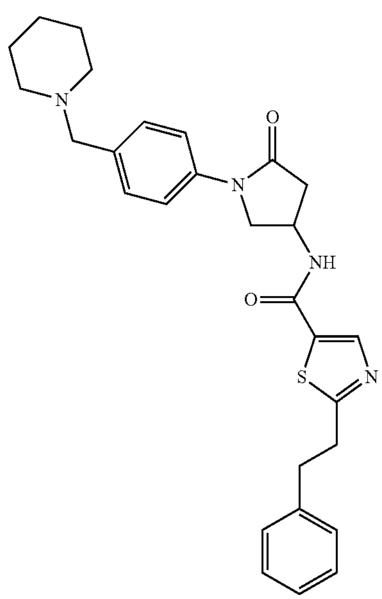 [SMILES: O=C(NC1CC(=O)N(c2ccc(CN3CCCCC3)cc2)C1)c1cnc(CCc2ccccc2)s1] | N-[5-oxo-1-[4-(1-piperidylmethyl)phenyl]pyrrolidin-3-yl]-2-(2-phenylethyl)thiazole-5-carboxamide | HCl | 9.3531 |

TABLE 17-continued

ATX activity (Quanta Red assay)

| EXAMPLE | STRUCTURE | NAME | SALT | AVERAGE IC50 (MEAN, μM) |
|---|---|---|---|---|
| F207 | 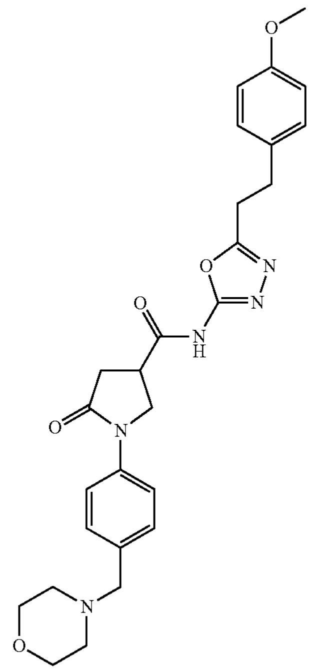 [SMILES: COc1ccc(CCc2nnc(NC(=O)C3CC(=O)N(c4ccc(CN5CCOCC5)cc4)C3)o2)cc1] | N-[5-[2-(4-methoxyphenyl)ethyl]-1,3,4-oxadiazol-2-yl]-1-[4-(morpholinomethyl)phenyl]-5-oxo-pyrrolidine-3-carboxamide | — | 2.4454 |
| F208 | 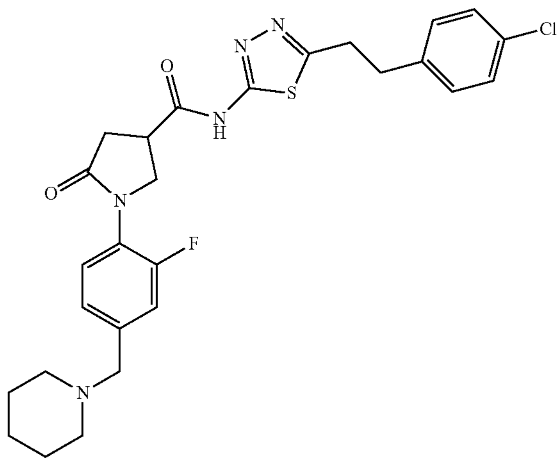 [SMILES: O=C(Nc1nnc(CCc2ccc(Cl)cc2)s1)C1CC(=O)N(c2ccc(CN3CCCCC3)cc2F)C1] | 1-[4-(4-{5-[2-(4-Chlorophenyl)-ethyl]-[1,3,4]thiadiazol-2-ylcarbamoyl}-2-oxo-pyrrolidin-1-yl)-3-fluoro-benzyl]-piperidinium; chloride | HCl | — |

TABLE 17-continued

| | ATX activity (Quanta Red assay) | | | |
|---|---|---|---|---|
| EXAMPLE | STRUCTURE | NAME | SALT | AVERAGE IC50 (MEAN, μM) |
| F209 | | 4-[4-(4-{5-[2-(4-Chlorophenyl)-ethyl]-[1,3,4]thiadiazol-2-ylcarbamoyl}-2-oxo-pyrrolidin-1-yl)-3-fluoro-benzyl]morpholin-4-ium; chloride | HCl | — |
| F210 | | 1-[4-(4-{5-[2-(4-Chlorophenyl)-ethyl]-[1,3,4]thiadiazol-2-ylcarbamoyl}-2-oxo-pyrrolidin-1-yl)-3-fluoro-benzyl]-4-methyl-piperidinium; chloride | HCl | — |

TABLE 17-continued

| | ATX activity (Quanta Red assay) | | | |
|---|---|---|---|---|
| EXAMPLE | STRUCTURE | NAME | SALT | AVERAGE IC50 (MEAN, μM) |
| F211 | | 1-{4-[(Ethyl-methyl-amino)-methyl]-phenyl}-5-oxo-pyrrolidine-3-carboxylic acid {5-[2-(4-chloro-phenyl)-ethyl]-[1,3,4]thiadiazol-2-yl}-amide | — | 0.009 |
| F212 | | (3S)-N-[5-[2-(4-chlorophenyl)ethyl]-1,3,4-thiadiazol-2-yl]-1-[4-(2-oxa-7-azaspiro[3.4]octan-7-ylmethyl)phenyl]-5-oxo-pyrrolidine-3-carboxamide | — | 0.001 |

TABLE 17-continued
ATX activity (Quanta Red assay)
| EX-AM-PLE | STRUCTURE | NAME | SALT | AVERAGE IC50 (MEAN, μM) |
|---|---|---|---|---|
| F213 | 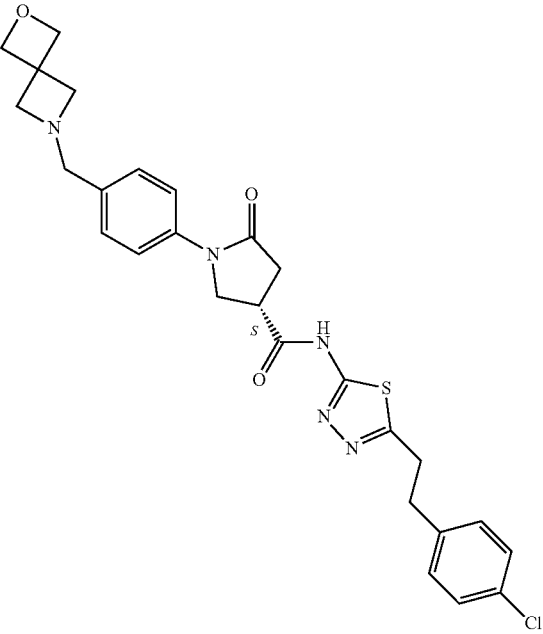 | (3S)-N-[5-[2-(4-chlorophenyl)ethyl]-1,3,4-thiadiazol-2-yl]-1-[4-(2-oxa-6-azaspiro[3.3]heptan-6-ylmethyl)phenyl]-5-oxo-pyrrolidine-3-carboxamide | — | 0.001 |
| F214 | 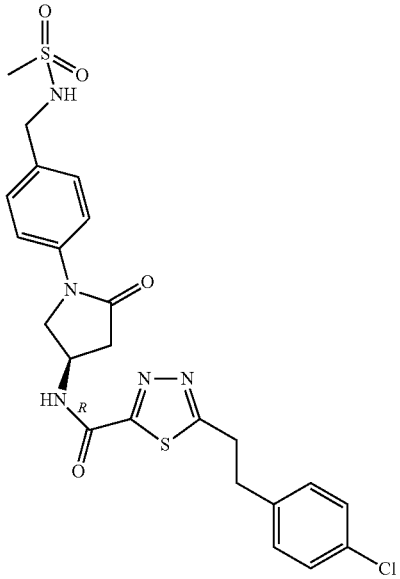 | 5-[2-(4-chlorophenyl)ethyl]-N-[(3R)-1-[4-(methanesulfonamido-methyl)phenyl]-5-oxo-pyrrolidin-3-yl]-1,3,4-thiadiazole-2-carboxamide | — | 0.134 |

TABLE 17-continued

ATX activity (Quanta Red assay)

| EXAMPLE | STRUCTURE | NAME | SALT | AVERAGE IC50 (MEAN, μM) |
|---|---|---|---|---|
| F215 | 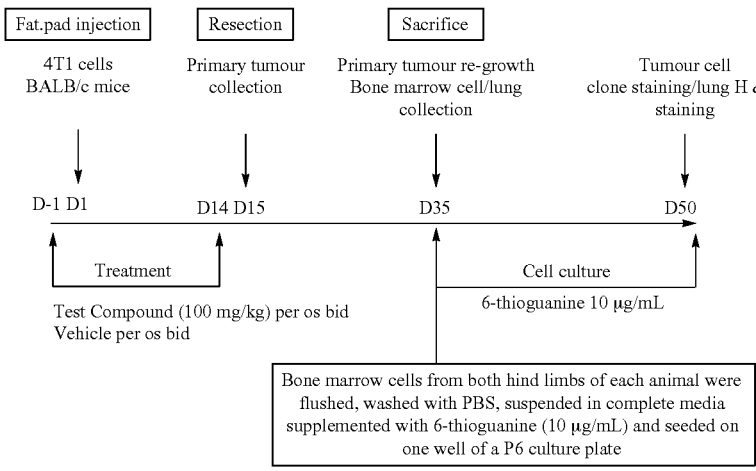 | 1-(4-Morpholin-4-ylmethyl-phenyl)-5-oxo-pyrrolidine-3-carboxylic acid {5-[2-(4-fluoro-phenyl)-ethyl]-[1,3,4]thiadiazol-2-yl}-amide; hydrochloride | HCl | 0.003 |

In Vivo Data
ATX 4 T1 Orthotopic, Metastatic Breast Cancer Mouse Model

Procedure

On day −1 dosing of the test compound by gavage (100 mg/kg of test compound in 1% methylcellulose solution, twice daily with the second dose 8 hours after the first and assuming a mouse weight of 20 g) was commenced on female BALB/c mice 6 weeks of age (Charles River). The test compound (Example F93) was dosed for 15 days (day −1 to day 14)

On day 1 4T1 cells ($10^5$ in 10 μl of PBS) were injected into the fat pad of the $4^{th}$ mammary gland of the mice. Before injection, cells were stored at room temperature for a period that did not exceed 2 hours at which time a new batch of cell suspension was prepared. At day 15 animals were anaesthetised and primary tumours were surgically removed. Primary tumours were weighed, fixed with paraformaldehyde (PFA 4%) for 48 hours, dehydrated for 24 hours in 70% ethanol and embedded in paraffin. Mice were then monitored for an additional 3-week period. At this time they were sacrificed. Re-grown primary tumours were collected, weighed, fixed with PFA, dehydrated with 70% ethanol and embedded in paraffin as described above.

Bone marrow cells from both hind limbs of each animal were flushed with PBS, suspended in RPMI 1640 medium containing 10% FBS supplemented with 6-thioguanine (10 μg/mL) and seeded on a well of a 6-well culture plate. After a two-week incubation period at 37° C., tumour colonies were stained with crystal violet and counted. The levels of disseminated tumour cells in bone were expressed as the number of colonies per well.

At the time of animal sacrifice, lungs were inflated with PFA prior to removal, then fixed with PFA for 48 hours, dehydrated with ethanol and embedded in paraffin as described above for primary tumour samples. 5 um sections were cut every 50 um through the lungs and the number and total volume of the metastases was determined using the assumption that the metastases were spherical.

Figure 2:
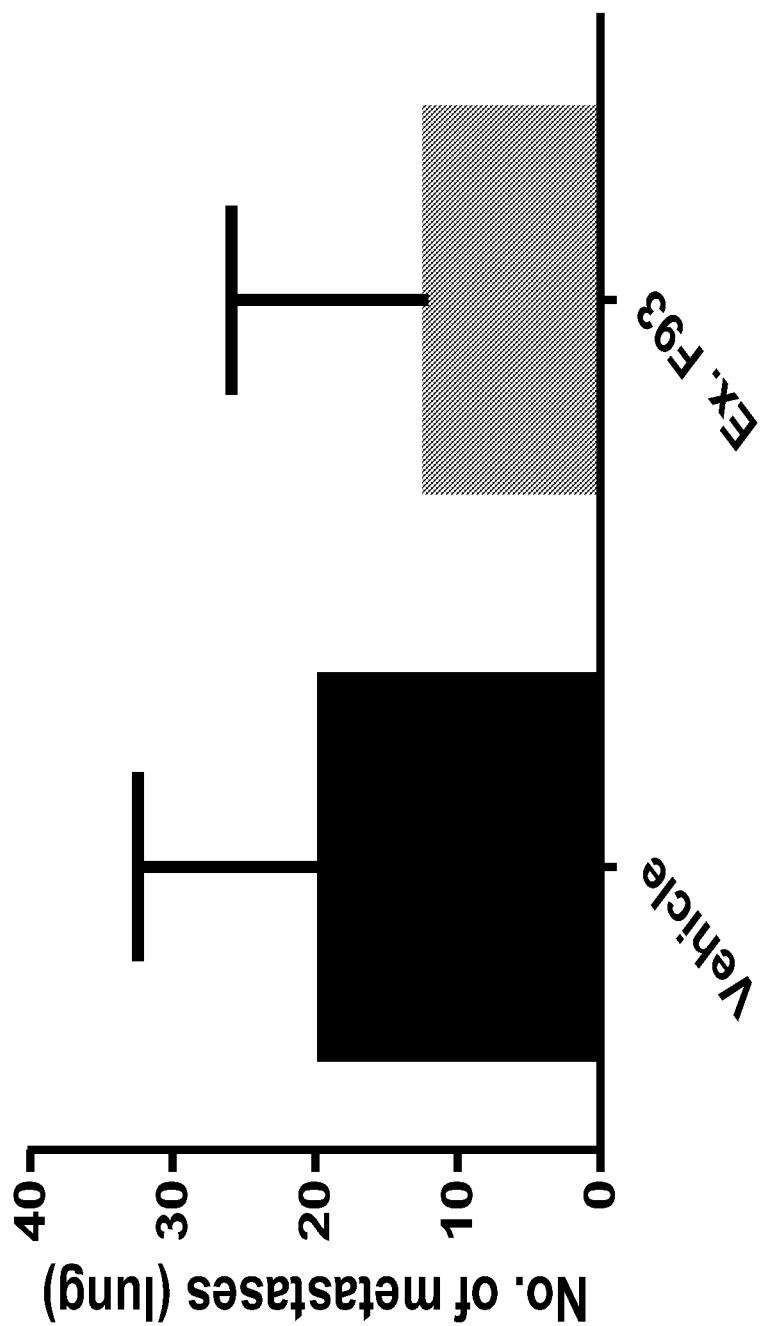
FIG. 2 shows the number of lung metastases for Example F93 compared to the vehicle, in the 4T1 orthotopic metastatic breast cancer model, described hereinbelow.
Figure 3:
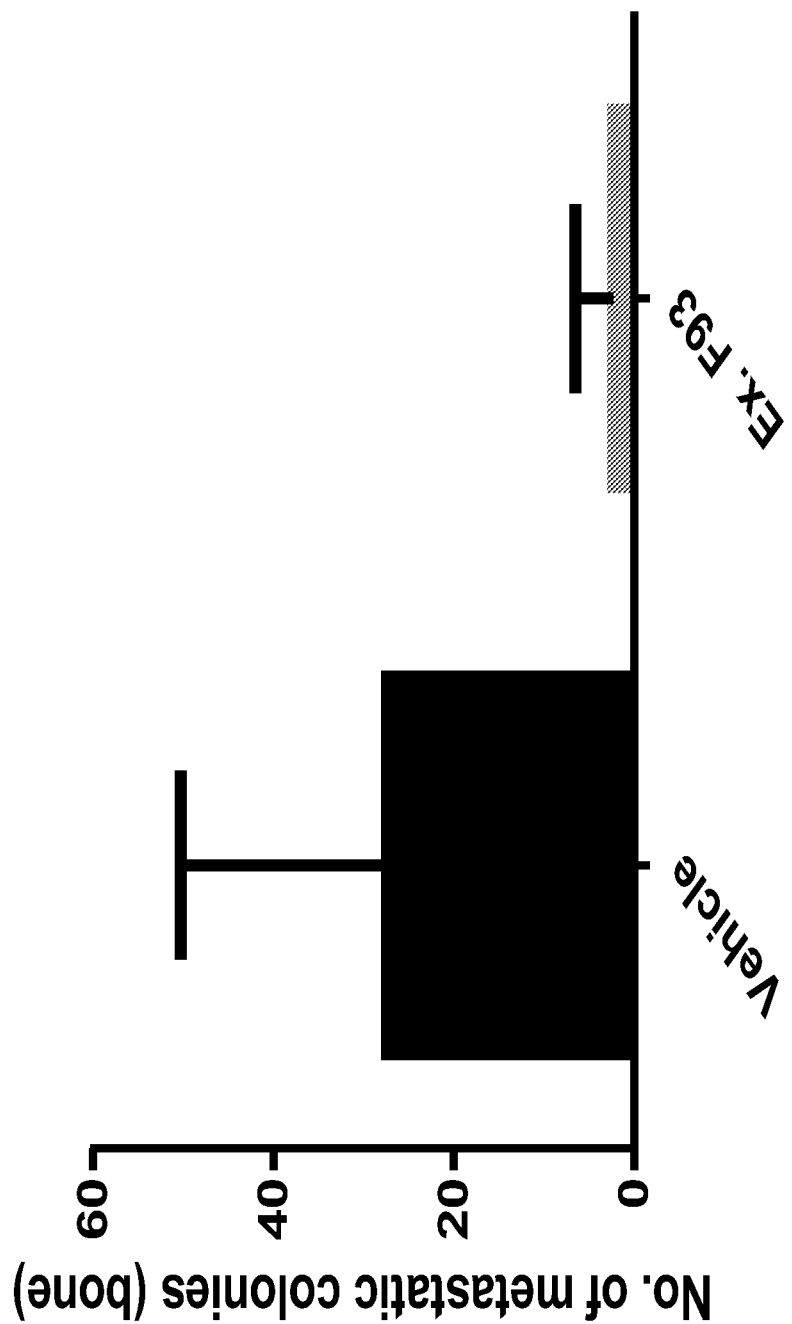
FIG. 3 shows the effect on bone metastatic colony formation in the presence of Example F93 compared to the vehicle, in the 4T1 orthotopic metastatic breast cancer model, described hereinbelow.

The results are summarised in FIGS. 1 to 3. In which:

FIG. 1 shows total volume of lung metastases for Example F93 compared to the vehicle, in the 4T1 orthotopic metastatic breast cancer model.

FIG. 2 shows the number of lung metastases for Example F93 compared to the vehicle, in the 4T1 orthotopic metastatic breast cancer model.

FIG. 3 shows the effect on bone metastatic colony formation in the presence of Example F93 compared to the vehicle, in the 4T1 orthotopic metastatic breast cancer model.

REFERENCES

1) Aznavoorian et al., 1990, "Signal transduction for chemotaxis and haptotaxis by matrix molecules in tumor cells", *The Journal of Cell Biology*, Vol. 110, pp. 1427-1438.
2) Baumforth et al., 2005, "Induction of autotaxin by the Epstein-Barr virus promotes the growth and survival of Hodgkin lymphoma cells", *Blood*, Vol. 106, pp. 2138-2146.
3) Boucharaba et al., 2004, "Platelet-derived lysophosphatidic acid supports the progression of osteolytic bone metastases in breast cancer", *J Clin Invest.*, 114:1714-25.
4) Boucher et al., 2005, "Potential involvement of adipocyte insulin resistance in obesity-associated up-regulation of adipocyte lysophospholipase D/autotaxin expression", *Diabetologia*, Vol. 248, pp. 569-577.
5) Choi et al., 2010, "LPA receptors: subtypes and biological actions", *Annu Rev Pharmacol Toxicol.*, 50:157-86.
6) Cui et al., 2007, "Synthesis and biological evaluation of phosphonate derivatives as autotaxin (ATX) inhibitors", *Bioorganic & Medicinal Chemistry Letters*, Vol. 17, pp. 1634-1640.
7) Cui et al., 2008, "α- and β-Substituted phosphonate analogs of LPA as autotaxin inhibitors", *Bioorganic & Medicinal Chemistry*, Vol. 16, pp. 2212-2225.
8) Ferry et al., 2008, "S32826, A Nanomolar Inhibitor of Autotaxin: Discovery, Synthesis and Applications as a Pharmacological Tool," *J. Pharmacol. Exp. Ther.*, Vol. 327, pp. 809-819.
9) Gajewiak et al., 2008, "Synthesis, Pharmacology, and Cell Biology of sn-2-Aminooxy Analogues of Lysophosphatidic Acid", *Org. Lett.*, Vol. 10, No. 6, pp. 1111-1114.
10) Hausman et al., 2001, "The biology of white adipocyte proliferation", *Obes. Rev.*, Vol. 2, pp. 239-254.
11) Houben A J, Moolenaar W H, 2011, "Autotaxin and LPA receptor signaling in cancer", *Cancer Metastasis Rev.*, 30(3-4):557-65.
12) Inoue et al., 2004, "Initiation of neuropathic pain requires lysophosphatidic acid receptor signalling", *Nat. Med.*, Vol. 10, pp. 712-718.
13) Inoue et al., 2008, "Autotaxin, a synthetic enzyme of lysophosphatidic acid (LPA), mediates the induction of nerve-injured neuropathic pain", *Molecular Pain*, Vol. 4, p. 6.
14) Jiang et al., 2007, "Substituted Phosphonate Analogues of Lysophosphatidic Acid (LPA) Selectively Inhibit Production and Action of LPA", *Chem. Med. Chem.*, Vol. 2, pp. 679-690.
15) Kanda et al., 2008, "Autotaxin, an ectoenzyme that produces lysophosphatidic acid, promotes the entry of lymphocytes into secondary lymphoid organs", *Nat. Immunol.*, Vol. 9, pp. 415-423.
16) Kremer et al., 2012, "Serum autotaxin is increased in pruritus of cholestasis, but not of other origin, and Responds to therapeutic interventions" *Hepatology*, Vol 56, pp 1391-1400.
17) Knowlden S, Georas S N., 2014, "The autotaxin-LPA axis emerges as a novel regulator of lymphocyte homing and inflammation", *J Immunol.*, 192(3):851-7
18) Leblanc R and Peyruchaud O., 2014, "New insights into the autotaxin/LPA axis in cancer development and metastasis", *Exp Cell Res*
19) Lin et al., 2009, "The absence of LPA2 attenuates tumor formation in an experimental model of colitis-associated cancer", *Gastroenteroloqy*, Vol. 136, No. 5, pp. 1711-1720.
20) Liu et al., 2009, "Expression of Autotaxin and Lysophosphatidic Acid Receptors Increases Mammary Tumorigenesis, Invasion, and Metastases", *Cancer Cell*, Vol. 15, No. 6, pp. 539-550, published 2 Jun. 2009.
21) Marshall et al., 2012, "Effect of inhibition of the lysophosphatidic acid receptor 1 on metastasis and metastatic dormancy in breast cancer", *J Natl Cancer Inst.*, 104:1306-19
22) Masuda et al., 2008, "Serum autotaxin measurement in haematological malignancies: a promising marker for follicular lymphoma", *Br. J. Haematol.*, Vol. 143, pp. 60-70.
23) Meyer zu Heringdorf et al., 2007, "Lysophospholipid receptors: signalling, pharmacology and regulation by lysophospholipid metabolism", *Biochim. Biophys. Acta*, Vol. 1768, pp. 923-940.
24) Moolenaar W H, et al., 2013, "Autotaxin in embryonic development", *Biochim Biophys Acta.*, 2013; 1831:13-9
25) Murakami et al., 2008, "Identification of the orphan GPCR, P2Y10 receptor as the sphingosine-1-phosphate and lysophosphatidic acid receptor", *Biochemical and Biophysical Research Communications*, Vol. 371, pp. 707-712.
26) Nakamura et al., 2007, "Serum lysophospholipase D/autotaxin may be a new nutritional assessment marker: study on prostate cancer patients", *Ann. Clin. Biochem.* Vol. 44, pp. 549-556.
27) Nakao et al., 2014, "Serum autotaxin levels correlate with pruritus in patients with atopic dermatitis", *Journal of Investigative Dermatoloaqy* 134, 1745-1747; doi: 10.1038/jid.2014.24; published online 6 Feb. 2014
28) Nakasaki et al., 2008, "Involvement of the Lysophosphatidic Acid-Generating Enzyme Autotaxin in Lymphocyte-Endothelial Cell Interactions", *Am. J. Pathol.*, Vol. 173, pp. 1566-1576.
29) Nishimura et al., 2014, "ENPP2 contributes to adipose tissue expansion and insulin resistance in diet-induced obesity", *Diabetes*, 63(12):4154-64
30) Pamuklar et al., 2009, "Autotaxin/lysopholipase D and lysophosphatidic acid regulate murine hemostasis and thrombosis," *J. Biol. Chem.*, e-publication 12 Jan. 2009.
31) Pradere et al., 2007, "LPA1 receptor activation promotes renal interstitial fibrosis", *J. Am. Soc. Nephrol.*, Vol. 18, pp. 3110-3118.
32) Reynolds G., "The autotaxin-lysophosphatidate axis plays a key role in the pathogenesis of Hepatitis C virus-associated Hepatocellular carcinoma", Oral Presentation at the European Congress of Pathology 2014, London.

33) Siess et al., 1999, "Lysophosphatidic acid mediates the rapid activation of platelets and endothelial cells by mildly oxidized low density lipoprotein and accumulates in human atherosclerotic lesions", *Proc. Natl. Acad. Sci. USA*, Vol. 96, pp. 6931-6936.
34) Saga et al., 2014, "A Novel Highly Potent Autotaxin/ENPP2 Inhibitor Produces Prolonged Decreases in Plasma Lysophosphatidic Acid Formation In Vivo and Regulates Urethral Tension", *PLoS ONE* 9(4): e93230. doi:10.1371/journal.pone.0093230
35) Siess et al., 2004, "Thrombogenic and atherogenic activities of lysophosphatidic acid", *Cell Biochem.*, Vol. 92, pp. 1086-1094.
36) Tabata et al., 2007, "The orphan GPCR GPR87 was deorphanized and shown to be a lysophosphatidic acid receptor", *Biochem. Biophys. Res. Commun.*, Vol. 363, pp. 861-866.
37) Tager et al., 2008, "The lysophosphatidic acid receptor LPA1 links pulmonary fibrosis to lung injury by mediating fibroblast recruitment and vascular leak", *Nat. Med.*, Vol. 14, pp. 45-54.
38) Taghavi et al., 2008, "In vitro genetic screen identifies a cooperative role for LPA signaling and c-Myc in cell transformation", *Oncogene*, Vol. 27, pp. 6806-6816.
39) Tigyi, 2001, "Physiological responses to lysophosphatidic acid and related glycerophospholipids", *Prostaglandins*, Vol. 64, pp. 47-62.
40) van Meeteren et al., 2005, "Inhibition of autotaxin by lysophosphatidic acid and sphingosine 1-phosphate", *J. Biol. Chem.*, Vol. 280, pp. 21155-21161.
41) Van Meeteren et al., 2007, "Regulation and biological activities of the autotaxin-LPA axis", *Prog. Lipid Res.*, Vol. 46, pp. 145-160.
42) Watanabe et al., 2007, "Both plasma lysophosphatidic acid and serum autotaxin levels are increased in chronic hepatitis C", *J Clin Gastroenterol.*, July; 41(6):616-23
43) Wu et al., 2010, "Autotaxin expression and its connection with the TNF-alpha-NF-kappaB axis inhuman hepatocellular carcinoma" *Molecular Cancer*, 9:71
44) Zhang et al. (2012), "Autotaxin through lysophosphatidic acid stimulates polarization, motility, and transendothelial migration of naive T cells", *J Immunol.*, 89:3914-24
45) Zhang et al., 2009, "Dual Activity Lysophosphatidic Acid Receptor Pan-Antagonist/Autotaxin Inhibitor Reduces Breast Cancer Cell Migration In vitro and Causes Tumor Regression In vivo", *Cancer Res.*, Vol. 69, No. 13, pp. 5441-5449.
46) Zhao et al., 2007, "Distinctive gene expression of prostatic stromal cells cultured from diseased versus normal tissues.", *J. Cell Physiol.*, Vol. 210, pp. 111-121.

The invention claimed is:

1. A compound, or a pharmaceutically acceptable salt thereof, having the structural formula (I) shown below:

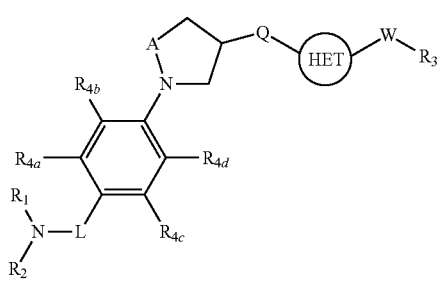

(I)

wherein:
$R_1$ and $R_2$ are independently selected from H, (1-8C)alkyl, (4-7C)cycloalkyl, 4-7 membered heterocyclyl, 5-6 membered heteroaryl, —S(O)$_y$R$_a$ or C(O)R$_a$, wherein R$_a$ is selected from H, (1-4C)alkyl or (1-4C)alkoxy, y is 0, 1 or 2, and wherein any (1-8C)alkyl, (4-7C)cycloalkyl, 4-7 membered heterocyclyl or 5-6 membered heteroaryl is optionally substituted by one or more substituents selected from oxo, (1-4C)alkyl, halo, cyano, nitro, hydroxyl, amino, (1-4C)haloalkyl, (1-4C)alkoxy, (1-4C)haloalkoxy, carboxyl, carbamoyl, sulphamoyl, NR$_b$R$_c$, OR$_b$, C(O)R$_b$, C(O)OR$_b$, OC(O)R$_b$, C(O)N(R$_b$)R$_c$, N(R$_b$)C(O)R$_c$, S(O)$_y$R$_b$ (where y is 0, 1 or 2), SO$_2$N(R$_b$)R$_c$, N(R$_b$)SO$_2$R$_c$ or (CH$_2$)$_z$NR$_b$R$_c$ (where z is 1, 2 or 3), (4-6C)heterocycyl, 6 membered aryl or 5 or 6 membered heteroaryl, wherein R$_b$ and R$_c$ are each independently selected from H or (1-4C)alkyl; or $R_1$ and $R_2$ are linked such that, together with the nitrogen atom to which they are attached, they form a 4 to 10 membered mono or bicyclic heterocyclic ring which is optionally substituted by one or more substituents selected from oxo, (1-4C)alkyl, halo, cyano, nitro, hydroxyl, amino, (1-4C)haloalkyl, (1-4C)alkoxy, (1-4C)haloalkoxy, carboxyl, carbamoyl, sulphamoyl, NR$_d$R$_e$, OR$_d$, C(O)R$_d$, C(O)OR$_d$, OC(O)R$_d$, C(O)N(R$_e$)R$_d$, N(R$_e$)C(O)R$_d$, S(O)$_y$R$_d$ (where y is 0, 1 or 2), SO$_2$N(R$_e$)R$_d$, N(R$_e$)SO$_2$R$_d$ or (CH$_2$)$_z$NR$_d$R$_e$ (where z is 1, 2 or 3), (4-6C)heterocycyl, 6 membered aryl or 5 or 6 membered heteroaryl, wherein R$_d$ and R$_e$ are each independently selected from H or (1-4C)alkyl;

L is a (1-3C)alkylene optionally substituted by fluoro, (1-2C)alkyl or oxo;

$R_{4a}$, $R_{4b}$, $R_{4c}$ and $R_{4d}$ are each independently selected from H, halo, (1-2C)alkyl, cyano, nitro, hydroxyl, amino, (1-2C)haloalkyl, (1-2C)alkoxy, or (1-2C)haloalkoxy;

A is C(=X) or CR$_f$R$_g$;
wherein X is O, NH or S; and
R$_f$ and R$_g$ are independently selected from H or (1-2C)alkyl;

Q is selected from —NH—S(O)$_y$—, —S(O)$_y$—NH—, —C(O)NR$_h$—, —NR$_h$C(O)—, —NR$_h$—S(O)(NH)—, —S(O)(NH)—NR$_h$—, —C(O)O—, —OC(O)—, —CH$_2$CH$_2$—, —CH$_2$NR$_h$— or —NR$_h$CH$_2$—, wherein y is 0, 1 or 2 and R$_h$ is selected from H or (1-2C)alkyl;

HET is a 5 or 6 membered nitrogen containing heteroaryl optionally substituted with one or more substituents selected from H, (1-4C)alkyl, halo, cyano, nitro, hydroxyl, amino, (1-4C)haloalkyl, (1-4C)alkoxy, (1-4C)haloalkoxy, carboxyl, carbamoyl, amido or sulphamoyl;

W is either a group of the formula:

-Q$_1$-R$_i$— wherein:
Q$_1$ is attached to HET and is —C(O)— or —CH$_2$—; and
R$_i$ is attached to R$_3$ and is selected from —CHR$_j$—, —NR$_j$—, or —O—, wherein R$_j$ is selected from H or (1-2C)alkyl;

or W is a group of the formula:

R$_k$-Q$_2$- wherein:
Q$_2$ is attached to R$_3$ and is selected from —C(O)— or —CH$_2$—; and
R$_k$ is attached to HET and is selected from CHR$_l$, NR$_l$, O or S(O)$_y$, wherein y is 0, 1 or 2 and R is H or (1-4C)alkyl;
R$_3$ is selected from (1-6C)alkyl, phenyl, (4-8C)carbocyclyl, heteroaryl or heterocyclyl, each of which is optionally substituted with one or more substituents selected from (1-4C)alkyl, halo, (1-4C)haloalkyl, (1-4C)alkoxy, (1-4C)haloalkoxy, (3-6C)cycloalkyl, (3-6C)cycloalkyl(1-2C)alkyl, (2-4C)alkenyl or (2-4C)alkynyl.

2. A compound according to claim 1, wherein L is a methylene.

3. A compound according to claim 1, wherein R$_{4a}$, R$_{4b}$, R$_{4c}$ and R$_{4d}$ are each independently selected from H, fluoro, methyl or CF$_3$.

4. A compound according to claim 1, wherein R$_{4a}$, R$_{4b}$ and R$_{4c}$ are H, and R$_{4d}$ is selected from H or fluoro.

5. A compound, or a pharmaceutically acceptable salt thereof according to claim 1, wherein said compound has the structure (Ia) shown below:

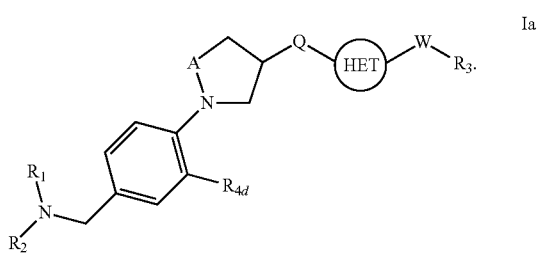

Ia

6. A compound according to claim 1, where R$_1$ and R$_2$ are independently selected from H, (1-6C)alkyl, 4-6 membered heterocyclyl, —S(O)$_2$R$_a$ or C(O)R$_a$, wherein R$_a$ is selected from H or methyl, and wherein any (1-6C)alkyl, or 4-6 membered heterocyclyl is optionally substituted by one or more substituents selected from methyl, fluoro or hydroxyl; or
R$_1$ and R$_2$ are linked such that, together with the nitrogen atom to which they are attached, they form a 4 to 10 membered mono or bicyclic heterocyclic ring which is optionally substituted by one or more substituents selected from oxo, methyl, fluoro, hydroxyl or C(O)OR$_d$, wherein R$_d$ is selected from H or (1-4C)alkyl.

7. A compound according to claim 1, wherein A is C(=O) or CH$_2$.

8. A compound according to claim 1, wherein Q is selected from —C(O)NH—, —NHC(O)—, —CH$_2$NH— or —NHCH$_2$.

9. A compound according to claim 1, wherein HET is a 5 or 6 membered nitrogen containing heteroaryl optionally substituted with one or more substituents selected from H, methyl, fluoro hydroxyl, amino, CF$_3$, OMe or OCF$_3$.

10. A compound according to claim 1, wherein HET is a 5 or 6 membered nitrogen containing heteroaryl.

11. A compound according to claim 1, wherein W is either a group of the formula:

-Q$_1$-R$_j$— wherein:
Q$_1$ is attached to HET and is —C(O)— or —CH$_2$—; and
R$_j$ is attached to R$_3$ and is selected from —CH$_2$— or —O;

or W is a group of the formula:

—R$_k$-Q$_2$- wherein:
Q$_2$ is attached to R$_3$ and is selected from —CH$_2$—; and
R$_k$ is attached to HET and is NH or S.

12. A compound according to claim 1, wherein R$_3$ is selected from (1-6C)alkyl, phenyl, (4-8C)carbocyclyl, 5- or 6 membered heteroaryl or 4- to 6 membered heterocyclyl, each of which is optionally substituted with one or more substituents selected from (1-4C)alkyl, halo, (1-4C)fluoroalkyl, (1-4C)alkoxy, (1-4C)fluoroalkoxy, cyclopropyl, cyclobutyl, (2-4C)alkenyl or (2-4C)alkynyl.

13. A compound according to claim 1, wherein R$_3$ is selected from (1-4C)alkyl, phenyl, (5-6C)carbocyclyl, or 5- to 6 membered heterocyclyl, each of which is optionally substituted with one or more substituents selected from methyl, halo, CF$_3$ or OMe.

14. A compound according to claim 1 selected from any one of the following:
(3 S)—N-[5-[2-(4-chlorophenyl)ethyl]-1,3,4-thiadiazol-2-yl]-1-[4-[[methyl(tetrahydrofuran-3-yl)amino]methyl]phenyl]-5-oxo-pyrrolidine-3-carboxamide;
(3 S)—N-[5-[2-(4-chlorophenyl)ethyl]-1,3,4-thiadiazol-2-yl]-1-[4-[[methyl(oxetan-3-yl)amino]methyl]phenyl]-5-oxo-pyrrolidine-3-carboxamide;
(3 S)—N-[5-[2-(4-chlorophenyl)ethyl]-1,3,4-thiadiazol-2-yl]-1-[4-(morpholinomethyl)phenyl]-5-oxo-pyrrolidine-3-carboxamide;
(3 S)—N-[5-[2-(4-chlorophenyl)ethyl]-1,3,4-thiadiazol-2-yl]-1-[4-[[methyl(tetrahydropyran-4-yl)amino]methyl]phenyl]-5-oxo-pyrrolidine-3-carboxamide;
(3 S)-1-[4-(azepan-1-ylmethyl)phenyl]-N-[5-[2-(4-chlorophenyl)ethyl]-1,3,4-thiadiazol-2-yl]-5-oxo-pyrrolidine-3-carboxamide;
(3 S)—N-[5-[2-(4-chlorophenyl)ethyl]-1,3,4-thiadiazol-2-yl]-1-[4-[(4-methyl-1-piperidyl)methyl]phenyl]-5-oxo-pyrrolidine-3-carboxamide;
(3 S)—N-[5-[2-(4-chlorophenyl)ethyl]-1,3,4-thiadiazol-2-yl]-5-oxo-1-[4-(1-piperidylmethyl)phenyl]pyrrolidine-3-carboxamide;
(3 S)—N-[5-[2-(4-chlorophenyl)ethyl]-1,3,4-thiadiazol-2-yl]-1-[4-[[2-methoxyethyl(methyl)amino]methyl]phenyl]-5-oxo-pyrrolidine-3-carboxamide;
N-[5-[2-(4-chlorophenyl)ethyl]-1,3,4-thiadiazol-2-yl]-1-[4-[(4-methyl-1-piperidyl)methyl]phenyl]-5-oxo-pyrrolidine-3-carboxamide;
N-[5-(2-cyclohexylethyl)-1,3,4-thiadiazol-2-yl]-1-[4-(1,4-oxazepan-4-ylmethyl)phenyl]-5-oxo-pyrrolidine-3-carboxamide;
(3 S)-1-[4-(morpholinomethyl)phenyl]-5-oxo-N-[5-[2-[4-(trifluoromethyl)phenyl]ethyl]-1,3,4-thiadiazol-2-yl]pyrrolidine-3-carboxamide;
N-[5-[2-(4-chlorophenyl)ethyl]-1,3,4-thiadiazol-2-yl]-1-[4-(diethyl aminomethyl)phenyl]-5-oxo-pyrrolidine-3-carboxamide;
N-[5-[2-(4-chlorophenyl)ethyl]-1,3,4-thiadiazol-2-yl]-5-oxo-1-[4-(1-piperidylmethyl)phenyl]pyrrolidine-3-carboxamide;
N-[5-[2-(4-chlorophenyl)ethyl]-1,3,4-thiadiazol-2-yl]-1-[4-[[2-methoxyethyl(methyl)amino]methyl]phenyl]-5-oxo-pyrrolidine-3-carboxamide;
N-[5-[2-(4-chlorophenyl)ethyl]-1,3,4-thiadiazol-2-yl]-1-[4-(1,4-oxazepan-4-ylmethyl)phenyl]-5-oxo-pyrrolidine-3-carboxamide;

N-[5-[2-(4-chlorophenyl)ethyl]-1,3,4-thiadiazol-2-yl]-1-[4-[(4-hydroxy-1-piperidyl)methyl]phenyl]-5-oxo-pyrrolidine-3-carboxamide;
(3 S)-1-[4-(3-azabicyclo[3.1.0]hexan-3-ylmethyl)phenyl]-N-[5-[2-(4-chlorophenyl)ethyl]-1,3,4-thiadiazol-2-yl]-5-oxo-pyrrolidine-3-carboxamide;
(3 S)—N-[5-[2-(4-chlorophenyl)ethyl]-1,3,4-thiadiazol-2-yl]-1-[4-(1,4-oxazepan-4-ylmethyl)phenyl]-5-oxo-pyrrolidine-3-carboxamide;
N-[5-[2-(4-chlorophenyl)ethyl]-1,3,4-thiadiazol-2-yl]-5-oxo-1-[4-[(tetrahydropyran-4-ylamino)methyl]phenyl]pyrrolidine-3-carboxamide;
N-[5-(2-cyclohexylethyl)-1,3,4-thiadiazol-2-yl]-5-oxo-1-[4-(1-piperidylmethyl)phenyl]pyrrolidine-3-carboxamide;
N-[5-(2-cyclopentylethyl)-1,3,4-thiadiazol-2-yl]-1-[4-(morpholinomethyl)phenyl]-5-oxo-pyrrolidine-3-carboxamide;
(3 S)—N-[5-[2-(4-fluorophenyl)ethyl]-1,3,4-thiadiazol-2-yl]-1-[4-(morpholinomethyl)phenyl]-5-oxo-pyrrolidine-3-carboxamide;
N-[5-[2-(4-chlorophenyl)ethyl]-1,3,4-thiadiazol-2-yl]-1-[4-[[methyl(propyl)amino]methyl]phenyl]-5-oxo-pyrrolidine-3-carboxamide;
1-[4-(3-azabicyclo[3.1.0]hexan-3-ylmethyl)phenyl]-N-[5-[2-(4-chlorophenyl)ethyl]-1,3,4-thiadiazol-2-yl]-5-oxo-pyrrolidine-3-carboxamide;
N-[5-[2-(4-chlorophenyl)ethyl]-1,3,4-thiadiazol-2-yl]-1-[4-[[methyl(tetrahydropyran-4-yl)amino]methyl]phenyl]-5-oxo-pyrrolidine-3-carboxamide;
N-[5-[2-(4-chlorophenyl)ethyl]-1,3,4-thiadiazol-2-yl]-1-[4-[[ethyl(isobutyl)amino]methyl]phenyl]-5-oxo-pyrrolidine-3-carboxamide;
N-[5-(2-cyclopentylethyl)-1,3,4-thiadiazol-2-yl]-1-[4-[(4-fluoro-1-piperidyl)methyl]phenyl]-5-oxo-pyrrolidine-3-carboxamide;
1-[4-(azepan-1-ylmethyl)phenyl]-N-[5-[2-(4-chlorophenyl)ethyl]-1,3,4-thiadiazol-2-yl]-5-oxo-pyrrolidine-3-carboxamide;
N-[5-(2-cyclopentylethyl)-1,3,4-thiadiazol-2-yl]-1-[4-[(3,3-difluoro-1-piperidyl)methyl]phenyl]-5-oxo-pyrrolidine-3-carboxamide;
N-[5-[2-(4-chlorophenyl)ethyl]-1,3,4-thiadiazol-2-yl]-1-[4-[(dipropylamino)methyl]phenyl]-5-oxo-pyrrolidine-3-carboxamide;
N-[5-[2-(4-chlorophenyl)ethyl]-1,3,4-thiadiazol-2-yl]-1-[4-[(4-methylpiperazin-1-yl)methyl]phenyl]-5-oxo-pyrrolidine-3-carboxamide;
1-[4-(morpholinomethyl)phenyl]-5-oxo-N-[5-(2-phenylethyl)thiazol-2-yl]pyrrolidine-3-carboxamide;
N-[5-[2-(4-chlorophenyl)ethyl]-1,3,4-thiadiazol-2-yl]-1-[4-[[(2S,6R)-2,6-dimethylmorpholin-4-yl]methyl]phenyl]-5-oxo-pyrrolidine-3-carboxamide;
N-[5-[2-(4-chlorophenyl)ethyl]-1,3,4-thiadiazol-2-yl]-1-[4-[[ethyl(propyl)amino]methyl]phenyl]-5-oxo-pyrrolidine-3-carboxamide;
N-[5-[2-(4-chlorophenyl)ethyl]-1,3,4-thiadiazol-2-yl]-1-[4-(morpholinomethyl)phenyl]-5-oxo-pyrrolidine-3-carboxamide;
N-[5-(2-cyclopentylethyl)-1,3,4-thiadiazol-2-yl]-1-[4-(1,4-oxazepan-4-ylmethyl)phenyl]-5-oxo-pyrrolidine-3-carboxamide;
N-[5-(2-cyclopentylethyl)-1,3,4-thiadiazol-2-yl]-1-[4-[(4,4-difluoro-1-piperidyl)methyl]phenyl]-5-oxo-pyrrolidine-3-carboxamide;
N-[3-[2-(4-chlorophenyl)ethyl]-1H-pyrazol-5-yl]-1-[4-(morpholinomethyl)phenyl]-5-oxo-pyrrolidine-3-carboxamide;
N-[5-[2-(4-chlorophenyl)ethyl]-1,3,4-thiadiazol-2-yl]-1-[4-[[(2S,6S)-2,6-dimethylmorpholin-4-yl]methyl]phenyl]-5-oxo-pyrrolidine-3-carboxamide;
(3 S)—N-[6-[2-(4-fluorophenyl)ethyl]pyridazin-3-yl]-1-[4-[[methyl(tetrahydropyran-4-yl)amino]methyl]phenyl]-5-oxo-pyrrolidine-3-carboxamide;
N-[5-[2-(4-chlorophenyl)ethyl]-1,3,4-thiadiazol-2-yl]-1-[4-[[ethyl(isopropyl)amino]methyl]phenyl]-5-oxo-pyrrolidine-3-carboxamide;
5-[2-(4-chlorophenyl)ethyl]-N-[1-[4-(morpholinomethyl)phenyl]-5-oxo-pyrrolidin-3-yl]-1,3,4-thiadiazole-2-carboxamide;
5-[2-(4-chlorophenyl)ethyl]-N-[1-[4-(1,4-oxazepan-4-ylmethyl)phenyl]-5-oxo-pyrrolidin-3-yl]-1,3,4-thiadiazole-2-carboxamide;
5-[2-(4-chlorophenyl)ethyl]-N-[(3R)-1-[4-(morpholinomethyl)phenyl]-5-oxo-pyrrolidin-3-yl]-1,3,4-thiadiazole-2-carboxamide;
5-[2-(4-chlorophenyl)ethyl]-N-[(3R)-1-[4-(morpholinomethyl)phenyl]pyrrolidin-3-yl]-1,3,4-thiadiazole-2-carboxamide;
5-[2-(4-chlorophenyl)ethyl]-N-[(3R)-5-oxo-1-[4-(1-piperidylmethyl)phenyl]pyrrolidin-3-yl]-1,3,4-thiadiazole-2-carboxamide;
5-[2-(4-chlorophenyl)ethyl]-N-[(3 S)-5-oxo-1-[4-(1-piperidylmethyl)phenyl]pyrrolidin-3-yl]-1,3,4-thiadiazole-2-carboxamide;
N-[1-[4-(azepan-1-ylmethyl)phenyl]-5-oxo-pyrrolidin-3-yl]-5-[2-(4-chlorophenyl)ethyl]-1,3,4-thiadiazole-2-carboxamide;
5-[2-(4-chlorophenyl)ethyl]-N-[(3 S)-1-[4-(morpholinomethyl)phenyl]-5-oxo-pyrrolidin-3-yl]-1,3,4-thiadiazole-2-carboxamide;
5-[2-(4-chlorophenyl)ethyl]-N-[1-[4-[(4-methyl-1-piperidyl)methyl]phenyl]-5-oxo-pyrrolidin-3-yl]-1,3,4-thiadiazole-2-carboxamide;
5-[2-(4-chlorophenyl)ethyl]-N-[(3 S)-1-[4-[(4-methyl-1-piperidyl)methyl]phenyl]-5-oxo-pyrrolidin-3-yl]-1,3,4-thiadiazole-2-carboxamide;
5-[2-(4-chlorophenyl)ethyl]-N-[(3R)-1-[4-[(4-methyl-1-piperidyl)methyl]phenyl]-5-oxo-pyrrolidin-3-yl]-1,3,4-thiadiazole-2-carboxamide;
5-[2-(4-chlorophenyl)ethyl]-N-[5-oxo-1-[4-(1-piperidylmethyl)phenyl]pyrrolidin-3-yl]-1,3,4-thiadiazole-2-carboxamide;
N-[1-[4-(3-azabicyclo[3.1.0]hexan-3-ylmethyl)phenyl]-5-oxo-pyrrolidin-3-yl]-5-[2-(4-chlorophenyl)ethyl]-1,3,4-thiadiazole-2-carboxamide;
5-[2-(4-chlorophenyl)ethyl]-N-[(3R)-5-oxo-1-[4-[(3-oxopiperazin-1-yl)methyl]phenyl]pyrrolidin-3-yl]-1,3,4-thiadiazole-2-carboxamide;
5-[2-(4-chlorophenyl)ethyl]-N-[1-[4-[[2-methoxyethyl(methyl)amino]methyl]phenyl]-5-oxo-pyrrolidin-3-yl]-1,3,4-thiadiazole-2-carboxamide;
5-[2-(4-chlorophenyl)ethyl]-N-[(3R)-5-oxo-1-[4-(1-piperidylmethyl)phenyl]pyrrolidin-3-yl]isoxazole-3-carboxamide;
5-[2-(4-chlorophenyl)ethyl]-N-[5-oxo-1-[4-(1-piperidylmethyl)phenyl]pyrrolidin-3-yl]isoxazole-3-carboxamide;
5-[2-(4-chlorophenyl)ethyl]-N-[(3 S)-5-oxo-1-[4-(1-piperidylmethyl)phenyl]pyrrolidin-3-yl]isoxazole-3-carboxamide;

(3 S)—N-[5-[2-(4-chlorophenyl)ethyl]isoxazol-3-yl]-5-oxo-1-[4-(1-piperidylmethyl)phenyl]pyrrolidine-3-carboxamide;
N-[5-(2-cyclohexylethyl)-1,3,4-thiadiazol-2-yl]-1-[4-(morpholinomethyl)phenyl]-5-oxo-pyrrolidine-3-carboxamide;
(3 S)—N-[6-[2-(4-fluorophenyl)ethyl]pyridazin-3-yl]-1-[4-[[methyl(tetrahydrofuran-3-yl)amino]methyl]phenyl]-5-oxo-pyrrolidine-3-carboxamide;
N-[6-[2-(4-fluorophenyl)ethyl]pyridazin-3-yl]-1-[4-(morpholinomethyl)phenyl]-5-oxo-pyrrolidine-3-carboxamide;
N-[5-[2-(4-methoxyphenyl)ethyl]-1,3,4-thiadiazol-2-yl]-1-[4-(morpholinomethyl)phenyl]-5-oxo-pyrrolidine-3-carboxamide;
N-[5-[2-(4-chlorophenyl)ethyl]-1,3,4-thiadiazol-2-yl]-5-oxo-1-[4-(pyrrolidin-1-ylmethyl)phenyl]pyrrolidine-3-carboxamide;
(3 S)—N-[5-[2-(4-chlorophenyl)ethyl]isoxazol-3-yl]-1-[4-[[methyl(tetrahydrofuran-3-yl)amino]methyl]phenyl]-5-oxo-pyrrolidine-3-carboxamide;
4-[[[5-[2-(4-chlorophenyl)ethyl]-1,3,4-thiadiazol-2-yl]amino]methyl]-1-[4-(morpholinomethyl)phenyl]pyrrolidin-2-one;
N-[5-[(4-fluorophenyl)methylsulfanyl]-1,3,4-thiadiazol-2-yl]-1-[4-(morpholinomethyl)phenyl]-5-oxo-pyrrolidine-3-carboxamide;
(3 S)—N-[6-[2-(4-fluorophenyl)ethyl]pyridazin-3-yl]-1-[4-[[methyl(oxetan-3-yl)amino]methyl]phenyl]-5-oxo-pyrrolidine-3-carboxamide;
N-[5-[2-(4-chlorophenyl)ethyl]-1,3,4-thiadiazol-2-yl]-1-[4-(1,4-diazepan-1-ylmethyl)phenyl]-5-oxo-pyrrolidine-3-carboxamide;
1 tert-butyl 4-[[4-[4-[[5-[2-(4-chlorophenyl)ethyl]-1,3,4-thiadiazol-2-yl]carbamoyl]-2-oxo-pyrrolidin-1-yl]phenyl]methyl]piperazine-1-carboxylate;
1-[4-(morpholinomethyl)phenyl]-5-oxo-N-[5-(2-phenylethyl)isoxazol-3-yl]pyrrolidine-3-carboxamide;
N-[5-[2-(4-chlorophenyl)ethyl]-1,3,4-thiadiazol-2-yl]-1-[4-[[isopropyl(methyl)amino]methyl]phenyl]-5-oxo-pyrrolidine-3-carboxamide;
N-[5-[2-(4-chlorophenyl)ethyl]-1,3,4-thiadiazol-2-yl]-5-oxo-1-[4-(piperazin-1-ylmethyl)phenyl]pyrrolidine-3-carboxamide;
(3R)—N-[5-[2-(4-chlorophenyl)ethyl]-1,3,4-thiadiazol-2-yl]-1-[4-(morpholinomethyl)phenyl]-5-oxo-pyrrolidine-3-carboxamide;
1-[4-(morpholinomethyl)phenyl]-5-oxo-N-[6-(2-phenylethyl)pyridazin-3-yl]pyrrolidine-3-carboxamide;
(3R)—N-[5-[2-(4-chlorophenyl)ethyl]-1,3,4-thiadiazol-2-yl]-5-oxo-1-[4-(1-piperidylmethyl)phenyl]pyrrolidine-3-carboxamide;
(3 S)-5-oxo-1-[4-(1-piperidylmethyl)phenyl]-N-[5-(2-tetrahydropyran-2-ylethyl)-1,3,4-thiadiazol-2-yl]pyrrolidine-3-carboxamide;
(3 S)-1-[4-(morpholinomethyl)phenyl]-5-oxo-N-[5-(2-tetrahydropyran-2-ylethyl)-1,3,4-thiadiazol-2-yl]pyrrolidine-3-carboxamide;
N-[5-(2-cyclopentylethyl)-1,3,4-thiadiazol-2-yl]-5-oxo-1-[4-(1-piperidylmethyl)phenyl]pyrrolidine-3-carboxamide;
5-[2-(4-chlorophenyl)ethyl]-N-[(3 S)-1-[4-(morpholinomethyl)phenyl]pyrrolidin-3-yl]-1,3,4-thiadiazole-2-carboxamide;
5-[2-(4-fluorophenyl)ethyl]-N-[5-oxo-1-[4-(1-piperidylmethyl)phenyl]pyrrolidin-3-yl]-1,3,4-thiadiazole-2-carboxamide;
5-[2-(4-chlorophenyl)ethyl]-N-[(3R)-1-[4-[(4-hydroxy-4-methyl-1-piperidyl)methyl]phenyl]-5-oxo-pyrrolidin-3-yl]-1,3,4-thiadiazole-2-carboxamide;
5-[2-(4-chlorophenyl)ethyl]-N-[(3R)-1-[4-[[(3-hydroxy-3-methyl-butyl)amino]methyl]phenyl]-5-oxo-pyrrolidin-3-yl]-1,3,4-thiadiazole-2-carboxamide hydrochloride;
5-[2-(4-chlorophenyl)ethyl]-N-[(3R)-1-[4-[[(3-hydroxy-3-methyl-butyl)-methyl-amino]methyl]phenyl]-5-oxo-pyrrolidin-3-yl]-1,3,4-thiadiazole-2-carboxamide;
N-[5-oxo-1-[4-(1-piperidylmethyl)phenyl]pyrrolidin-3-yl]-5-(2-phenylethyl)-1,3,4-thiadiazole-2-carboxamide;
5-[2-(4-fluorophenyl)ethyl]-N-[(3R)-5-oxo-1-[4-(1-piperidylmethyl)phenyl]pyrrolidin-3-yl]isoxazole-3-carboxamide;
5-[2-(4-fluorophenyl)ethyl]-N-[(3 S)-5-oxo-1-[4-(1-piperidylmethyl)phenyl]pyrrolidin-3-yl]isoxazole-3-carboxamide;
N-[5-oxo-1-[4-(1-piperidylmethyl)phenyl]pyrrolidin-3-yl]-5-(2-phenylethyl)isoxazole-3-carboxamide;
1-[4-(morpholinomethyl)phenyl]-5-oxo-N-[5-(2-phenylethyl)-1,3,4-thiadiazol-2-yl]pyrrolidine-3-carboxamide;
N-[5-[2-(4-chlorophenyl)ethyl]-1,3,4-thiadiazol-2-yl]-1-[4-[(dimethylamino)methyl]phenyl]-5-oxo-pyrrolidine-3-carboxamide;
(3 S)—N-[6-[2-(4-fluorophenyl)ethyl]pyridazin-3-yl]-5-oxo-1-[4-(1-piperidylmethyl)phenyl]pyrrolidine-3-carboxamide;
1-[4-(morpholinomethyl)phenyl]-5-oxo-N-[5-(2-phenylethyl)-1H-pyrazol-3-yl]pyrrolidine-3-carboxamide;
(3 S)—N-[6-[2-(4-fluorophenyl)ethyl]pyridazin-3-yl]-1-[4-(morpholinomethyl)phenyl]-5-oxo-pyrrolidine-3-carboxamide;
N-[5-(3-methylpentyl)-1,3,4-thiadiazol-2-yl]-1-[4-(morpholinomethyl)phenyl]-5-oxo-pyrrolidine-3-carboxamide;
N-[5-(3-methylpentyl)-1,3,4-thiadiazol-2-yl]-5-oxo-1-[4-(1-piperidylmethyl)phenyl]pyrrolidine-3-carboxamide;
4-[[5-[2-(4-chlorophenyl)ethyl]-1,3,4-thiadiazol-2-yl]methylamino]-1-[4-(morpholinomethyl)phenyl]pyrrolidin-2-one;
N-[[4-[4-[[5-[2-(4-chlorophenyl)ethyl]-1,3,4-thiadiazol-2-yl]carbamoyl]-2-oxo-pyrrolidin-1-yl]phenyl]methyl]-1-methyl-piperidine-4-carboxamide;
(3 S)-1-[4-(morpholinomethyl)phenyl]-5-oxo-N-[5-(2-tetrahydrofuran-2-ylethyl)-1,3,4-thiadiazol-2-yl]pyrrolidine-3-carboxamide;
N-[5-(cyclohexoxymethyl)thiazol-2-yl]-1-[4-(morpholinomethyl)phenyl]-5-oxo-pyrrolidine-3-carboxamide;
1-[4-(morpholinomethyl)phenyl]-5-oxo-N-[5-(2-tetrahydropyran-4-ylethyl)-1,3,4-thiadiazol-2-yl]pyrrolidine-3-carboxamide;
5-oxo-1-[4-(1-piperidylmethyl)phenyl]-N-[5-(2-tetrahydropyran-4-yl ethyl)-1,3,4-thiadiazol-2-yl]pyrrolidine-3-carboxamide;
(3 S)-5-oxo-1-[4-(1-piperidylmethyl)phenyl]-N-[5-(2-tetrahydropyran-4-ylethyl)-1,3,4-thiadiazol-2-yl]pyrrolidine-3-carboxamide;
(3 S)-5-oxo-1-[4-(1-piperidylmethyl)phenyl]-N-[5-(2-tetrahydrofuran-2-ylethyl)-1,3,4-thiadiazol-2-yl]pyrrolidine-3-carboxamide;
N-[5-[2-(4-chlorophenyl)ethyl]-1-methyl-pyrazol-3-yl]-1-[4-(morpholinomethyl)phenyl]-5-oxo-pyrrolidine-3-carboxamide;

5-[2-(4-chlorophenyl)ethyl]-N-[(3R)-1-[4-[(4-methylpiperazin-1-yl)methyl]phenyl]-5-oxo-pyrrolidin-3-yl]-1,3,4-thiadiazole-2-carboxamide;
N-[5-oxo-1-[4-(1-piperidylmethyl)phenyl]pyrrolidin-3-yl]-5-(2-phenylethyl)-1,3,4-oxadiazole-2-carboxamide;
5-[2-(2-furyl)ethyl]-N-[5-oxo-1-[4-(1-piperidylmethyl)phenyl]pyrrolidin-3-yl]-1,3,4-thiadiazole-2-carboxamide;
5-[(4-chlorophenyl)methylamino]-N-[5-oxo-1-[4-(1-piperidylmethyl)phenyl]pyrrolidin-3-yl]-1,3,4-thiadiazole-2-carboxamide;
N-[5-oxo-1-[4-(1-piperidylmethyl)phenyl]pyrrolidin-3-yl]-5-(2-phenylethyl)thiazole-2-carboxamide;
N-[5-oxo-1-[4-(1-piperidylmethyl)phenyl]pyrrolidin-3-yl]-3-(2-phenylethyl)isoxazole-5-carboxamide;
N-[3-[2-(4-methoxyphenyl)ethyl]isoxazol-5-yl]-1-[4-(morpholinomethyl)phenyl]-5-oxo-pyrrolidine-3-carboxamide;
1-[4-(morpholinomethyl)phenyl]-5-oxo-N-[3-(2-phenylethyl)isoxazol-5-yl]pyrrolidine-3-carboxamide;
1-[4-(morpholinomethyl)phenyl]-5-oxo-N-[2-(2-phenylethyl)thiazol-5-yl]pyrrolidine-3-carboxamide;
N-[5-[2-(4-chlorophenyl)ethyl]-2-methyl-pyrazol-3-yl]-1-[4-(morpholinomethyl)phenyl]-5-oxo-pyrrolidine-3-carboxamide;
1-[4-(aminomethyl)phenyl]-N-[5-[2-(4-chlorophenyl)ethyl]-1,3,4-thiadiazol-2-yl]-5-oxo-pyrrolidine-3-carboxamide;
N-[5-oxo-1-[4-(1-piperidylmethyl)phenyl]pyrrolidin-3-yl]-3-(2-phenylethyl)-1H-pyrazole-5-carboxamide;
N-[5-oxo-1-[4-(1-piperidylmethyl)phenyl]pyrrolidin-3-yl]-6-(2-phenylethyl)pyridazine-3-carboxamide;
N-[5-oxo-1-[4-(1-piperidylmethyl)phenyl]pyrrolidin-3-yl]-2-(2-phenylethyl)thiazole-5-carboxamide;
N-[5-[2-(4-methoxyphenyl)ethyl]-1,3,4-oxadiazol-2-yl]-1-[4-(morpholinomethyl)phenyl]-5-oxo-pyrrolidine-3-carboxamide;
1-[4-(4-{5-[2-(4-Chloro-phenyl)-ethyl]-[1,3,4]thiadiazol-2-ylcarbamoyl}-2-oxo-pyrrolidin-1-yl)-3-fluoro-benzyl]-piperidinium; chloride;
4-[4-(4-{5-[2-(4-Chloro-phenyl)-ethyl]-[1,3,4]thiadiazol-2-ylcarbamoyl}-2-oxo-pyrrolidin-1-yl)-3-fluoro-benzyl]-morpholin-4-ium; chloride;
1-[4-(4-{5-[2-(4-Chloro-phenyl)-ethyl]-[1,3,4]thiadiazol-2-ylcarbamoyl}-2-oxo-pyrrolidin-1-yl)-3-fluoro-benzyl]-4-methyl-piperidinium; chloride;
1-{4-[(Ethyl-methyl-amino)-methyl]-phenyl}-5-oxo-pyrrolidine-3-carboxylic acid {5-[2-(4-chloro-phenyl)-ethyl]-[1,3,4]thiadiazol-2-yl}-amide;
(3 S)—N-[5-[2-(4-chlorophenyl)ethyl]-1,3,4-thiadiazol-2-yl]-1-[4-(2-oxa-7-azaspiro[3.4]octan-7-ylmethyl)phenyl]-5-oxo-pyrrolidine-3-carboxamide;
(3 S)—N-[5-[2-(4-chlorophenyl)ethyl]-1,3,4-thiadiazol-2-yl]-1-[4-(2-oxa-6-azaspiro[3.3]heptan-6-ylmethyl)phenyl]-5-oxo-pyrrolidine-3-carboxamide;
5-[2-(4-chlorophenyl)ethyl]-N-[(3R)-1-[4-(methanesulfonamidomethyl)phenyl]-5-oxo-pyrrolidin-3-yl]-1,3,4-thiadiazole-2-carboxamide;
1-(4-Morpholin-4-ylmethyl-phenyl)-5-oxo-pyrrolidine-3-carboxylic acid {5-[2-(4-fluoro-phenyl)-ethyl]-[1,3,4]thiadiazol-2-yl}-amide; hydrochloride.

15. A pharmaceutical composition comprising a compound according to claim 1, or a pharmaceutically acceptable salt thereof, in admixture with a pharmaceutically acceptable diluent or carrier.

16. A method of treating a proliferative disorder in a patient in need of such treatment, said method comprising administering to said patient a therapeutically effective amount of a compound according to claim 1, or a pharmaceutically acceptable salt thereof.

17. A method of treating cancer in a patient in need of such treatment, said method comprising administering to said patient a therapeutically effective amount of a compound according to claim 1, or a pharmaceutically acceptable salt or solvate thereof.

18. A method of treating a benign proliferative disorder in a patient in need of such treatment, said method comprising administering to said patient a therapeutically effective amount of a compound according to claim 1, or a pharmaceutically acceptable salt thereof.

19. A method of treating fibrosis in a patient in need of such treatment, said method comprising administering to said patient a therapeutically effective amount of a compound according to claim 1, or a pharmaceutically acceptable salt thereof.

20. A method of treating lung fibrosis in a patient in need of such treatment, said method comprising administering to said patient a therapeutically effective amount of a compound according to claim 1, or a pharmaceutically acceptable salt thereof.

21. A method of treating renal fibrosis in a patient in need of such treatment, said method comprising administering to said patient a therapeutically effective amount of a compound according to claim 1, or a pharmaceutically acceptable salt thereof.

22. A method of treating hepatic fibrosis in a patient in need of such treatment, said method comprising administering to said patient a therapeutically effective amount of a compound according to claim 1, or a pharmaceutically acceptable salt thereof.

23. A method of treating skin fibrosis in a patient in need of such treatment, said method comprising administering to said patient a therapeutically effective amount of a compound according to claim 1, or a pharmaceutically acceptable salt thereof.

24. A method of treating inflammation, pain, diabetes mellitus, hypertension, atherosclerosis, thrombosis, urethral obstructive disease, hepatitis B and C and/or pruritus in a patient in need of such treatment, said method comprising administering to said patient a therapeutically effective amount of a compound according to claim 1, or a pharmaceutically acceptable salt thereof.

25. A method of treating cancer in a patient in need of such treatment, said method comprising administering to said patient a combination of a therapeutically effective amount of a compound according to claim 1, or a pharmaceutically acceptable salt thereof, and one or more additional therapies.

26. A combination of a compound, or a pharmaceutically acceptable salt thereof, according to claim 1, with one or more additional therapeutic agents for the use in the treatment of cancer, inflammation, pain, diabetes mellitus, hypertension, atherosclerosis, thrombosis, urethral obstructive disease, fibrosis, hepatitis B and C and/or pruritus.

* * * * *